US008436013B2

(12) United States Patent
Liu et al.

(10) Patent No.: US 8,436,013 B2
(45) Date of Patent: May 7, 2013

(54) COMPOUNDS AND METHODS FOR TREATMENT OF ALPHA-1 ANTITRYPSIN DEFICIENCY

(75) Inventors: Chen Liu, Gainesville, FL (US); David A. Ostrov, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 575 days.

(21) Appl. No.: 12/500,540

(22) Filed: Jul. 9, 2009

(65) Prior Publication Data

US 2010/0076018 A1 Mar. 25, 2010

Related U.S. Application Data

(63) Continuation of application No. PCT/US2007/022717, filed on Oct. 26, 2007.

(60) Provisional application No. 60/879,913, filed on Jan. 10, 2007, provisional application No. 60/900,406, filed on Feb. 9, 2007, provisional application No. 60/939,617, filed on May 22, 2007, provisional application No. 60/945, 079, filed on Jun. 19, 2007, provisional application No. 60/945,336, filed on Jun. 20, 2007.

(51) Int. Cl.
| | |
|---|---|
| *A61K 31/47* | (2006.01) |
| *A61K 31/38* | (2006.01) |
| *A61K 31/36* | (2006.01) |
| *A61K 31/22* | (2006.01) |
| *A61K 31/185* | (2006.01) |
| *A61K 31/075* | (2006.01) |
| *A61K 31/01* | (2006.01) |
| *A01N 43/06* | (2006.01) |
| *A01N 43/30* | (2006.01) |
| *A01N 37/02* | (2006.01) |
| *A01N 37/00* | (2006.01) |
| *A01N 31/14* | (2006.01) |
| *A01N 27/00* | (2006.01) |
| *C07C 215/16* | (2006.01) |
| *C07C 409/00* | (2006.01) |
| *C07C 333/28* | (2006.01) |
| *C07C 317/44* | (2006.01) |
| *C07C 69/76* | (2006.01) |
| *C07C 41/00* | (2006.01) |
| *C07C 43/02* | (2006.01) |
| *C07C 43/20* | (2006.01) |
| *C07C 33/00* | (2006.01) |

(52) U.S. Cl.
USPC .......... 514/311; 514/444; 514/448; 514/464; 514/546; 514/577; 514/718; 514/762; 546/178; 549/60; 549/81; 549/436; 560/106; 568/630; 568/808

(58) Field of Classification Search .................. 514/311, 514/444, 448, 464, 546, 577, 718, 762; 546/178; 549/60, 81, 436; 560/106; 568/630, 808
See application file for complete search history.

(56) References Cited

U.S. PATENT DOCUMENTS 5,753,692 A * 5/1998 Chang et al. ............... 514/444
6,403,646 B1 6/2002 Perlmutter et al.

FOREIGN PATENT DOCUMENTS

WO WO 0152830 A2 * 7/2001

OTHER PUBLICATIONS

Teckman, Journal of Pediatric Gastroenterology and Nutrition, 2004, Lippincott Williams & Wilkins, vol. 39, pp. 34-37.*
Bernier et. al., Trends in Endocrinology and Metabolism, 2004, Elsevier, vol. 15, No. 5, pp. 222-228.*
Burrows et. al., PNAS, 2000, National Academy of Sciences, vol. 97, No. 4, pp. 1796-1801.*
Abusriwill et. al., Current Opinion in Pulmonary Medicine, 2006, Lippincott Williams & Wilkins, vol. 12, pp. 125-131.*
Sandhaus, Thorax, 2004, British Thoracic Society, vol. 59, pp. 904-909.*
Wilson et. al., Chest, 2000, American College of Chest Physicians, vol. 118, pp. 867-871.*
Rios-Santamarina et. al., European Journal of Pharmaceutical Sciences, 2004, Elsevier, vol. 22, pp. 271-277.*
Burrows et al., Chemical chaperones mediate increased secretion of mutant α1-antitrypsin (α1-AT) Z: A potential pharmacological strategy for prevention of liver injury and emphysema in a1-AT deficiency. PNAS, vol. 97, No. 4, pp. 1796-1801 (2000).
Van Hest, "Biosynthetic-Synthetic Polymer Conjugates", Journal of Macromolecular Science, Part C: Polymer Reviews, 47:63-92 (2007).
Carrell et al., :Alpha 1-Antitrypsin Deficiency; A Model for Conformational Diseases N. Engl J Med, vol. 346, No. 1, (2002).
Lomas et al., "Polymerisation Underlies Alpha1-Antitrypsin Deficiency, Dementia and Other Serpinopathies", Frontiers in Bioscience 9, 2873-2891 (2004).
ATS Board of Directors, "Standards for the Diagnosis and Management of Individuals with Alpha-1 Antitrypsin Deficiency", American Journal of Respiratory and Critical Care Medicine, vol. 168, pp. 818-900 (2003).
International Search Report and Written Opinion dated Jan. 30, 2009 in corresponding PCT application No. PCT/US07/22717.

(Continued)

*Primary Examiner* — Shengjun Wang
*Assistant Examiner* — Sarah Pihonak
(74) *Attorney, Agent, or Firm* — Edwards Wildman Palmer LLP; Peter F. Corless; Mark D. Russett

(57) ABSTRACT

The invention features compositions and methods that are useful for treating or preventing AAT deficiency and associated conditions. In addition, the invention provides methods for identifying compounds useful for treatment of AAT deficiency and associated conditions.

8 Claims, 8 Drawing Sheets

OTHER PUBLICATIONS

Gooptu et al., "Crystallographic and Cellular Characterisation of Two Mechanisms Stabilising the Native Fold of $\alpha_1$-Antitrypsin: Implications for Disease and Drug Design", Journal of Molecular Biology, vol. 387(4):857-868 (2009), accessed at http://www.sciencedirect.com/science/article/pii/S0022283609001429.

Mallya et al., "Small molecules block the polymerisation of Z $\alpha_1$-antitrypsin and increase the clearance of intracellular aggregates", J Med. Chem. 50(22) 5357-5363 (2007).

* cited by examiner

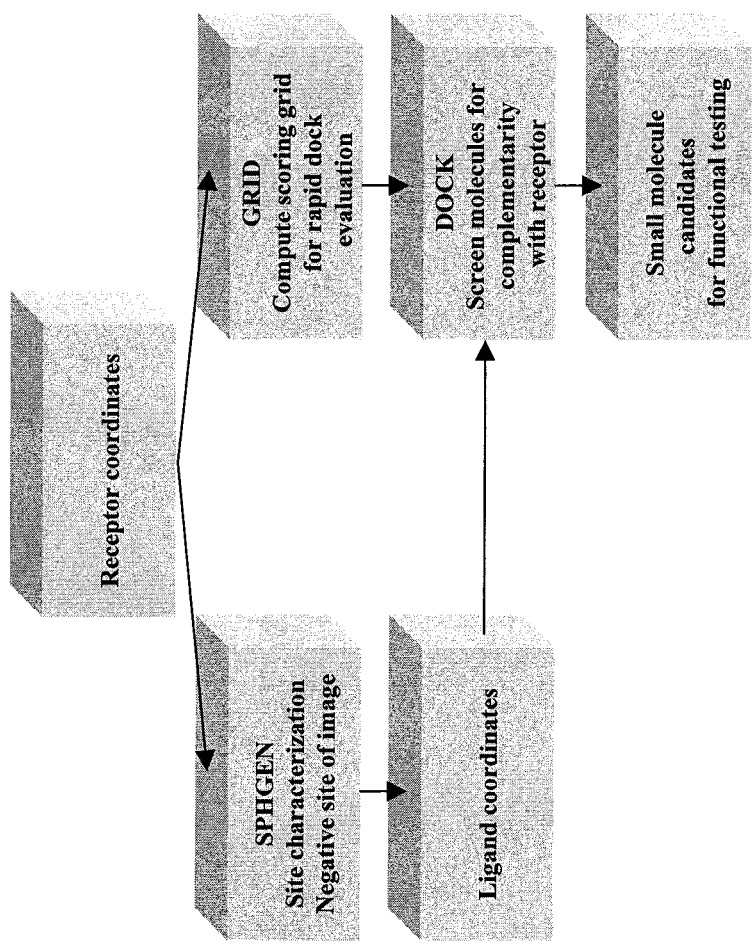
Figure 1. *In silico* molecular docking strategy

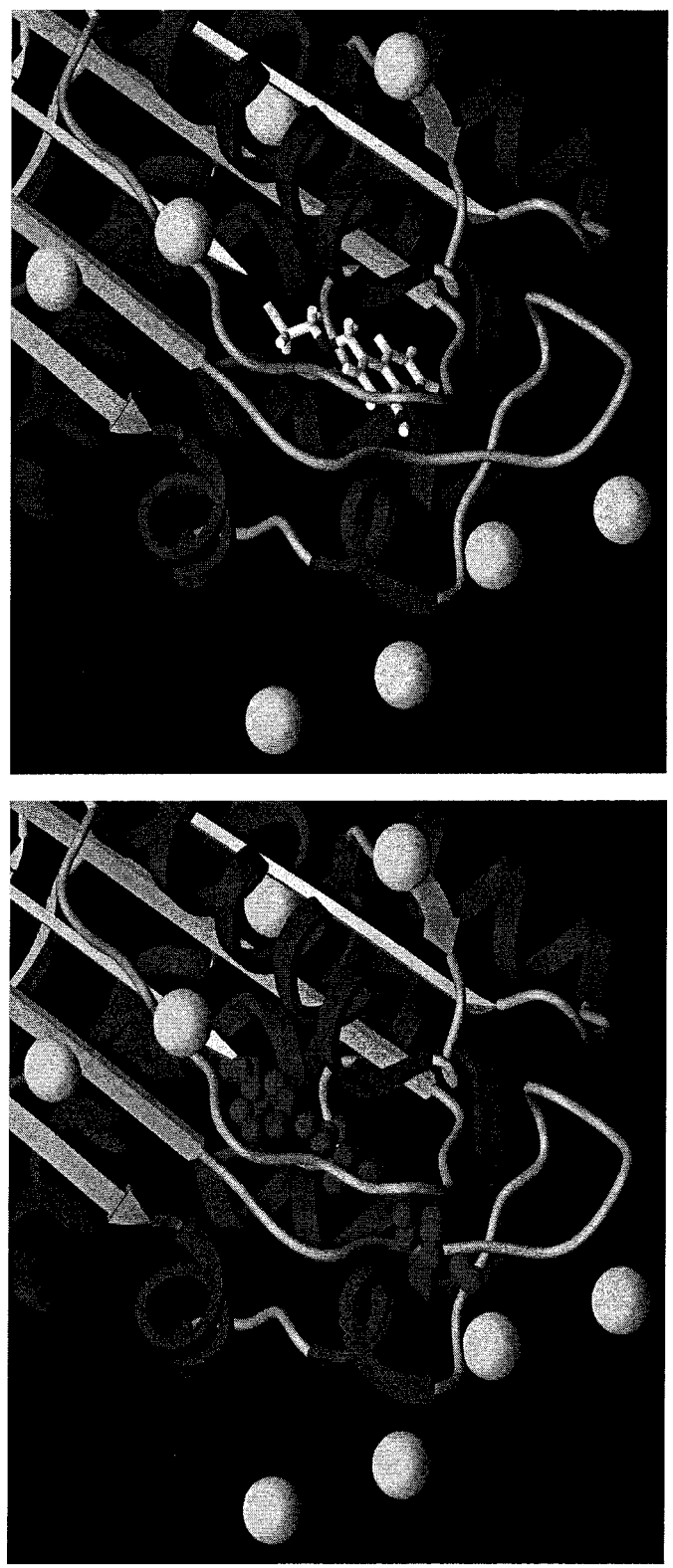
Figure 2. The crystal structure of mutant AAT provides the basis for molecular docking.

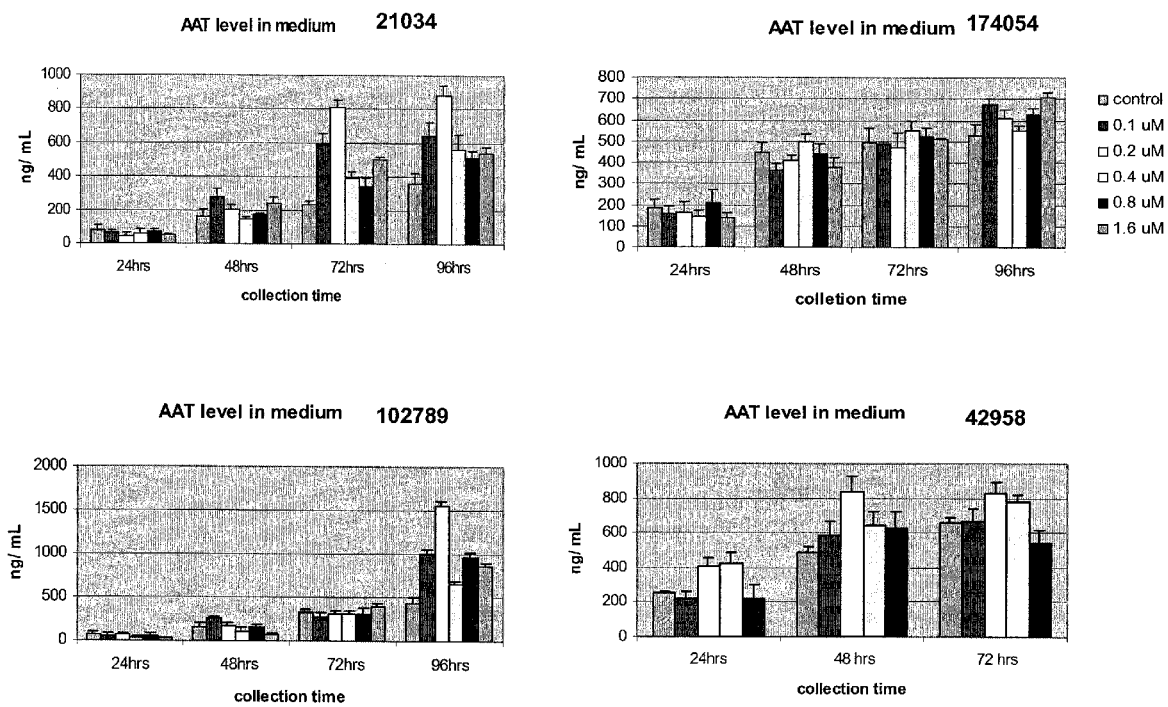
Figure 3. Effects of small molecule compounds on AAT secretion in cells.

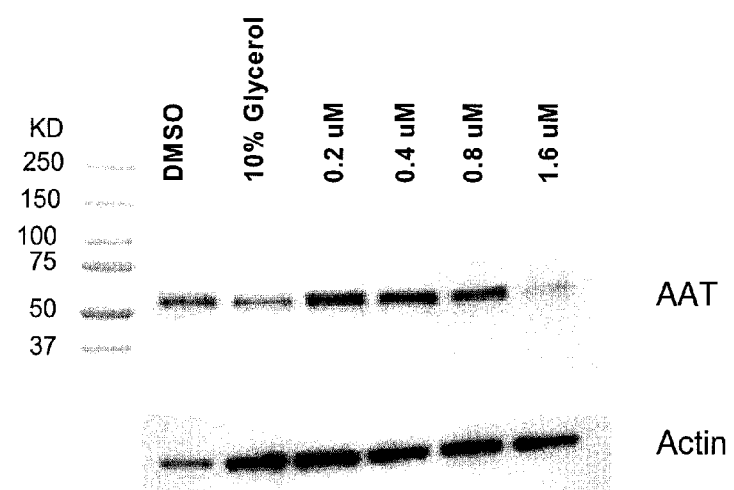
Figure 4. Polymer inhibitor (NCI/NSC 102789) reduces the ATZ accumulation in cells.

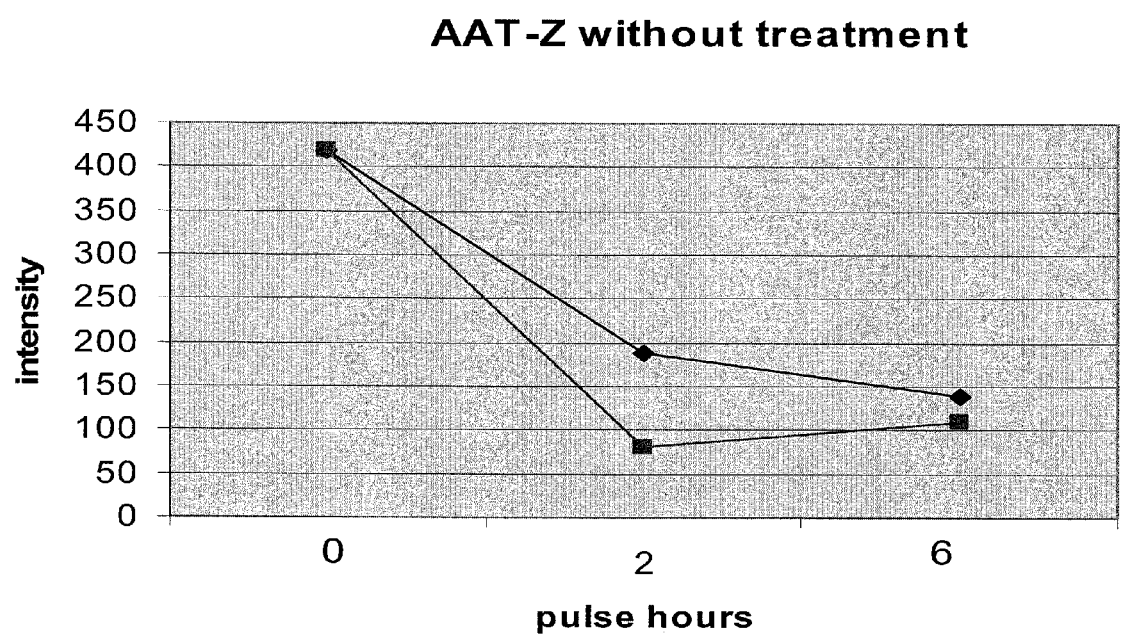
Figure 5A. Polymer inhibitor (NCI/NSC102789) increases ATZ secretion.

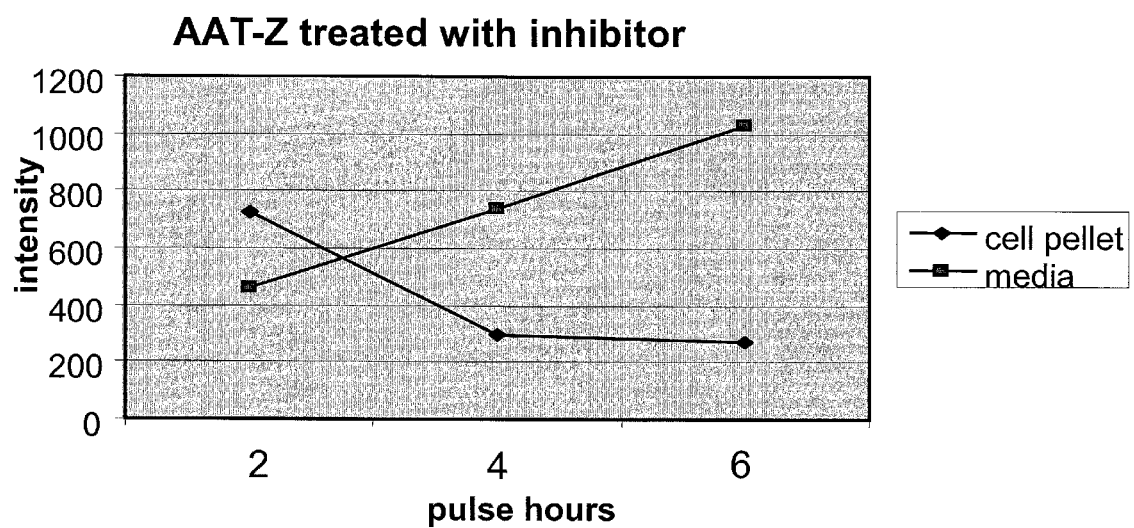
Figure 5B. Polymer inhibitor (NCI/NSC102789) increases ATZ secretion.

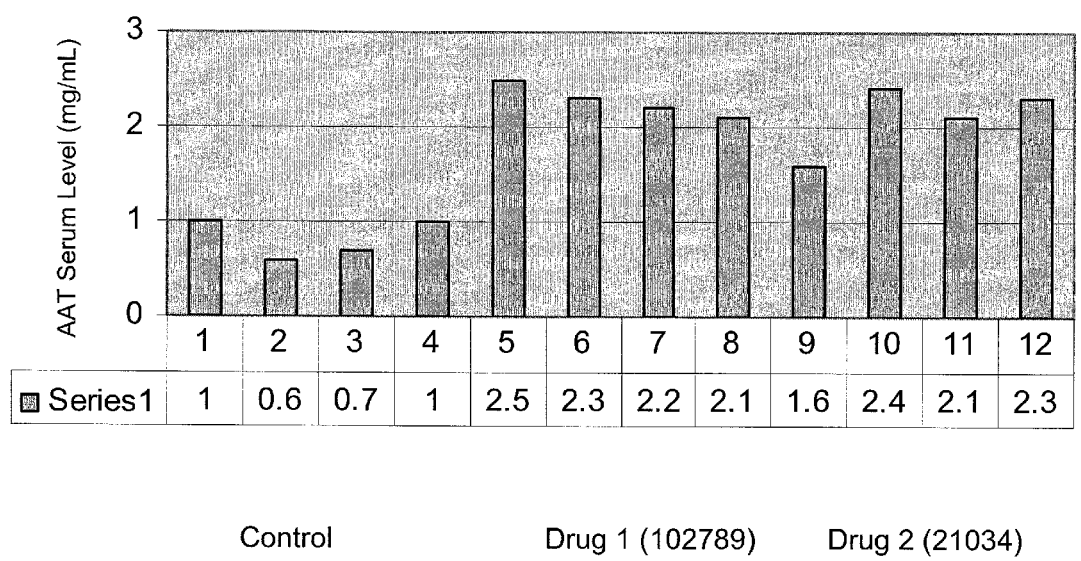
Figure 6. Compounds can increase AAT secretion in transgenic animals.

COMPOUNDS AND METHODS FOR TREATMENT OF ALPHA-1 ANTITRYPSIN DEFICIENCY

RELATED APPLICATIONS

This application is a continuation of International Application No. PCT/US2007/022717 having an International filing date of Oct. 26, 2007 incorporated herein by reference which claims the benefit of U.S. Provisional Patent Application No. 60/879,913, filed Jan. 10, 2007, U.S. Provisional Patent Application No. 60/900,406, filed Feb. 9, 2007, U.S. Provisional Patent Application No. 60/939,617, filed May 22, 2007, U.S. Provisional Patent Application No. 60/945,079, filed Jun. 19, 2007, and U.S. Provisional Patent Application No. 60/945,336, filed Jun. 20, 2007. The contents of each of these applications are incorporated herein by reference.

GOVERNMENT SUPPORT

This work was funded in part by grant HL080222 from NIH. The U.S. Government has certain rights in the invention.

BACKGROUND OF THE INVENTION

Alpha-1 antitrypsin (AAT) deficiency is an autosomal recessive genetic disorder causing both lung and liver diseases, for which there is no effective treatment. The most common genotype of AAT deficiency is genotype PiZZ, which encodes mutant AAT, referred to as Z protein (ATZ). It affects 1 in 1,800 live births in Northern European and North American populations. The fundamental pathological process of the AAT deficiency is the accumulation of mutant AAT as polymers within hepatocytes. The resultant low levels of AAT in the serum, result in lung damage by proteinases, and eventually emphysema. Though not entirely clear, the protein accumulation in hepatocytes appears to play a crucial role in the development of liver diseases, including cirrhosis and hepatocellular carcinoma.

AAT is a member of the serine proteinase inhibitor family[1]. Its main function is to protect tissue from the damage caused by various proteinases during inflammatory responses[2, 3]. The liver is the main source of AAT. Deficiency in AAT causes both lung and liver diseases[4]. There is no effective treatment available, except for symptomatic control and replacement therapy[5]. A current focus on new treatment modalities is gene therapy[6]. Although gene therapy may alleviate lung disease, the liver disorders are expected to remain. The ideal treatment would be a therapeutic intervention that promotes ATZ secretion from hepatocytes, which could cure both lung and liver diseases, and probably other diseases that are associated with AAT deficiency, such as panniculitis, vasculitis, pancreatitis or renal disease[7].

The prototype of AAT deficiency (PiZZ) affects 1 in 1,800 live births in Northern European and North American populations[8, 9]. The disease is associated with mutation of the gene, AAT[10]. The Z form of AAT is a mutation that results from the substitution of lysine for glutamate at position 342, and accounts for the defective secretion and mutant molecule accumulation in the endoplasmic reticulum of hepatocytes[11-14]. In ZZ homozygotes, the low serum level of AAT predisposes the patients to lung disease, such as emphysema. In a subgroup of AAT deficiency patients, liver diseases also occur, which include chronic hepatitis, cirrhosis, and hepatocellular carcinoma[15]. In fact, AAT deficiency-associated liver disease is the most common genetic liver disease in children and the most common genetic diagnosis for liver transplantation[16]. However, the pathogenesis of the liver disease is poorly understood.

The lung disease in AAT deficiency patients is usually of an earlier onset than in patients with chronic obstructive pulmonary disease (COPD) and often appears to be out of proportion to their smoking history. The typical pattern shows lower lobe predominant or pan-lobular emphysema[17, 18]. The pathogenesis of emphysema associated with AAT deficiency is closely related to neutrophil elastase. Leucocyte elastase, a neutrophil enzyme, can bind to the active site of AAT and permanently inactivates it, which causes elastin degradation, and lung tissue injury and destruction[19, 20] Smoking is a definite compounding factor for the development of lung disease. Other genetic factors and environmental conditions are also implicated in the pathogenesis of AAT-associated lung disease[21].

The current concept for AAT deficiency-associated liver cell injury is "gain of function"[16, 22]. In another words, it is related to the protein accumulation within hepatocytes (and, hence, is actually a storage disorder). The supporting evidence was mainly derived from studies using mice transgenic for mutant human AAT[23-25]. Although the detailed kinetics of mutant AAT within a hepatocyte are still not completely defined, several groups have demonstrated that the mutation of AAT affects the gap between the third and fifth strands of the "A" sheet of the protein, which results in dimerization[26-28]. The dimerized proteins eventually form polymers, which are retained in the ER. It is also possible that some unidentified cellular factors play a role in the turnover of the mutant AAT, though the details are still unknown. Recent studies have shown that chemical chaperons can reverse the cellular mislocalization or misfolding of mutant protein[29, 30]. It has been shown that 4-phenylbutyric acid (PBA) can increase blood levels of AAT in a human ATZ transgenic model[29]. Its potential clinical effectiveness is currently undergoing evaluation).

It is still unclear how the retained protein causes cell damage. Recent studies by Teckman et al. suggested that the accumulation could initiate cellular responses[31, 32]. Among the responses is increased numbers of autophagosomes[31, 32]. It is known that autophagy is associated with cell stress, differentiation and morphogenesis[33]. The autophagic response in the hepatocytes with mutant AAT is probably a protective mechanism for host cells. Interestingly, both AAT and mitochondria are present in the autophagosomes[31]. Moreover, the mitochondria that are not surrounded by the autophagic vacuolar membranes are invariably damaged to a certain extent, indicating mitochondria may be involved in mutant AAT associated liver cell injury. Many studies have attributed the mitochondrion as one of the key players regulating program cell death (apoptosis)[34, 35]. Therefore, a working hypothesis is that the accumulation of mutant AAT may subject the host cell undergoing apoptosis through signaling pathways related to the mitochondria. Supporting this notion, Perlmutter et al. have shown that activated caspase-3 is increased in the ATZ mouse liver[16]. These observations indicate that hepatocyte apoptosis may be an important mechanism for ATZ-related liver damage.

Clinical studies have indicated that the protein accumulation alone could not explain all the cases of the liver diseases, implying that other factors may play a role in the pathogenesis, such as environmental factors and genetic traits[16, 36, 37]. It has been shown that increasing ambient temperature causes an increase in the polymerization of mutant AAT[11]. The phenomenon has been employed as an in vitro assay to study biochemical mechanisms of AAT polymerization. Systemic diseases also affect liver disease incidence and severity, probably through cytokines. It is known that several cytokines such as IL-1 or IL-6, affect expression levels of AAT[38-40]. However, little is known on how these cytokines are involved in the disease process. In the case of IL-6, its signal is transmitted through STAT3 (signal transducer and activator of transcription 3). The binding site of STAT3 has been identified in the enhancer region of the AAT gene[41].

It appears that mutant AAT retention through polymerization is a key mechanism of hepatocyte damage. It is also the cause for low level of AAT in the serum.

Except for symptomatic control and replacement therapy, there is currently no effective treatment available for AAT deficiency.

SUMMARY OF THE INVENTION

The invention features compositions and methods that are useful for treating and/or preventing AAT deficiency and conditions related to AAT deficiency, and methods for identifying compounds useful for such treatment.

In one aspect, the invention provides a method of treating alpha-1 antitrypsin (AAT) deficiency in a subject in need of such treatment, the method comprising administering to the subject a compound capable of disrupting polymerization of the mutant Z form of AAT under conditions such that AAT deficiency is treated.

In one aspect, the invention provides a method of treating a condition related to or associated with alpha-1 antitrypsin (AAT) deficiency in a subject in need of such treatment, the method comprising administering to the subject a compound capable of disrupting polymerization of the mutant Z form of AAT under conditions such that a condition related to or associated with AAT deficiency is treated.

In another aspect, the invention provides a method of reducing the accumulation of the mutant Z form of alpha-1 antitrypsin (AAT) in a cell (e.g., a hepatocyte), the method comprising contacting the cell with a compound capable of disrupting polymerization of the mutant Z form of AAT under conditions such that accumulation of the mutant Z form of alpha-1 antitrypsin in the cell is reduced.

In yet another aspect, the invention provides a method of increasing the secretion of alpha-1 antitrypsin (AAT) from a cell (e.g., a hepatocyte) producing a mutant Z form of AAT, the method comprising contacting the cell with a compound capable of disrupting polymerization of the mutant Z form of AAT under conditions such that secretion of AAT from the cell is increased.

In still another aspect, the invention provides a method for inhibiting the polymerization of the mutant Z form of alpha-1 antitrypsin (AAT) in a cell (e.g., a hepatocyte), comprising contacting the mutant Z form of alpha-1 antitrypsin with a compound capable of disrupting polymerization of the mutant Z form of AAT under conditions such that polymerization of the mutant Z form of alpha-1 antitrypsin in the cell is reduced (e.g., the amount of or accumulation of the mutant Z form of alpha-1 antitrypsin in the cell is reduced).

In a still further aspect, the invention provides a method for treating a subject diagnosed as having AAT deficiency (e.g., due to the subject producing a mutant form of AAT), the method comprising administering to the subject a pharmaceutically effective amount of a compound capable of disrupting polymerization of the mutant Z form of AAT.

In another aspect, the invention provides a method of increasing the amount of a biochemically functional conformation of an AAT protein in a cell (e.g., a hepatocyte or a lung cell), the method comprising contacting the cell with an effective amount of a compound capable of disrupting polymerization of the mutant Z form of AAT, with the proviso that the compound is not 4-phenylbutyrate; under conditions such that the amount of a biochemically functional conformation of an AAT protein is increased in the cell.

In another aspect, the invention provides a pharmaceutical composition comprising a compound capable of disrupting polymerization of the mutant Z form of AAT, or a pharmaceutically acceptable salt thereof, in a pharmaceutically acceptable vehicle, with the proviso that the a compound capable of disrupting polymerization of the mutant Z form of AAT is not a 4-phenylbutyrate.

In another aspect, the invention provides an oral dosage form comprising a compound capable of disrupting polymerization of the mutant Z form of AAT, or a pharmaceutically acceptable salt thereof, in a pharmaceutically acceptable vehicle, with the proviso that the compound capable of disrupting polymerization of the mutant Z form of AAT is not a 4-phenylbutyrate.

In a further aspect, the invention provides a kit for the treatment of AAT deficiency, the kit comprising an effective amount of the amount of a compound capable of disrupting polymerization of the mutant Z form of AAT; and instructions for administering the compound capable of disrupting polymerization of the mutant Z form of AAT to a subject to treat AAT deficiency.

In any of the above methods, pharmaceutical compositions, oral dosage forms, or kits of the invention, the compound can be a compound identified by computational screening, and/or can be a compound selected from the following: 5-(2-Bromo-ethoxy-methyl)-quinolin-8-ol, 3,4-methylenedioxy-6-nitrocinnamic acid, 4-hydroxyantipyrine, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl-benzene, 2-acetyl-5-chlorothiophene, or 1,9-decadiene; or a pharmaceutically acceptable salt thereof. In certain embodiments, the compound is 1,9-decadiene. In certain embodiments, the compound is 3,4-methylenedioxy-6-nitrocinnamic acid Also provided are methods, including computational screening methods, for identifying compounds which can bind to an AAT monomer or polymer, and compounds which can inhibit or disrupt polymerization or aggregation of the mutant Z form of AAT.

In one aspect, the invention provides a computer for producing a three-dimensional representation of a) a molecule or molecular complex, wherein said molecule or molecular complex comprises a binding site in the P6-P3 region of an AAT protein monomer defined by structure coordinates of amino acid residues in the P6-P3 region of the AAT protein; or b) a three-dimensional representation of a homologue of said molecule or molecular complex, wherein said homologue comprises a binding pocket that has a root mean square deviation from the backbone atoms of said amino acids of not more than about 2.0 (more preferably not more than 1.5) angstroms, wherein said computer comprises: (i) a machine-readable data storage medium comprising a data storage material encoded with machine-readable data, wherein said data comprises the structure coordinates of structure coordinates of amino acid residues in the P6-P3 region of the AAT protein; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

In another aspect, the invention provides a method for evaluating the potential of a chemical entity to associate with a) a molecule or molecular complex comprising a binding pocket defined by structure coordinates of AAT protein monomer amino acid residues in the P6-P3 region of the AAT protein, or b) a homologue of said molecule or molecular complex, wherein said homologue comprises a binding pocket that has a root mean square deviation from the backbone atoms of said amino acids of not more than 2.0 (more preferably 1.5) angstroms, the method comprising the steps of: i) employing computational means to perform a fitting operation between the chemical entity and a binding pocket of the molecule or molecular complex; and ii) analyzing the results of the fitting operation to quantify the association between the chemical entity and the binding pocket.

In yet another aspect, the invention provides a method for identifying a potential agonist or antagonist of mutant AAT polymerization, the method comprising the steps of: a) using the atomic coordinates of AAT protein monomer amino acid residues in the P6-P3 region of the AAT protein to generate a three-dimensional structure of an AAT binding site; and b) employing the three-dimensional structure to design or select the potential agonist or antagonist.

In another aspect, the invention provides a method of treating or preventing liver damage in a subject suffering from or susceptible to alpha-1 antitrypsin (AAT) deficiency, the method comprising administering to the subject a compound capable of disrupting polymerization of the mutant Z form of AAT under conditions such that liver damage in the subject is treated or prevented.

In another aspect, wherein the method further comprises the step of identifying the subject as suffering from or susceptible to AAT-deficiency-related liver damage prior to the step of administering to the subject the compound capable of disrupting polymerization of the mutant Z form of AAT. In certain embodiments, the method further comprises the step of determining the efficacy of administration to the subject of the compound capable of disrupting polymerization of the mutant Z form of AAT. In certain embodiments, the step of determining the efficacy of administration to the subject of the compound comprises testing liver function of the subject before and after administration of the compound, and comparing the liver function determined before administration of the compound and after administration of the compound.

In another aspect, the invention provides a method of treating or preventing liver damage in a subject suffering from or susceptible to alpha-1 antitrypsin (AAT) deficiency, the method comprising administering to the subject an effective amount of a compound capable of increasing secretion of the mutant Z form of AAT from a hepatocyte.

In another aspect, the invention provides a method of preserving liver function in a subject suffering from or susceptible to alpha-1 antitrypsin (AAT) deficiency, the method comprising administering to the subject a compound capable of disrupting polymerization of the mutant Z form of AAT under conditions such that liver function in the subject is preserved.

In another aspect, the invention provides a method of preserving liver function in a subject suffering from or susceptible to alpha-1 antitrypsin (AAT) deficiency, the method comprising administering to the subject a compound capable of increasing secretion of the mutant Z foam of AAT from a hepatocyte, under conditions such that liver function in the subject is preserved.

In another aspect, the invention provides a packaged pharmaceutical formulation for the treatment or prevention of liver damage in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the treatment or prevention of liver damage in the subject.

In another aspect, the invention provides a packaged pharmaceutical formulation for preserving liver function in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the preservation of liver function in the subject.

In another aspect, the invention provides a packaged pharmaceutical formulation for the treatment or prevention of liver damage in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a hepatocyte; and instructions for administering the compound capable of disrupting polymerization of the mutant Z form of AAT to a subject suffering from or susceptible to AAT deficiency for the treatment or prevention of liver damage in the subject.

In another aspect, the invention provides a packaged pharmaceutical formulation for preserving liver function in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a hepatocyte; and instructions for administering the compound capable of disrupting polymerization of the mutant Z form of AAT to a subject suffering from or susceptible to AAT deficiency for the preservation of liver function in the subject.

In another aspect, the invention provides a method of treating or preventing lung damage in a subject suffering from or susceptible to alpha-1 antitrypsin (AAT) deficiency, the method comprising administering to the subject a compound capable of disrupting polymerization of the mutant Z form of AAT under conditions such that lung damage in the subject is treated or prevented. In certain embodiments, the method further comprises the step of identifying the subject as suffering from or susceptible to AAT-deficiency-related lung damage prior to the step of administering to the subject the compound capable of disrupting polymerization of the mutant Z form of AAT. In certain embodiments, the method further comprises the step of determining the efficacy of administration to the subject of the compound capable of disrupting polymerization of the mutant Z form of AAT. In certain embodiments, the method includes the step of determining the efficacy of administration to the subject of the compound comprises monitoring or testing lung function of the subject before and after administration of the compound, and comparing the lung function determined before administration of the compound and after administration of the compound.

In another aspect, the invention provides a method of treating or preventing lung damage in a subject suffering from or susceptible to alpha-1 antitrypsin (AAT) deficiency, the method comprising administering to the subject an effective amount of a compound capable of increasing secretion of the mutant Z form of AAT from a cell, e.g., a hepatocyte or lung cell.

In another aspect, the invention provides a method of preserving lung function in a subject suffering from or susceptible to alpha-1 antitrypsin (AAT) deficiency, the method comprising administering to the subject a compound capable of disrupting polymerization of the mutant Z form of AAT under conditions such that lung function in the subject is preserved.

In another aspect, the invention provides a method of preserving lung function in a subject suffering from or susceptible to alpha-1 antitrypsin (AAT) deficiency, the method comprising administering to the subject a compound capable of increasing secretion of the mutant Z form of AAT from a cell, e.g., a hepatocyte or lung cell, under conditions such that lung function in the subject is preserved.

In another aspect, the invention provides a packaged pharmaceutical formulation for the treatment or prevention of lung damage in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and
instructions for administering the compound capable of disrupting polymerization of the mutant Z form of AAT to a subject suffering from or susceptible to AAT deficiency for the treatment or prevention of lung damage in the subject.

In another aspect, the invention provides a packaged pharmaceutical formulation for preserving lung function in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the preservation of lung function in the subject.

In another aspect, the invention provides a packaged pharmaceutical formulation for the treatment or prevention of lung damage in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a cell, e.g., a hepatocyte or lung cell; and instructions for administering the compound capable of disrupting polymerization of the mutant Z form of AAT to a subject suffering from or susceptible to AAT deficiency for the treatment or prevention of lung damage in the subject.

In another aspect, the invention provides a packaged pharmaceutical formulation for preserving lung function in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a cell, e.g., a hepatocyte or lung cell; and instructions for administering the compound capable of disrupting polymerization of the mutant Z form of AAT to a subject suffering from or susceptible to AAT deficiency for the preservation of lung function in the subject.

In another aspect, the invention relates to the use of a compound described herein (e.g., a compound of Table 1, infra) for the manufacture of a medicament for the treatment (or prevention) of AAT deficiency in a subject. In another aspect, the invention relates to the use of a compound described herein (e.g., a compound of Table 1, infra) for the manufacture of a medicament for the treatment (or prevention) of liver damage in a subject. In another aspect, the invention relates to the use of a compound described herein (e.g., a compound of Table 1, infra) for the manufacture of a medicament for the treatment (or prevention) of lung damage in a subject.

Other aspects and embodiments of the invention are described herein.

BRIEF DESCRIPTION OF THE DRAWINGS

FIG. 1 is a scheme illustrating a computational screening method for identifying candidate compounds for binding to and/or stabilizing a mutant AAT protein and/or treating AAT deficiency.

FIG. 2. The crystal structure of mutant AAT provides the basis for molecular docking. The interaction site between AAT monomers is depicted as magenta spheres. Blue spheres mark the boundary of the scoring grid to calculate potential interactions between small molecules and AAT. Molecular docking selected $C_{12}H_{12}BrNO_2$ out of approximately 140,000 small molecules for binding the AAT monomer interaction site. $C_{12}H_{12}BrNO_2$ is shown in the predicted bound position in AAT.

FIG. 3. Effects of small molecule compounds on AAT secretion in cells. The CHO-ATZ cells were treated with various concentrations of NCI compounds. The culture supernatants were harvested for ELISA analysis. The data represent the means from 4-separate experiments. As seen in the figure, compounds 1,9-decadiene and 3,4-methylenedioxy-6-nitrocinnamic acid (NSC 21034) effectively enhance ATZ secretion in the cells. Since the compounds were prepared with DMSO, all the control cells were also treated with comparable concentrations of DMSO.

FIG. 4. Polymer inhibitor (1,9-decadiene) reduces the ATZ accumulation in cells. Cells were treated with polymer inhibitor and harvested for Western blot analysis. It shows that the inhibitor can effectively reduce the accumulation of ATZ in cells.

FIG. 5. Polymer inhibitor (1,9-decadiene) increases ATZ secretion. The cells were labeled with $^{35}S$ and harvested at the indicated time points. The protein extracts were immunoprecipitated using anti-AAT antibody. The immunocomplexes were then resolved in PAGE gel. The intensity of AAT bands were then quantified and calculated. FIG. 5A is the cells treated with DMSO control; FIG. 5B represents result of cells with polymer inhibitor treatment. It shows that the inhibitor increases the ATZ secretion in the supernatant.

FIG. 6. Compounds according to the invention can increase AAT secretion in transgenic animals. The animals were treated for two weeks. Serum AAT levels were determined by ELISA assay. The figure shows that Drug 1 and Drug 2 enhance AAT serum level by more than two-fold.

DETAILED DESCRIPTION OF THE INVENTION

Definitions

Figure 7:
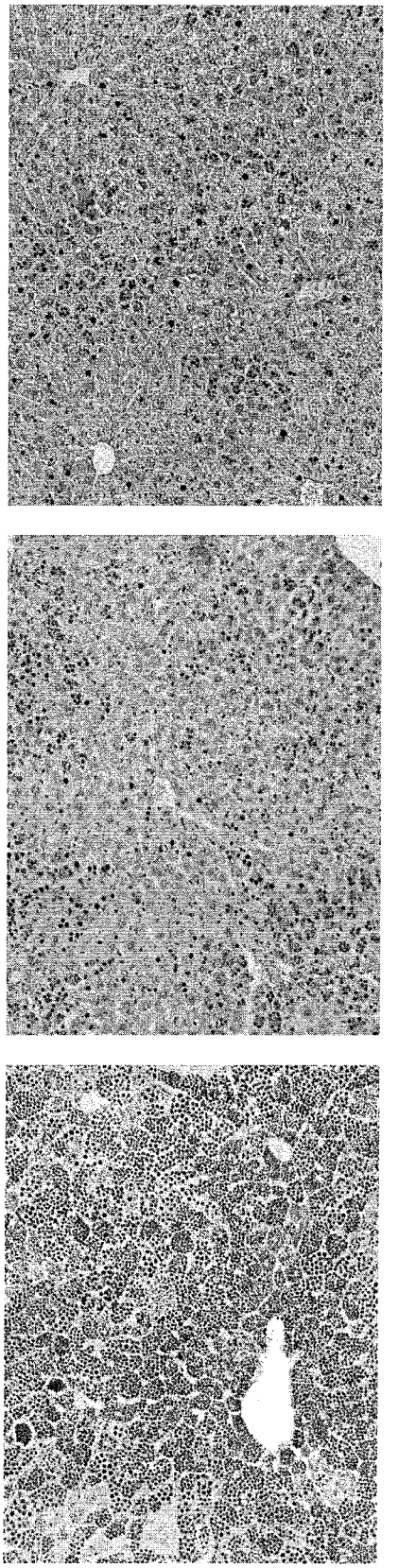
FIG. 7. Compounds according to the invention decrease AAT accumulation and reduce inflammation in liver cells compared to control. AAT-Z transgenic mice were treated by i.p. injection of a compound or control for 7 days, followed by collection of liver tissue. The Figure shows that Drug 1 and Drug 2, when administered to animals, decrease AAT accumulation in hepatocytes as demonstrated by PASD staining. The treatment also reduced live tissue inflammation compared to animals treated with a control.

By "reduces" or "increases" is meant a negative or positive alteration, respectively, of at least 10%, 25%, 50%, 75%, or 100%.

By "a biochemically functional conformation" is meant that a protein has a tertiary structure that permits the protein to be biologically active. When a mutant AAT protein assumes a biochemically functional conformation its biological activity is increased. Accordingly, a mutant protein having a biochemically functional conformation may, to some degree, functionally substitute for a wild-type protein.

By "subject" is meant a warm-blooded animal, including a mammal, including a human, or a non-human mammal, such as a bovine, equine, canine, ovine, or feline.

The term "treating" or "treated" refers to administering a compound described herein to a subject with the purpose to cure, heal, alleviate, relieve, alter, remedy, ameliorate, improve, or affect a disease or condition, the symptoms of the disease or condition or the predisposition toward the disease or condition.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

"An effective amount" refers to an amount of a compound, which confers a therapeutic effect on the treated subject. The therapeutic effect may be objective (i.e., measurable by some test or marker) or subjective (i.e., subject gives an indication of or feels an effect). An effective amount of a compound described herein may range from about 1 mg/Kg to about 5000 mg/Kg body weight. Effective doses will also vary depending on route of administration, as well as the possibility of co-usage with other agents.

Compounds of the Invention

It has been found that certain compounds are capable of preventing aggregation or polymerization of mutant AAT proteins. Such compounds are sometimes referred to herein as "AAT-binding" or "mutant AAT-stabilizing" compounds. In certain embodiments, a compound of the invention can bind to and/or stabilize mutant AAT proteins and prevent polymerization.

In certain embodiments, a compound of the invention can prevent, inhibit, or disrupt (e.g., reduce by at least 10%, 25%, 50%, 75%, or 100%) the polymerization or aggregation of mutant AAT proteins, e.g., by binding to a binding site in an AAT protein and blocking binding of one AAT protein to another AAT protein.

In certain embodiments, a compound of the invention can increase secretion of AAT protein (e.g., a mutant AAT protein) from a cell, which can increase AAT serum levels in the blood. This can treat or prevent diseases and conditions, such as liver and lung diseases or damage, associated with AAT deficiency.

In certain embodiments, a compound of the invention is a non-polymeric (e.g., small molecule) compound having a molecular weight less than about 1000 daltons, less than 800, less than 600, less than 500, less than 400, or less than about 300 daltons. In certain embodiments, an active compound can increase the amount (e.g., from or in a cell) of a stably-folded and/or physiologically active mutant protein by at least 10%, 15%, 20%, 25%, 50%, 75%, or 100% compared to an untreated control cell or protein.

Examples of compounds of the invention include the compounds of Table 1, and pharmaceutically acceptable salts thereof.

As used herein, the term "pharmaceutically acceptable salt," is a salt formed from an acid and a basic group of one of the compounds of the invention (e.g., of Table 1, infra). Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable salt" also refers to a salt prepared from a compound of the invention (e.g., of Table 1) having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, e.g., a compound of Table 1, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

Methods of the Invention

The invention features compositions and methods that are useful for preventing polymerization of mutant AAT proteins in vitro or in vivo. And for treatment of conditions associated with AAT deficiency.

The invention is generally based on the discovery that certain compounds can be used to prevent the aggregation or polymerization of mutant AAT proteins (such as ATZ) or to increase the amount of physiologically active AAT protein in a cell. Without wishing to be bound by any particular theory, these compounds are believed to prevent the aggregation or polymerization of mutant AAT proteins by binding to the AAT protein, e.g., at or near the in the P6-P3 region of the protein.

In one aspect, the invention provides a method of treating alpha-1 antitrypsin (AAT) deficiency, or a condition related to AAT deficiency, in a subject in need of such treatment, the method comprising administering to the subject a compound capable of disrupting polymerization of the mutant Z form of AAT under conditions such that AAT deficiency, or a condition related to AAT deficiency, is treated.

Conditions related to AAT deficiency include conditions related to the buildup of AAT in hepatocytes, and/or low levels of AAT in serum, for example, lung damage, emphysema, panniculitis, vasculitis (including anticytoplasmic neutrophilic antibody (C-ANCA)-positive vasculitis (Wegener's granulomatosis), pancreatitis, renal disease, liver damage, and liver diseases such as chronic hepatitis, cirrhosis, and liver cancer (e.g., hepatocellular carcinoma). In certain embodiments, the present methods are also useful for decreasing neutrophil elastase activity, thereby treating or preventing conditions associated with increased neutrophil elastase activity, such as damage to or destruction of pulmonary tissues. For example, by increasing the AAT levels in serum, neutrophil elastase activity, and the tissue damage associated with increased neutrophil elastase activity, can be decreased.

In another aspect, the invention provides a method of reducing the accumulation of the mutant Z form of alpha-1 antitrypsin (AAT) in a cell, the method comprising contacting the cell with a compound capable of disrupting polymerization of the mutant Z form of AAT under conditions such that accumulation of the mutant Z form of alpha-1 antitrypsin in the cell is reduced.

in yet another aspect, the invention provides a method of increasing the secretion of alpha-1 antitrypsin (AAT) from a cell (e.g., a hepatocyte) producing a mutant Z form of AAT, the method comprising contacting the cell with a compound capable of disrupting polymerization of the mutant Z form of AAT under conditions such that secretion of AAT from the cell is increased.

In still another aspect, the invention provides a method for inhibiting the polymerization of the mutant Z form of alpha-1 antitrypsin (AAT) in a cell, comprising contacting the mutant Z form of alpha-1 antitrypsin with a compound capable of disrupting polymerization of the mutant Z form of AAT under conditions such that polymerization of the mutant Z form of alpha-1 antitrypsin in the cell is reduced.

In a still further aspect, the invention provides a method for treating a subject diagnosed as having AAT deficiency (e.g., due to the subject producing a mutant form of AAT), the method comprising administering to the subject a pharmaceutically effective amount of a compound capable of disrupting polymerization of the mutant Z form of AAT.

In another aspect, the invention provides a method of increasing the amount of a biochemically functional conformation of an AAT protein in a cell, the method comprising contacting the cell with an effective amount of a compound capable of disrupting polymerization of the mutant Z form of AAT, with the proviso that the compound is not 4-phenylbutyrate; under conditions such that the amount of a biochemically functional conformation of an AAT protein is increased in the cell.

In another aspect, the invention provides a method of treating or preventing liver damage in a subject suffering from or susceptible to alpha-1 antitrypsin (AAT) deficiency, the method comprising administering to the subject a compound capable of disrupting polymerization of the mutant Z form of AAT under conditions such that liver damage in the subject is treated or prevented. In certain embodiments, the method further comprises the step of identifying the subject as suffering from or susceptible to AAT-deficiency-related liver damage prior to the step of administering to the subject the compound capable of disrupting polymerization of the mutant Z form of AAT. In certain embodiments, the method further comprises the step of determining the efficacy of administration to the subject of the compound capable of disrupting polymerization of the mutant Z form of AAT. In certain embodiments, the step of determining the efficacy of administration to the subject of the compound comprises monitoring or testing liver function of the subject before and after administration of the compound, and comparing the liver function determined before administration of the compound and after administration of the compound.

In another aspect, the invention provides a method of treating or preventing liver damage in a subject suffering from or susceptible to alpha-1 antitrypsin (AAT) deficiency, the method comprising administering to the subject an effective amount of a compound capable of increasing secretion of the mutant Z form of AAT from a hepatocyte.

In another aspect, the invention provides a method of preserving liver function in a subject suffering from or susceptible to alpha-1 antitrypsin (AAT) deficiency, the method comprising administering to the subject a compound capable of disrupting polymerization of the mutant Z form of AAT under conditions such that liver function in the subject is preserved.

In another aspect, the invention provides a method of preserving liver function in a subject suffering from or susceptible to alpha-1 antitrypsin (AAT) deficiency, the method comprising administering to the subject a compound capable of increasing secretion of the mutant Z form of AAT from a hepatocyte, under conditions such that liver function in the subject is preserved.

In another aspect, the invention provides a method of treating or preventing lung damage in a subject suffering from or susceptible to alpha-1 antitrypsin (AAT) deficiency, the method comprising administering to the subject a compound capable of disrupting polymerization of the mutant Z form of AAT under conditions such that lung damage in the subject is treated or prevented. In certain embodiments, the method further comprises the step of identifying the subject as suffering from or susceptible to AAT-deficiency-related lung damage prior to the step of administering to the subject the compound capable of disrupting polymerization of the mutant Z form of AAT. In certain embodiments, the method further comprises the step of determining the efficacy of administration to the subject of the compound capable of disrupting polymerization of the mutant Z form of AAT. In certain embodiments, the method includes the step of determining the efficacy of administration to the subject of the compound comprises monitoring or testing lung function of the subject before and after administration of the compound, and comparing the lung function determined before administration of the compound and after administration of the compound.

In another aspect, the invention provides a method of treating or preventing lung damage in a subject suffering from or susceptible to alpha-1 antitrypsin (AAT) deficiency, the method comprising administering to the subject an effective amount of a compound capable of increasing secretion of the mutant Z form of AAT from a lung cell or a hepatocyte. This may have beneficial effects on preventing or relieving lung injury or emphysema by increasing the serum level of AAT.

In another aspect, the invention provides a method of preserving lung function in a subject suffering from or susceptible to alpha-1 antitrypsin (AAT) deficiency, the method comprising administering to the subject a compound capable of disrupting polymerization of the mutant Z form of AAT under conditions such that lung function in the subject is preserved.

In another aspect, the invention provides a method of preserving lung function in a subject suffering from or susceptible to alpha-1 antitrypsin (AAT) deficiency, the method comprising administering to the subject a compound capable of increasing secretion of the mutant Z form of AAT from a lung cell, under conditions such that lung function in the subject is preserved.

In any of the above methods, the compound can be a compound identified by computational screening, and/or can be a compound selected from the following: 5-(2-Bromo-ethoxy-methyl)-quinolin-8-ol, 3,4-methylenedioxy-6-nitrocinnamic acid, 4-hydroxyantipyrine, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl-benzene, 2-acetyl-5-chlorothiophene, or 1,9-decadiene; or a pharmaceutically acceptable salt thereof. In certain embodiments, the compound is 1,9-decadiene. In certain embodiments, the compound is 3,4-methylenedioxy-6-nitrocinnamic acid. In certain embodiments, mixtures of the above-referenced compounds can be employed. In certain embodiments, the compound is not 4-phenylbutyrate.

These compounds can be used alone or in combination with one or more additional compounds to treat or prevent conditions associated with mutant AAT proteins, including AAT deficiency; for example, liver damage and lung damage.

In certain embodiments, a subject is a subject identified (e.g., by clinical diagnosis or testing) as being in need of treatment, e.g., a treatment described herein.

Methods of stabilizing mutant proteins using a proteasomal inhibitor, an autophagy inhibitor, a lysosomal inhibitor, an inhibitor of protein transport from the ER to the Golgi, an Hsp90 chaperone inhibitor, a heat shock response activator, and a histone deacetylase inhibitor are also described in co-pending U.S. Provisional Patent Application No. 60/703,068, which was filed on Jul. 27, 2005, the contents of which are incorporated herein by reference.

Pharmaceutical Compositions

The present invention features pharmaceutical preparations comprising compounds together with pharmaceutically acceptable carriers, where the compounds provide for the generation of a mutant protein in a biochemically functional conformation. Such preparations have both therapeutic and prophylactic applications. In one embodiment, a pharmaceutical composition includes compound capable of inhibiting mutant AAT protein polymerization (e.g., a compound of Table 1) or a pharmaceutically acceptable salt thereof. Compounds of the invention may be administered as part of a pharmaceutical composition. The compositions should be sterile and contain a therapeutically effective amount of the active compound in a unit of weight or volume suitable for administration to a subject. The compositions and combinations of the invention can be part of a pharmaceutical pack, where each of the compounds is present in individual dosage amounts.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In another aspect, the invention provides a pharmaceutical composition comprising a compound capable of disrupting polymerization of the mutant Z form of AAT, or a pharmaceutically acceptable salt thereof, in a pharmaceutically acceptable vehicle, with the proviso that the a compound capable of disrupting polymerization of the mutant Z form of AAT is not 4-phenylbutyrate.

In another aspect, the invention provides an oral dosage form comprising a compound capable of disrupting polymerization of the mutant Z form of AAT, or a pharmaceutically acceptable salt thereof, in a pharmaceutically acceptable vehicle, with the proviso that the compound capable of disrupting polymerization of the mutant Z form of AAT is not a 4-phenylbutyrate.

In any of the above aspects, the compound can be a compound identified by computational screening, and/or can be a compound selected from the following: 542-Bromo-ethoxy-methyl)-quinolin-8-ol, 3,4-methylenedioxy-6-nitrocinnamic acid, 4-hydroxyantipyrine, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl-benzene, 2-acetyl-5-chlorothiophene, or 1,9-decadiene; or a pharmaceutically acceptable salt thereof. In certain embodiments, the compound is 1,9-decadiene. In certain embodiments, the compound is 3,4-methylenedioxy-6-nitrocinnamic acid. In certain embodiments, mixtures of the above-referenced compounds can be employed. In certain embodiments, the compound is not 4-phenylbutyrate.

Pharmaceutical compositions of the invention to be used for prophylactic or therapeutic administration should be sterile. Sterility is readily accomplished by filtration through sterile filtration membranes (e.g., 0.2 µm membranes), by gamma irradiation, or any other suitable means known to those skilled in the art. Therapeutic compound compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

The compounds may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with the molecules of the present invention, and with each other, in a manner such that there is no interaction that would substantially impair the desired pharmaceutical efficacy.

Compounds of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine;

monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject suffering from or susceptible to AAT deficiency, an effective amount is, e.g., in certain embodiments, an amount sufficient to increase the level of a correctly folded or physiologically active AAT protein in a cell, or, in certain embodiments, an amount sufficient to reduce the amount of a mutant AAT protein in a cell or tissue. With respect to a subject having a disease or disorder related to a mutant AAT protein, an effective amount is an amount sufficient to stabilize, slow, or reduce a symptom associated with an AAT-deficiency-associated pathology such as lung or liver disease. Generally, doses of the compounds of the present invention would be from about 0.01 mg/kg per day to about 1000 mg/kg per day, e.g., from about 0.1 mg/kg per day to about 100 mg/kg per day. It is expected that doses ranging from about 1 to about 1000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one embodiment, a composition of the invention is administered orally. Oral administration may provide certain advantages, e.g., for treatment or prevention of liver damage, oral administration can provide a high concentration of the drug to hepatic circulation and thus to the liver. Other modes of administration include rectal; topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Compositions comprising a composition of the invention can be added to a physiological fluid, such as to the intravitreal humor. For CNS administration, a variety of techniques are available for promoting transfer of the therapeutic across the blood brain barrier including disruption by surgery or injection, drugs which transiently open adhesion contact between the CNS vasculature endothelial cells, and compounds that facilitate translocation through such cells. Oral administration can be preferred for prophylactic treatment because of the convenience to the patient as well as the dosing schedule. Oral administration is also beneficial because of the first passage effect on the liver, which may reduce the systemic side effects.

Pharmaceutical compositions of the invention can optionally further contain one or more additional proteins as desired, including plasma proteins, proteases, and other biological material, so long as it does not cause adverse effects upon administration to a subject. Suitable proteins or biological material may be obtained from human or mammalian plasma by any of the purification methods known and available to those skilled in the art; from supernatants, extracts, or lysates of recombinant tissue culture, viruses, yeast, bacteria, or the like that contain a gene that expresses a human or mammalian plasma protein which has been introduced according to standard recombinant DNA techniques; or from the fluids (e.g., blood, milk, lymph, urine or the like) or transgenic animals that contain a gene that expresses a human plasma protein which has been introduced according to standard transgenic techniques.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising a mutant AAT-stabilizing compound of the present invention can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least −70° C., but can also be stored at higher temperatures of at least 0° C., or between about 0.1° C. and about 42° C., depending on the properties of the composition. It is generally known to the skilled artisan that proteins and polypeptides are sensitive to changes in pH, temperature, and a multiplicity of other factors that may affect therapeutic efficacy.

In certain embodiments a desirable route of administration can be by pulmonary aerosol. Techniques for preparing aerosol delivery systems containing polypeptides are well known to those of skill in the art. Generally, such systems should utilize components that will not significantly impair the biological properties of the antibodies, such as the paratope binding capacity (see, for example, Sciarra and Cutie, "Aerosols," in *Remington's Pharmaceutical Sciences*, 18th edition, 1990, pp 1694-1712; incorporated by reference). Those of skill in the art can readily modify the various parameters and conditions for producing polypeptide aerosols without resorting to undue experimentation.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly(2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono-di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 µm, can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3dioleyloxy)-propyl]-N,N,N-trimethylammonium chloride (DOTMA) and dimethyl dioctadecylammonium bromide (DDAB). Methods for making liposomes are well known in the art and have been described in many publications, for example, in DE 3,218, 121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/03307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terephthalates, polyvinyl alcohols, polyvinyl ethers, polyvinyl esters, poly-vinyl halides, polyvinylpyrrolidone, polyglycolides, polysiloxanes, polyureathanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), polyvinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Nanoparticles are a colloidal carrier system that has been shown to improve the efficacy of the encapsulated drug by prolonging the serum half-life. Polyalkylcyanoacrylates (PACAs) nanoparticles are a polymer colloidal drug delivery system that is in clinical development, as described by Stella et al., J. Pharm. Sci., 2000. 89: p. 1452-1464; Brigger et al., Int. J. Pharm., 2001. 214: p. 37-42; Calvo et al., Pharm. Res., 2001. 18: p. 1157-1166; and Li et al., Biol. Pharm. Bull., 2001. 24: p. 662-665. Biodegradable poly(hydroxyl acids), such as the copolymers of poly(lactic acid) (PLA) and poly(lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier have the ability to be freeze-dried and reconstituted in solution without aggregation; (iv) that the carrier be biodegradable; (v) that the carrier system be of small size; and (vi) that the carrier enhance the particles persistence.

Nanoparticles are synthesized using virtually any biodegradable shell known in the art. In one embodiment, a polymer, such as poly(lactic-acid) (PLA) or poly(lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charge nucleic acid aptamers. Nanoparticles are also modified with polyethylene glycol (PEG), which also increases the half-life and stability of the particles in circulation. Alternatively, the COOH group is converted to an N-hydroxysuccinimide (NHS) ester for covalent conjugation to amine-modified aptamers.

Biocompatible polymers useful in the composition and methods of the invention include, but are not limited to, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetage phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpyrrolidone, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutylmethacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) and combinations of any of these. In one embodiment, the nanoparticles of the invention include PEG-PLGA polymers.

Compositions of the invention may also be delivered topically. For topical delivery, the compositions are provided in any pharmaceutically acceptable excipient that is approved for topical delivery.

Those of skill in the art will recognize that the best treatment regimens for using compounds of the present invention to treat AAT deficiency can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained from the initial clinical trials and the needs of a particular patient.

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 g/Kg body weight. Of course, this dosage amount may be adjusted upward or downward, as is routinely done in such treatment protocols, depending on the results of the initial clinical trials and the needs of a particular patient.

Screening Methods and Systems

In another aspect, the invention provides a machine readable storage medium which comprises the structural coordinates of an AAT binding site identified herein, (e.g., a binding site in the P6-P3 region of an AAT protein monomer, e.g., one or more (preferably 2, 3, 4, 5, 6, 7, 8, 9, 10, 11, 12, 13, 14, 15, 16, 17, 18, 19 or 20) of residues 173-184, 327-333 and 352, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Such compounds are potential inhibitors of mutant AAT protein polymerization or aggregation.

According to another aspect, the invention provides a computer for producing a) a three-dimensional representation of a molecule or molecular complex, wherein said molecule or molecular complex comprises a binding site in the P6-P3 region of an AAT protein monomer defined by structure coordinates of amino acid residues in the P6-P3 region of the AAT protein (e.g., one or more (e.g., 2, 3, 4, 5, 6, 7, 8, 9, 10, 11, 12, 13, 14, 15, 16, 17, 18, 19 or 20) of residues 173-184, 327-333 and 352); or b) a three-dimensional representation of a homologue of said molecule or molecular complex, wherein said homologue comprises a binding pocket that has a root mean square deviation from the backbone atoms of said amino acids of not more than about 2.0 (more preferably not more than 1.5) angstroms, wherein said computer comprises:

(i) a machine-readable data storage medium comprising a data storage material encoded with machine-readable data, wherein said data comprises the structure coordinates of structure coordinates of amino acid residues in the P6-P3 region of the AAT protein;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding site.

In another embodiment, the invention provides a computer for producing a three-dimensional representation of a molecule or molecular complex defined by structure coordinates of all of the AAT (or mutant AAT) amino acids, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms In exemplary embodiments, the computer or computer system can include components which are conventional in the art, e.g., as disclosed in U.S. Pat. No. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding site of an AAT protein (including a mutant AAT protein) may inhibit mutant AAT protein polymerization or aggregation, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket defined by structure coordinates of AAT protein monomer amino acid residues in the P6-P3 region of the AAT protein (e.g., one or more (e.g., 2, 3, 4, 5, 6, 7, 8, 9, 10, 11, 12, 13, 14, 15, 16, 17, 18, 19 or 20) of residues 173-184, 327-333 and 352), as described herein, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:
 i) employing computational means to perform a fitting operation between the chemical entity and a binding pocket of the molecule or molecular complex; and
 ii) analyzing the results of the fitting operation to quantify the association between the chemical entity and the binding pocket. This embodiment relates to evaluating the potential of a chemical entity to associate with or bind to a binding site of AAT protein.

The term "chemical entity", as used herein, refers to chemical compounds, complexes of at least two chemical compounds, and fragments of such compounds or complexes.

In certain embodiments, the method evaluates the potential of a chemical entity to associate with a molecule or molecular complex defined by structure coordinates of all of the amino acids of AAT protein, as described herein, or a homologue of said molecule or molecular complex having a root mean square deviation from the backbone atoms of said amino acids of not more than 2.0 (more preferably not more than 1.5) angstroms.

In a further embodiment, the structural coordinates one of the binding pockets described herein can be utilized in a method for identifying a potential agonist or antagonist of a molecule comprising an AAT binding site. This method comprises the steps of:
 a) using the atomic coordinates of AAT protein monomer amino acid residues in the P6-P3 region of the AAT protein (e.g., one or more (e.g., 2, 3, 4, 5, 6, 7, 8, 9, 10, 11, 12, 13, 14, 15, 16, 17, 18, 19 or 20) of residues 173-184, 327-333 and 352), as described herein, with a root mean square deviation from the backbone atoms of said amino acids of not more than about 2.0 (more preferably not more than 1.5) angstroms, to generate a three-dimensional structure of molecule comprising an AAT binding site;
 b) employing the three-dimensional structure to design or select the potential agonist or antagonist. The method further includes the optional steps of c) synthesizing the agonist or antagonist; and d) contacting the agonist or antagonist with the molecule to determine the ability of the potential agonist or antagonist to interact with the molecule.

In another embodiment, the invention provides a method for identifying a potential agonist or antagonist of mutant AAT polymerization, the method comprising the steps of:
 a) using the atomic coordinates of AAT protein monomer amino acid residues in the P6-P3 region (e.g., one or more (e.g., 2, 3, 4, 5, 6, 7, 8, 9, 10, 11, 12, 13, 14, 15, 16, 17, 18, 19 or 20) of residues 173-184, 327-333 and 352) of the AAT protein to generate a three-dimensional structure of an AAT binding site;
 b) employing the three-dimensional structure to design or select the potential agonist or antagonist.

The present inventors' elucidation of heretofore unknown binding sites of AAT proteins provides the necessary information for designing new chemical entities and compounds that may interact with AAT proteins, in whole or in part, and may therefore modulate (e.g., inhibit) the polymerization of mutant AAT proteins.

The design of compounds that bind to or inhibit AAT binding sites according to this invention generally involves consideration of several factors. First, the entity must be capable of physically and structurally associating with parts or all of the AAT binding site. Non-covalent molecular interactions important in this association include hydrogen bonding, van der Waals interactions, hydrophobic interactions and electrostatic interactions. Second, the entity must be able to assume a conformation that allows it to associate with the AAT binding site(s) directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on an AAT binding site may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding site. This may be achieved, e.g., by testing the ability of the molecule to inhibit AAT polymerization, e.g., using assays described herein or known in the art. In this manner, synthesis of inoperative compounds may be avoided.

A potential inhibitor of an AAT binding site may be computationally evaluated by means of a series of steps in which chemical entities or fragments are screened and selected for their ability to associate with the AAT binding site.

One skilled in the art may use one of several methods to screen chemical entities or fragments for their ability to associate with an AAT binding site. This process may begin by visual inspection of, for example, an AAT binding site on the computer screen based on the an AAT structure coordinates described herein, or other coordinates which define a similar shape generated from the machine-readable storage medium. Selected fragments or chemical entities may then be positioned in a variety of orientations, or docked, within that binding site as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding site.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology 4, pp. 777-781 (1994)).

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silica screening of virtual libraries of compounds, e.g., as described herein (see, e.g., Example 1). Many thousands of compounds can be rapidly screened and the best virtual compounds can be selected for further screening (e.g., by synthesis and in vitro testing). Small molecule databases can be screened for chemical entities or compounds that can bind, in whole or in part, to an AAT binding site. In this screening, the quality of fit of such entities to the binding site may be judged either by shape complementarity or by estimated interaction energy.

Screening Assays

As discussed herein, useful compounds correct or prevent protein misfolding by increasing the amount of a mutant protein that is in a biochemically active conformation. Any number of methods are available for carrying out screening assays to identify such compounds. In one approach, a mutant AAT protein that fails to adopt a wild-type protein conformation resulting polymerization or aggregation is expressed in a cell (e.g., a cell in vitro or in vivo); the cell is contacted with a candidate compound; and the effect of the compound on the polymerization of the mutant AAT protein is assayed using any method known in the art or described herein. Useful compounds decrease the amount of mutant AAT protein polymerization by at least 10%, 15%, or 20%, or preferably by 25%, 50%, or 75%; or most preferably by at least 100%, 200%, 300% or even 400%.

If desired, the efficacy of the identified compound is assayed in an animal model of AAT deficiency (e.g., a transgenic mouse model).

Test Compounds and Extracts

In general, compounds capable of inhibiting AZT polymerization in a cell are identified from large libraries of either natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, large numbers of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods.

Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity in correcting a misfolded protein should be employed whenever possible.

When a crude extract is found to prevent mutant AAT polymer formation, further fractionation of the positive lead extract is necessary to isolate chemical constituents responsible for the observed effect. Thus, the goal of the extraction, fractionation, and purification process is the careful characterization and identification of a chemical entity within the crude extract that prevents mutant AAT polymer formation. Methods of fractionation and purification of such heterogenous extracts are known in the art. If desired, compounds shown to be useful agents for the treatment of any pathology related to a misfolded protein or protein aggregation are chemically modified according to methods known in the art.

Combination Therapies

Compositions of the invention useful for the treatment of AAT deficiency (or conditions related thereto) can optionally be combined with additional therapies. For example, 4-phenylbutyric acid has been shown to have potential therapeutic effect in AAT models.

Kits

The invention provides kits for the treatment or prevention of AAT deficiency or symptoms thereof. In one embodiment, the kit includes a pharmaceutical pack comprising an effective amount of a compound of the invention for treatment of AAT deficiency. Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments. In certain embodiments, the kit further comprises a second compound for treatment of AAT deficiency, e.g., 4-phenylbutyric acid.

If desired compositions of the invention or combinations thereof are provided together with instructions for administering them to a subject having or at risk of developing AAT deficiency. The instructions will generally include information about the use of the compounds for the treatment or prevention of AAT deficiency. In other embodiments, the instructions include at least one of the following: description of the compound or combination of compounds; dosage schedule and administration for treatment of AAT deficiency or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

In one aspect, the invention provides a kit for the treatment of AAT deficiency, the kit comprising an effective amount of the amount of a compound capable of disrupting polymerization of the mutant Z form of AAT; and instructions for administering the compound capable of disrupting polymerization of the mutant Z form of AAT to a subject to treat AAT deficiency.

In another aspect, the invention provides a packaged pharmaceutical formulation for the treatment or prevention of liver damage in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the treatment or prevention of liver damage in the subject.

In another aspect, the invention provides a packaged pharmaceutical formulation for preserving liver function in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the preservation of liver function in the subject.

In another aspect, the invention provides a packaged pharmaceutical formulation for the treatment or prevention of liver damage in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a hepatocyte; and instructions for administering the compound capable of disrupting polymerization of the mutant Z form of AAT to a subject suffering from or susceptible to AAT deficiency for the treatment.

In another aspect, the invention provides a packaged pharmaceutical formulation for preserving liver function in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a hepatocyte; and instructions for administering the compound capable of disrupting polymerization of the mutant Z form of AAT to a subject suffering from or susceptible to AAT deficiency for the preservation of liver function in the subject.

In another aspect, the invention provides a packaged pharmaceutical formulation for the treatment or prevention of lung damage in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the treatment or prevention of lung damage in the subject.

In another aspect, the invention provides a packaged pharmaceutical formulation for preserving lung function in a subject suffering from or susceptible to alpha-1 antitrypsin (AAT) deficiency, the packaged pharmaceutical formulation comprising: an effective amount of the amount of a compound capable of disrupting polymerization of the mutant Z form of AAT; and instructions for administering the compound capable of disrupting polymerization of the mutant Z form of AAT to a subject suffering from or susceptible to AAT deficiency for the preservation of lung function in the subject.

In another aspect, the invention provides a packaged pharmaceutical formulation for the treatment or prevention of lung damage in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a lung cell; and instructions for administering the compound capable of disrupting polymerization of the mutant Z form of AAT to a subject suffering from or susceptible to AAT deficiency for the treatment or prevention of long damage in the subject.

In another aspect, the invention provides a packaged pharmaceutical formulation for preserving lung function in a subject suffering from or susceptible to alpha-1 antitrypsin (AAT) deficiency, the packaged pharmaceutical formulation comprising: an effective amount of the amount of a compound capable of increasing secretion of the mutant Z form of AAT from a lung cell; and instructions for administering the compound capable of disrupting polymerization of the mutant Z form of AAT to a subject suffering from or susceptible to AAT deficiency for the preservation of lung function in the subject.

The following examples are provided to illustrate the invention, not to limit it.

EXAMPLES

Example 1

Identification of Small Molecules Directed to AAT Target Site

The crystal structure of the AAT polymer provided the basis for selection of potential small molecule inhibitors. A significant finding in understanding polymer formation in AAT deficiency is the conserved mode of interaction between monomers that yield plaque-causing polymers. The atomic interactions at the interface between monomers were characterized by x-ray crystallography[67]. Residues from the P6-P3 region of one monomer insert into a gap in the β-sheet of an adjacent monomer. We utilized the atomic positions of the residues in the P6-P3 region as the site selected for molecular docking to disrupt polymer.

We positioned spheres at the selected site to allow the molecular docking program, DOCK5.1.0, to match spheres with atoms in potential ligands (small molecules in this case). During the molecular docking calculation, orientations are sampled to match the largest number of spheres to potential ligand atoms. The spheres are depicted in FIG. 2.

The atomic positions and chemical characteristics of residues in close proximity (within 4 Å) to the selected site were used to establish a scoring grid to evaluate potential interactions with small molecules. Blue spheres in FIG. 2 mark the boundaries of the scoring grid utilized in this preliminary study. Two types of interaction were scored: van der Waals contact and electrostatic interactions. A scoring grid was calculated to estimate the interaction between potential ligands and the AAT target site.

We utilized DOCK5.1.0 to perform docking molecular dynamic simulations. The coordinates for approximately 140,000 compounds (all of which are available through the NCI/DTP) were used as the ligand database for molecular docking site. Each small molecule was positioned in the selected site in 100 different orientations, and the best orientations and their scores (contact and electrostatic) were calculated. The scored compounds were ranked and certain highest scoring compounds are shown in Table 1. The top scoring compound, $C_{12}H_{12}BrNO_2$, is shown in the selected site of AAT in FIG. 2 (right panel).

Research Design and Methods

Database Preparation

The National Cancer Institute/Developmental Therapeutics Program (NCI/DTP) maintains a repository of approximately 220,000 samples (the plated compound set) which are non-proprietary and offered to the extramural research community for the discovery and development of new agents for the treatment of cancer, AIDS, or opportunistic infections afflicting patients with cancer or AIDS (Monga and Sausville 2002). The three-dimensional coordinates for the NCI/DTP plated compound set was obtained in the MDL SD format and converted to the mol2 format by the DOCK utility program SDF2MOL2 (UCSF). Partial atomic charges, solvation energies and van der Waals parameters for the ligands were calculated using SYBDB (Tripos, Inc.) and added to the plated compound set mol2 file.

Molecular Docking

All docking calculations were performed with the Oct. 15, 2002, development version of DOCK, v5.1.0 (Charifson et al. 1999; Ewing et al. 2001). The general features of DOCK include rigid orienting of ligands to receptor spheres, AMBER energy scoring, GB/SA solvation scoring, contact scoring, internal non-bonded energy scoring, ligand flexibility and both rigid and torsional simplex minimization (Gschwend et al.; Good et al. 1995). Unlike previously distributed versions, this release incorporates automated matching, internal energy (used in flexible docking), scoring function hierarchy and new minimizer termination criteria.

The coordinates for the crystal structure of mutant ATZ (see, e.g., Huntington JA, et al., Journal of Molecular Biology 1999; 293:449-55), were used in the molecular docking calculations. The atomic positions of the residues in the P6-P3 region were used for the site selected for molecular docking, with the aim of disrupting polymer formation with small molecules. The site consists of residues 173-184, 327-333 and 352 in the crystal structure of PDB code 1QMB (accessed at http://www.rcsb.org/pdb/explore.do?structureId=1QMB). The PDB file is shown in the attached Appendix A, which is incorporated herein by reference.

To prepare the site for docking, all water molecules were removed. Protonation of receptor residues was performed with Sybyl (Tripos, St. Louis, Mo.). The structure was explored using sets of spheres to describe potential binding pockets. The number of orientations per molecule was 100. Intermolecular AMBER energy scoring (vdw+columbic), contact scoring and bump filtering were implemented in DOCK5.1.0 (Gschwend et al.). SETOR (Evans 1993) and GRASP (Petrey and Honig 2003) were used to generate molecular graphic images.

The approach is generally illustrated in FIG. 1. Compounds identified using virtual screening are shown in Table 1.

TABLE 1

| Compound Name/Chemical Formula/ CAS Number | Structure | Energy Score |
|---|---|---|
| 5-(2-Bromo-ethoxy-methyl)-quinolin-8-ol $C_{12}H_{12}BrNO_2$ 91844-22-3 NSC174054 | 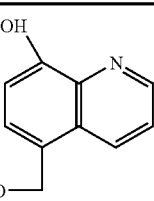 | −21.1 |

TABLE 1-continued

| Compound Name/Chemical Formula/ CAS Number | Structure | Energy Score |
|---|---|---|
| 3,4-methylenedioxy-6-nitrocinnamic acid $C_{10}H_7NO_6$ 6315-90-8 NSC21034 | 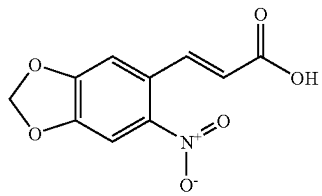 [SMILES: O=C(O)/C=C/c1cc2c(cc1[N+](=O)[O-])OCO2] | −19.9 |
| 4-hydroxyantipyrine 3H-Pyrazol-3-one, 1,2-dihydro-4-hydroxy-1,5-dimethyl-2-phenyl- $C_{11}H_{12}N_2O_2$ 1672-63-5 | 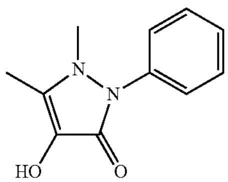 | −17.7 |
| 5-Nitro-1-naphthol $C_{10}H_7NO_3$ 6304-46-7 NSC42958 | 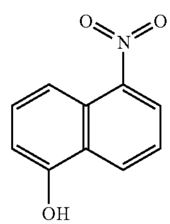 [SMILES: O=[N+]([O-])c1cccc2c(O)cccc12] | −17.0 |
| 3'-acetoxy acetophenone $C_{10}H_{10}O_3$ 2454-35-5 | 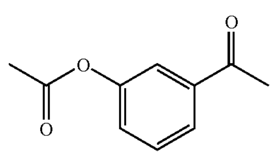 | −14.6 |
| 2-Ethyl-3-methyl-3-thiophen-2-yl-oxirane-2-carboxylic acid, sodium salt $C_{10}H_{12}O_3S$•Na 6304-48-9 | | −13.4 |
| 2-Bromo-1,5-dimethoxy-3-methyl-benzene $C_9H_{11}BrO_2$ 13321-73-8 | 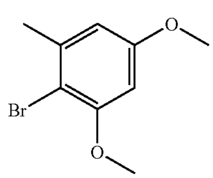 | −12.9 |
| 2-acetyl-5-chlorothiophene $C_6H_5ClOS$ 6310-09-4 | 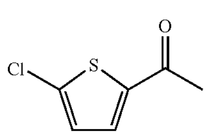 | −12.6 |
| 1,9-decadiene $C_{10}H_{18}$ 1647-16-1 NSC102789 | 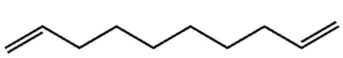 | −10.7 |

Example 2

Cell Models for AAT Deficiency

Establishment of Human PiZZ Cell Line.

The liver biopsy tissue from a 4-month-old infant with PiZZ was used for generating the cell line. The cell culture procedure was used according to an established protocol. Forty-eight hours after the cell attached to the plate, lentivirus containing human telomerase catalytic domain TERT was added to the cells for 12 hours in the presence of polybrene. The cells were continuously cultured in the culture medium. After two months, a cell line was established and referred to as AT01. The cells exhibit epithelial growth pattern. The cells have a doubling time approximately 36 hours. To determine whether the cells have hepatic phenotype, total RNA was extracted from AT01 cells and the control hepatoma cell line, Huh7, for RT-PCR analysis using human albumin-specific primers. The AT01 cells express albumin, though at lower levels compared to the Huh7 cells. The cells produce ATZ, as confirmed by monoclonal anti-ATZ antibody. It is noted that Huh7 cells produces a second band, suggesting different protein modification, such as glycosylation.

The possible explanations for the lower level expression of ATZ in AT01 cells are: firstly, the cell culture may not exhibit fully differentiated hepatic phenotype. The lower level of albumin expression is consistent with this postulate; secondly, signals are required for AAT expression. The potential signals may be derived from cytokines, which are not present in the culture medium; lastly, if ATZ protein is toxic, the adaptive cells would produce lower levels of the protein for growth advantage.

Based on the hypothesis that liver-specific transcription factors would up-regulate α1-AT gene expression, we transfected the AT01 cells with the plasmid pCMVHNF3 containing HNF3α gene. Expression of HNF3 slightly upregulated ATZ protein expression. Further experiments with constitutive HNF3 expression may enhance the ATZ expression in these cells.

Hepatoma Cell Line that Stably Expresses ATM or ATZ.

To have a robust cell culture system for AAT study, we transfected a human hepatoma cell line, Huh7, with either wild type AAT (ATM) or mutant AAT (ATZ) expression vector under RSV promoter control. The vector also contains a neomycin resistance gene that permits G418 selection for stable cell lines.

Stable cell lines for both ATM and ATZ were established. There is no overt abnormality in these cell lines. Huh7, Huh-ATM, and Huh-ATZ exhibit similar growth potential. Protein expression was confirmed by Western blot analysis. Polymers were only formed in Huh-ATZ cells. Moreover, we also determined the AAT expression level in the culture medium. Huh-ATM cells express much high levels of AAT in the supernatant, while Huh-ATZ cells only express the endogenous AAT, suggesting that the ATZ is trapped inside the cells as protein polymers.

Example 3

Compounds listed in Table 1 were obtained from NCI/DTP. The compounds were dissolved in DMSO. As the first step, the compounds were tested in CHO-ATZ cells. Various concentrations of the compounds were added to the cells. The supernatants were harvested at time points: 24, 48, and 72 hours. The samples were then used for ELISA assay for human AAT. Among the 9 compounds tested, many showed effectiveness to increase the ATZ secretion, and two compounds showed effectiveness to increase the ATZ secretion at the micromolar range.

Because DMSO was used as a solvent, and previous work has indicated that DMSO by itself increases AAT secretion, we tested the effect of DMSO on AAT secretion in our cell system. At the highest possible concentration, DMSO would have slightly increased the secretion of ATZ in CHO cells; however, the effect can be monitored through adequate controls.

Compounds were used to treat CHO-ATZ cells at various concentrations. Cell supernatant was harvested at different time points. ELISA test was performed to determine the level of ATZ in the supernatant. The cells were also harvested for Western blot analysis.

As shown in FIG. 3, two compounds, NSC 21034 (3,4-methylenedioxy-6-nitrocinnamic acid) and NSC 102789 (1,9-decadiene) appear to be effective for inhibition of ATZ secretion.

We then examined these two potentially effective inhibitors. The cells were treated by the inhibitors, followed by protein extraction and Western blot analysis. Comparing with controls, the cells treated with these inhibitors showed reduced amount of ATZ, as shown in FIG. 4 for 1,9-decadiene, suggesting that the compounds indeed enhanced the secretion of the ATZ.

To further test the two compounds, a pulse-chase experiment, which is more definitive to demonstrate the protein secretion, was performed. As shown in FIGS. 5A and 5B, the two compounds indeed increased the secretion of ATZ in CHO cells. A non-denaturing gel was used to analyze cell extracts from compound-treated CHO ATZ cells. Again, the treated cells exhibited fewer polymers in comparison with controls.

Two test compounds were administered to transgenic mice (four animals per group, including control) carrying a human ATZ transgene to determine whether the compounds are capable of increasing AAT secretion in a transgenic animal model. The animals were treated for two weeks. Serum AAT levels were determined by ELISA assay. FIG. 6 shows that Drug 1 (1,9-decadiene) and Drug 2 (3,4-methylenedioxy-6-nitrocinnamic acid) can enhance AAT serum level by more than two-fold.

Compounds according to the invention decrease AAT accumulation and reduce inflammation in liver cells compared to control. AAT-Z transgenic mice were treated by i.p. injection of a compound or control for 7 days, followed by collection of liver tissue. FIG. 7 shows that Drug 1 and Drug 2, when administered to animals, decrease AAT accumulation in hepatocytes as demonstrated by periodic acid-Schiff with diastases digestion (PASD) staining. Drug treatment also reduced live tissue inflammation compared to animals treated with a control.

These experiments suggest that interfering with polymer formation enhances ATZ secretion rather than ATZ degradation. In summary, these experiments demonstrate the feasibility of the molecular docking approach for identifying effective and specific ATZ-polymer inhibitors.

References

1. Huber R, Carrell R W. Implications of the three-dimensional structure of alpha 1-antitrypsin for structure and function of serpins. Biochemistry 1989; 28:8951-66.
2. MacDonald J L, Johnson C E. Pathophysiology and treatment of alpha 1-antitrypsin deficiency. Am J Health Syst Pharm 1995; 52:481-9; quiz 544-5.
3. Morgan K, Kalsheker N A. Regulation of the serine proteinase inhibitor (SERPIN) gene alpha 1-antitrypsin: a paradigm for other SERPINs. Int J Biochem Cell Biol 1997; 29:1501-11.
4. Needham M, Stockley R A. Alpha 1-antitrypsin deficiency. 3: Clinical manifestations and natural history. Thorax 2004; 59:441-5.
5. Barker A F, Siemsen F, Pasley D, D'Silva R, Buist A S. Replacement therapy for hereditary alpha1-antitrypsin deficiency. A program for long-term administration. Chest 1994; 105:1406-10.
6. Stecenko A A, Brigham K L. Gene therapy progress and prospects: alpha-1 antitrypsin. Gene Ther 2003; 10:95-9.
7. Mazodier P, Elzouki A N, Segelmark M, Eriksson S. Systemic necrotizing vasculitides in severe alpha1-antitrypsin deficiency. Qjm 1996; 89:599-611.
8. Perlmutter D H. Alpha-1-antitrypsin deficiency. Semin Liver Dis 1998; 18:217-25.
9. Teckman J H, Qu D, Perlmutter D H. Molecular pathogenesis of liver disease in alpha1-antitrypsin deficiency. Hepatology 1996; 24:1504-16.
10. Brantly M, Nukiwa T, Crystal R G. Molecular basis of alpha-1-antitrypsin deficiency. Am J Med 1988; 84:13-31.
11. Lomas D A, Evans D L, Finch J T, Carrell R W. The mechanism of Z alpha-1-antitrypsin accumulation in the liver. Nature 1992; 357:605-7.
12. Lomas D A. Loop-sheet polymerization: the structural basis of Z alpha 1-antitrypsin accumulation in the liver. Clin Sci (Lond) 1994; 86:489-95.
13. Lomas D A, Mahadeva R. Alpha1-antitrypsin polymerization and the serpinopathies: pathobiology and prospects for therapy. J Clin invest 2002; 110:1585-90.
14. Carrell R W, Lomas D A. Conformational disease. Lancet 1997; 350:134-8.
15. Sveger T, Eriksson S. The liver in adolescents with alpha 1-antitrypsin deficiency. Hepatology 1995; 22:514-7.
16. Perlmutter D H. Liver injury in alpha1-antitrypsin deficiency: an aggregated protein induces mitochondrial injury. J Clin Invest 2002; 110:1579-83.
17. Cuvelier A, Muir J F, Hellot M F, Benhamou D, Martin J P, Benichou J, Sesboue R. Distribution of alpha(1)-antitrypsin alleles in patients with bronchiectasis. Chest 2000; 117:415-9.
18. Hill A T, Campbell E J, Ward A M, Stockley R A. Chronic obstructive pulmonary disease, with and without alpha-1-antitrypsin deficiency: management practices in the U.K. Respir Med 1999; 93:481-90.
19. Niemann M A, Baggott J E, Miller E J. Inhibition of human serine proteases by SPAAT, the C-terminal 44-residue peptide from alpha1-antitrypsin. Biochim Biophys Acta 1997; 1340:123-30.
20. Janciauskiene S, Zelvyte I, Jansson L, Stevens T. Divergent effects of alpha1-antitrypsin on neutrophil activation, in vitro. Biochem Biophys Res Commun 2004; 315:288-96.
21. DeMeo D L, Silverman E K. Alpha1-antitrypsin deficiency. 2: genetic aspects of alpha(1)-antitrypsin deficiency: phenotypes and genetic modifiers of emphysema risk. Thorax 2004; 59:259-64.
22. Perlmutter D H. The cellular response to aggregated proteins associated with human disease. J Clin Invest 2002; 110:1219-20.
23. Ali R, Perfumo S, della Rocca C, Amicone L, Pozzi L, McCullagh P, Millward-Sadler H, Edwards Y, Povey S, Tripodi M. Evaluation of a transgenic mouse model for alpha-1-antitrypsin (AAT) related liver disease. Ann Hum Genet. 1994; 58:305-20.

24. Archibald A L, McClenaghan M, Hornsey V, Simons J P, Clark A J. High-level expression of biologically active human alpha 1-antitrypsin in the milk of transgenic mice. Proc Natl Acad Sci USA 1990; 87:5178-82.
25. Carlson J A, Rogers B B, Sifers R N, Finegold M J, Clift S M, DeMayo F J, Bullock D W, Woo S L. Accumulation of PiZ alpha 1-antitrypsin causes liver damage in transgenic mice. J Clin Invest 1989; 83:1183-90.
26. Carrell R W, Lomas D A, Sidhar S, Foreman R. Alpha 1-antitrypsin deficiency. A conformational disease. Chest 1996; 110:243 S-247S.
27. Carrell R W, Lomas D A. Alpha1-antitrypsin deficiency— a model for conformational diseases. N Engl 3 Med 2002; 346:45-53.
28. Lomas D A. Loop-sheet polymerization: the mechanism of alpha1-antitrypsin deficiency. Respir Med 2000; 94 Suppl C:S3-6.
29. Burrows J A, Willis L K, Perlmutter D H. Chemical chaperones mediate increased secretion of mutant alpha 1-antitrypsin (alpha 1-AT) Z: A potential pharmacological strategy for prevention of liver injury and emphysema in alpha 1-AT deficiency. Proc Natl Acad Sci USA 2000; 97:1796-801.
30. Marcus N Y, Perlmutter D H. Glucosidase and mannosidase inhibitors mediate increased secretion of mutant alpha1 antitrypsin Z. J Biol Chem 2000; 275:1987-92.
31. Teckman lift Perlmutter D H. Retention of mutant alpha (1)-antitrypsin Z in endoplasmic reticulum is associated with an autophagic response. Am J Physiol Gastrointest Liver Physiol 2000; 279:G961-74.
32. Teckman J H, An J K, Loethen S, Perlmutter D H. Fasting in alpha1-antitrypsin deficient liver: constitutive [correction of consultative] activation of autophagy. Am J Physiol Gastrointest Liver Physiol 2002; 283:G1156-65.
33. Schwartz A L, Brandt R A, Geuze H, Ciechanover A. Stress-induced alterations in autophagic pathway: relationship to ubiquitin system. Am J Physiol 1992; 262: C1031-8.
34. Hacki J, Egger L, Monney L, Conus S, Rosse T, Fellay I, Bonier C. Apoptotic crosstalk between the endoplasmic reticulum and mitochondria controlled by Bcl-2. Oncogene 2000; 19:2286-95.
35. Wei M C, Zong W X, Cheng E H, Lindsten T, Panoutsakopoulou V, Ross A J, Roth K A, MacGregor G R, Thompson C B, Korsmeyer S J. Proapoptotic BAX and BAK: a requisite gateway to mitochondrial dysfunction and death. Science 2001; 292:727-30.
36. Massi G. Pathogenesis and pathology of liver disease associated with alpha 1-antitrypsin deficiency. Chest 1996; 110:251 S-255S.
37. Perlmutter D H. Liver injury in alpha 1-antitrypsin deficiency. Clin Liver Dis 2000; 4:387-408, vi.
38. Baumann H, Prowse K R, Won K A, Marinkovic S, Jahreis G P. Regulation of acute phase protein genes by hepatocyte-stimulating factors, monokines and glucocorticoids. Tokai J Exp Clin Med 1988; 13:277-92.
39. Castell J V, Gomez-Lechon M J, David M, Andus T, Geiger T, Trullenque R, Fabra R, Heinrich P C. Interleukin-6 is the major regulator of acute phase protein synthesis in adult human hepatocytes. FEBS Lett 1989; 242:237-9.
40. Yiangou M, Paraskeva E, Hsieh C C, Markou E, Victoratos P, Scouras Z, Papaconstantinou J. Induction of a subgroup of acute phase protein genes in mouse liver by hyperthermia. Biochim Biophys Acta 1998; 1396:191-206.
41. Kalsheker N, Morley S, Morgan K. Gene regulation of the serine proteinase inhibitors alpha1-antitrypsin and alpha1-antichymotrypsin. Biochem Soc Trans 2002; 30:93-8.
42. Paiva A M, Vanderwall D E, Blanchard J S, Kozarich T W, Williamson J M, Kelly T M. Inhibitors of dihydrodipicolinate reductase, a key enzyme of the diaminopimelate pathway of Mycobacterium tuberculosis. Biochimica Et Biophysica Acta 2001; 1545:67-77.
43. Shoichet B K, McGovern S L, Wei B, Irwin J J. Lead discovery using molecular docking. Current Opinion in Chemical Biology 2002; 6:439-46.
44. Doman T N, McGovern S L, Witherbee B J, Kasten T P, Kurumbail R, Stallings W C, Connolly D T, Shoichet B K. Molecular docking and high-throughput screening for novel inhibitors of protein tyrosine phosphatase-1B. Journal of Medicinal Chemistry 2002; 45:2213-21.
45. Iwata Y, Arisawa M, Hamada R, Kita Y, Mizutani M Y, Tomioka N, Itai A, Miyamoto S. Discovery of novel aldose reductase inhibitors using a protein structure-based approach: 3D-database search followed by design and synthesis. Journal of Medicinal Chemistry 2001; 44:1718-28.
46. Enyedy I J, Ling Y, Nacro K, Tomita Y, Wu X, Cao Y, Guo R, Li B, Zhu X, Huang Y, Long Y Q, Roller P P, Yang D, Wang S. Discovery of small-molecule inhibitors of Bcl-2 through structure-based computer screening. Journal of Medicinal Chemistry 2001; 44:4313-24.
47. Enyedy I J, Lee S L, Kuo A H, Dickson R B, Lin C Y, Wang S. Structure-based approach for the discovery of bis-benzamidines as novel inhibitors of matriptase. Journal of Medicinal Chemistry 2001; 44:1349-55.
48. Pang Y P, Xu K, Kollmeyer T M, Perola E, McGrath W J, Green D T, Mangel W F. Discovery of a new inhibitor lead of adenovirus proteinase: steps toward selective, irreversible inhibitors of cysteine proteinases. Febs Letters 2001; 502:93-7.
49. Gruneberg S, Stubbs M T, Klebe G. Successful virtual screening for novel inhibitors of human carbonic anhydrase: strategy and experimental confirmation. Journal of Medicinal Chemistry 2002; 45:3588-602.
50. Freymann D M, Wenck M A, Engel J C, Feng J, Focia P J, Eakin A E, Craig S P. Efficient identification of inhibitors targeting the closed active site conformation of the HPRT from Trypanosoma cruzi. Chemistry & Biology 2000; 7:957-68.
51. Honma T, Yoshizumi T, Hashimoto N, Hayashi K, Kawanishi N, Fukasawa K, Takaki T, Ikeura C, Ikuta M, Suzuki_Takahashi I, Hayama T, Nishimura S, Morishima H. A novel approach for the development of selective Cdk4 inhibitors: library design based on locations of Cdk4 specific amino acid residues. Journal of Medicinal Chemistry 2001; 44:4628-40.
52. Honma T, Hayashi K, Aoyama T, Hashimoto N, Machida T, Fukasawa K, Iwama T, Ikeura C, Ikuta M, Suzuki_Takahashi I, Iwasawa Y, Hayama T, Nishimura S, Morishima H. Structure-based generation of a new class of potent Cdk4 inhibitors: new de novo design strategy and library design. Journal of Medicinal Chemistry 2001; 44:4615-27.
53. Liebeschuetz J W, Jones S D, Morgan P J, Murray C W, Rimmer A D, Roscoe J M, Waszkowycz B, Welsh P M, Wylie W A, Young S C, Martin H, Mahler J, Brady L, Wilkinson K. PRO_SELECT: combining structure-based drug design and array-based chemistry for rapid lead discovery. 2. The development of a series of highly potent and selective factor Xa inhibitors. Journal of Medicinal Chemistry 2002; 45:1221-32.
54. Boehm H J, Boehringer M, Bur D, Gmuender H, Huber W, Klaus W, Kostrewa D, Kuehn H, Luebbers T, Meunier_Keller N, Mueller F. Novel inhibitors of DNA gyrase: 3D structure based biased needle screening, hit validation by biophysical methods, and 3D guided optimization. A promising alternative to random screening. Journal of Medicinal Chemistry 2000; 43:2664-74.
55. Schapira M, Raaka B M, Samuels H H, Abagyan R. Rational discovery of novel nuclear hormone receptor antagonists. Proceedings of the National Academy of Sciences of the United States of America 2000; 97:1008-13.
56. Ho C M, Marshall G R. Cavity search: an algorithm for the isolation and display of cavity-like binding regions. J Comput Aided Mol Des 1990; 4:337-54.
57. Ho C M, Marshall G R. DBMAKER: a set of programs to generate three-dimensional databases based upon user-specified criteria. J Comput Aided Mol Des 1995; 9:65-86.
58. Dammkoehler R A, Karasek S F, Shands E F, Marshall G R. Constrained search of conformational hyperspace. J Comput Aided Mol Des 1989; 3:3-21.
59. Carney S A, Tahara H, Swartz C D, Risinger J I, He H, Moore A B, Haseman J K, Barrett J C, Dixon D. Immortalization of human uterine leiomyoma and myometrial cell lines after induction of telomerase activity: molecular and phenotypic characteristics. Lab Invest 2002; 82:719-28.
60. Cascio S M. Novel strategies for immortalization of human hepatocytes. Artif Organs 2001; 25:529-38.
61. Dycaico M J, Grant S G, Felts K, Nichols W S, Geller S A, Hager J H, Pollard A J, Kohler S W, Short H P, Jirik F R, et al. Neonatal hepatitis induced by alpha 1-antitrypsin: a transgenic mouse model. Science 1988; 242:1409-12.
62. Geller S A, Nichols W S, Dycaico M J, Felts K A, Sorge J A. Histopathology of alpha 1-antitrypsin liver disease in a transgenic mouse model. Hepatology 1990; 12:40-7.
63. Geller S A, Nichols W S, Kim S, Tolmachoff T, Lee S, Dycaico M J, Felts K, Sorge J A. Hepatocarcinogenesis is the sequel to hepatitis in Z#2 alpha 1-antitrypsin transgenic mice: histopathological and DNA ploidy studies. Hepatology 1994; 19:389-97.
64. Rudnick D A, Liao Y, An J K, Muglia L J, Perlmutter D H, Teckman J H. Analyses of hepatocellular proliferation in a mouse model of alpha-1-antitrypsin deficiency. Hepatology 2004; 39:1048-55.
65. Hidvegi T, Schmidt B Z, Hale P, Perlmutter D H. Accumulation of mutant alpha1-antitrypsin Z in the endoplasmic reticulum activates caspases-4 and -12, NFkappaB, and BAP31 but not the unfolded protein response. J Biol Chem 2005; 280:39002-15.
66. Teckman J H. Lack of effect of oral 4-phenylbutyrate on serum alpha-1-antitrypsin in patients with alpha-1-antitrypsin deficiency: a preliminary study. J Pediatr Gastroenterol Nutr 2004; 39:34-7.
67. Huntington J A, Pannu N S, Hazes B, Read R J, Lomas D A, Carrell R W. A 2.6 A structure of a serpin polymer and implications for conformational disease. Journal of Molecular Biology 1999; 293:449-55.
68. Gomez-Lechon M J, Lopez P, Donato T, Montoya A, Larrauri A, Gimenez P, Trullenque R, Fabra R, Castell J V. Culture of human hepatocytes from small surgical liver biopsies. Biochemical characterization and comparison with in vivo. In Vitro Cell Dev Biol 1990; 26:67-74.
69. Monga M, Sausville E A. Developmental therapeutics program at the NCI: molecular target and drug discovery process. Leukemia: Official Journal of the Leukemia Society of America, Leukemia Research Fund, U.K 2002; 16:520-6.
70. Irwin J J, Shoichet B K. ZINC—a free database of commercially available compounds for virtual screening. J Chem Inf Model 2005; 45:177-82.
71. Ewing T J, Makino S, Skillman A G, Kuntz I D. DOCK 4.0: search strategies for automated molecular docking of flexible molecule databases. Journal of Computer-Aided Molecular Design 2001; 15:411-28.
72. Charifson P S, Corkery J J, Murcko M A, Walters W P. Consensus scoring: A method for obtaining improved hit rates from docking databases of three-dimensional structures into proteins. Journal of Medicinal Chemistry 1999; 42:5100-9.
73. Gschwend D A, Good A C, Kuntz I D. Molecular docking towards drug discovery. Journal of Molecular Recognition: Jmr; 9:175-86.
74. Good A C, Ewing T J, Gschwend D A, Kuntz I D. New molecular shape descriptors: application in database screening. Journal of Computer-Aided Molecular Design 1995; 9:1-12.
75. Evans S V. SETOR: hardware-lighted three-dimensional solid model representations of macromolecules. J. Mol. Graphics. 1993; 11:134-8, 127-8.
76. Petrey D, Honig B. GRASP2: visualization, surface properties, and electrostatics of macromolecular structures and sequences. Methods in Enzymology 2003; 374:492-509.
77. Perlmutter D H, Travis J, Punsal P I. Elastase regulates the synthesis of its inhibitor, alpha 1-proteinase inhibitor, and exaggerates the defect in homozygous PiZZ alpha 1 PI deficiency. J Clin Invest 1988; 81:1774-80.
78. Zhu H, Zhao H, Collins C D, Eckenrode S E, Run Q, McIndoe R A, Crawford J M, Nelson D R, She J X, Liu C. Gene expression associated with interferon alfa antiviral activity in an HCV replicon cell line. Hepatology 2003; 37:1180-8.
79. Shang X Z, Zhu H, Lin K, Tu Z, Chen J, Nelson D R, Liu C. Stabilized beta-catenin promotes hepatocyte proliferation and inhibits TNFalpha-induced apoptosis. Lab Invest 2004; 84:332-41.
80. Parfrey H, Mahadeva R, Ravenhill N A, Zhou A, Dafforn T R, Foreman R C, Lomas D A. Targeting a surface cavity of alpha 1-antitrypsin to prevent conformational disease. J Biol Chem 2003; 278:33060-6.
81. Hassanein A M, Glanz S M, Kessler H P, Eskin T A, Liu C. beta-Catenin is expressed aberrantly in tumors expressing shadow cells. Pilomatricoma, craniopharyngioma, and calcifying odontogenic cyst. Am J Clin Pathol 2003; 120:732-6.

Other Embodiments

From the foregoing description, it will be apparent that variations and modifications may be made to the invention described herein to adopt it to various usages and conditions. Such embodiments are also within the scope of the following claims.

All patents and publications mentioned in this specification are herein incorporated by reference to the same extent as if each independent patent and publication was specifically and individually indicated to be incorporated by reference.

APPENDIX A

```
HEADER    SERINE PROTEASE INHIBITOR          24-SEP-99   1QMB
TITLE     CLEAVED ALPHA-1-ANTITRYPSIN POLYMER
COMPND    MOL_ID: 1;
COMPND    2   MOLECULE: ALPHA-1-ANTITRYPSIN;
COMPND    3   CHAIN: A, B;
```

APPENDIX A-continued

```
COMPND    4    SYNONYM: ALPHA-1-PROTEINASE INHIBITOR, ALPHA-1-PI;
COMPND    5    ENGINEERED: YES;
COMPND    6    MUTATION: YES
SOURCE         MOL_ID: 1;
SOURCE    2    ORGANISM_SCIENTIFIC: *HOMO SAPIENS*;
SOURCE    3    EXPRESSION_SYSTEM: *ESCHERICHIA COLI*
KEYWDS         SERPIN, ANTITRYPSIN, POLYMER, CLEAVED
EXPDTA         X-RAY DIFFRACTION
AUTHOR         J. A. HUNTINGTON, N. S. PANNU, B. HAZES, R. J. READ, D. A. LOMAS,
AUTHOR    2    R. W. CARRELL
REVDAT    1    06-FEB-00 1QMB    0
JRNL      AUTH    J. A. HUNTINGTON, N. S. PANNU, B. HAZES, R. J. READ,
JRNL      AUTH 2  D. A. LOMAS, R. W. CARRELL
JRNL      TITL    A 2.6A STRUCTURE OF A SERPIN POLYMER AND
JRNL      TITL 2  IMPLICATIONS FOR CONFORMATIONAL DISEASE
JRNL      REF     J. MOL. BIOL.           V. 293 449 1999
JRNL      REFN    ASTM JMOBAK UK ISSN 0022-2836
REMARK    2
REMARK    2    RESOLUTION. 2.6 ANGSTROMS.
REMARK    3
REMARK    3    REFINEMENT.
REMARK    3     PROGRAM     :CNS 0.9
REMARK    3     AUTHORS     :BRUNGER, ADAMS, CLORE, DELANO, GROS,
REMARK    3                  GROSSE-KUNSTLEVE, JIANG, KUSZEWSKI, NILGES,
REMARK    3                  PANNU, READ, RICE, SIMONSON, WARREN
REMARK    3
REMARK    3    REFINEMENT TARGET: NULL
REMARK    3
REMARK    3    DATA USED IN REFINEMENT.
REMARK    3     RESOLUTION RANGE HIGH (ANGSTROMS):2.60
REMARK    3     RESOLUTION RANGE LOW  (ANGSTROMS) :27.27
REMARK    3     DATA CUTOFF            (SIGMA(F)):0.0
REMARK    3     OUTLIER CUTOFF HIGH (RMS(ABS(F))):1038103.31
REMARK    3     COMPLETENESS (WORKING + TEST)   (%):73.8
REMARK    3     NUMBER OF REFLECTIONS             :17423
REMARK    3
REMARK    3    FIT TO DATA USED IN REFINEMENT.
REMARK    3     CROSS-VALIDATION METHOD          :THROUGHOUT
REMARK    3     FREE R VALUE TEST SET SELECTION :RANDOM
REMARK    3     R VALUE          (WORKING SET): 0.212
REMARK    3     FREE R VALUE                  :0.258
REMARK    3     FREE R VALUE TEST SET SIZE (%): 5.0
REMARK    3     FREE R VALUE TEST SET COUNT    :875
REMARK    3     ESTIMATED ERROR OF FREE R VALUE :0.009
REMARK    3
REMARK    3    FIT IN THE HIGHEST RESOLUTION BIN.
REMARK    3     TOTAL NUMBER OF BINS USED           :6
REMARK    3     BIN RESOLUTION RANGE HIGH       (A): 2.57
REMARK    3     BIN RESOLUTION RANGE LOW        (A): 2.73
REMARK    3     BIN COMPLETENESS (WORKING + TEST) (%): 13.2
REMARK    3     REFLECTIONS IN BIN    (WORKING SET): 501
REMARK    3     BIN R VALUE        (WORKING SET): 0.409
REMARK    3     BIN FREE R VALUE              :0.373
REMARK    3     BIN FREE R VALUE TEST SET SIZE (%): 4.9
REMARK    3     BIN FREE R VALUE TEST SET COUNT   :26
REMARK    3     ESTIMATED ERROR OF BIN FREE R VALUE: 0.073
REMARK    3
REMARK    3    NUMBER OF NON-HYDROGEN ATOMS USED IN REFINEMENT.
REMARK    3     PROTEIN ATOMS        :2873
REMARK    3     NUCLEIC ACID ATOMS    :0
REMARK    3     HETEROGEN ATOMS       :0
REMARK    3     SOLVENT ATOMS       :23
REMARK    3
REMARK    3    B VALUES.
REMARK    3     FROM WILSON PLOT       (A**2): 58.0
REMARK    3     MEAN B VALUE    (OVERALL, A**2): 69.7
REMARK    3     OVERALL ANISOTROPIC B VALUE.
REMARK    3      B11 (A**2): 0.06
REMARK    3      B22 (A**2): 0.06
REMARK    3      B33 (A**2): −0.12
REMARK    3      B12 (A**2): −4.68
REMARK    3      B13 (A**2): 0.00
REMARK    3      B23 (A**2): 0.00
REMARK    3
REMARK    3    ESTIMATED COORDINATE ERROR.
REMARK    3     ESD FROM LUZZATI PLOT      (A): 0.43
REMARK    3     ESD FROM SIGMAA          (A): 0.81
REMARK    3     LOW RESOLUTION CUTOFF      (A): 5.00
REMARK    3
REMARK    3    CROSS-VALIDATED ESTIMATED COORDINATE ERROR.
```

APPENDIX A-continued

```
REMARK    3   ESD FROM C-V LUZZATI PLOT    (A): 0.41
REMARK    3   ESD FROM C-V SIGMAA          (A): 0.73
REMARK    3
REMARK    3   RMS DEVIATIONS FROM IDEAL VALUES.
REMARK    3   BOND LENGTHS         (A): 0.005
REMARK    3   BOND ANGLES          (DEGREES): 1.2
REMARK    3   DIHEDRAL ANGLES      (DEGREES): 23.6
REMARK    3   IMPROPER ANGLES      (DEGREES): 0.59
REMARK    3
REMARK    3   ISOTROPIC THERMAL MODEL: RESTRAINED
REMARK    3
REMARK    3   ISOTROPIC THERMAL FACTOR RESTRAINTS.    RMS    SIGMA
REMARK    3   MAIN-CHAIN BOND      (A**2): 4.00; 1.50
REMARK    3   MAIN-CHAIN ANGLE     (A**2): 6.25; 2.00
REMARK    3   SIDE-CHAIN BOND      (A**2): 8.74; 2.00
REMARK    3   SIDE-CHAIN ANGLE     (A**2): 11.86; 2.50
REMARK    3
REMARK    3   BULK SOLVENT MODELING.
REMARK    3   METHOD USED: FLAT MODEL
REMARK    3   KSOL: 0.321472
REMARK    3   BSOL: 50.9487
REMARK    3
REMARK    3   NCS MODEL: NONE
REMARK    3
REMARK    3   NCS RESTRAINTS.                RMS SIGMA/WEIGHT
REMARK    3    GROUP 1 POSITIONAL      (A): NULL; NULL
REMARK    3    GROUP 1 B-FACTOR       (A**2): NULL; NULL
REMARK    3
REMARK    3   PARAMETER FILE 1  :PROTEIN_REP.PARAM
REMARK    3   PARAMETER FILE 2  :WATER_REP.PARAM
REMARK    3   TOPOLOGY FILE 1   :PROTEIN.TOP
REMARK    3   TOPOLOGY FILE 2   :WATER.TOP
REMARK    3
REMARK    3   OTHER REFINEMENT REMARKS: NULL
REMARK    4
REMARK    4   1QMB COMPLIES WITH FORMAT V. 2.3, 09-JULY-1998
REMARK  100
REMARK  100   THIS ENTRY HAS BEEN PROCESSED BY EBI ON 24-SEP-1999.
REMARK  100   THE EBI ID CODE IS EBI-4086.
REMARK  200
REMARK  200   EXPERIMENTAL DETAILS
REMARK  200   EXPERIMENT TYPE         :X-RAY DIFFRACTION
REMARK  200   DATE OF DATA COLLECTION    :15-MAY-1999
REMARK  200   TEMPERATURE      (KELVIN): 100
REMARK  200   PH              :8.5
REMARK  200   NUMBER OF CRYSTALS USED       :1
REMARK  200
REMARK  200   SYNCHROTRON       (Y/N): Y
REMARK  200   RADIATION SOURCE       :SRS BEAMLINE PX9.6
REMARK  200   BEAMLINE          :PX9.6
REMARK  200   X-RAY GENERATOR MODEL     :NULL
REMARK  200   MONOCHROMATIC OR LAUE    (M/L): M
REMARK  200   WAVELENGTH OR RANGE       (A): 0.9
REMARK  200   MONOCHROMATOR         :SI FILTER
REMARK  200   OPTICS            :MIRRORS
REMARK  200
REMARK  200   DETECTOR TYPE         :CCD
REMARK  200   DETECTOR MANUFACTURER     :ADSC
REMARK  200   INTENSITY-INTEGRATION SOFTWARE: MOSFLM
REMARK  200   DATA SCALING SOFTWARE     :SCALA
REMARK  200
REMARK  200   NUMBER OF UNIQUE REFLECTIONS   :17423
REMARK  200   RESOLUTION RANGE HIGH     (A): 2.57
REMARK  200   RESOLUTION RANGE LOW      (A): 27.27
REMARK  200   REJECTION CRITERIA (SIGMA(I)): NONE
REMARK  200
REMARK  200   OVERALL.
REMARK  200   COMPLETENESS FOR RANGE   (%): 71.5
REMARK  200   DATA REDUNDANCY       :3.9
REMARK  200   R MERGE          (I): 0.209
REMARK  200   R SYM            (I): 0.183
REMARK  200   <I/SIGMA(I)> FOR THE DATA SET: 13.73
REMARK  200
REMARK  200   IN THE HIGHEST RESOLUTION SHELL.
REMARK  200   HIGHEST RESOLUTION SHELL, RANGE HIGH (A): 2.57
REMARK  200   HIGHEST RESOLUTION SHELL, RANGE LOW (A): 2.71
REMARK  200   COMPLETENESS FOR SHELL   (%): 12.5
REMARK  200   DATA REDUNDANCY IN SHELL    :1.6
REMARK  200   R MERGE FOR SHELL       (I): 1.0
REMARK  200   R SYM FOR SHELL         (I): 1.0
```

APPENDIX A-continued

```
REMARK  200   <I/SIGMA(I)> FOR SHELL          :0.3
REMARK  200
REMARK  200   DIFFRACTION PROTOCOL: SINGLE WAVELENGTH
REMARK  200   METHOD USED TO DETERMINE THE STRUCTURE: MOLECULAR REPLACEMENT
REMARK  200   SOFTWARE USED: AMORE
REMARK  200   STARTING MODEL: PDB ETRY 7API
REMARK  200
REMARK  200   REMARK: MOLECULAR REPLACEMENT WAS CONDUCTED IN THE ABSENCE
REMARK  200    OF S4A
REMARK  280
REMARK  280   CRYSTAL
REMARK  280   SOLVENT CONTENT, VS (%): 73
REMARK  280   MATTHEWS COEFFICIENT, VM (ANGSTROMS**3/DA): 4.46
REMARK  280
REMARK  280   CRYSTALLIZATION CONDITIONS: 0.2M TRI-SODIUM CITRATE,
REMARK  280    0.1M TRIS, PH 8.5, 30% PEG 400
REMARK  290
REMARK  290   CRYSTALLOGRAPHIC SYMMETRY
REMARK  290   SYMMETRY OPERATORS FOR SPACE GROUP: P 31 2 1
REMARK  290
REMARK  290      SYMOP  SYMMETRY
REMARK  290     NNNMMM  OPERATOR
REMARK  290       1555  X, Y, Z
REMARK  290       2555  −Y, X − Y, Z + 1/3
REMARK  290       3555  Y − X, −X, Z + 2/3
REMARK  290       4555  Y, X, −Z
REMARK  290       5555  X − Y, −Y, 2/3 − Z
REMARK  290       6555  −X, Y − X, 1/3 − Z
REMARK  290
REMARK  290    WHERE NNN -> OPERATOR NUMBER
REMARK  290          MMM -> TRANSLATION VECTOR
REMARK  290
REMARK  290   CRYSTALLOGRAPHIC SYMMETRY TRANSFORMATIONS
REMARK  290   THE FOLLOWING TRANSFORMATIONS OPERATE ON THE ATOM/HETATM
REMARK  290   RECORDS IN THIS ENTRY TO PRODUCE CRYSTALLOGRAPHICALLY
REMARK  290   RELATED MOLECULES.
REMARK  290     SMTRY1   1    1.000000   0.000000   0.000000    0.00000
REMARK  290     SMTRY2   1    0.000000   1.000000   0.000000    0.00000
REMARK  290     SMTRY3   1    0.000000   0.000000   1.000000    0.00000
REMARK  290     SMTRY1   2   −0.500000  −0.866025   0.000000    0.00000
REMARK  290     SMTRY2   2    0.866025  −0.500000   0.000000    0.00000
REMARK  290     SMTRY3   2    0.000000   0.000000   1.000000   36.88333
REMARK  290     SMTRY1   3   −0.500000   0.866025   0.000000    0.00000
REMARK  290     SMTRY2   3   −0.866025  −0.500000   0.000000    0.00000
REMARK  290     SMTRY3   3    0.000000   0.000000   1.000000   73.76667
REMARK  290     SMTRY1   4   −0.500000   0.866025   0.000000    0.00000
REMARK  290     SMTRY2   4    0.866025   0.500000   0.000000    0.00000
REMARK  290     SMTRY3   4    0.000000   0.000000  −1.000000    0.00000
REMARK  290     SMTRY1   5    1.000000   0.000000   0.000000    0.00000
REMARK  290     SMTRY2   5    0.000000  −1.000000   0.000000    0.00000
REMARK  290     SMTRY3   5    0.000000   0.000000  −1.000000   73.76667
REMARK  290     SMTRY1   6   −0.500000  −0.866025   0.000000    0.00000
REMARK  290     SMTRY2   6   −0.866025   0.500000   0.000000    0.00000
REMARK  290     SMTRY3   6    0.000000   0.000000  −1.000000   36.88333
REMARK  290
REMARK  290   REMARK: NULL
REMARK  300
REMARK  300   BIOMOLECULE: 1
REMARK  300   THIS ENTRY CONTAINS THE CRYSTALLOGRAPHIC ASYMMETRIC UNIT
REMARK  300   WHICH CONSISTS OF 2 CHAIN(S). SEE REMARK 350 FOR
REMARK  300   INFORMATION ON GENERATING THE BIOLOGICAL MOLECULE(S).
REMARK  350
REMARK  350   GENERATING THE BIOMOLECULE
REMARK  350   COORDINATES FOR A COMPLETE MULTIMER REPRESENTING THE KNOWN
REMARK  350   BIOLOGICALLY SIGNIFICANT OLIGOMERIZATION STATE OF THE
REMARK  350   MOLECULE CAN BE GENERATED BY APPLYING BIOMT TRANSFORMATIONS
REMARK  350   GIVEN BELOW. BOTH NON-CRYSTALLOGRAPHIC AND
REMARK  350   CRYSTALLOGRAPHIC OPERATIONS ARE GIVEN.
REMARK  350
REMARK  350   BIOMOLECULE: 1
REMARK  350   APPLY THE FOLLOWING TO CHAINS: A, B
REMARK  350     BIOMT1   1    1.000000   0.000000   0.000000    0.00000
REMARK  350     BIOMT2   1    0.000000   1.000000   0.000000    0.00000
REMARK  350     BIOMT3   1    0.000000   0.000000   1.000000    0.00000
REMARK  400
REMARK  400   COMPOUND
REMARK  400    CRYSTAL TRIALS WERE SET UP FOR S195A THROMBIN AND M358R
REMARK  400    ALPHA-1-ANTITRYPSIN. THE CRYSTALS CONTAINED ONLY P7-P6
REMARK  400    CLEAVED ALPHA-1-ANTITRYPSIN AND THE REMAINING MOTHERLIQOUR
REMARK  400    WAS PREDOMINANTLY S195A THROMBIN.
```

APPENDIX A-continued

```
REMARK   470
REMARK   470 MISSING ATOM
REMARK   470 THE FOLLOWING RESIDUES HAVE MISSING ATOMS (M = MODEL NUMBER;
REMARK   470 RES = RESIDUE NAME; C = CHAIN IDENTIFIER; SSEQ = SEQUENCE NUMBER;
REMARK   470 I = INSERTION CODE):
REMARK   470   M RES CSSEQI ATOMS
REMARK   470     LYS  A    125  CG  CD   CE   NZ
REMARK   470     LYS  A    155  CG  CD   CE   NZ
REMARK   470     ARG  A    178  CG  CD   NE   CZ   NH1   NH2
REMARK   470     ARG  A    196  CG  CD   NE   CZ   NH1   NH2
REMARK   470     LYS  A    233  CG  CD   CE   NZ
REMARK   470     LYS  A    234  CG  CD   CE   NZ
REMARK   470     LYS  A    274  CG  CD   CE   NZ
REMARK   470     ASP  A    280  CG  OD1  OD2
REMARK   470     LYS  B    365  CG  CD   CE   NZ
REMARK   470     LYS  B    380  CG  CD   CE   NZ
REMARK   500
REMARK   500 GEOMETRY AND STEREOCHEMISTRY
REMARK   500 SUBTOPIC: COVALENT BOND ANGLES
REMARK   500
REMARK   500 THE STEREOCHEMICAL PARAMETERS OF THE FOLLOWING RESIDUES
REMARK   500 HAVE VALUES WHICH DEVIATE FROM EXPECTED VALUES BY MORE
REMARK   500 THAN 6*RMSD (M = MODEL NUMBER; RES = RESIDUE NAME; C = CHAIN
REMARK   500 IDENTIFIER; SSEQ = SEQUENCE NUMBER; I = INSERTION CODE).
REMARK   500
REMARK   500 STANDARD TABLE:
REMARK   500 FORMAT: (10X, I3, 1X, A3, 1X, A1, I4, A1, 3(1X, A4, 2X), 12X, F5.1)
REMARK   500
REMARK   500 EXPECTED VALUES: ENGH AND HUBER, 1991
REMARK   500
REMARK   500   M RES CSSEQI ATM1 ATM2 ATM3
REMARK   500     THR  A     85  N-CA-C    ANGL. DEV. = -9.6 DEGREES
REMARK   500     LEU  A    245  N-CA-C    ANGL. DEV. = -8.3 DEGREES
REMARK   500     SER  A    292  N-CA-C    ANGL. DEV. = -9.7 DEGREES
REMARK   500     ASP  A    298  N-CA-C    ANGL. DEV. = -11.1 DEGREES
REMARK   500
REMARK   500 REMARK: NULL
REMARK   500
REMARK   500 GEOMETRY AND STEREOCHEMISTRY
REMARK   500 SUBTOPIC: TORSION ANGLES
REMARK   500
REMARK   500 TORSION ANGLES OUTSIDE THE EXPECTED RAMACHANDRAN REGIONS:
REMARK   500 (M = MODEL NUMBER; RES = RESIDUE NAME; C = CHAIN IDENTIFIER;
REMARK   500 SSEQ = SEQUENCE NUMBER; I = INSERTION CODE).
REMARK   500 STANDARD TABLE:
REMARK   500 FORMAT: (10X, I3, 1X, A3, 1X, A1, I4, A1, 4X, F7.2, 3X, F7.2)
REMARK   500
REMARK   500   M RES CSSEQI      PSI       PHI
REMARK   500
REMARK   500     GLU  A     86   129.86   -73.12
REMARK   500     SER  A    108    55.27   -47.90
REMARK   525
REMARK   525 SOLVENT
REMARK   525 SOME ATOMS COULD NOT BE ASSIGNED TO THE OLIGOMER, BY ANY
REMARK   525 SYMMETRY OPERATION TO WITHIN 5.00 ANGSTROM
REMARK   525
REMARK   525   M RES CSSEQI    X      Y       Z    SYMM-TRANS CLOSEST
REMARK   525                                                  DIST.
REMARK   525     1  HOH    404   19.130  39.155  14.205   001  555  5.2
REMARK   525     1  HOH    405   32.703  23.131  26.372   001  555  7.0
REMARK   525     1  HOH    410  -11.932  33.910  30.933   001  555  7.3
REMARK   525     1  HOH    413   16.797  64.247  34.336   001  555  6.0
REMARK   525     1  HOH    414   -9.929  34.038  46.262   001  555  7.5
REMARK   525     1  HOH    418  -16.283  64.098  70.960   001  555  6.7
REMARK   800
REMARK   800 SITE
REMARK   800 SITE_IDENTIFIER: P7
REMARK   800 SITE_DESCRIPTION: ABERREANT CLEAVAGE SITE
REMARK   900
REMARK   900 RELATED ENTRIES
REMARK   900 RELATED ID: 7API    RELATED DB: PDB
REMARK   900  MODIFIED ALPHA-1-ANTITRYPSIN/MODIFIED ALPHA-1-PROTEINASE
REMARK   900  INHIBITOR (TETRAGONAL FORM 1)
REMARK   900 RELATED ID: 8API    RELATED DB: PDB
REMARK   900  MODIFIED ALPHA-1-ANTITRYPSIN/MODIFIED ALPHA-1-PROTEINASE
REMARK   900  INHIBITOR (HEXAGONAL)
REMARK   900 RELATED ID: 9API    RELATED DB: PDB
REMARK   900  MODIFIED ALPHA-1-ANTITRYPSIN/MODIFIED ALPHA-1-PROTEINASE
REMARK   900  INHIBITOR (TETRAGONAL FORM 2)
REMARK   900 RELATED ID: 1PSI    RELATED DB: PDB
```

APPENDIX A-continued

```
REMARK   900   INTACT RECOMBINED ALPHA-1-ANTITRYPSIN MUTANT PHE 51 TO LEU
REMARK   900   RELATED ID: 2PSI   RELATED DB: PDB
REMARK   900   INTACT WILDTYPE RECOMBINANT ALPHA-1-ANTITRYPSIN
REMARK   900   RELATED ID: 1KCT   RELATED DB: PDB
REMARK   900   ALPHA1-ANTITRYPSIN
REMARK   900   RELATED ID: 1ATU   RELATED DB: PDB
REMARK   900   UNCLEAVED ALPHA-1-ANTITRYPSIN
REMARK   999
REMARK   999   SEQUENCE
REMARK   999   PREVIOUSLY UNIDENTIFIED CLEAVAGE SITE
REMARK   999   CHAIN BREAK SER 45 A---SER 47 A MISSING RESIDUE ASN 46 A
REMARK   999   CHAIN BREAK ASN 278 A---ASP 280 A MISSING RESIDUE GLU 279 A
REMARK   999
DBREF    1QMB   A     25    45  SWS   P01009  A1AT_HUMAN     49    69
DBREF    1QMB   A     47   278  SWS   P01009  A1AT_HUMAN     71   302
DBREF    1QMB   A    280   352  SWS   P01009  A1AT_HUMAN    304   376
DBREF    1QMB   B    353   394  SWS   P01009  A1AT_HUMAN    377   418
SEQADV   1QMB   GLN  A    115  SWS   P01009  ALA     99 CONFLICT
SEQADV   1QMB   ARG  A    358  SWS   P01009  MET    382 ENGINEERED
SEQRES    1 A  326  LYS  ILE  THR  PRO  ASN  LEU  ALA  GLU  PHE  ALA  PHE  SER  LEU
SEQRES    2 A  326  TYR  ARG  GLN  LEU  ALA  HIS  GLN  SER  SER  THR  ASN  ILE  PHE
SEQRES    3 A  326  PHE  SER  PRO  VAL  SER  ILE  ALA  THR  ALA  PHE  ALA  MET  LEU
SEQRES    4 A  326  SER  LEU  GLY  THR  LYS  ALA  ASP  THR  HIS  ASP  GLU  ILE  LEU
SEQRES    5 A  326  GLU  GLY  LEU  ASN  PHE  ASN  LEU  THR  GLU  ILE  PRO  GLU  ALA
SEQRES    6 A  326  ALA  ILE  HIS  GLU  GLY  PHE  GLN  GLU  LEU  LEU  ARG  THR  LEU
SEQRES    7 A  326  ASN  GLN  PRO  ASP  SER  GLN  LEU  GLN  LEU  THR  THR  GLY  ASN
SEQRES    8 A  326  GLY  LEU  PHE  LEU  SER  GLU  GLY  LEU  LYS  LEU  VAL  ASP  LYS
SEQRES    9 A  326  PHE  LEU  GLU  ASP  VAL  LYS  LYS  LEU  TYR  HIS  SER  GLU  ALA
SEQRES   10 A  326  PHE  THR  VAL  ASN  PHE  GLY  ASP  THR  GLU  GLU  ALA  LYS  LYS
SEQRES   11 A  326  GLN  ILE  ASN  ASP  TYR  VAL  GLU  LYS  GLY  THR  GLN  GLY  LYS
SEQRES   12 A  326  ILE  VAL  ASP  LEU  VAL  LYS  GLU  LEU  ASP  ARG  ASP  THR  VAL
SEQRES   13 A  326  PHE  ALA  LEU  VAL  ASN  TYR  ILE  PHE  PHE  LYS  GLY  LYS  TRP
SEQRES   14 A  326  GLU  ARG  PRO  PHE  GLU  VAL  LYS  ASP  THR  GLU  GLU  GLU  ASP
SEQRES   15 A  326  PHE  HIS  VAL  ASP  GLN  VAL  THR  THR  VAL  LYS  VAL  PRO  MET
SEQRES   16 A  326  MET  LYS  ARG  LEU  GLY  MET  PHE  ASN  ILE  GLN  HIS  CYS  LYS
SEQRES   17 A  326  LYS  LEU  SER  SER  TRP  VAL  LEU  LEU  MET  LYS  TYR  LEU  GLY
SEQRES   18 A  326  ASN  ALA  THR  ALA  ILE  PHE  PHE  LEU  PRO  ASP  GLU  GLY  LYS
SEQRES   19 A  326  LEU  GLN  HIS  LEU  GLU  ASN  GLU  LEU  THR  HIS  ASP  ILE  ILE
SEQRES   20 A  326  THR  LYS  PHE  LEU  GLU  ASN  ASP  ARG  ARG  SER  ALA  SER  LEU
SEQRES   21 A  326  HIS  LEU  PRO  LYS  LEU  SER  ILE  THR  GLY  THR  TYR  ASP  LEU
SEQRES   22 A  326  LYS  SER  VAL  LEU  GLY  GLN  LEU  GLY  ILE  THR  LYS  VAL  PHE
SEQRES   23 A  326  SER  ASN  GLY  ALA  ASP  LEU  SER  GLY  VAL  THR  GLU  GLU  ALA
SEQRES   24 A  326  PRO  LEU  LYS  LEU  SER  LYS  ALA  VAL  HIS  LYS  ALA  VAL  LEU
SEQRES   25 A  326  THR  ILE  ASP  GLU  LYS  GLY  THR  GLU  ALA  ALA  GLY  ALA  MET
SEQRES   26 A  326  PHE
SEQRES    1 B   42  LEU  GLU  ALA  ILE  PRO  ARG  SER  ILE  PRO  PRO  GLU  VAL  LYS
SEQRES    2 B   42  PHE  ASN  ALA  PRO  PHE  VAL  PHE  LEU  MET  ILE  GLU  GLN  ASN
SEQRES    3 B   42  THR  LYS  SER  PRO  LEU  PHE  MET  GLY  LYS  VAL  VAL  ASN  PRO
SEQRES    4 B   42  THR  GLN  LYS
FORMUL    3  HOH   *23(H2 O1)
HELIX     1   1 ILE  A    26  SER  A    45  1                                  20
HELIX     2   2 SER  A    53  SER  A    65  1                                  13
HELIX     3   3 LEU  A    66  THR  A    68  5                                   3
HELIX     4   4 LYS  A    69  LEU  A    80  1                                  12
HELIX     5   5 PRO  A    88  ASN  A   104  1                                  17
HELIX     6   6 VAL  A   127  TYR  A   138  1                                  12
HELIX     7   7 ASP  A   149  THR  A   165  1                                  17
HELIX     8   8 LYS  A   259  GLU  A   266  1                                   8
HELIX     9   9 THR  A   268  ASN  A   278  1                                  11
HELIX    10  10 LEU  A   299  GLN  A   305  1                                   7
HELIX    11  11 THR  A   309  SER  A   313  5                                   5
SHEET     1 A  6 GLU  A   141  VAL  A   145  0
SHEET     2 A  6 GLN  A   111  SER  A   121  1 N  LEU  A   118  O  GLU  A   141
SHEET     3 A  6 PHE  A   182  LYS  A   193 -1 N  LYS  A   191  O  GLN  A   111
SHEET     4 A  6 GLY  A   344  PHE  A   352 -1 N  MET  A   351  O  ASN  A   186
SHEET     5 A  6 VAL  A   333  ILE  A   340 -1 N  THR  A   339  O  GLU  A   346
SHEET     6 A  6 LEU  A   291  ASP  A   298 -1 N  TYR  A   297  O  HIS  A   334
SHEET     1 B  3 ARG  A   282  PRO  A   289  0
SHEET     2 B  3 THR  A   214  PHE  A   227 -1 N  PHE  A   227  O  ARG  A   282
SHEET     3 B  3 GLU  A   204  ASP  A   211 -1 N  ASP  A   211  O  THR  A   214
SHEET     1 C  3 GLN  A   230  CYS  A   232  0
SHEET     2 C  3 SER  A   237  TYR  A   244 -1 N  VAL  A   239  O  GLN  A   230
SHEET     3 C  3 ALA  A   248  PRO  A   255 -1 N  LEU  A   254  O  TRP  A   238
SHEET     1 D  2 PHE  B   370  GLU  B   376  0
SHEET     2 D  2 SER  B   381  VAL  B   388 -1 N  VAL  B   388  O  PHE  B   370
SITE      1 P7  1 PHE A 352
CRYST1  108.590 108.590 110.650  90.00  90.00 120.00 P 31 2 1      12
ORIGX1      1.000000  0.000000  0.000000        0.00000
ORIGX2      0.000000  1.000000  0.000000        0.00000
ORIGX3      0.000000  0.000000  1.000000        0.00000
```

APPENDIX A-continued

| SCALE1 | 0.009209 | 0.005317 | 0.000000 | 0.00000 | | | | | | | |
|---|---|---|---|---|---|---|---|---|---|---|---|
| SCALE2 | 0.000000 | 0.010633 | 0.000000 | 0.00000 | | | | | | | |
| SCALE3 | 0.000000 | 0.000000 | 0.009037 | 0.00000 | | | | | | | |
| ATOM | 1 | N | LYS | A | 25 | 3.965 | 39.881 | 56.789 | 1.00 | 69.02 | N |
| ATOM | 2 | CA | LYS | A | 25 | 2.601 | 39.519 | 57.274 | 1.00 | 77.03 | C |
| ATOM | 3 | C | LYS | A | 25 | 1.528 | 40.005 | 56.309 | 1.00 | 77.77 | C |
| ATOM | 4 | O | LYS | A | 25 | 0.420 | 39.467 | 56.274 | 1.00 | 77.70 | O |
| ATOM | 5 | CB | LYS | A | 25 | 2.344 | 40.119 | 58.663 | 1.00 | 75.77 | C |
| ATOM | 6 | CG | LYS | A | 25 | 1.031 | 39.665 | 59.300 | 1.00 | 83.70 | C |
| ATOM | 7 | CD | LYS | A | 25 | 1.004 | 39.980 | 60.793 | 1.00 | 98.19 | C |
| ATOM | 8 | CE | LYS | A | 25 | −0.166 | 39.293 | 61.493 | 1.00 | 100.36 | C |
| ATOM | 9 | NZ | LYS | A | 25 | −0.099 | 39.424 | 62.979 | 1.00 | 94.94 | N |
| ATOM | 10 | N | ILE | A | 26 | 1.860 | 41.032 | 55.533 | 1.00 | 77.27 | N |
| ATOM | 11 | CA | ILE | A | 26 | 0.926 | 41.590 | 54.560 | 1.00 | 73.66 | C |
| ATOM | 12 | C | ILE | A | 26 | 1.529 | 41.568 | 53.164 | 1.00 | 72.38 | C |
| ATOM | 13 | O | ILE | A | 26 | 0.869 | 41.942 | 52.192 | 1.00 | 70.24 | O |
| ATOM | 14 | CB | ILE | A | 26 | 0.539 | 43.057 | 54.893 | 1.00 | 67.55 | C |
| ATOM | 15 | CG1 | ILE | A | 26 | 1.792 | 43.934 | 54.958 | 1.00 | 63.49 | C |
| ATOM | 16 | CG2 | ILE | A | 26 | −0.223 | 43.112 | 56.204 | 1.00 | 69.62 | C |
| ATOM | 17 | CD1 | ILE | A | 26 | 1.504 | 45.406 | 55.181 | 1.00 | 52.20 | C |
| ATOM | 18 | N | THR | A | 27 | 2.781 | 41.128 | 53.071 | 1.00 | 68.72 | N |
| ATOM | 19 | CA | THR | A | 27 | 3.464 | 41.064 | 51.783 | 1.00 | 72.37 | C |
| ATOM | 20 | C | THR | A | 27 | 2.602 | 40.355 | 50.749 | 1.00 | 70.67 | C |
| ATOM | 21 | O | THR | A | 27 | 2.459 | 40.826 | 49.620 | 1.00 | 67.16 | O |
| ATOM | 22 | CB | THR | A | 27 | 4.809 | 40.322 | 51.885 | 1.00 | 75.26 | C |
| ATOM | 23 | OG1 | THR | A | 27 | 5.672 | 41.013 | 52.797 | 1.00 | 85.50 | O |
| ATOM | 24 | CG2 | THR | A | 27 | 5.481 | 40.258 | 50.522 | 1.00 | 74.79 | C |
| ATOM | 25 | N | PRO | A | 28 | 2.019 | 39.204 | 51.120 | 1.00 | 70.37 | N |
| ATOM | 26 | CA | PRO | A | 28 | 1.170 | 38.463 | 50.185 | 1.00 | 65.08 | C |
| ATOM | 27 | C | PRO | A | 28 | −0.056 | 39.268 | 49.761 | 1.00 | 68.05 | C |
| ATOM | 28 | O | PRO | A | 28 | −0.481 | 39.200 | 48.604 | 1.00 | 68.18 | O |
| ATOM | 29 | CB | PRO | A | 28 | 0.807 | 37.208 | 50.973 | 1.00 | 66.10 | C |
| ATOM | 30 | CG | PRO | A | 28 | 0.841 | 37.683 | 52.398 | 1.00 | 72.78 | C |
| ATOM | 31 | CD | PRO | A | 28 | 2.093 | 38.513 | 52.419 | 1.00 | 67.66 | C |
| ATOM | 32 | N | ASN | A | 29 | −0.619 | 40.030 | 50.697 | 1.00 | 67.06 | N |
| ATOM | 33 | CA | ASN | A | 29 | −1.789 | 40.848 | 50.402 | 1.00 | 68.09 | C |
| ATOM | 34 | C | ASN | A | 29 | −1.423 | 41.872 | 49.342 | 1.00 | 68.72 | C |
| ATOM | 35 | O | ASN | A | 29 | −2.181 | 42.099 | 48.399 | 1.00 | 66.45 | O |
| ATOM | 36 | CB | ASN | A | 29 | −2.290 | 41.566 | 51.657 | 1.00 | 73.21 | C |
| ATOM | 37 | CG | ASN | A | 29 | −2.751 | 40.604 | 52.738 | 1.00 | 81.26 | C |
| ATOM | 38 | OD1 | ASN | A | 29 | −1.934 | 39.972 | 53.407 | 1.00 | 95.07 | O |
| ATOM | 39 | ND2 | ASN | A | 29 | −4.067 | 40.481 | 52.908 | 1.00 | 69.37 | N |
| ATOM | 40 | N | LEU | A | 30 | −0.256 | 42.490 | 49.505 | 1.00 | 69.62 | N |
| ATOM | 41 | CA | LEU | A | 30 | 0.213 | 43.478 | 48.543 | 1.00 | 72.32 | C |
| ATOM | 42 | C | LEU | A | 30 | 0.480 | 42.780 | 47.224 | 1.00 | 72.26 | C |
| ATOM | 43 | O | LEU | A | 30 | −0.102 | 43.127 | 46.196 | 1.00 | 80.07 | O |
| ATOM | 44 | CB | LEU | A | 30 | 1.506 | 44.148 | 49.017 | 1.00 | 74.13 | C |
| ATOM | 45 | CG | LEU | A | 30 | 1.464 | 45.089 | 50.221 | 1.00 | 77.51 | C |
| ATOM | 46 | CD1 | LEU | A | 30 | 2.783 | 45.848 | 50.281 | 1.00 | 70.82 | C |
| ATOM | 47 | CD2 | LEU | A | 30 | 0.299 | 46.065 | 50.096 | 1.00 | 78.46 | C |
| ATOM | 48 | N | ALA | A | 31 | 1.371 | 41.795 | 47.262 | 1.00 | 66.65 | N |
| ATOM | 49 | CA | ALA | A | 31 | 1.719 | 41.041 | 46.072 | 1.00 | 58.77 | C |
| ATOM | 50 | C | ALA | A | 31 | 0.472 | 40.811 | 45.241 | 1.00 | 59.40 | C |
| ATOM | 51 | O | ALA | A | 31 | 0.430 | 41.166 | 44.067 | 1.00 | 65.17 | O |
| ATOM | 52 | CB | ALA | A | 31 | 2.336 | 39.712 | 46.461 | 1.00 | 65.43 | C |
| ATOM | 53 | N | GLU | A | 32 | −0.557 | 40.245 | 45.861 | 1.00 | 61.93 | N |
| ATOM | 54 | CA | GLU | A | 32 | −1.793 | 39.970 | 45.145 | 1.00 | 67.78 | C |
| ATOM | 55 | C | GLU | A | 32 | −2.550 | 41.241 | 44.747 | 1.00 | 66.01 | C |
| ATOM | 56 | O | GLU | A | 32 | −3.247 | 41.258 | 43.734 | 1.00 | 67.11 | O |
| ATOM | 57 | CB | GLU | A | 32 | −2.680 | 39.039 | 45.972 | 1.00 | 65.04 | C |
| ATOM | 58 | CG | GLU | A | 32 | −3.286 | 37.893 | 45.154 | 1.00 | 77.88 | C |
| ATOM | 59 | CD | GLU | A | 32 | −2.246 | 37.088 | 44.363 | 1.00 | 84.07 | C |
| ATOM | 60 | OE1 | GLU | A | 32 | −1.308 | 36.525 | 44.976 | 1.00 | 76.79 | O |
| ATOM | 61 | OE2 | GLU | A | 32 | −2.375 | 37.015 | 43.119 | 1.00 | 89.15 | O |
| ATOM | 62 | N | PHE | A | 33 | −2.416 | 42.305 | 45.535 | 1.00 | 62.21 | N |
| ATOM | 63 | CA | PHE | A | 33 | −3.070 | 43.564 | 45.196 | 1.00 | 58.27 | C |
| ATOM | 64 | C | PHE | A | 33 | −2.438 | 44.077 | 43.911 | 1.00 | 61.82 | C |
| ATOM | 65 | O | PHE | A | 33 | −3.122 | 44.557 | 43.005 | 1.00 | 59.10 | O |
| ATOM | 66 | CB | PHE | A | 33 | −2.868 | 44.608 | 46.294 | 1.00 | 60.07 | C |
| ATOM | 67 | CG | PHE | A | 33 | −3.253 | 46.003 | 45.876 | 1.00 | 61.83 | C |
| ATOM | 68 | CD1 | PHE | A | 33 | −4.588 | 46.351 | 45.706 | 1.00 | 64.67 | C |
| ATOM | 69 | CD2 | PHE | A | 33 | −2.278 | 46.956 | 45.610 | 1.00 | 57.97 | C |
| ATOM | 70 | CE1 | PHE | A | 33 | −4.943 | 47.628 | 45.273 | 1.00 | 55.71 | C |
| ATOM | 71 | CE2 | PHE | A | 33 | −2.626 | 48.234 | 45.175 | 1.00 | 53.73 | C |
| ATOM | 72 | CZ | PHE | A | 33 | −3.958 | 48.569 | 45.007 | 1.00 | 49.15 | C |
| ATOM | 73 | N | ALA | A | 34 | −1.115 | 43.975 | 43.851 | 1.00 | 60.16 | N |
| ATOM | 74 | CA | ALA | A | 34 | −0.367 | 44.418 | 42.686 | 1.00 | 63.31 | C |
| ATOM | 75 | C | ALA | A | 34 | −0.909 | 43.716 | 41.450 | 1.00 | 59.82 | C |
| ATOM | 76 | O | ALA | A | 34 | −1.194 | 44.350 | 40.434 | 1.00 | 59.89 | O |
| ATOM | 77 | CB | ALA | A | 34 | 1.114 | 44.104 | 42.865 | 1.00 | 58.90 | C |

APPENDIX A-continued

| ATOM | 78 | N | PHE | A | 35 | −1.064 | 42.402 | 41.550 | 1.00 | 53.41 | N |
|---|---|---|---|---|---|---|---|---|---|---|---|
| ATOM | 79 | CA | PHE | A | 35 | −1.566 | 41.615 | 40.439 | 1.00 | 48.43 | C |
| ATOM | 80 | C | PHE | A | 35 | −3.008 | 41.959 | 40.112 | 1.00 | 50.51 | C |
| ATOM | 81 | O | PHE | A | 35 | −3.363 | 42.103 | 38.942 | 1.00 | 49.92 | O |
| ATOM | 82 | CB | PHE | A | 35 | −1.423 | 40.134 | 40.760 | 1.00 | 49.90 | C |
| ATOM | 83 | CG | PHE | A | 35 | −0.009 | 39.727 | 41.035 | 1.00 | 55.96 | C |
| ATOM | 84 | CD1 | PHE | A | 35 | 0.999 | 40.026 | 40.122 | 1.00 | 56.40 | C |
| ATOM | 85 | CD2 | PHE | A | 35 | 0.325 | 39.077 | 42.217 | 1.00 | 58.59 | C |
| ATOM | 86 | CE1 | PHE | A | 35 | 2.321 | 39.690 | 40.382 | 1.00 | 50.57 | C |
| ATOM | 87 | CE2 | PHE | A | 35 | 1.648 | 38.735 | 42.490 | 1.00 | 56.97 | C |
| ATOM | 88 | CZ | PHE | A | 35 | 2.649 | 39.044 | 41.568 | 1.00 | 55.97 | C |
| ATOM | 89 | N | SER | A | 36 | −3.838 | 42.097 | 41.142 | 1.00 | 51.16 | N |
| ATOM | 90 | CA | SER | A | 36 | −5.241 | 42.441 | 40.933 | 1.00 | 51.76 | C |
| ATOM | 91 | C | SER | A | 36 | −5.279 | 43.706 | 40.103 | 1.00 | 50.21 | C |
| ATOM | 92 | O | SER | A | 36 | −5.776 | 43.722 | 38.978 | 1.00 | 49.53 | O |
| ATOM | 93 | CB | SER | A | 36 | −5.940 | 42.703 | 42.267 | 1.00 | 53.43 | C |
| ATOM | 94 | OG | SER | A | 36 | −5.892 | 41.562 | 43.104 | 1.00 | 69.85 | O |
| ATOM | 95 | N | LEU | A | 37 | −4.728 | 44.767 | 40.676 | 1.00 | 54.84 | N |
| ATOM | 96 | CA | LEU | A | 37 | −4.677 | 46.064 | 40.024 | 1.00 | 53.45 | C |
| ATOM | 97 | C | LEU | A | 37 | −4.050 | 45.976 | 38.637 | 1.00 | 54.09 | C |
| ATOM | 98 | O | LEU | A | 37 | −4.559 | 46.560 | 37.681 | 1.00 | 57.77 | O |
| ATOM | 99 | CB | LEU | A | 37 | −3.888 | 47.045 | 40.895 | 1.00 | 57.26 | C |
| ATOM | 100 | CG | LEU | A | 37 | −3.689 | 48.477 | 40.389 | 1.00 | 52.66 | C |
| ATOM | 101 | CD1 | LEU | A | 37 | −5.027 | 49.123 | 40.104 | 1.00 | 43.71 | C |
| ATOM | 102 | CD2 | LEU | A | 37 | −2.931 | 49.272 | 41.434 | 1.00 | 54.61 | C |
| ATOM | 103 | N | TYR | A | 38 | −2.945 | 45.246 | 38.524 | 1.00 | 51.57 | N |
| ATOM | 104 | CA | TYR | A | 38 | −2.278 | 45.116 | 37.238 | 1.00 | 53.80 | C |
| ATOM | 105 | C | TYR | A | 38 | −3.217 | 44.578 | 36.171 | 1.00 | 59.33 | C |
| ATOM | 106 | O | TYR | A | 38 | −3.385 | 45.191 | 35.116 | 1.00 | 60.96 | O |
| ATOM | 107 | CB | TYR | A | 38 | −1.055 | 44.200 | 37.341 | 1.00 | 50.55 | C |
| ATOM | 108 | CG | TYR | A | 38 | −0.453 | 43.875 | 35.993 | 1.00 | 46.09 | C |
| ATOM | 109 | CD1 | TYR | A | 38 | −1.049 | 42.938 | 35.150 | 1.00 | 48.70 | C |
| ATOM | 110 | CD2 | TYR | A | 38 | 0.683 | 44.543 | 35.533 | 1.00 | 53.35 | C |
| ATOM | 111 | CE1 | TYR | A | 38 | −0.534 | 42.676 | 33.883 | 1.00 | 52.23 | C |
| ATOM | 112 | CE2 | TYR | A | 38 | 1.206 | 44.289 | 34.266 | 1.00 | 50.49 | C |
| ATOM | 113 | CZ | TYR | A | 38 | 0.590 | 43.354 | 33.446 | 1.00 | 51.51 | C |
| ATOM | 114 | OH | TYR | A | 38 | 1.086 | 43.097 | 32.189 | 1.00 | 50.32 | O |
| ATOM | 115 | N | ARG | A | 39 | −3.819 | 43.424 | 36.441 | 1.00 | 61.04 | N |
| ATOM | 116 | CA | ARG | A | 39 | −4.729 | 42.809 | 35.487 | 1.00 | 56.59 | C |
| ATOM | 117 | C | ARG | A | 39 | −5.803 | 43.793 | 35.022 | 1.00 | 59.54 | C |
| ATOM | 118 | O | ARG | A | 39 | −6.282 | 43.714 | 33.891 | 1.00 | 65.34 | O |
| ATOM | 119 | CB | ARG | A | 39 | −5.361 | 41.556 | 36.101 | 1.00 | 46.87 | C |
| ATOM | 120 | CG | ARG | A | 39 | −4.323 | 40.528 | 36.526 | 1.00 | 56.40 | C |
| ATOM | 121 | CD | ARG | A | 39 | −4.906 | 39.133 | 36.679 | 1.00 | 63.28 | C |
| ATOM | 122 | NE | ARG | A | 39 | −3.887 | 38.154 | 37.065 | 1.00 | 73.13 | N |
| ATOM | 123 | CZ | ARG | A | 39 | −3.504 | 37.914 | 38.319 | 1.00 | 78.44 | C |
| ATOM | 124 | NH1 | ARG | A | 39 | −4.056 | 38.577 | 39.329 | 1.00 | 75.57 | N |
| ATOM | 125 | NH2 | ARG | A | 39 | −2.561 | 37.013 | 38.564 | 1.00 | 74.28 | N |
| ATOM | 126 | N | GLN | A | 40 | −6.166 | 44.733 | 35.886 | 1.00 | 60.91 | N |
| ATOM | 127 | CA | GLN | A | 40 | −7.170 | 45.729 | 35.531 | 1.00 | 62.85 | C |
| ATOM | 128 | C | GLN | A | 40 | −6.609 | 46.725 | 34.522 | 1.00 | 66.88 | C |
| ATOM | 129 | O | GLN | A | 40 | −7.250 | 47.031 | 33.514 | 1.00 | 69.20 | O |
| ATOM | 130 | CB | GLN | A | 40 | −7.642 | 46.466 | 36.781 | 1.00 | 56.39 | C |
| ATOM | 131 | CG | GLN | A | 40 | −8.427 | 45.586 | 37.720 | 1.00 | 69.08 | C |
| ATOM | 132 | CD | GLN | A | 40 | −9.723 | 45.113 | 37.099 | 1.00 | 83.39 | C |
| ATOM | 133 | OE1 | GLN | A | 40 | −10.315 | 44.129 | 37.545 | 1.00 | 95.07 | O |
| ATOM | 134 | NE2 | GLN | A | 40 | −10.178 | 45.819 | 36.067 | 1.00 | 85.83 | N |
| ATOM | 135 | N | LEU | A | 41 | −5.408 | 47.223 | 34.802 | 1.00 | 68.47 | N |
| ATOM | 136 | CA | LEU | A | 41 | −4.740 | 48.182 | 33.927 | 1.00 | 65.05 | C |
| ATOM | 137 | C | LEU | A | 41 | −4.375 | 47.544 | 32.589 | 1.00 | 67.93 | C |
| ATOM | 138 | O | LEU | A | 41 | −4.346 | 48.210 | 31.554 | 1.00 | 64.22 | O |
| ATOM | 139 | CB | LEU | A | 41 | −3.469 | 48.711 | 34.599 | 1.00 | 60.16 | C |
| ATOM | 140 | CG | LEU | A | 41 | −3.601 | 49.437 | 35.944 | 1.00 | 57.46 | C |
| ATOM | 141 | CD1 | LEU | A | 41 | −2.217 | 49.694 | 36.515 | 1.00 | 48.99 | C |
| ATOM | 142 | CD2 | LEU | A | 41 | −4.351 | 50.742 | 35.763 | 1.00 | 48.66 | C |
| ATOM | 143 | N | ALA | A | 42 | −4.089 | 46.248 | 32.619 | 1.00 | 69.92 | N |
| ATOM | 144 | CA | ALA | A | 42 | −3.719 | 45.529 | 31.408 | 1.00 | 72.07 | C |
| ATOM | 145 | C | ALA | A | 42 | −4.939 | 45.340 | 30.523 | 1.00 | 73.41 | C |
| ATOM | 146 | O | ALA | A | 42 | −4.833 | 45.299 | 29.302 | 1.00 | 71.77 | O |
| ATOM | 147 | CB | ALA | A | 42 | −3.120 | 44.178 | 31.768 | 1.00 | 67.99 | C |
| ATOM | 148 | N | HIS | A | 43 | −6.099 | 45.240 | 31.161 | 1.00 | 78.17 | N |
| ATOM | 149 | CA | HIS | A | 43 | −7.363 | 45.044 | 30.470 | 1.00 | 82.97 | C |
| ATOM | 150 | C | HIS | A | 43 | −7.904 | 46.353 | 29.888 | 1.00 | 83.59 | C |
| ATOM | 151 | O | HIS | A | 43 | −8.438 | 46.393 | 28.779 | 1.00 | 85.80 | O |
| ATOM | 152 | CB | HIS | A | 43 | −8.374 | 44.449 | 31.454 | 1.00 | 89.79 | C |
| ATOM | 153 | CG | HIS | A | 43 | −9.700 | 44.130 | 30.840 | 1.00 | 100.68 | C |
| ATOM | 154 | ND1 | HIS | A | 43 | −10.489 | 45.086 | 30.239 | 1.00 | 102.89 | N |
| ATOM | 155 | CD2 | HIS | A | 43 | −10.380 | 42.963 | 30.741 | 1.00 | 101.26 | C |
| ATOM | 156 | CE1 | HIS | A | 43 | −11.599 | 44.523 | 29.796 | 1.00 | 103.85 | C |
| ATOM | 157 | NE2 | HIS | A | 43 | −11.558 | 43.235 | 30.088 | 1.00 | 104.07 | N |

APPENDIX A-continued

| | | | | | | | | | | |
|---|---|---|---|---|---|---|---|---|---|---|
| ATOM | 158 | N | GLN | A | 44 | −7.729 | 47.425 | 30.646 | 1.00 | 86.72 | N |
| ATOM | 159 | CA | GLN | A | 44 | −8.213 | 48.748 | 30.283 | 1.00 | 91.61 | C |
| ATOM | 160 | C | GLN | A | 44 | −7.636 | 49.442 | 29.038 | 1.00 | 97.72 | C |
| ATOM | 161 | O | GLN | A | 44 | −8.375 | 50.135 | 28.334 | 1.00 | 102.74 | O |
| ATOM | 162 | CB | GLN | A | 44 | −8.051 | 49.665 | 31.502 | 1.00 | 91.82 | C |
| ATOM | 163 | CG | GLN | A | 44 | −8.359 | 51.125 | 31.266 | 1.00 | 94.80 | C |
| ATOM | 164 | CD | GLN | A | 44 | −7.804 | 51.993 | 32.370 | 1.00 | 91.24 | C |
| ATOM | 165 | OE1 | GLN | A | 44 | −8.179 | 51.854 | 33.532 | 1.00 | 86.05 | O |
| ATOM | 166 | NE2 | GLN | A | 44 | −6.888 | 52.885 | 32.014 | 1.00 | 98.35 | N |
| ATOM | 167 | N | SER | A | 45 | −6.346 | 49.261 | 28.753 | 1.00 | 108.25 | N |
| ATOM | 168 | CA | SER | A | 45 | −5.716 | 49.942 | 27.616 | 1.00 | 113.24 | C |
| ATOM | 169 | C | SER | A | 45 | −6.174 | 49.484 | 26.229 | 1.00 | 115.54 | C |
| ATOM | 170 | O | SER | A | 45 | −6.503 | 50.307 | 25.370 | 1.00 | 109.16 | O |
| ATOM | 171 | CB | SER | A | 45 | −4.186 | 49.841 | 27.729 | 1.00 | 107.89 | C |
| ATOM | 172 | OG | SER | A | 45 | −3.739 | 48.508 | 27.555 | 1.00 | 107.56 | O |
| ATOM | 173 | N | SER | A | 47 | −3.286 | 48.736 | 23.949 | 1.00 | 87.79 | N |
| ATOM | 174 | CA | SER | A | 47 | −2.013 | 48.212 | 24.430 | 1.00 | 85.38 | C |
| ATOM | 175 | C | SER | A | 47 | −0.997 | 49.330 | 24.641 | 1.00 | 82.65 | C |
| ATOM | 176 | O | SER | A | 47 | −0.634 | 50.043 | 23.703 | 1.00 | 75.54 | O |
| ATOM | 177 | CB | SER | A | 47 | −1.453 | 47.195 | 23.440 | 1.00 | 88.89 | C |
| ATOM | 178 | OG | SER | A | 47 | −0.223 | 46.669 | 23.908 | 1.00 | 105.60 | O |
| ATOM | 179 | N | THR | A | 48 | −0.532 | 49.464 | 25.879 | 1.00 | 80.11 | N |
| ATOM | 180 | CA | THR | A | 48 | 0.428 | 50.499 | 26.235 | 1.00 | 69.77 | C |
| ATOM | 181 | C | THR | A | 48 | 1.377 | 50.007 | 27.316 | 1.00 | 66.96 | C |
| ATOM | 182 | O | THR | A | 48 | 1.057 | 49.065 | 28.043 | 1.00 | 70.21 | O |
| ATOM | 183 | CB | THR | A | 48 | −0.305 | 51.730 | 26.770 | 1.00 | 66.45 | C |
| ATOM | 184 | OG1 | THR | A | 48 | −1.273 | 52.149 | 25.805 | 1.00 | 79.66 | O |
| ATOM | 185 | CG2 | THR | A | 48 | 0.671 | 52.870 | 27.051 | 1.00 | 59.61 | C |
| ATOM | 186 | N | ASN | A | 49 | 2.545 | 50.635 | 27.419 | 1.00 | 53.09 | N |
| ATOM | 187 | CA | ASN | A | 49 | 3.499 | 50.247 | 28.449 | 1.00 | 49.30 | C |
| ATOM | 188 | C | ASN | A | 49 | 2.830 | 50.490 | 29.796 | 1.00 | 48.33 | C |
| ATOM | 189 | O | ASN | A | 49 | 2.157 | 51.502 | 29.987 | 1.00 | 50.46 | O |
| ATOM | 190 | CB | ASN | A | 49 | 4.773 | 51.095 | 28.377 | 1.00 | 47.76 | C |
| ATOM | 191 | CG | ASN | A | 49 | 5.558 | 50.877 | 27.103 | 1.00 | 50.61 | C |
| ATOM | 192 | OD1 | ASN | A | 49 | 5.735 | 49.747 | 26.655 | 1.00 | 55.06 | O |
| ATOM | 193 | ND2 | ASN | A | 49 | 6.058 | 51.962 | 26.525 | 1.00 | 53.59 | N |
| ATOM | 194 | N | ILE | A | 50 | 3.007 | 49.567 | 30.731 | 1.00 | 45.89 | N |
| ATOM | 195 | CA | ILE | A | 50 | 2.418 | 49.726 | 32.052 | 1.00 | 44.82 | C |
| ATOM | 196 | C | ILE | A | 50 | 3.496 | 49.825 | 33.122 | 1.00 | 45.18 | C |
| ATOM | 197 | O | ILE | A | 50 | 4.466 | 49.067 | 33.118 | 1.00 | 48.14 | O |
| ATOM | 198 | CB | ILE | A | 50 | 1.498 | 48.539 | 32.408 | 1.00 | 46.62 | C |
| ATOM | 199 | CG1 | ILE | A | 50 | 0.295 | 48.515 | 31.471 | 1.00 | 41.37 | C |
| ATOM | 200 | CG2 | ILE | A | 50 | 1.027 | 48.647 | 33.857 | 1.00 | 42.76 | C |
| ATOM | 201 | CD1 | ILE | A | 50 | −0.638 | 47.364 | 31.741 | 1.00 | 40.49 | C |
| ATOM | 202 | N | PHE | A | 51 | 3.330 | 50.773 | 34.032 | 1.00 | 39.12 | N |
| ATOM | 203 | CA | PHE | A | 51 | 4.276 | 50.929 | 35.119 | 1.00 | 43.87 | C |
| ATOM | 204 | C | PHE | A | 51 | 3.592 | 51.628 | 36.276 | 1.00 | 47.30 | C |
| ATOM | 205 | O | PHE | A | 51 | 3.042 | 52.715 | 36.109 | 1.00 | 51.18 | O |
| ATOM | 206 | CB | PHE | A | 51 | 5.491 | 51.744 | 34.687 | 1.00 | 36.91 | C |
| ATOM | 207 | CG | PHE | A | 51 | 6.602 | 51.746 | 35.706 | 1.00 | 49.54 | C |
| ATOM | 208 | CD1 | PHE | A | 51 | 7.350 | 50.592 | 35.943 | 1.00 | 51.84 | C |
| ATOM | 209 | CD2 | PHE | A | 51 | 6.889 | 52.891 | 36.446 | 1.00 | 53.09 | C |
| ATOM | 210 | CE1 | PHE | A | 51 | 8.368 | 50.577 | 36.903 | 1.00 | 46.62 | C |
| ATOM | 211 | CE2 | PHE | A | 51 | 7.907 | 52.889 | 37.410 | 1.00 | 51.49 | C |
| ATOM | 212 | CZ | PHE | A | 51 | 8.646 | 51.730 | 37.638 | 1.00 | 50.43 | C |
| ATOM | 213 | N | PHE | A | 52 | 3.615 | 50.993 | 37.443 | 1.00 | 46.67 | N |
| ATOM | 214 | CA | PHE | A | 52 | 3.005 | 51.564 | 38.636 | 1.00 | 48.47 | C |
| ATOM | 215 | C | PHE | A | 52 | 3.689 | 51.038 | 39.894 | 1.00 | 54.09 | C |
| ATOM | 216 | O | PHE | A | 52 | 4.458 | 50.073 | 39.839 | 1.00 | 53.35 | O |
| ATOM | 217 | CB | PHE | A | 52 | 1.503 | 51.248 | 38.682 | 1.00 | 46.74 | C |
| ATOM | 218 | CG | PHE | A | 52 | 1.181 | 49.781 | 38.865 | 1.00 | 54.67 | C |
| ATOM | 219 | CD1 | PHE | A | 52 | 1.438 | 48.861 | 37.854 | 1.00 | 54.41 | C |
| ATOM | 220 | CD2 | PHE | A | 52 | 0.599 | 49.326 | 40.049 | 1.00 | 55.53 | C |
| ATOM | 221 | CE1 | PHE | A | 52 | 1.119 | 47.514 | 38.018 | 1.00 | 49.95 | C |
| ATOM | 222 | CE2 | PHE | A | 52 | 0.279 | 47.982 | 40.221 | 1.00 | 48.24 | C |
| ATOM | 223 | CZ | PHE | A | 52 | 0.539 | 47.076 | 39.203 | 1.00 | 51.66 | C |
| ATOM | 224 | N | SER | A | 53 | 3.413 | 51.682 | 41.025 | 1.00 | 56.56 | N |
| ATOM | 225 | CA | SER | A | 53 | 3.998 | 51.277 | 42.299 | 1.00 | 56.41 | C |
| ATOM | 226 | C | SER | A | 53 | 2.941 | 50.750 | 43.253 | 1.00 | 56.67 | C |
| ATOM | 227 | O | SER | A | 53 | 2.240 | 51.528 | 43.905 | 1.00 | 63.25 | O |
| ATOM | 228 | CB | SER | A | 53 | 4.717 | 52.455 | 42.959 | 1.00 | 61.44 | C |
| ATOM | 229 | OG | SER | A | 53 | 5.111 | 52.125 | 44.281 | 1.00 | 60.52 | O |
| ATOM | 230 | N | PRO | A | 54 | 2.812 | 49.418 | 43.352 | 1.00 | 55.75 | N |
| ATOM | 231 | CA | PRO | A | 54 | 1.822 | 48.818 | 44.249 | 1.00 | 53.04 | C |
| ATOM | 232 | C | PRO | A | 54 | 1.936 | 49.375 | 45.670 | 1.00 | 53.92 | C |
| ATOM | 233 | O | PRO | A | 54 | 0.962 | 49.878 | 46.230 | 1.00 | 59.59 | O |
| ATOM | 234 | CB | PRO | A | 54 | 2.153 | 47.332 | 44.168 | 1.00 | 49.60 | C |
| ATOM | 235 | CG | PRO | A | 54 | 2.611 | 47.180 | 42.750 | 1.00 | 52.03 | C |
| ATOM | 236 | CD | PRO | A | 54 | 3.529 | 48.374 | 42.596 | 1.00 | 56.53 | C |
| ATOM | 237 | N | VAL | A | 55 | 3.132 | 49.294 | 46.243 | 1.00 | 48.51 | N |

APPENDIX A-continued

| ATOM | 238 | CA | VAL | A | 55 | 3.363 | 49.794 | 47.593 | 1.00 | 50.36 | C |
|---|---|---|---|---|---|---|---|---|---|---|---|
| ATOM | 239 | C | VAL | A | 55 | 2.804 | 51.201 | 47.754 | 1.00 | 47.74 | C |
| ATOM | 240 | O | VAL | A | 55 | 2.091 | 51.488 | 48.716 | 1.00 | 48.61 | O |
| ATOM | 241 | CB | VAL | A | 55 | 4.877 | 49.824 | 47.931 | 1.00 | 58.54 | C |
| ATOM | 242 | CG1 | VAL | A | 55 | 5.096 | 50.432 | 49.318 | 1.00 | 56.79 | C |
| ATOM | 243 | CG2 | VAL | A | 55 | 5.454 | 48.411 | 47.875 | 1.00 | 55.47 | C |
| ATOM | 244 | N | SER | A | 56 | 3.133 | 52.068 | 46.800 | 1.00 | 47.60 | N |
| ATOM | 245 | CA | SER | A | 56 | 2.690 | 53.460 | 46.810 | 1.00 | 47.44 | C |
| ATOM | 246 | C | SER | A | 56 | 1.171 | 53.609 | 46.906 | 1.00 | 54.54 | C |
| ATOM | 247 | O | SER | A | 56 | 0.654 | 54.237 | 47.835 | 1.00 | 54.08 | O |
| ATOM | 248 | CB | SER | A | 56 | 3.194 | 54.166 | 45.551 | 1.00 | 40.50 | C |
| ATOM | 249 | OG | SER | A | 56 | 2.821 | 55.532 | 45.548 | 1.00 | 47.84 | O |
| ATOM | 250 | N | ILE | A | 57 | 0.462 | 53.031 | 45.939 | 1.00 | 55.83 | N |
| ATOM | 251 | CA | ILE | A | 57 | −1.000 | 53.091 | 45.897 | 1.00 | 51.49 | C |
| ATOM | 252 | C | ILE | A | 57 | −1.636 | 52.505 | 47.151 | 1.00 | 50.79 | C |
| ATOM | 253 | O | ILE | A | 57 | −2.613 | 53.042 | 47.674 | 1.00 | 50.31 | O |
| ATOM | 254 | CB | ILE | A | 57 | −1.553 | 52.313 | 44.681 | 1.00 | 43.98 | C |
| ATOM | 255 | CG1 | ILE | A | 57 | −0.968 | 52.883 | 43.391 | 1.00 | 35.74 | C |
| ATOM | 256 | CG2 | ILE | A | 57 | −3.075 | 52.401 | 44.649 | 1.00 | 36.61 | C |
| ATOM | 257 | CD1 | ILE | A | 57 | −1.447 | 52.183 | 42.154 | 1.00 | 28.58 | C |
| ATOM | 258 | N | ALA | A | 58 | −1.069 | 51.398 | 47.620 | 1.00 | 54.67 | N |
| ATOM | 259 | CA | ALA | A | 58 | −1.564 | 50.694 | 48.795 | 1.00 | 56.60 | C |
| ATOM | 260 | C | ALA | A | 58 | −1.467 | 51.481 | 50.095 | 1.00 | 56.90 | C |
| ATOM | 261 | O | ALA | A | 58 | −2.470 | 51.656 | 50.788 | 1.00 | 59.08 | O |
| ATOM | 262 | CB | ALA | A | 58 | −0.832 | 49.365 | 48.943 | 1.00 | 59.71 | C |
| ATOM | 263 | N | THR | A | 59 | −0.269 | 51.952 | 50.432 | 1.00 | 54.46 | N |
| ATOM | 264 | CA | THR | A | 59 | −0.091 | 52.693 | 51.677 | 1.00 | 57.53 | C |
| ATOM | 265 | C | THR | A | 59 | −0.890 | 53.992 | 51.683 | 1.00 | 52.84 | C |
| ATOM | 266 | O | THR | A | 59 | −1.324 | 54.448 | 52.738 | 1.00 | 53.90 | O |
| ATOM | 267 | CB | THR | A | 59 | 1.407 | 53.023 | 51.962 | 1.00 | 56.57 | C |
| ATOM | 268 | OG1 | THR | A | 59 | 1.773 | 54.237 | 51.298 | 1.00 | 59.90 | O |
| ATOM | 269 | CG2 | THR | A | 59 | 2.309 | 51.892 | 51.480 | 1.00 | 45.28 | C |
| ATOM | 270 | N | ALA | A | 60 | −1.090 | 54.579 | 50.506 | 1.00 | 48.78 | N |
| ATOM | 271 | CA | ALA | A | 60 | −1.839 | 55.828 | 50.395 | 1.00 | 49.16 | C |
| ATOM | 272 | C | ALA | A | 60 | −3.306 | 55.629 | 50.771 | 1.00 | 50.36 | C |
| ATOM | 273 | O | ALA | A | 60 | −3.895 | 56.468 | 51.452 | 1.00 | 48.99 | O |
| ATOM | 274 | CB | ALA | A | 60 | −1.731 | 56.382 | 48.978 | 1.00 | 43.32 | C |
| ATOM | 275 | N | PHE | A | 61 | −3.891 | 54.521 | 50.325 | 1.00 | 53.37 | N |
| ATOM | 276 | CA | PHE | A | 61 | −5.288 | 54.213 | 50.622 | 1.00 | 50.02 | C |
| ATOM | 277 | C | PHE | A | 61 | −5.434 | 53.583 | 51.992 | 1.00 | 52.26 | C |
| ATOM | 278 | O | PHE | A | 61 | −6.380 | 53.876 | 52.726 | 1.00 | 56.84 | O |
| ATOM | 279 | CB | PHE | A | 61 | −5.860 | 53.287 | 49.556 | 1.00 | 45.44 | C |
| ATOM | 280 | CG | PHE | A | 61 | −6.391 | 54.014 | 48.362 | 1.00 | 49.92 | C |
| ATOM | 281 | CD1 | PHE | A | 61 | −7.644 | 54.620 | 48.407 | 1.00 | 43.52 | C |
| ATOM | 282 | CD2 | PHE | A | 61 | −5.627 | 54.132 | 47.205 | 1.00 | 49.30 | C |
| ATOM | 283 | CE1 | PHE | A | 61 | −8.134 | 55.336 | 47.314 | 1.00 | 38.28 | C |
| ATOM | 284 | CE2 | PHE | A | 61 | −6.105 | 54.847 | 46.105 | 1.00 | 54.73 | C |
| ATOM | 285 | CZ | PHE | A | 61 | −7.364 | 55.452 | 46.161 | 1.00 | 45.89 | C |
| ATOM | 286 | N | ALA | A | 62 | −4.492 | 52.712 | 52.332 | 1.00 | 52.67 | N |
| ATOM | 287 | CA | ALA | A | 62 | −4.496 | 52.057 | 53.628 | 1.00 | 48.92 | C |
| ATOM | 288 | C | ALA | A | 62 | −4.456 | 53.141 | 54.692 | 1.00 | 49.63 | C |
| ATOM | 289 | O | ALA | A | 62 | −5.041 | 52.997 | 55.760 | 1.00 | 58.04 | O |
| ATOM | 290 | CB | ALA | A | 62 | −3.280 | 51.162 | 53.762 | 1.00 | 47.61 | C |
| ATOM | 291 | N | MET | A | 63 | −3.764 | 54.232 | 54.378 | 1.00 | 55.13 | N |
| ATOM | 292 | CA | MET | A | 63 | −3.617 | 55.360 | 55.294 | 1.00 | 56.57 | C |
| ATOM | 293 | C | MET | A | 63 | −4.911 | 56.160 | 55.401 | 1.00 | 57.94 | C |
| ATOM | 294 | O | MET | A | 63 | −5.310 | 56.586 | 56.490 | 1.00 | 59.98 | O |
| ATOM | 295 | CB | MET | A | 63 | −2.487 | 56.276 | 54.814 | 1.00 | 47.20 | C |
| ATOM | 296 | CG | MET | A | 63 | −2.011 | 57.280 | 55.845 | 1.00 | 47.05 | C |
| ATOM | 297 | SD | MET | A | 63 | −0.742 | 58.370 | 55.191 | 1.00 | 58.33 | S |
| ATOM | 298 | CE | MET | A | 63 | −1.575 | 59.946 | 55.294 | 1.00 | 55.00 | C |
| ATOM | 299 | N | LEU | A | 64 | −5.560 | 56.365 | 54.262 | 1.00 | 57.18 | N |
| ATOM | 300 | CA | LEU | A | 64 | −6.806 | 57.111 | 54.220 | 1.00 | 57.40 | C |
| ATOM | 301 | C | LEU | A | 64 | −7.868 | 56.443 | 55.084 | 1.00 | 63.25 | C |
| ATOM | 302 | O | LEU | A | 64 | −8.532 | 57.107 | 55.880 | 1.00 | 63.78 | O |
| ATOM | 303 | CB | LEU | A | 64 | −7.306 | 57.206 | 52.781 | 1.00 | 53.68 | C |
| ATOM | 304 | CG | LEU | A | 64 | −8.620 | 57.950 | 52.573 | 1.00 | 44.14 | C |
| ATOM | 305 | CD1 | LEU | A | 64 | −8.483 | 59.357 | 53.113 | 1.00 | 54.72 | C |
| ATOM | 306 | CD2 | LEU | A | 64 | −8.960 | 57.978 | 51.095 | 1.00 | 40.61 | C |
| ATOM | 307 | N | SER | A | 65 | −8.011 | 55.127 | 54.920 | 1.00 | 68.52 | N |
| ATOM | 308 | CA | SER | A | 65 | −8.995 | 54.328 | 55.657 | 1.00 | 64.71 | C |
| ATOM | 309 | C | SER | A | 65 | −9.043 | 54.658 | 57.145 | 1.00 | 64.38 | C |
| ATOM | 310 | O | SER | A | 65 | −10.086 | 54.531 | 57.785 | 1.00 | 69.39 | O |
| ATOM | 311 | CB | SER | A | 65 | −8.691 | 52.841 | 55.490 | 1.00 | 57.94 | C |
| ATOM | 312 | OG | SER | A | 65 | −7.505 | 52.496 | 56.179 | 1.00 | 48.43 | O |
| ATOM | 313 | N | LEU | A | 66 | −7.901 | 55.065 | 57.687 | 1.00 | 66.86 | N |
| ATOM | 314 | CA | LEU | A | 66 | −7.781 | 55.433 | 59.094 | 1.00 | 58.65 | C |
| ATOM | 315 | C | LEU | A | 66 | −8.875 | 56.433 | 59.458 | 1.00 | 58.01 | C |
| ATOM | 316 | O | LEU | A | 66 | −9.448 | 56.379 | 60.544 | 1.00 | 60.07 | O |
| ATOM | 317 | CB | LEU | A | 66 | −6.401 | 56.053 | 59.337 | 1.00 | 53.85 | C |

APPENDIX A-continued

| ATOM | 318 | CG | LEU | A | 66 | −5.407 | 55.367 | 60.282 | 1.00 | 54.92 | C |
|---|---|---|---|---|---|---|---|---|---|---|---|
| ATOM | 319 | CD1 | LEU | A | 66 | −5.686 | 53.879 | 60.399 | 1.00 | 43.59 | C |
| ATOM | 320 | CD2 | LEU | A | 66 | −4.001 | 55.620 | 59.765 | 1.00 | 46.81 | C |
| ATOM | 321 | N | GLY | A | 67 | −9.168 | 57.340 | 58.532 | 1.00 | 55.70 | N |
| ATOM | 322 | CA | GLY | A | 67 | −10.187 | 58.343 | 58.777 | 1.00 | 61.04 | C |
| ATOM | 323 | C | GLY | A | 67 | −11.487 | 58.063 | 58.055 | 1.00 | 62.59 | C |
| ATOM | 324 | O | GLY | A | 67 | −12.296 | 58.968 | 57.836 | 1.00 | 60.08 | O |
| ATOM | 325 | N | THR | A | 68 | −11.685 | 56.802 | 57.684 | 1.00 | 67.26 | N |
| ATOM | 326 | CA | THR | A | 68 | −12.888 | 56.379 | 56.982 | 1.00 | 65.54 | C |
| ATOM | 327 | C | THR | A | 68 | −13.664 | 55.434 | 57.893 | 1.00 | 66.35 | C |
| ATOM | 328 | O | THR | A | 68 | −13.085 | 54.807 | 58.781 | 1.00 | 66.67 | O |
| ATOM | 329 | CB | THR | A | 68 | −12.530 | 55.652 | 55.668 | 1.00 | 63.99 | C |
| ATOM | 330 | OG1 | THR | A | 68 | −11.712 | 56.502 | 54.854 | 1.00 | 70.89 | O |
| ATOM | 331 | CG2 | THR | A | 68 | −13.780 | 55.318 | 54.892 | 1.00 | 77.99 | C |
| ATOM | 332 | N | LYS | A | 69 | −14.973 | 55.336 | 57.680 | 1.00 | 67.32 | N |
| ATOM | 333 | CA | LYS | A | 69 | −15.802 | 54.469 | 58.508 | 1.00 | 73.29 | C |
| ATOM | 334 | C | LYS | A | 69 | −16.824 | 53.660 | 57.711 | 1.00 | 75.99 | C |
| ATOM | 335 | O | LYS | A | 69 | −16.945 | 53.820 | 56.499 | 1.00 | 79.38 | O |
| ATOM | 336 | CB | LYS | A | 69 | −16.519 | 55.314 | 59.563 | 1.00 | 74.44 | C |
| ATOM | 337 | CG | LYS | A | 69 | −15.578 | 56.155 | 60.407 | 1.00 | 78.21 | C |
| ATOM | 338 | CD | LYS | A | 69 | −16.238 | 56.621 | 61.691 | 1.00 | 83.04 | C |
| ATOM | 339 | CE | LYS | A | 69 | −15.194 | 57.113 | 62.682 | 1.00 | 92.70 | C |
| ATOM | 340 | NZ | LYS | A | 69 | −15.735 | 57.228 | 64.065 | 1.00 | 98.62 | N |
| ATOM | 341 | N | ALA | A | 70 | −17.549 | 52.782 | 58.399 | 1.00 | 80.56 | N |
| ATOM | 342 | CA | ALA | A | 70 | −18.578 | 51.954 | 57.769 | 1.00 | 81.36 | C |
| ATOM | 343 | C | ALA | A | 70 | −18.070 | 51.202 | 56.544 | 1.00 | 80.04 | C |
| ATOM | 344 | O | ALA | A | 70 | −16.958 | 50.675 | 56.546 | 1.00 | 78.82 | O |
| ATOM | 345 | CB | ALA | A | 70 | −19.783 | 52.822 | 57.381 | 1.00 | 75.69 | C |
| ATOM | 346 | N | ASP | A | 71 | −18.899 | 51.152 | 55.504 | 1.00 | 82.38 | N |
| ATOM | 347 | CA | ASP | A | 71 | −18.540 | 50.465 | 54.269 | 1.00 | 84.74 | C |
| ATOM | 348 | C | ASP | A | 71 | −17.367 | 51.132 | 53.576 | 1.00 | 82.23 | C |
| ATOM | 349 | O | ASP | A | 71 | −16.396 | 50.464 | 53.221 | 1.00 | 81.79 | O |
| ATOM | 350 | CB | ASP | A | 71 | −19.725 | 50.415 | 53.299 | 1.00 | 93.62 | C |
| ATOM | 351 | CG | ASP | A | 71 | −20.780 | 49.411 | 53.715 | 1.00 | 101.13 | C |
| ATOM | 352 | OD1 | ASP | A | 71 | −21.639 | 49.750 | 54.559 | 1.00 | 98.11 | O |
| ATOM | 353 | OD2 | ASP | A | 71 | −20.744 | 48.272 | 53.200 | 1.00 | 109.55 | O |
| ATOM | 354 | N | THR | A | 72 | −17.459 | 52.445 | 53.377 | 1.00 | 76.64 | N |
| ATOM | 355 | CA | THR | A | 72 | −16.386 | 53.178 | 52.718 | 1.00 | 75.89 | C |
| ATOM | 356 | C | THR | A | 72 | −15.036 | 52.682 | 53.244 | 1.00 | 70.05 | C |
| ATOM | 357 | O | THR | A | 72 | −14.071 | 52.574 | 52.491 | 1.00 | 69.02 | O |
| ATOM | 358 | CB | THR | A | 72 | −16.520 | 54.711 | 52.948 | 1.00 | 71.00 | C |
| ATOM | 359 | OG1 | THR | A | 72 | −16.514 | 54.990 | 54.348 | 1.00 | 84.16 | O |
| ATOM | 360 | CG2 | THR | A | 72 | −17.822 | 55.229 | 52.366 | 1.00 | 67.67 | C |
| ATOM | 361 | N | HIS | A | 73 | −14.991 | 52.348 | 54.533 | 1.00 | 64.96 | N |
| ATOM | 362 | CA | HIS | A | 73 | −13.773 | 51.852 | 55.175 | 1.00 | 67.32 | C |
| ATOM | 363 | C | HIS | A | 73 | −13.415 | 50.454 | 54.691 | 1.00 | 69.71 | C |
| ATOM | 364 | O | HIS | A | 73 | −12.428 | 50.259 | 53.977 | 1.00 | 67.96 | O |
| ATOM | 365 | CB | HIS | A | 73 | −13.948 | 51.840 | 56.702 | 1.00 | 69.48 | C |
| ATOM | 366 | CG | HIS | A | 73 | −12.924 | 51.019 | 57.430 | 1.00 | 71.23 | C |
| ATOM | 367 | ND1 | HIS | A | 73 | −13.067 | 49.664 | 57.639 | 1.00 | 74.02 | N |
| ATOM | 368 | CD2 | HIS | A | 73 | −11.729 | 51.359 | 57.972 | 1.00 | 74.97 | C |
| ATOM | 369 | CE1 | HIS | A | 73 | −12.006 | 49.205 | 58.281 | 1.00 | 78.98 | C |
| ATOM | 370 | NE2 | HIS | A | 73 | −11.179 | 50.213 | 58.494 | 1.00 | 73.70 | N |
| ATOM | 371 | N | ASP | A | 74 | −14.226 | 49.484 | 55.096 | 1.00 | 69.07 | N |
| ATOM | 372 | CA | ASP | A | 74 | −14.018 | 48.096 | 54.728 | 1.00 | 70.88 | C |
| ATOM | 373 | C | ASP | A | 74 | −13.797 | 47.967 | 53.229 | 1.00 | 68.45 | C |
| ATOM | 374 | O | ASP | A | 74 | −12.945 | 47.203 | 52.780 | 1.00 | 74.12 | O |
| ATOM | 375 | CB | ASP | A | 74 | −15.235 | 47.274 | 55.137 | 1.00 | 77.91 | C |
| ATOM | 376 | CG | ASP | A | 74 | −15.620 | 47.492 | 56.583 | 1.00 | 80.77 | C |
| ATOM | 377 | OD1 | ASP | A | 74 | −14.746 | 47.327 | 57.460 | 1.00 | 86.51 | O |
| ATOM | 378 | OD2 | ASP | A | 74 | −16.795 | 47.827 | 56.843 | 1.00 | 85.33 | O |
| ATOM | 379 | N | GLU | A | 75 | −14.575 | 48.724 | 52.465 | 1.00 | 64.55 | N |
| ATOM | 380 | CA | GLU | A | 75 | −14.498 | 48.708 | 51.011 | 1.00 | 61.87 | C |
| ATOM | 381 | C | GLU | A | 75 | −13.074 | 48.973 | 50.543 | 1.00 | 61.77 | C |
| ATOM | 382 | O | GLU | A | 75 | −12.590 | 48.338 | 49.606 | 1.00 | 68.81 | O |
| ATOM | 383 | CB | GLU | A | 75 | −15.431 | 49.768 | 50.446 | 1.00 | 58.02 | C |
| ATOM | 384 | CG | GLU | A | 75 | −15.935 | 49.479 | 49.066 | 1.00 | 55.97 | C |
| ATOM | 385 | CD | GLU | A | 75 | −16.799 | 50.603 | 48.564 | 1.00 | 68.43 | C |
| ATOM | 386 | OE1 | GLU | A | 75 | −16.273 | 51.733 | 48.436 | 1.00 | 62.10 | O |
| ATOM | 387 | OE2 | GLU | A | 75 | −18.000 | 50.360 | 48.313 | 1.00 | 65.02 | O |
| ATOM | 388 | N | ILE | A | 76 | −12.409 | 49.919 | 51.195 | 1.00 | 60.17 | N |
| ATOM | 389 | CA | ILE | A | 76 | −11.035 | 50.251 | 50.849 | 1.00 | 60.57 | C |
| ATOM | 390 | C | ILE | A | 76 | −10.131 | 49.075 | 51.198 | 1.00 | 61.63 | C |
| ATOM | 391 | O | ILE | A | 76 | −9.581 | 48.417 | 50.315 | 1.00 | 63.62 | O |
| ATOM | 392 | CB | ILE | A | 76 | −10.535 | 51.497 | 51.622 | 1.00 | 61.72 | C |
| ATOM | 393 | CG1 | ILE | A | 76 | −11.339 | 52.730 | 51.218 | 1.00 | 64.11 | C |
| ATOM | 394 | CG2 | ILE | A | 76 | −9.060 | 51.741 | 51.328 | 1.00 | 61.88 | C |
| ATOM | 395 | CD1 | ILE | A | 76 | −10.857 | 54.007 | 51.881 | 1.00 | 69.14 | C |
| ATOM | 396 | N | LEU | A | 77 | −9.988 | 48.822 | 52.495 | 1.00 | 60.73 | N |
| ATOM | 397 | CA | LEU | A | 77 | −9.153 | 47.740 | 52.996 | 1.00 | 57.01 | C |

APPENDIX A-continued

| ATOM | 398 | C | LEU | A | 77 | −9.334 | 46.446 | 52.215 | 1.00 | 63.13 | C |
|---|---|---|---|---|---|---|---|---|---|---|---|
| ATOM | 399 | O | LEU | A | 77 | −8.357 | 45.785 | 51.867 | 1.00 | 71.63 | O |
| ATOM | 400 | CB | LEU | A | 77 | −9.455 | 47.500 | 54.476 | 1.00 | 49.45 | C |
| ATOM | 401 | CG | LEU | A | 77 | −8.420 | 47.986 | 55.497 | 1.00 | 58.89 | C |
| ATOM | 402 | CD1 | LEU | A | 77 | −7.933 | 49.373 | 55.149 | 1.00 | 57.51 | C |
| ATOM | 403 | CD2 | LEU | A | 77 | −9.042 | 47.973 | 56.882 | 1.00 | 64.30 | C |
| ATOM | 404 | N | GLU | A | 78 | −10.583 | 46.089 | 51.933 | 1.00 | 61.60 | N |
| ATOM | 405 | CA | GLU | A | 78 | −10.876 | 44.865 | 51.196 | 1.00 | 60.61 | C |
| ATOM | 406 | C | GLU | A | 78 | −10.374 | 44.921 | 49.761 | 1.00 | 59.39 | C |
| ATOM | 407 | O | GLU | A | 78 | −9.867 | 43.927 | 49.244 | 1.00 | 52.60 | O |
| ATOM | 408 | CB | GLU | A | 78 | −12.379 | 44.587 | 51.220 | 1.00 | 65.56 | C |
| ATOM | 409 | CG | GLU | A | 78 | −12.748 | 43.347 | 52.012 | 1.00 | 70.48 | C |
| ATOM | 410 | CD | GLU | A | 78 | −14.133 | 43.434 | 52.613 | 1.00 | 81.51 | C |
| ATOM | 411 | OE1 | GLU | A | 78 | −15.097 | 43.701 | 51.860 | 1.00 | 84.09 | O |
| ATOM | 412 | OE2 | GLU | A | 78 | −14.253 | 43.231 | 53.842 | 1.00 | 84.06 | O |
| ATOM | 413 | N | GLY | A | 79 | −10.521 | 46.081 | 49.125 | 1.00 | 61.11 | N |
| ATOM | 414 | CA | GLY | A | 79 | −10.055 | 46.251 | 47.761 | 1.00 | 57.87 | C |
| ATOM | 415 | C | GLY | A | 79 | −8.543 | 46.095 | 47.668 | 1.00 | 65.21 | C |
| ATOM | 416 | O | GLY | A | 79 | −8.008 | 45.794 | 46.601 | 1.00 | 72.11 | O |
| ATOM | 417 | N | LEU | A | 80 | −7.848 | 46.305 | 48.784 | 1.00 | 65.80 | N |
| ATOM | 418 | CA | LEU | A | 80 | −6.394 | 46.166 | 48.820 | 1.00 | 62.35 | C |
| ATOM | 419 | C | LEU | A | 80 | −6.029 | 44.702 | 49.072 | 1.00 | 66.77 | C |
| ATOM | 420 | O | LEU | A | 80 | −4.905 | 44.382 | 49.465 | 1.00 | 66.78 | O |
| ATOM | 421 | CB | LEU | A | 80 | −5.797 | 47.051 | 49.922 | 1.00 | 58.21 | C |
| ATOM | 422 | CG | LEU | A | 80 | −5.905 | 48.571 | 49.757 | 1.00 | 49.86 | C |
| ATOM | 423 | CD1 | LEU | A | 80 | −5.236 | 49.263 | 50.938 | 1.00 | 50.73 | C |
| ATOM | 424 | CD2 | LEU | A | 80 | −5.242 | 48.996 | 48.460 | 1.00 | 48.35 | C |
| ATOM | 425 | N | ASN | A | 81 | −7.001 | 43.823 | 48.843 | 1.00 | 69.82 | N |
| ATOM | 426 | CA | ASN | A | 81 | −6.837 | 42.383 | 49.020 | 1.00 | 70.04 | C |
| ATOM | 427 | C | ASN | A | 81 | −6.591 | 41.957 | 50.457 | 1.00 | 68.89 | C |
| ATOM | 428 | O | ASN | A | 81 | −5.637 | 41.240 | 50.753 | 1.00 | 70.02 | O |
| ATOM | 429 | CB | ASN | A | 81 | −5.721 | 41.864 | 48.113 | 1.00 | 73.77 | C |
| ATOM | 430 | CG | ASN | A | 81 | −6.123 | 41.869 | 46.651 | 1.00 | 86.94 | C |
| ATOM | 431 | OD1 | ASN | A | 81 | −6.939 | 41.055 | 46.217 | 1.00 | 94.21 | O |
| ATOM | 432 | ND2 | ASN | A | 81 | −5.570 | 42.801 | 45.887 | 1.00 | 89.33 | N |
| ATOM | 433 | N | PHE | A | 82 | −7.473 | 42.409 | 51.342 | 1.00 | 70.03 | N |
| ATOM | 434 | CA | PHE | A | 82 | −7.413 | 42.078 | 52.760 | 1.00 | 73.00 | C |
| ATOM | 435 | C | PHE | A | 82 | −8.750 | 41.469 | 53.152 | 1.00 | 77.20 | C |
| ATOM | 436 | O | PHE | A | 82 | −9.804 | 41.922 | 52.704 | 1.00 | 76.90 | O |
| ATOM | 437 | CB | PHE | A | 82 | −7.172 | 43.333 | 53.608 | 1.00 | 74.16 | C |
| ATOM | 438 | CG | PHE | A | 82 | −5.749 | 43.815 | 53.596 | 1.00 | 83.28 | C |
| ATOM | 439 | CD1 | PHE | A | 82 | −4.748 | 43.089 | 54.239 | 1.00 | 83.41 | C |
| ATOM | 440 | CD2 | PHE | A | 82 | −5.403 | 44.988 | 52.930 | 1.00 | 80.64 | C |
| ATOM | 441 | CE1 | PHE | A | 82 | −3.422 | 43.526 | 54.220 | 1.00 | 79.79 | C |
| ATOM | 442 | CE2 | PHE | A | 82 | −4.082 | 45.432 | 52.905 | 1.00 | 77.44 | C |
| ATOM | 443 | CZ | PHE | A | 82 | −3.089 | 44.699 | 53.551 | 1.00 | 76.32 | C |
| ATOM | 444 | N | ASN | A | 83 | −8.706 | 40.429 | 53.974 | 1.00 | 85.19 | N |
| ATOM | 445 | CA | ASN | A | 83 | −9.929 | 39.792 | 54.435 | 1.00 | 89.25 | C |
| ATOM | 446 | C | ASN | A | 83 | −10.105 | 40.270 | 55.864 | 1.00 | 90.90 | C |
| ATOM | 447 | O | ASN | A | 83 | −9.501 | 39.717 | 56.784 | 1.00 | 90.57 | O |
| ATOM | 448 | CB | ASN | A | 83 | −9.791 | 38.270 | 54.415 | 1.00 | 91.70 | C |
| ATOM | 449 | CG | ASN | A | 83 | −11.101 | 37.573 | 54.102 | 1.00 | 91.60 | C |
| ATOM | 450 | OD1 | ASN | A | 83 | −11.363 | 37.204 | 52.954 | 1.00 | 95.89 | O |
| ATOM | 451 | ND2 | ASN | A | 83 | −11.940 | 37.405 | 55.116 | 1.00 | 83.45 | N |
| ATOM | 452 | N | LEU | A | 84 | −10.914 | 41.310 | 56.044 | 1.00 | 93.91 | N |
| ATOM | 453 | CA | LEU | A | 84 | −11.148 | 41.873 | 57.368 | 1.00 | 99.37 | C |
| ATOM | 454 | C | LEU | A | 84 | −11.355 | 40.777 | 58.405 | 1.00 | 102.55 | C |
| ATOM | 455 | O | LEU | A | 84 | −10.857 | 40.873 | 59.529 | 1.00 | 100.15 | O |
| ATOM | 456 | CB | LEU | A | 84 | −12.337 | 42.829 | 57.324 | 1.00 | 100.23 | C |
| ATOM | 457 | CG | LEU | A | 84 | −12.069 | 44.009 | 56.386 | 1.00 | 102.73 | C |
| ATOM | 458 | CD1 | LEU | A | 84 | −13.255 | 44.952 | 56.401 | 1.00 | 104.61 | C |
| ATOM | 459 | CD2 | LEU | A | 84 | −10.796 | 44.734 | 56.820 | 1.00 | 98.11 | C |
| ATOM | 460 | N | THR | A | 85 | −12.093 | 39.737 | 58.031 | 1.00 | 105.58 | N |
| ATOM | 461 | CA | THR | A | 85 | −12.282 | 38.618 | 58.937 | 1.00 | 107.19 | C |
| ATOM | 462 | C | THR | A | 85 | −11.070 | 37.751 | 58.610 | 1.00 | 111.38 | C |
| ATOM | 463 | O | THR | A | 85 | −10.908 | 37.318 | 57.472 | 1.00 | 121.60 | O |
| ATOM | 464 | CB | THR | A | 85 | −13.616 | 37.864 | 58.662 | 1.00 | 107.74 | C |
| ATOM | 465 | OG1 | THR | A | 85 | −13.953 | 37.082 | 59.812 | 1.00 | 114.37 | O |
| ATOM | 466 | CG2 | THR | A | 85 | −13.509 | 36.937 | 57.455 | 1.00 | 104.05 | C |
| ATOM | 467 | N | GLU | A | 86 | −10.207 | 37.553 | 59.603 | 1.00 | 107.25 | N |
| ATOM | 468 | CA | GLU | A | 86 | −8.957 | 36.785 | 59.491 | 1.00 | 112.92 | C |
| ATOM | 469 | C | GLU | A | 86 | −7.872 | 37.672 | 60.070 | 1.00 | 112.28 | C |
| ATOM | 470 | O | GLU | A | 86 | −7.367 | 37.435 | 61.167 | 1.00 | 119.19 | O |
| ATOM | 471 | CB | GLU | A | 86 | −8.566 | 36.471 | 58.038 | 1.00 | 114.58 | C |
| ATOM | 472 | CG | GLU | A | 86 | −9.155 | 35.195 | 57.452 | 1.00 | 121.91 | C |
| ATOM | 473 | CD | GLU | A | 86 | −8.568 | 34.864 | 56.088 | 1.00 | 121.61 | C |
| ATOM | 474 | OE1 | GLU | A | 86 | −8.618 | 35.729 | 55.188 | 1.00 | 117.19 | O |
| ATOM | 475 | OE2 | GLU | A | 86 | −8.057 | 33.738 | 55.914 | 1.00 | 124.16 | O |
| ATOM | 476 | N | ILE | A | 87 | −7.520 | 38.703 | 59.310 | 1.00 | 107.37 | N |
| ATOM | 477 | CA | ILE | A | 87 | −6.502 | 39.655 | 59.724 | 1.00 | 101.57 | C |

APPENDIX A-continued

| | | | | | | | | | | |
|---|---|---|---|---|---|---|---|---|---|---|
| ATOM | 478 | C | ILE | A | 87 | −7.189 | 40.974 | 60.091 | 1.00 | 92.80 | C |
| ATOM | 479 | O | ILE | A | 87 | −7.695 | 41.683 | 59.225 | 1.00 | 91.76 | O |
| ATOM | 480 | CB | ILE | A | 87 | −5.463 | 39.868 | 58.589 | 1.00 | 104.35 | C |
| ATOM | 481 | CG1 | ILE | A | 87 | −4.391 | 40.865 | 59.032 | 1.00 | 107.17 | C |
| ATOM | 482 | CG2 | ILE | A | 87 | −6.161 | 40.322 | 57.313 | 1.00 | 105.22 | C |
| ATOM | 483 | CD1 | ILE | A | 87 | −3.206 | 40.948 | 58.084 | 1.00 | 104.73 | C |
| ATOM | 484 | N | PRO | A | 88 | −7.230 | 41.306 | 61.393 | 1.00 | 88.67 | N |
| ATOM | 485 | CA | PRO | A | 88 | −7.864 | 42.542 | 61.861 | 1.00 | 86.27 | C |
| ATOM | 486 | C | PRO | A | 88 | −7.144 | 43.798 | 61.381 | 1.00 | 87.42 | C |
| ATOM | 487 | O | PRO | A | 88 | −5.918 | 43.820 | 61.269 | 1.00 | 88.21 | O |
| ATOM | 488 | CB | PRO | A | 88 | −7.831 | 42.387 | 63.379 | 1.00 | 85.62 | C |
| ATOM | 489 | CG | PRO | A | 88 | −6.564 | 41.627 | 63.600 | 1.00 | 83.89 | C |
| ATOM | 490 | CD | PRO | A | 88 | −6.631 | 40.568 | 62.520 | 1.00 | 86.25 | C |
| ATOM | 491 | N | GLU | A | 89 | −7.918 | 44.841 | 61.100 | 1.00 | 89.76 | N |
| ATOM | 492 | CA | GLU | A | 89 | −7.366 | 46.103 | 60.624 | 1.00 | 89.99 | C |
| ATOM | 493 | C | GLU | A | 89 | −6.296 | 46.612 | 61.574 | 1.00 | 84.59 | C |
| ATOM | 494 | O | GLU | A | 89 | −5.281 | 47.158 | 61.144 | 1.00 | 86.30 | O |
| ATOM | 495 | CB | GLU | A | 89 | −8.479 | 47.143 | 60.489 | 1.00 | 93.77 | C |
| ATOM | 496 | CG | GLU | A | 89 | −9.179 | 47.469 | 61.790 | 1.00 | 98.66 | C |
| ATOM | 497 | CD | GLU | A | 89 | −10.519 | 48.130 | 61.569 | 1.00 | 104.46 | C |
| ATOM | 498 | OE1 | GLU | A | 89 | −11.414 | 47.481 | 60.987 | 1.00 | 103.71 | O |
| ATOM | 499 | OE2 | GLU | A | 89 | −10.677 | 49.299 | 61.975 | 1.00 | 113.54 | O |
| ATOM | 500 | N | ALA | A | 90 | −6.530 | 46.429 | 62.868 | 1.00 | 80.82 | N |
| ATOM | 501 | CA | ALA | A | 90 | −5.579 | 46.861 | 63.880 | 1.00 | 78.10 | C |
| ATOM | 502 | C | ALA | A | 90 | −4.191 | 46.312 | 63.540 | 1.00 | 77.99 | C |
| ATOM | 503 | O | ALA | A | 90 | −3.174 | 46.973 | 63.757 | 1.00 | 76.76 | O |
| ATOM | 504 | CB | ALA | A | 90 | −6.027 | 46.367 | 65.254 | 1.00 | 76.16 | C |
| ATOM | 505 | N | ALA | A | 91 | −4.159 | 45.100 | 62.995 | 1.00 | 80.52 | N |
| ATOM | 506 | CA | ALA | A | 91 | −2.904 | 44.461 | 62.627 | 1.00 | 80.43 | C |
| ATOM | 507 | C | ALA | A | 91 | −2.515 | 44.787 | 61.185 | 1.00 | 83.19 | C |
| ATOM | 508 | O | ALA | A | 91 | −1.349 | 44.646 | 60.812 | 1.00 | 87.83 | O |
| ATOM | 509 | CB | ALA | A | 91 | −3.008 | 42.947 | 62.821 | 1.00 | 76.61 | C |
| ATOM | 510 | N | ILE | A | 92 | −3.485 | 45.214 | 60.376 | 1.00 | 79.62 | N |
| ATOM | 511 | CA | ILE | A | 92 | −3.206 | 45.575 | 58.985 | 1.00 | 67.73 | C |
| ATOM | 512 | C | ILE | A | 92 | −2.347 | 46.837 | 59.003 | 1.00 | 68.35 | C |
| ATOM | 513 | O | ILE | A | 92 | −1.274 | 46.877 | 58.396 | 1.00 | 68.24 | O |
| ATOM | 514 | CB | ILE | A | 92 | −4.501 | 45.877 | 58.187 | 1.00 | 58.67 | C |
| ATOM | 515 | CG1 | ILE | A | 92 | −5.395 | 44.638 | 58.123 | 1.00 | 60.22 | C |
| ATOM | 516 | CG2 | ILE | A | 92 | −4.152 | 46.295 | 56.777 | 1.00 | 57.27 | C |
| ATOM | 517 | CD1 | ILE | A | 92 | −6.693 | 44.861 | 57.353 | 1.00 | 48.83 | C |
| ATOM | 518 | N | HIS | A | 93 | −2.830 | 47.859 | 59.712 | 1.00 | 65.68 | N |
| ATOM | 519 | CA | HIS | A | 93 | −2.128 | 49.137 | 59.841 | 1.00 | 64.00 | C |
| ATOM | 520 | C | HIS | A | 93 | −0.802 | 48.921 | 60.560 | 1.00 | 66.65 | C |
| ATOM | 521 | O | HIS | A | 93 | 0.212 | 49.530 | 60.228 | 1.00 | 61.37 | O |
| ATOM | 522 | CB | HIS | A | 93 | −2.969 | 50.134 | 60.647 | 1.00 | 64.87 | C |
| ATOM | 523 | CG | HIS | A | 93 | −4.282 | 50.484 | 60.015 | 1.00 | 63.83 | C |
| ATOM | 524 | ND1 | HIS | A | 93 | −4.376 | 51.117 | 58.793 | 1.00 | 65.91 | N |
| ATOM | 525 | CD2 | HIS | A | 93 | −5.554 | 50.304 | 60.444 | 1.00 | 58.00 | C |
| ATOM | 526 | CE1 | HIS | A | 93 | −5.649 | 51.310 | 58.497 | 1.00 | 64.78 | C |
| ATOM | 527 | NE2 | HIS | A | 93 | −6.385 | 50.827 | 59.482 | 1.00 | 60.58 | N |
| ATOM | 528 | N | GLU | A | 94 | −0.830 | 48.053 | 61.563 | 1.00 | 77.73 | N |
| ATOM | 529 | CA | GLU | A | 94 | 0.355 | 47.727 | 62.343 | 1.00 | 82.68 | C |
| ATOM | 530 | C | GLU | A | 94 | 1.424 | 47.150 | 61.405 | 1.00 | 78.93 | C |
| ATOM | 531 | O | GLU | A | 94 | 2.621 | 47.345 | 61.617 | 1.00 | 76.82 | O |
| ATOM | 532 | CB | GLU | A | 94 | −0.032 | 46.714 | 63.429 | 1.00 | 92.85 | C |
| ATOM | 533 | CG | GLU | A | 94 | 1.023 | 46.446 | 64.492 | 1.00 | 109.40 | C |
| ATOM | 534 | CD | GLU | A | 94 | 0.528 | 45.493 | 65.578 | 1.00 | 115.61 | C |
| ATOM | 535 | OE1 | GLU | A | 94 | −0.443 | 45.846 | 66.284 | 1.00 | 114.62 | O |
| ATOM | 536 | OE2 | GLU | A | 94 | 1.106 | 44.392 | 65.724 | 1.00 | 112.22 | O |
| ATOM | 537 | N | GLY | A | 95 | 0.970 | 46.456 | 60.360 | 1.00 | 78.97 | N |
| ATOM | 538 | CA | GLY | A | 95 | 1.869 | 45.857 | 59.386 | 1.00 | 74.55 | C |
| ATOM | 539 | C | GLY | A | 95 | 2.461 | 46.868 | 58.420 | 1.00 | 74.27 | C |
| ATOM | 540 | O | GLY | A | 95 | 3.662 | 46.839 | 58.144 | 1.00 | 72.81 | O |
| ATOM | 541 | N | PHE | A | 96 | 1.616 | 47.756 | 57.895 | 1.00 | 73.61 | N |
| ATOM | 542 | CA | PHE | A | 96 | 2.062 | 48.804 | 56.974 | 1.00 | 67.25 | C |
| ATOM | 543 | C | PHE | A | 96 | 3.127 | 49.655 | 57.658 | 1.00 | 68.38 | C |
| ATOM | 544 | O | PHE | A | 96 | 4.009 | 50.222 | 57.010 | 1.00 | 61.29 | O |
| ATOM | 545 | CB | PHE | A | 96 | 0.882 | 49.695 | 56.572 | 1.00 | 54.45 | C |
| ATOM | 546 | CG | PHE | A | 96 | 0.276 | 49.333 | 55.255 | 100 | 59.18 | C |
| ATOM | 547 | CD1 | PHE | A | 96 | 0.967 | 49.574 | 54.073 | 1.00 | 64.78 | C |
| ATOM | 548 | CD2 | PHE | A | 96 | −0.968 | 48.716 | 55.191 | 1.00 | 59.56 | C |
| ATOM | 549 | CE1 | PHE | A | 96 | 0.427 | 49.201 | 52.842 | 1.00 | 67.63 | C |
| ATOM | 550 | CE2 | PHE | A | 96 | −1.519 | 48.337 | 53.964 | 1.00 | 54.05 | C |
| ATOM | 551 | CZ | PHE | A | 96 | −0.818 | 48.580 | 52.789 | 1.00 | 59.15 | C |
| ATOM | 552 | N | GLN | A | 97 | 3.028 | 49.726 | 58.982 | 1.00 | 73.10 | N |
| ATOM | 553 | CA | GLN | A | 97 | 3.948 | 50.495 | 59.805 | 1.00 | 71.81 | C |
| ATOM | 554 | C | GLN | A | 97 | 5.354 | 49.916 | 59.749 | 1.00 | 71.29 | C |
| ATOM | 555 | O | GLN | A | 97 | 6.332 | 50.654 | 59.618 | 1.00 | 69.88 | O |
| ATOM | 556 | CB | GLN | A | 97 | 3.460 | 50.501 | 61.250 | 1.00 | 69.15 | C |
| ATOM | 557 | CG | GLN | A | 97 | 4.182 | 51.483 | 62.142 | 1.00 | 78.56 | C |

APPENDIX A-continued

| ATOM | 558 | CD | GLN | A | 97 | 3.696 | 51.414 | 63.571 | 1.00 | 85.25 | C |
|---|---|---|---|---|---|---|---|---|---|---|---|
| ATOM | 559 | OE1 | GLN | A | 97 | 3.959 | 52.309 | 64.371 | 1.00 | 89.31 | O |
| ATOM | 560 | NE2 | GLN | A | 97 | 2.985 | 50.341 | 63.904 | 1.00 | 90.86 | N |
| ATOM | 561 | N | GLU | A | 98 | 5.446 | 48.593 | 59.853 | 1.00 | 70.32 | N |
| ATOM | 562 | CA | GLU | A | 98 | 6.732 | 47.912 | 59.819 | 1.00 | 71.32 | C |
| ATOM | 563 | C | GLU | A | 98 | 7.265 | 47.778 | 58.404 | 1.00 | 70.91 | C |
| ATOM | 564 | O | GLU | A | 98 | 8.477 | 47.818 | 58.190 | 1.00 | 68.85 | O |
| ATOM | 565 | CB | GLU | A | 98 | 6.626 | 46.534 | 60.472 | 1.00 | 81.23 | C |
| ATOM | 566 | CG | GLU | A | 98 | 6.381 | 46.587 | 61.975 | 1.00 | 103.23 | C |
| ATOM | 567 | CD | GLU | A | 98 | 7.310 | 47.565 | 62.685 | 1.00 | 110.69 | C |
| ATOM | 568 | OE1 | GLU | A | 98 | 8.540 | 47.487 | 62.470 | 1.00 | 114.04 | O |
| ATOM | 569 | OE2 | GLU | A | 98 | 6.809 | 48.410 | 63.460 | 1.00 | 111.81 | O |
| ATOM | 570 | N | LEU | A | 99 | 6.362 | 47.616 | 57.441 | 1.00 | 70.21 | N |
| ATOM | 571 | CA | LEU | A | 99 | 6.766 | 47.501 | 56.043 | 1.00 | 68.13 | C |
| ATOM | 572 | C | LEU | A | 99 | 7.409 | 48.816 | 55.620 | 1.00 | 67.97 | C |
| ATOM | 573 | O | LEU | A | 99 | 8.409 | 48.832 | 54.898 | 1.00 | 62.68 | O |
| ATOM | 574 | CB | LEU | A | 99 | 5.558 | 47.222 | 55.146 | 1.00 | 71.09 | C |
| ATOM | 575 | CG | LEU | A | 99 | 5.822 | 47.314 | 53.637 | 1.00 | 72.78 | C |
| ATOM | 576 | CD1 | LEU | A | 99 | 6.673 | 46.143 | 53.181 | 1.00 | 71.95 | C |
| ATOM | 577 | CD2 | LEU | A | 99 | 4.503 | 47.325 | 52.888 | 1.00 | 75.65 | C |
| ATOM | 578 | N | LEU | A | 100 | 6.823 | 49.919 | 56.077 | 1.00 | 65.92 | N |
| ATOM | 579 | CA | LEU | A | 100 | 7.338 | 51.238 | 55.744 | 1.00 | 68.00 | C |
| ATOM | 580 | C | LEU | A | 100 | 8.659 | 51.492 | 58.461 | 1.00 | 71.33 | C |
| ATOM | 581 | O | LEU | A | 100 | 9.632 | 51.936 | 55.845 | 1.00 | 72.68 | O |
| ATOM | 582 | CB | LEU | A | 100 | 6.315 | 52.322 | 56.108 | 1.00 | 59.01 | C |
| ATOM | 583 | CG | LEU | A | 100 | 5.000 | 52.325 | 55.318 | 1.00 | 49.32 | C |
| ATOM | 584 | CD1 | LEU | A | 100 | 4.172 | 53.522 | 55.735 | 1.00 | 56.58 | C |
| ATOM | 585 | CD2 | LEU | A | 100 | 5.273 | 52.378 | 53.826 | 1.00 | 39.37 | C |
| ATOM | 586 | N | ARG | A | 101 | 8.698 | 51.203 | 57.759 | 1.00 | 68.64 | N |
| ATOM | 587 | CA | ARG | A | 101 | 9.916 | 51.399 | 58.532 | 1.00 | 70.06 | C |
| ATOM | 588 | C | ARG | A | 101 | 11.072 | 50.637 | 57.894 | 1.00 | 69.83 | C |
| ATOM | 589 | O | ARG | A | 101 | 12.202 | 51.127 | 57.856 | 1.00 | 65.84 | O |
| ATOM | 590 | CB | ARG | A | 101 | 9.713 | 50.925 | 59.977 | 1.00 | 74.47 | C |
| ATOM | 591 | CG | ARG | A | 101 | 11.000 | 50.858 | 60.799 | 1.00 | 82.74 | C |
| ATOM | 592 | CD | ARG | A | 101 | 10.740 | 50.559 | 62.278 | 1.00 | 89.78 | C |
| ATOM | 593 | NE | ARG | A | 101 | 10.236 | 51.721 | 63.011 | 1.00 | 93.18 | N |
| ATOM | 594 | CZ | ARG | A | 101 | 9.005 | 51.830 | 63.508 | 1.00 | 92.92 | C |
| ATOM | 595 | NH1 | ARG | A | 101 | 8.133 | 50.840 | 63.356 | 1.00 | 85.11 | N |
| ATOM | 596 | NH2 | ARG | A | 101 | 8.646 | 52.932 | 64.157 | 1.00 | 86.66 | N |
| ATOM | 597 | N | THR | A | 102 | 10.774 | 49.447 | 57.376 | 1.00 | 71.30 | N |
| ATOM | 598 | CA | THR | A | 102 | 11.783 | 48.596 | 56.748 | 1.00 | 72.49 | C |
| ATOM | 599 | C | THR | A | 102 | 12.227 | 49.058 | 55.365 | 1.00 | 72.28 | C |
| ATOM | 600 | O | THR | A | 102 | 13.421 | 49.058 | 55.066 | 1.00 | 76.12 | O |
| ATOM | 601 | CB | THR | A | 102 | 11.294 | 47.138 | 56.626 | 1.00 | 71.63 | C |
| ATOM | 602 | OG1 | THR | A | 102 | 10.945 | 46.642 | 57.925 | 1.00 | 74.97 | O |
| ATOM | 603 | CG2 | THR | A | 102 | 12.388 | 46.257 | 56.024 | 1.00 | 62.26 | C |
| ATOM | 604 | N | LEU | A | 103 | 11.272 | 49.431 | 54.518 | 1.00 | 65.54 | N |
| ATOM | 605 | CA | LEU | A | 103 | 11.605 | 49.894 | 53.176 | 1.00 | 57.73 | C |
| ATOM | 606 | C | LEU | A | 103 | 12.498 | 51.131 | 53.254 | 1.00 | 61.03 | C |
| ATOM | 607 | O | LEU | A | 103 | 13.126 | 51.513 | 52.266 | 1.00 | 57.94 | O |
| ATOM | 608 | CB | LEU | A | 103 | 10.332 | 50.236 | 52.395 | 1.00 | 53.93 | C |
| ATOM | 609 | CG | LEU | A | 103 | 9.379 | 49.109 | 51.994 | 1.00 | 50.95 | C |
| ATOM | 610 | CD1 | LEU | A | 103 | 8.124 | 49.706 | 51.373 | 1.00 | 45.77 | C |
| ATOM | 611 | CD2 | LEU | A | 103 | 10.070 | 48.168 | 51.015 | 1.00 | 47.52 | C |
| ATOM | 612 | N | ASN | A | 104 | 12.559 | 51.744 | 54.436 | 1.00 | 62.09 | N |
| ATOM | 613 | CA | ASN | A | 104 | 13.359 | 52.949 | 54.640 | 1.00 | 64.29 | C |
| ATOM | 614 | C | ASN | A | 104 | 14.736 | 52.775 | 55.272 | 1.00 | 71.65 | C |
| ATOM | 615 | O | ASN | A | 104 | 15.321 | 53.732 | 55.771 | 1.00 | 73.23 | O |
| ATOM | 616 | CB | ASN | A | 104 | 12.555 | 53.960 | 55.447 | 1.00 | 54.19 | C |
| ATOM | 617 | CG | ASN | A | 104 | 11.494 | 54.636 | 54.615 | 1.00 | 60.20 | C |
| ATOM | 618 | OD1 | ASN | A | 104 | 11.801 | 55.396 | 53.691 | 1.00 | 53.96 | O |
| ATOM | 619 | ND2 | ASN | A | 104 | 10.234 | 54.356 | 54.925 | 1.00 | 60.75 | N |
| ATOM | 620 | N | GLN | A | 105 | 15.255 | 51.556 | 55.251 | 1.00 | 82.76 | N |
| ATOM | 621 | CA | GLN | A | 105 | 16.578 | 51.293 | 55.797 | 1.00 | 86.19 | C |
| ATOM | 622 | C | GLN | A | 105 | 17.344 | 50.487 | 54.752 | 1.00 | 91.74 | C |
| ATOM | 623 | O | GLN | A | 105 | 17.682 | 49.323 | 54.969 | 1.00 | 91.59 | O |
| ATOM | 624 | CB | GLN | A | 105 | 16.473 | 50.506 | 57.102 | 1.00 | 85.21 | C |
| ATOM | 625 | CG | GLN | A | 105 | 15.518 | 51.113 | 58.110 | 1.00 | 91.91 | C |
| ATOM | 626 | CD | GLN | A | 105 | 15.593 | 50.432 | 59.460 | 1.00 | 98.67 | C |
| ATOM | 627 | OE1 | GLN | A | 105 | 14.723 | 50.617 | 60.313 | 1.00 | 100.80 | O |
| ATOM | 628 | NE2 | GLN | A | 105 | 16.645 | 49.643 | 59.667 | 1.00 | 103.40 | N |
| ATOM | 629 | N | PRO | A | 106 | 17.609 | 51.104 | 53.588 | 1.00 | 94.81 | N |
| ATOM | 630 | CA | PRO | A | 106 | 18.331 | 50.481 | 52.475 | 1.00 | 93.94 | C |
| ATOM | 631 | C | PRO | A | 106 | 19.681 | 49.869 | 52.849 | 1.00 | 93.86 | C |
| ATOM | 632 | O | PRO | A | 106 | 20.287 | 50.219 | 53.861 | 1.00 | 91.09 | O |
| ATOM | 633 | CB | PRO | A | 106 | 18.474 | 51.628 | 51.481 | 1.00 | 92.64 | C |
| ATOM | 634 | CG | PRO | A | 106 | 17.219 | 52.412 | 51.707 | 1.00 | 94.08 | C |
| ATOM | 635 | CD | PRO | A | 106 | 17.150 | 52.455 | 53.213 | 1.00 | 94.20 | C |
| ATOM | 636 | N | ASP | A | 107 | 20.145 | 48.952 | 52.012 | 1.00 | 94.92 | N |
| ATOM | 637 | CA | ASP | A | 107 | 21.412 | 48.274 | 52.230 | 1.00 | 92.02 | C |

APPENDIX A-continued

| | | | | | | | | | | | |
|---|---|---|---|---|---|---|---|---|---|---|---|
| ATOM | 638 | C | ASP | A | 107 | 22.557 | 49.173 | 51.781 | 1.00 | 90.94 | C |
| ATOM | 639 | O | ASP | A | 107 | 23.483 | 48.721 | 51.107 | 1.00 | 92.76 | O |
| ATOM | 640 | CB | ASP | A | 107 | 21.438 | 46.971 | 51.432 | 1.00 | 101.84 | C |
| ATOM | 641 | CG | ASP | A | 107 | 21.906 | 45.791 | 52.253 | 1.00 | 102.51 | C |
| ATOM | 642 | OD1 | ASP | A | 107 | 21.250 | 45.484 | 53.273 | 1.00 | 94.37 | O |
| ATOM | 643 | OD2 | ASP | A | 107 | 22.924 | 45.170 | 51.874 | 1.00 | 109.62 | O |
| ATOM | 644 | N | SER | A | 108 | 22.474 | 50.447 | 52.154 | 1.00 | 89.24 | N |
| ATOM | 645 | CA | SER | A | 108 | 23.485 | 51.452 | 51.821 | 1.00 | 94.43 | C |
| ATOM | 646 | C | SER | A | 108 | 23.792 | 51.594 | 50.329 | 1.00 | 94.93 | C |
| ATOM | 647 | O | SER | A | 108 | 23.837 | 52.709 | 49.804 | 1.00 | 100.50 | O |
| ATOM | 648 | CB | SER | A | 108 | 24.787 | 51.175 | 52.587 | 1.00 | 92.11 | C |
| ATOM | 649 | OG | SER | A | 108 | 25.404 | 49.977 | 52.155 | 1.00 | 100.44 | O |
| ATOM | 650 | N | GLN | A | 109 | 24.011 | 50.472 | 49.651 | 1.00 | 91.46 | N |
| ATOM | 651 | CA | GLN | A | 109 | 24.317 | 50.485 | 48.223 | 1.00 | 84.17 | C |
| ATOM | 652 | C | GLN | A | 109 | 23.033 | 50.700 | 47.430 | 1.00 | 78.10 | C |
| ATOM | 653 | O | GLN | A | 109 | 23.054 | 50.917 | 46.216 | 1.00 | 70.56 | O |
| ATOM | 654 | CB | GLN | A | 109 | 24.954 | 49.159 | 47.819 | 1.00 | 81.46 | C |
| ATOM | 655 | CG | GLN | A | 109 | 26.077 | 48.723 | 48.730 | 1.00 | 80.10 | C |
| ATOM | 656 | CD | GLN | A | 109 | 26.633 | 47.371 | 48.346 | 1.00 | 87.43 | C |
| ATOM | 657 | OE1 | GLN | A | 109 | 27.239 | 47.212 | 47.284 | 1.00 | 76.72 | O |
| ATOM | 658 | NE2 | GLN | A | 109 | 26.420 | 46.382 | 49.206 | 1.00 | 92.56 | N |
| ATOM | 659 | N | LEU | A | 110 | 21.914 | 50.640 | 48.137 | 1.00 | 71.26 | N |
| ATOM | 660 | CA | LEU | A | 110 | 20.616 | 50.819 | 47.517 | 1.00 | 70.31 | C |
| ATOM | 661 | C | LEU | A | 110 | 19.921 | 52.046 | 48.078 | 1.00 | 73.12 | C |
| ATOM | 662 | O | LEU | A | 110 | 19.960 | 52.292 | 49.285 | 1.00 | 75.05 | O |
| ATOM | 663 | CB | LEU | A | 110 | 19.746 | 49.589 | 47.770 | 1.00 | 70.38 | C |
| ATOM | 664 | CG | LEU | A | 110 | 18.312 | 49.658 | 47.248 | 1.00 | 61.50 | C |
| ATOM | 665 | CD1 | LEU | A | 110 | 18.337 | 49.830 | 45.735 | 1.00 | 69.86 | C |
| ATOM | 666 | CD2 | LEU | A | 110 | 17.560 | 48.396 | 47.641 | 1.00 | 45.49 | C |
| ATOM | 667 | N | GLN | A | 111 | 19.299 | 52.824 | 47.195 | 1.00 | 68.57 | N |
| ATOM | 668 | CA | GLN | A | 111 | 18.564 | 54.005 | 47.621 | 1.00 | 56.44 | C |
| ATOM | 669 | C | GLN | A | 111 | 17.088 | 53.680 | 47.494 | 1.00 | 53.46 | C |
| ATOM | 670 | O | GLN | A | 111 | 16.597 | 53.395 | 46.397 | 1.00 | 49.16 | O |
| ATOM | 671 | CB | GLN | A | 111 | 18.880 | 55.217 | 46.744 | 1.00 | 53.33 | C |
| ATOM | 672 | CG | GLN | A | 111 | 20.331 | 55.649 | 46.733 | 1.00 | 56.62 | C |
| ATOM | 673 | CD | GLN | A | 111 | 20.516 | 57.019 | 46.103 | 1.00 | 59.41 | C |
| ATOM | 674 | OE1 | GLN | A | 111 | 20.068 | 58.026 | 46.652 | 1.00 | 60.52 | O |
| ATOM | 675 | NE2 | GLN | A | 111 | 21.170 | 57.064 | 44.943 | 1.00 | 52.93 | N |
| ATOM | 676 | N | LEU | A | 112 | 16.392 | 53.702 | 48.624 | 1.00 | 47.51 | N |
| ATOM | 677 | CA | LEU | A | 112 | 14.965 | 53.433 | 48.653 | 1.00 | 46.89 | C |
| ATOM | 678 | C | LEU | A | 112 | 14.337 | 54.288 | 49.743 | 1.00 | 54.61 | C |
| ATOM | 679 | O | LEU | A | 112 | 14.713 | 54.196 | 50.914 | 1.00 | 59.80 | O |
| ATOM | 680 | CB | LEU | A | 112 | 14.702 | 51.957 | 48.928 | 1.00 | 40.76 | C |
| ATOM | 681 | CG | LEU | A | 112 | 13.219 | 51.589 | 48.905 | 1.00 | 42.28 | C |
| ATOM | 682 | CD1 | LEU | A | 112 | 12.670 | 51.763 | 47.503 | 1.00 | 53.56 | C |
| ATOM | 683 | CD2 | LEU | A | 112 | 13.043 | 50.159 | 49.358 | 1.00 | 53.56 | C |
| ATOM | 684 | N | THR | A | 113 | 13.378 | 55.121 | 49.349 | 1.00 | 59.79 | N |
| ATOM | 685 | CA | THR | A | 113 | 12.704 | 56.021 | 50.279 | 1.00 | 60.51 | C |
| ATOM | 686 | C | THR | A | 113 | 11.208 | 56.105 | 50.004 | 1.00 | 57.28 | C |
| ATOM | 687 | O | THR | A | 113 | 10.768 | 55.911 | 48.871 | 1.00 | 61.47 | O |
| ATOM | 688 | CB | THR | A | 113 | 13.283 | 57.446 | 50.164 | 1.00 | 62.37 | C |
| ATOM | 689 | OG1 | THR | A | 113 | 14.705 | 57.396 | 50.318 | 1.00 | 73.29 | O |
| ATOM | 690 | CG2 | THR | A | 113 | 12.698 | 58.356 | 51.231 | 1.00 | 76.40 | C |
| ATOM | 691 | N | THR | A | 114 | 10.431 | 56.392 | 51.045 | 1.00 | 51.71 | N |
| ATOM | 692 | CA | THR | A | 114 | 8.985 | 56.539 | 50.908 | 1.00 | 55.02 | C |
| ATOM | 693 | C | THR | A | 114 | 8.460 | 57.547 | 51.927 | 1.00 | 59.01 | C |
| ATOM | 694 | O | THR | A | 114 | 8.709 | 57.412 | 53.124 | 1.00 | 65.94 | O |
| ATOM | 695 | CB | THR | A | 114 | 8.244 | 55.209 | 51.131 | 1.00 | 49.62 | C |
| ATOM | 696 | OG1 | THR | A | 114 | 8.564 | 54.702 | 52.431 | 1.00 | 48.02 | O |
| ATOM | 697 | CG2 | THR | A | 114 | 8.622 | 54.193 | 50.066 | 1.00 | 38.39 | C |
| ATOM | 698 | N | GLY | A | 115 | 7.729 | 58.553 | 51.449 | 1.00 | 57.11 | N |
| ATOM | 699 | CA | GLY | A | 115 | 7.183 | 59.558 | 52.343 | 1.00 | 54.45 | C |
| ATOM | 700 | C | GLY | A | 115 | 5.686 | 59.779 | 52.202 | 1.00 | 58.93 | C |
| ATOM | 701 | O | GLY | A | 115 | 5.142 | 59.730 | 51.096 | 1.00 | 60.04 | O |
| ATOM | 702 | N | ASN | A | 116 | 5.016 | 60.006 | 53.330 | 1.00 | 58.22 | N |
| ATOM | 703 | CA | ASN | A | 116 | 3.579 | 60.264 | 53.335 | 1.00 | 56.73 | C |
| ATOM | 704 | C | ASN | A | 116 | 3.349 | 61.642 | 53.922 | 1.00 | 56.68 | C |
| ATOM | 705 | O | ASN | A | 116 | 3.745 | 61.918 | 55.055 | 1.00 | 56.75 | O |
| ATOM | 706 | CB | ASN | A | 116 | 2.813 | 59.252 | 54.192 | 1.00 | 59.70 | C |
| ATOM | 707 | CG | ASN | A | 116 | 2.910 | 57.848 | 53.665 | 1.00 | 58.21 | C |
| ATOM | 708 | OD1 | ASN | A | 116 | 2.774 | 57.617 | 52.468 | 1.00 | 60.15 | O |
| ATOM | 709 | ND2 | ASN | A | 116 | 3.131 | 56.891 | 54.561 | 1.00 | 58.45 | N |
| ATOM | 710 | N | GLY | A | 117 | 2.703 | 62.502 | 53.148 | 1.00 | 54.78 | N |
| ATOM | 711 | CA | GLY | A | 117 | 2.424 | 63.839 | 53.616 | 1.00 | 48.24 | C |
| ATOM | 712 | C | GLY | A | 117 | 0.935 | 64.087 | 53.646 | 1.00 | 53.87 | C |
| ATOM | 713 | O | GLY | A | 117 | 0.195 | 63.587 | 52.802 | 1.00 | 57.07 | O |
| ATOM | 714 | N | LEU | A | 118 | 0.497 | 64.857 | 54.632 | 1.00 | 58.48 | N |
| ATOM | 715 | CA | LEU | A | 118 | −0.909 | 65.200 | 54.779 | 1.00 | 58.11 | C |
| ATOM | 716 | C | LEU | A | 118 | −1.034 | 66.719 | 54.767 | 1.00 | 60.85 | C |
| ATOM | 717 | O | LEU | A | 118 | −0.637 | 67.391 | 55.721 | 1.00 | 65.21 | O |

APPENDIX A-continued

| ATOM | 718 | CB  | LEU | A | 118 | −1.455  | 64.649 | 56.101 | 1.00 | 52.51  | C |
|------|-----|-----|-----|---|-----|---------|--------|--------|------|--------|---|
| ATOM | 719 | CG  | LEU | A | 118 | −2.896  | 65.026 | 56.457 | 1.00 | 44.62  | C |
| ATOM | 720 | CD1 | LEU | A | 118 | −3.859  | 64.354 | 55.493 | 1.00 | 53.22  | C |
| ATOM | 721 | CD2 | LEU | A | 118 | −3.194  | 64.601 | 57.884 | 1.00 | 53.45  | C |
| ATOM | 722 | N   | PHE | A | 119 | −1.568  | 67.261 | 53.679 | 1.00 | 61.59  | N |
| ATOM | 723 | CA  | PHE | A | 119 | −1.746  | 68.702 | 53.573 | 1.00 | 57.12  | C |
| ATOM | 724 | C   | PHE | A | 119 | −3.169  | 69.054 | 53.959 | 1.00 | 57.68  | C |
| ATOM | 725 | O   | PHE | A | 119 | −4.122  | 68.585 | 53.338 | 1.00 | 54.82  | O |
| ATOM | 726 | CB  | PHE | A | 119 | −1.429  | 69.170 | 52.155 | 1.00 | 50.64  | C |
| ATOM | 727 | CG  | PHE | A | 119 | −0.014  | 68.908 | 51.759 | 1.00 | 49.44  | C |
| ATOM | 728 | CD1 | PHE | A | 119 | 0.407   | 67.616 | 51.451 | 1.00 | 47.28  | C |
| ATOM | 729 | CD2 | PHE | A | 119 | 0.925   | 69.934 | 51.779 | 1.00 | 49.56  | C |
| ATOM | 730 | CE1 | PHE | A | 119 | 1.746   | 67.347 | 51.174 | 1.00 | 44.66  | C |
| ATOM | 731 | CE2 | PHE | A | 119 | 2.265   | 69.679 | 51.504 | 1.00 | 46.08  | C |
| ATOM | 732 | CZ  | PHE | A | 119 | 2.677   | 68.382 | 51.202 | 1.00 | 43.70  | C |
| ATOM | 733 | N   | LEU | A | 120 | −3.289  | 69.871 | 55.002 | 1.00 | 58.64  | N |
| ATOM | 734 | CA  | LEU | A | 120 | −4.575  | 70.299 | 55.545 | 1.00 | 61.64  | C |
| ATOM | 735 | C   | LEU | A | 120 | −4.859  | 71.757 | 55.213 | 1.00 | 63.93  | C |
| ATOM | 736 | O   | LEU | A | 120 | −3.946  | 72.580 | 55.197 | 1.00 | 69.27  | O |
| ATOM | 737 | CB  | LEU | A | 120 | −4.557  | 70.141 | 57.064 | 1.00 | 54.56  | C |
| ATOM | 738 | CG  | LEU | A | 120 | −3.892  | 68.862 | 57.571 | 1.00 | 56.19  | C |
| ATOM | 739 | CD1 | LEU | A | 120 | −3.552  | 69.013 | 59.039 | 1.00 | 57.90  | C |
| ATOM | 740 | CD2 | LEU | A | 120 | −4.808  | 67.669 | 57.329 | 1.00 | 55.79  | C |
| ATOM | 741 | N   | SER | A | 121 | −6.120  | 72.080 | 54.952 | 1.00 | 65.07  | N |
| ATOM | 742 | CA  | SER | A | 121 | −6.477  | 73.460 | 54.652 | 1.00 | 69.45  | C |
| ATOM | 743 | C   | SER | A | 121 | −6.409  | 74.236 | 55.963 | 1.00 | 74.60  | C |
| ATOM | 744 | O   | SER | A | 121 | −6.803  | 73.730 | 57.014 | 1.00 | 70.60  | O |
| ATOM | 745 | CB  | SER | A | 121 | −7.888  | 73.543 | 54.079 | 1.00 | 62.14  | C |
| ATOM | 746 | OG  | SER | A | 121 | −8.837  | 73.125 | 55.041 | 1.00 | 66.83  | O |
| ATOM | 747 | N   | GLU | A | 122 | −5.908  | 75.463 | 55.897 | 1.00 | 80.69  | N |
| ATOM | 748 | CA  | GLU | A | 122 | −5.778  | 76.291 | 57.086 | 1.00 | 86.89  | C |
| ATOM | 749 | C   | GLU | A | 122 | −7.011  | 76.209 | 57.975 | 1.00 | 87.39  | C |
| ATOM | 750 | O   | GLU | A | 122 | −6.918  | 75.852 | 59.149 | 1.00 | 90.14  | O |
| ATOM | 751 | CB  | GLU | A | 122 | −5.519  | 77.745 | 56.688 | 1.00 | 92.25  | C |
| ATOM | 752 | CG  | GLU | A | 122 | −4.342  | 77.918 | 55.742 | 1.00 | 99.63  | C |
| ATOM | 753 | CD  | GLU | A | 122 | −3.950  | 79.370 | 55.552 | 1.00 | 106.66 | C |
| ATOM | 754 | OE1 | GLU | A | 122 | −4.856  | 80.210 | 55.357 | 1.00 | 106.68 | O |
| ATOM | 755 | OE2 | GLU | A | 122 | −2.736  | 79.669 | 55.587 | 1.00 | 108.74 | O |
| ATOM | 756 | N   | GLY | A | 123 | −8.168  | 76.532 | 57.413 | 1.00 | 90.51  | N |
| ATOM | 757 | CA  | GLY | A | 123 | −9.391  | 76.490 | 58.194 | 1.00 | 101.67 | C |
| ATOM | 758 | C   | GLY | A | 123 | −10.035 | 75.119 | 58.264 | 1.00 | 106.08 | C |
| ATOM | 759 | O   | GLY | A | 123 | −11.083 | 74.889 | 57.649 | 1.00 | 110.59 | O |
| ATOM | 760 | N   | LEU | A | 124 | −9.418  | 74.208 | 59.015 | 1.00 | 100.71 | N |
| ATOM | 761 | CA  | LEU | A | 124 | −9.947  | 72.852 | 59.158 | 1.00 | 94.86  | C |
| ATOM | 762 | C   | LEU | A | 124 | −9.775  | 72.333 | 60.576 | 1.00 | 90.47  | C |
| ATOM | 763 | O   | LEU | A | 124 | −8.718  | 72.493 | 61.183 | 1.00 | 86.62  | O |
| ATOM | 764 | CB  | LEU | A | 124 | −9.251  | 71.892 | 58.181 | 1.00 | 88.12  | C |
| ATOM | 765 | CG  | LEU | A | 124 | −9.654  | 70.411 | 58.243 | 1.00 | 81.37  | C |
| ATOM | 766 | CD1 | LEU | A | 124 | −11.151 | 70.261 | 57.993 | 1.00 | 75.66  | C |
| ATOM | 767 | CD2 | LEU | A | 124 | −8.860  | 69.626 | 57.211 | 1.00 | 71.45  | C |
| ATOM | 768 | N   | LYS | A | 125 | −10.826 | 71.714 | 61.099 | 1.00 | 88.04  | N |
| ATOM | 769 | CA  | LYS | A | 125 | −10.789 | 71.156 | 62.440 | 1.00 | 84.33  | C |
| ATOM | 770 | C   | LYS | A | 125 | −10.643 | 69.649 | 62.310 | 1.00 | 79.53  | C |
| ATOM | 771 | O   | LYS | A | 125 | −11.639 | 68.932 | 62.206 | 1.00 | 76.07  | O |
| ATOM | 772 | CB  | LYS | A | 125 | −12.074 | 71.501 | 63.193 | 1.00 | 81.76  | C |
| ATOM | 773 | N   | LEU | A | 126 | −9.401  | 69.172 | 62.300 | 1.00 | 71.39  | N |
| ATOM | 774 | CA  | LEU | A | 126 | −9.148  | 67.741 | 62.183 | 1.00 | 70.82  | C |
| ATOM | 775 | C   | LEU | A | 126 | −9.721  | 66.982 | 63.364 | 1.00 | 73.83  | C |
| ATOM | 776 | O   | LEU | A | 126 | −10.403 | 67.544 | 64.220 | 1.00 | 84.63  | O |
| ATOM | 777 | CB  | LEU | A | 126 | −7.645  | 67.441 | 62.100 | 1.00 | 63.45  | C |
| ATOM | 778 | CG  | LEU | A | 126 | −6.908  | 67.588 | 60.765 | 1.00 | 62.50  | C |
| ATOM | 779 | CD1 | LEU | A | 126 | −5.529  | 66.947 | 60.874 | 1.00 | 50.75  | C |
| ATOM | 780 | CD2 | LEU | A | 126 | −7.699  | 66.916 | 59.657 | 1.00 | 69.98  | C |
| ATOM | 781 | N   | VAL | A | 127 | −9.434  | 65.690 | 63.396 | 1.00 | 73.64  | N |
| ATOM | 782 | CA  | VAL | A | 127 | −9.883  | 64.821 | 64.466 | 1.00 | 73.08  | C |
| ATOM | 783 | C   | VAL | A | 127 | −8.612  | 64.224 | 65.066 | 1.00 | 79.24  | C |
| ATOM | 784 | O   | VAL | A | 127 | −8.106  | 63.210 | 64.585 | 1.00 | 85.77  | O |
| ATOM | 785 | CB  | VAL | A | 127 | −10.801 | 63.712 | 63.909 | 1.00 | 65.63  | C |
| ATOM | 786 | CG1 | VAL | A | 127 | −11.123 | 62.702 | 64.988 | 1.00 | 63.03  | C |
| ATOM | 787 | CG2 | VAL | A | 127 | −12.082 | 64.334 | 63.366 | 1.00 | 52.87  | C |
| ATOM | 788 | N   | ASP | A | 128 | −8.097  | 64.879 | 66.106 | 1.00 | 81.44  | N |
| ATOM | 789 | CA  | ASP | A | 128 | −6.867  | 64.465 | 66.781 | 1.00 | 83.05  | C |
| ATOM | 790 | C   | ASP | A | 128 | −6.411  | 63.041 | 66.506 | 1.00 | 78.42  | C |
| ATOM | 791 | O   | ASP | A | 128 | −5.319  | 62.830 | 65.980 | 1.00 | 78.36  | O |
| ATOM | 792 | CB  | ASP | A | 128 | −6.982  | 64.681 | 68.295 | 1.00 | 100.03 | C |
| ATOM | 793 | CG  | ASP | A | 128 | −6.795  | 66.138 | 68.693 | 1.00 | 107.49 | C |
| ATOM | 794 | OD1 | ASP | A | 128 | −5.820  | 66.763 | 68.214 | 1.00 | 101.66 | O |
| ATOM | 795 | OD2 | ASP | A | 128 | −7.612  | 66.655 | 69.490 | 1.00 | 111.00 | O |
| ATOM | 796 | N   | LYS | A | 129 | −7.237  | 62.063 | 66.856 | 1.00 | 73.72  | N |
| ATOM | 797 | CA  | LYS | A | 129 | −6.866  | 60.673 | 66.631 | 1.00 | 73.90  | C |

APPENDIX A-continued

| | | | | | | | | | | |
|---|---|---|---|---|---|---|---|---|---|---|
| ATOM | 798 | C | LYS | A | 129 | −6.315 | 60.436 | 65.223 | 1.00 | 73.80 | C |
| ATOM | 799 | O | LYS | A | 129 | −5.270 | 59.808 | 65.061 | 1.00 | 73.80 | O |
| ATOM | 800 | CB | LYS | A | 129 | −8.059 | 59.748 | 66.882 | 1.00 | 70.19 | C |
| ATOM | 801 | CG | LYS | A | 129 | −7.749 | 58.289 | 66.589 | 1.00 | 74.16 | C |
| ATOM | 802 | CD | LYS | A | 129 | −8.852 | 57.349 | 67.043 | 1.00 | 76.54 | C |
| ATOM | 803 | CE | LYS | A | 129 | −8.534 | 55.918 | 66.626 | 1.00 | 81.97 | C |
| ATOM | 804 | NZ | LYS | A | 129 | −7.156 | 55.514 | 67.039 | 1.00 | 85.58 | N |
| ATOM | 805 | N | PHE | A | 130 | −7.007 | 60.947 | 64.209 | 1.00 | 73.26 | N |
| ATOM | 806 | CA | PHE | A | 130 | −6.564 | 60.761 | 62.834 | 1.00 | 69.61 | C |
| ATOM | 807 | C | PHE | A | 130 | −5.130 | 61.221 | 62.619 | 1.00 | 72.44 | C |
| ATOM | 808 | O | PHE | A | 130 | −4.330 | 60.498 | 62.022 | 1.00 | 78.05 | O |
| ATOM | 809 | CB | PHE | A | 130 | −7.490 | 61.496 | 61.858 | 1.00 | 61.88 | C |
| ATOM | 810 | CG | PHE | A | 130 | −7.136 | 61.277 | 60.407 | 1.00 | 68.76 | C |
| ATOM | 811 | CD1 | PHE | A | 130 | −6.876 | 59.996 | 59.925 | 1.00 | 69.88 | C |
| ATOM | 812 | CD2 | PHE | A | 130 | −7.070 | 62.348 | 59.520 | 1.00 | 70.51 | C |
| ATOM | 813 | CE1 | PHE | A | 130 | −6.554 | 59.785 | 58.582 | 1.00 | 65.48 | C |
| ATOM | 814 | CE2 | PHE | A | 130 | −6.749 | 62.146 | 58.177 | 1.00 | 66.74 | C |
| ATOM | 815 | CZ | PHE | A | 130 | −6.492 | 60.862 | 57.710 | 1.00 | 63.29 | C |
| ATOM | 816 | N | LEU | A | 131 | −4.803 | 62.413 | 63.113 | 1.00 | 71.95 | N |
| ATOM | 817 | CA | LEU | A | 131 | −3.454 | 62.959 | 62.952 | 1.00 | 72.46 | C |
| ATOM | 818 | C | LEU | A | 131 | −2.398 | 62.145 | 63.690 | 1.00 | 74.25 | C |
| ATOM | 819 | O | LEU | A | 131 | −1.275 | 61.994 | 63.205 | 1.00 | 70.38 | O |
| ATOM | 820 | CB | LEU | A | 131 | −3.401 | 64.415 | 63.426 | 1.00 | 67.75 | C |
| ATOM | 821 | CG | LEU | A | 131 | −2.058 | 65.130 | 63.234 | 1.00 | 66.61 | C |
| ATOM | 822 | CD1 | LEU | A | 131 | −1.625 | 65.041 | 61.780 | 1.00 | 71.22 | C |
| ATOM | 823 | CD2 | LEU | A | 131 | −2.187 | 66.581 | 63.654 | 1.00 | 62.18 | C |
| ATOM | 824 | N | GLU | A | 132 | −2.759 | 61.624 | 64.861 | 1.00 | 75.34 | N |
| ATOM | 825 | CA | GLU | A | 132 | −1.841 | 60.821 | 65.663 | 1.00 | 76.10 | C |
| ATOM | 826 | C | GLU | A | 132 | −1.594 | 59.476 | 64.998 | 1.00 | 74.37 | C |
| ATOM | 827 | O | GLU | A | 132 | −0.514 | 58.901 | 65.126 | 1.00 | 77.18 | O |
| ATOM | 828 | CB | GLU | A | 132 | −2.419 | 60.572 | 67.054 | 1.00 | 86.83 | C |
| ATOM | 829 | CG | GLU | A | 132 | −2.771 | 61.817 | 67.839 | 1.00 | 101.06 | C |
| ATOM | 830 | CD | GLU | A | 132 | −3.550 | 61.485 | 69.096 | 1.00 | 106.76 | C |
| ATOM | 831 | OE1 | GLU | A | 132 | −4.623 | 60.856 | 68.973 | 1.00 | 110.16 | O |
| ATOM | 832 | OE2 | GLU | A | 132 | −3.092 | 61.847 | 70.201 | 1.00 | 113.73 | O |
| ATOM | 833 | N | ASP | A | 133 | −2.610 | 58.973 | 64.302 | 1.00 | 73.38 | N |
| ATOM | 834 | CA | ASP | A | 133 | −2.509 | 57.687 | 63.624 | 1.00 | 70.06 | C |
| ATOM | 835 | C | ASP | A | 133 | −1.619 | 57.754 | 62.390 | 1.00 | 65.80 | C |
| ATOM | 836 | O | ASP | A | 133 | −0.569 | 57.113 | 62.347 | 1.00 | 63.34 | O |
| ATOM | 837 | CB | ASP | A | 133 | −3.895 | 57.169 | 63.212 | 1.00 | 76.04 | C |
| ATOM | 838 | CG | ASP | A | 133 | −4.759 | 56.768 | 64.401 | 1.00 | 73.21 | C |
| ATOM | 839 | OD1 | ASP | A | 133 | −4.261 | 56.066 | 65.306 | 1.00 | 70.03 | O |
| ATOM | 840 | OD2 | ASP | A | 133 | −5.949 | 57.144 | 64.419 | 1.00 | 73.09 | O |
| ATOM | 841 | N | VAL | A | 134 | −2.034 | 58.524 | 61.387 | 1.00 | 61.62 | N |
| ATOM | 842 | CA | VAL | A | 134 | −1.252 | 58.632 | 60.159 | 1.00 | 64.14 | C |
| ATOM | 843 | C | VAL | A | 134 | 0.198 | 58.964 | 60.487 | 1.00 | 68.14 | C |
| ATOM | 844 | O | VAL | A | 134 | 1.128 | 58.420 | 59.887 | 1.00 | 72.43 | O |
| ATOM | 845 | CB | VAL | A | 134 | −1.823 | 59.713 | 59.209 | 1.00 | 56.45 | C |
| ATOM | 846 | CG1 | VAL | A | 134 | −3.262 | 59.382 | 58.854 | 1.00 | 49.57 | C |
| ATOM | 847 | CG2 | VAL | A | 134 | −1.735 | 61.079 | 59.854 | 1.00 | 62.38 | C |
| ATOM | 848 | N | LYS | A | 135 | 0.383 | 59.842 | 61.464 | 1.00 | 69.38 | N |
| ATOM | 849 | CA | LYS | A | 135 | 1.713 | 60.251 | 61.878 | 1.00 | 63.82 | C |
| ATOM | 850 | C | LYS | A | 135 | 2.443 | 59.090 | 62.559 | 1.00 | 60.29 | C |
| ATOM | 851 | O | LYS | A | 135 | 3.653 | 58.942 | 62.408 | 1.00 | 63.29 | O |
| ATOM | 852 | CB | LYS | A | 135 | 1.605 | 61.447 | 62.828 | 1.00 | 60.61 | C |
| ATOM | 853 | CG | LYS | A | 135 | 2.898 | 62.207 | 63.056 | 1.00 | 56.78 | C |
| ATOM | 854 | CD | LYS | A | 135 | 2.757 | 63.667 | 62.644 | 1.00 | 61.45 | C |
| ATOM | 855 | CE | LYS | A | 135 | 1.705 | 64.408 | 63.469 | 1.00 | 54.55 | C |
| ATOM | 856 | NZ | LYS | A | 135 | 2.119 | 64.618 | 64.878 | 1.00 | 50.52 | N |
| ATOM | 857 | N | LYS | A | 136 | 1.703 | 58.257 | 63.290 | 1.00 | 60.22 | N |
| ATOM | 858 | CA | LYS | A | 136 | 2.299 | 57.123 | 63.998 | 1.00 | 62.66 | C |
| ATOM | 859 | C | LYS | A | 136 | 2.407 | 55.834 | 63.185 | 1.00 | 62.16 | C |
| ATOM | 860 | O | LYS | A | 136 | 3.502 | 55.288 | 63.032 | 1.00 | 54.80 | O |
| ATOM | 861 | CB | LYS | A | 136 | 1.532 | 56.851 | 65.299 | 1.00 | 66.01 | C |
| ATOM | 862 | CG | LYS | A | 136 | 1.969 | 55.589 | 66.047 | 1.00 | 77.32 | C |
| ATOM | 863 | CD | LYS | A | 136 | 1.509 | 55.597 | 67.509 | 1.00 | 88.14 | C |
| ATOM | 864 | CE | LYS | A | 136 | 0.009 | 55.888 | 67.657 | 1.00 | 94.86 | C |
| ATOM | 865 | NZ | LYS | A | 136 | −0.879 | 54.859 | 67.043 | 1.00 | 76.78 | N |
| ATOM | 866 | N | LEU | A | 137 | 1.281 | 55.344 | 62.669 | 1.00 | 61.16 | N |
| ATOM | 867 | CA | LEU | A | 137 | 1.287 | 54.113 | 61.880 | 1.00 | 58.18 | C |
| ATOM | 868 | C | LEU | A | 137 | 1.907 | 54.290 | 60.508 | 1.00 | 60.47 | C |
| ATOM | 869 | O | LEU | A | 137 | 2.527 | 53.368 | 59.984 | 1.00 | 67.59 | O |
| ATOM | 870 | CB | LEU | A | 137 | −0.131 | 53.568 | 61.677 | 1.00 | 54.48 | C |
| ATOM | 871 | CG | LEU | A | 137 | −0.992 | 53.230 | 62.886 | 1.00 | 52.55 | C |
| ATOM | 872 | CD1 | LEU | A | 137 | −0.117 | 52.646 | 63.977 | 1.00 | 54.08 | C |
| ATOM | 873 | CD2 | LEU | A | 137 | −1.686 | 54.481 | 63.376 | 1.00 | 60.51 | C |
| ATOM | 874 | N | TYR | A | 138 | 1.747 | 55.468 | 59.919 | 1.00 | 57.61 | N |
| ATOM | 875 | CA | TYR | A | 138 | 2.277 | 55.686 | 58.586 | 1.00 | 59.80 | C |
| ATOM | 876 | C | TYR | A | 138 | 3.434 | 56.666 | 58.464 | 1.00 | 60.49 | C |
| ATOM | 877 | O | TYR | A | 138 | 3.790 | 57.077 | 57.358 | 1.00 | 56.15 | O |

APPENDIX A-continued

| ATOM | 878 | CB | TYR | A | 138 | 1.130 | 56.077 | 57.657 | 1.00 | 61.44 | C |
|---|---|---|---|---|---|---|---|---|---|---|---|
| ATOM | 879 | CG | TYR | A | 138 | 0.176 | 54.927 | 57.426 | 1.00 | 58.86 | C |
| ATOM | 880 | CD1 | TYR | A | 138 | 0.460 | 53.945 | 56.474 | 1.00 | 59.49 | C |
| ATOM | 881 | CD2 | TYR | A | 138 | −0.977 | 54.784 | 58.197 | 1.00 | 53.66 | C |
| ATOM | 882 | CE1 | TYR | A | 138 | −0.378 | 52.846 | 56.295 | 1.00 | 57.72 | C |
| ATOM | 883 | CE2 | TYR | A | 138 | −1.824 | 53.688 | 58.029 | 1.00 | 60.15 | C |
| ATOM | 884 | CZ | TYR | A | 138 | −1.517 | 52.723 | 57.077 | 1.00 | 60.99 | C |
| ATOM | 885 | OH | TYR | A | 138 | −2.341 | 51.634 | 56.908 | 1.00 | 62.46 | O |
| ATOM | 886 | N | HIS | A | 139 | 4.029 | 57.026 | 59.598 | 1.00 | 57.62 | N |
| ATOM | 887 | CA | HIS | A | 139 | 5.170 | 57.936 | 59.600 | 1.00 | 60.66 | C |
| ATOM | 888 | C | HIS | A | 139 | 4.856 | 59.160 | 58.749 | 1.00 | 60.79 | C |
| ATOM | 889 | O | HIS | A | 139 | 5.732 | 59.710 | 58.078 | 1.00 | 61.68 | O |
| ATOM | 890 | CB | HIS | A | 139 | 6.395 | 57.219 | 59.026 | 1.00 | 61.69 | C |
| ATOM | 891 | CG | HIS | A | 139 | 6.601 | 55.841 | 59.574 | 1.00 | 70.17 | C |
| ATOM | 892 | ND1 | HIS | A | 139 | 7.011 | 55.607 | 60.869 | 1.00 | 72.86 | N |
| ATOM | 893 | CD2 | HIS | A | 139 | 6.424 | 54.623 | 59.010 | 1.00 | 75.03 | C |
| ATOM | 894 | CE1 | HIS | A | 139 | 7.077 | 54.305 | 61.079 | 1.00 | 76.18 | C |
| ATOM | 895 | NE2 | HIS | A | 139 | 6.725 | 53.685 | 59.967 | 1.00 | 77.61 | N |
| ATOM | 896 | N | SER | A | 140 | 3.601 | 59.589 | 58.787 | 1.00 | 61.06 | N |
| ATOM | 897 | CA | SER | A | 140 | 3.173 | 60.724 | 57.990 | 1.00 | 57.31 | C |
| ATOM | 898 | C | SER | A | 140 | 3.565 | 62.086 | 58.526 | 1.00 | 56.93 | C |
| ATOM | 899 | O | SER | A | 140 | 3.753 | 62.284 | 59.729 | 1.00 | 60.23 | O |
| ATOM | 900 | CB | SER | A | 140 | 1.658 | 60.691 | 57.799 | 1.00 | 55.48 | C |
| ATOM | 901 | OG | SER | A | 140 | 1.235 | 61.784 | 57.005 | 1.00 | 65.11 | O |
| ATOM | 902 | N | GLU | A | 141 | 3.689 | 63.023 | 57.597 | 1.00 | 53.51 | N |
| ATOM | 903 | CA | GLU | A | 141 | 4.011 | 64.401 | 57.908 | 1.00 | 52.22 | C |
| ATOM | 904 | C | GLU | A | 141 | 2.728 | 65.174 | 57.629 | 1.00 | 54.02 | C |
| ATOM | 905 | O | GLU | A | 141 | 1.902 | 64.737 | 56.830 | 1.00 | 58.63 | O |
| ATOM | 906 | CB | GLU | A | 141 | 5.120 | 64.914 | 56.990 | 1.00 | 55.64 | C |
| ATOM | 907 | CG | GLU | A | 141 | 6.505 | 64.384 | 57.295 | 1.00 | 61.69 | C |
| ATOM | 908 | CD | GLU | A | 141 | 7.552 | 64.934 | 56.341 | 1.00 | 72.02 | C |
| ATOM | 909 | OE1 | GLU | A | 141 | 7.579 | 64.495 | 55.169 | 1.00 | 76.92 | O |
| ATOM | 910 | OE2 | GLU | A | 141 | 8.339 | 65.812 | 56.762 | 1.00 | 63.15 | O |
| ATOM | 911 | N | ALA | A | 142 | 2.557 | 66.313 | 58.290 | 1.00 | 53.06 | N |
| ATOM | 912 | CA | ALA | A | 142 | 1.371 | 67.131 | 58.089 | 1.00 | 49.47 | C |
| ATOM | 913 | C | ALA | A | 142 | 1.790 | 68.574 | 57.874 | 1.00 | 52.41 | C |
| ATOM | 914 | O | ALA | A | 142 | 2.744 | 69.051 | 58.482 | 1.00 | 59.73 | O |
| ATOM | 915 | CB | ALA | A | 142 | 0.447 | 67.026 | 59.297 | 1.00 | 43.48 | C |
| ATOM | 916 | N | PHE | A | 143 | 1.075 | 69.266 | 56.999 | 1.00 | 59.97 | N |
| ATOM | 917 | CA | PHE | A | 143 | 1.366 | 70.664 | 56.710 | 1.00 | 57.49 | C |
| ATOM | 918 | C | PHE | A | 143 | 0.051 | 71.406 | 56.515 | 1.00 | 55.72 | C |
| ATOM | 919 | O | PHE | A | 143 | −0.974 | 70.803 | 56.202 | 1.00 | 60.07 | O |
| ATOM | 920 | CB | PHE | A | 143 | 2.229 | 70.776 | 55.452 | 1.00 | 58.09 | C |
| ATOM | 921 | CG | PHE | A | 143 | 3.568 | 70.113 | 55.579 | 1.00 | 51.01 | C |
| ATOM | 922 | CD1 | PHE | A | 143 | 4.576 | 70.698 | 56.332 | 1.00 | 53.17 | C |
| ATOM | 923 | CD2 | PHE | A | 143 | 3.815 | 68.891 | 54.961 | 1.00 | 56.84 | C |
| ATOM | 924 | CE1 | PHE | A | 143 | 5.814 | 70.077 | 56.468 | 1.00 | 52.96 | C |
| ATOM | 925 | CE2 | PHE | A | 143 | 5.050 | 68.260 | 55.091 | 1.00 | 50.07 | C |
| ATOM | 926 | CZ | PHE | A | 143 | 6.050 | 68.853 | 55.846 | 1.00 | 47.79 | C |
| ATOM | 927 | N | THR | A | 144 | 0.085 | 72.718 | 56.701 | 1.00 | 56.29 | N |
| ATOM | 928 | CA | THR | A | 144 | −1.111 | 73.527 | 56.571 | 1.00 | 51.08 | C |
| ATOM | 929 | C | THR | A | 144 | −1.021 | 74.517 | 55.431 | 1.00 | 52.74 | C |
| ATOM | 930 | O | THR | A | 144 | −0.460 | 75.602 | 55.591 | 1.00 | 62.43 | O |
| ATOM | 931 | CB | THR | A | 144 | −1.386 | 74.313 | 57.865 | 1.00 | 52.24 | C |
| ATOM | 932 | OG1 | THR | A | 144 | −1.672 | 73.397 | 58.928 | 1.00 | 58.02 | O |
| ATOM | 933 | CG2 | THR | A | 144 | −2.564 | 75.249 | 57.675 | 1.00 | 57.25 | C |
| ATOM | 934 | N | VAL | A | 145 | −1.580 | 74.141 | 54.284 | 1.00 | 51.88 | N |
| ATOM | 935 | CA | VAL | A | 145 | −1.590 | 75.008 | 53.110 | 1.00 | 49.74 | C |
| ATOM | 936 | C | VAL | A | 145 | −2.955 | 75.671 | 52.974 | 1.00 | 52.70 | C |
| ATOM | 937 | O | VAL | A | 145 | −3.917 | 75.284 | 53.640 | 1.00 | 56.11 | O |
| ATOM | 938 | CB | VAL | A | 145 | −1.317 | 74.226 | 51.812 | 1.00 | 42.69 | C |
| ATOM | 939 | CG1 | VAL | A | 145 | 0.031 | 73.535 | 51.892 | 1.00 | 52.94 | C |
| ATOM | 940 | CG2 | VAL | A | 145 | −2.429 | 73.222 | 51.570 | 1.00 | 51.73 | C |
| ATOM | 941 | N | ASN | A | 146 | −3.032 | 76.681 | 52.116 | 1.00 | 57.53 | N |
| ATOM | 942 | CA | ASN | A | 146 | −4.287 | 77.376 | 51.885 | 1.00 | 61.52 | C |
| ATOM | 943 | C | ASN | A | 146 | −4.733 | 77.078 | 50.470 | 1.00 | 63.51 | C |
| ATOM | 944 | O | ASN | A | 146 | −4.264 | 77.698 | 49.514 | 1.00 | 60.18 | O |
| ATOM | 945 | CB | ASN | A | 146 | −4.121 | 78.882 | 52.068 | 1.00 | 69.21 | C |
| ATOM | 946 | CG | ASN | A | 146 | −5.397 | 79.639 | 51.774 | 1.00 | 69.31 | C |
| ATOM | 947 | OD1 | ASN | A | 146 | −5.752 | 79.850 | 50.616 | 1.00 | 62.32 | O |
| ATOM | 948 | ND2 | ASN | A | 146 | −6.106 | 80.038 | 52.826 | 1.00 | 82.57 | N |
| ATOM | 949 | N | PHE | A | 147 | −5.638 | 76.117 | 50.349 | 1.00 | 64.74 | N |
| ATOM | 950 | CA | PHE | A | 147 | −6.145 | 75.706 | 49.055 | 1.00 | 65.75 | C |
| ATOM | 951 | C | PHE | A | 147 | −6.864 | 76.837 | 48.333 | 1.00 | 65.20 | C |
| ATOM | 952 | O | PHE | A | 147 | −7.241 | 76.705 | 47.168 | 1.00 | 65.59 | O |
| ATOM | 953 | CB | PHE | A | 147 | −7.047 | 74.483 | 49.235 | 1.00 | 66.13 | C |
| ATOM | 954 | CG | PHE | A | 147 | −6.302 | 73.255 | 49.693 | 1.00 | 64.54 | C |
| ATOM | 955 | CD1 | PHE | A | 147 | −5.407 | 72.615 | 48.843 | 1.00 | 59.19 | C |
| ATOM | 956 | CD2 | PHE | A | 147 | −6.466 | 72.762 | 50.984 | 1.00 | 69.35 | C |
| ATOM | 957 | CE1 | PHE | A | 147 | −4.688 | 71.505 | 49.270 | 1.00 | 59.47 | C |

APPENDIX A-continued

| | | | | | | | | | | |
|---|---|---|---|---|---|---|---|---|---|---|
| ATOM | 958 | CE2 | PHE | A | 147 | −5.751 | 71.651 | 51.422 | 1.00 | 58.24 | C |
| ATOM | 959 | CZ | PHE | A | 147 | −4.860 | 71.022 | 50.563 | 1.00 | 57.83 | C |
| ATOM | 960 | N | GLY | A | 148 | −7.043 | 77.955 | 49.027 | 1.00 | 68.55 | N |
| ATOM | 961 | CA | GLY | A | 148 | −7.685 | 79.101 | 48.410 | 1.00 | 73.48 | C |
| ATOM | 962 | C | GLY | A | 148 | −6.738 | 79.636 | 47.353 | 1.00 | 74.53 | C |
| ATOM | 963 | O | GLY | A | 148 | −7.156 | 80.128 | 46.304 | 1.00 | 78.43 | O |
| ATOM | 964 | N | ASP | A | 149 | −5.446 | 79.538 | 47.650 | 1.00 | 72.62 | N |
| ATOM | 965 | CA | ASP | A | 149 | −4.394 | 79.971 | 46.746 | 1.00 | 66.96 | C |
| ATOM | 966 | C | ASP | A | 149 | −3.977 | 78.683 | 46.048 | 1.00 | 69.92 | C |
| ATOM | 967 | O | ASP | A | 149 | −2.929 | 78.115 | 46.351 | 1.00 | 76.03 | O |
| ATOM | 968 | CB | ASP | A | 149 | −3.220 | 80.532 | 47.550 | 1.00 | 72.94 | C |
| ATOM | 969 | CG | ASP | A | 149 | −2.219 | 81.275 | 46.688 | 1.00 | 90.72 | C |
| ATOM | 970 | OD1 | ASP | A | 149 | −1.971 | 80.841 | 45.541 | 1.00 | 99.79 | O |
| ATOM | 971 | OD2 | ASP | A | 149 | −1.668 | 82.292 | 47.164 | 1.00 | 95.51 | O |
| ATOM | 972 | N | THR | A | 150 | −4.813 | 78.212 | 45.127 | 1.00 | 73.45 | N |
| ATOM | 973 | CA | THR | A | 150 | −4.547 | 76.965 | 44.417 | 1.00 | 78.56 | C |
| ATOM | 974 | C | THR | A | 150 | −3.192 | 76.898 | 43.732 | 1.00 | 79.82 | C |
| ATOM | 975 | O | THR | A | 150 | −2.699 | 75.810 | 43.427 | 1.00 | 87.55 | O |
| ATOM | 976 | CB | THR | A | 150 | −5.662 | 76.660 | 43.387 | 1.00 | 77.76 | C |
| ATOM | 977 | OG1 | THR | A | 150 | −6.789 | 76.099 | 44.070 | 1.00 | 84.66 | O |
| ATOM | 978 | CG2 | THR | A | 150 | −5.184 | 75.673 | 42.332 | 1.00 | 75.45 | C |
| ATOM | 979 | N | GLU | A | 151 | −2.577 | 78.049 | 43.498 | 1.00 | 72.87 | N |
| ATOM | 980 | CA | GLU | A | 151 | −1.280 | 78.047 | 42.849 | 1.00 | 71.34 | C |
| ATOM | 981 | C | GLU | A | 151 | −0.175 | 77.764 | 43.868 | 1.00 | 71.95 | C |
| ATOM | 982 | O | GLU | A | 151 | 0.761 | 77.014 | 43.588 | 1.00 | 78.05 | O |
| ATOM | 983 | CB | GLU | A | 151 | −1.046 | 79.381 | 42.144 | 1.00 | 71.38 | C |
| ATOM | 984 | CG | GLU | A | 151 | −0.381 | 79.226 | 40.786 | 1.00 | 82.21 | C |
| ATOM | 985 | CD | GLU | A | 151 | −1.073 | 78.184 | 39.916 | 1.00 | 89.62 | C |
| ATOM | 986 | OE1 | GLU | A | 151 | −2.300 | 78.295 | 39.695 | 1.00 | 87.73 | O |
| ATOM | 987 | OE2 | GLU | A | 151 | −0.386 | 77.249 | 39.452 | 1.00 | 100.40 | O |
| ATOM | 988 | N | GLU | A | 152 | −0.297 | 78.356 | 45.052 | 1.00 | 68.96 | N |
| ATOM | 989 | CA | GLU | A | 152 | 0.681 | 78.165 | 46.117 | 1.00 | 68.07 | C |
| ATOM | 990 | C | GLU | A | 152 | 0.548 | 76.773 | 46.725 | 1.00 | 67.88 | C |
| ATOM | 991 | O | GLU | A | 152 | 1.549 | 76.122 | 47.031 | 1.00 | 71.07 | O |
| ATOM | 992 | CB | GLU | A | 152 | 0.488 | 79.220 | 47.216 | 1.00 | 77.35 | C |
| ATOM | 993 | CG | GLU | A | 152 | 1.247 | 78.933 | 48.518 | 1.00 | 84.86 | C |
| ATOM | 994 | CD | GLU | A | 152 | 2.733 | 79.248 | 48.431 | 1.00 | 91.40 | C |
| ATOM | 995 | OE1 | GLU | A | 152 | 3.295 | 79.179 | 47.317 | 1.00 | 97.72 | O |
| ATOM | 996 | OE2 | GLU | A | 152 | 3.342 | 79.552 | 49.482 | 1.00 | 87.00 | O |
| ATOM | 997 | N | ALA | A | 153 | −0.690 | 76.325 | 46.912 | 1.00 | 61.71 | N |
| ATOM | 998 | CA | ALA | A | 153 | −0.940 | 75.010 | 47.490 | 1.00 | 58.28 | C |
| ATOM | 999 | C | ALA | A | 153 | −0.372 | 73.948 | 46.559 | 1.00 | 57.68 | C |
| ATOM | 1000 | O | ALA | A | 153 | 0.220 | 72.960 | 47.000 | 1.00 | 58.25 | O |
| ATOM | 1001 | CB | ALA | A | 153 | −2.438 | 74.799 | 47.681 | 1.00 | 48.38 | C |
| ATOM | 1002 | N | LYS | A | 154 | −0.562 | 74.172 | 45.264 | 1.00 | 57.38 | N |
| ATOM | 1003 | CA | LYS | A | 154 | −0.086 | 73.265 | 44.231 | 1.00 | 52.57 | C |
| ATOM | 1004 | C | LYS | A | 154 | 1.440 | 73.250 | 44.295 | 1.00 | 56.15 | C |
| ATOM | 1005 | O | LYS | A | 154 | 2.063 | 72.192 | 44.208 | 1.00 | 57.89 | O |
| ATOM | 1006 | CB | LYS | A | 154 | −0.573 | 73.768 | 42.868 | 1.00 | 51.35 | C |
| ATOM | 1007 | CG | LYS | A | 154 | −0.896 | 72.689 | 41.858 | 1.00 | 53.91 | C |
| ATOM | 1008 | CD | LYS | A | 154 | −2.075 | 73.104 | 40.976 | 1.00 | 58.72 | C |
| ATOM | 1009 | CE | LYS | A | 154 | −1.783 | 74.372 | 40.187 | 1.00 | 67.79 | C |
| ATOM | 1010 | NZ | LYS | A | 154 | −2.985 | 74.898 | 39.478 | 1.00 | 61.43 | N |
| ATOM | 1011 | N | LYS | A | 155 | 2.030 | 74.435 | 44.468 | 1.00 | 61.60 | N |
| ATOM | 1012 | CA | LYS | A | 155 | 3.486 | 74.594 | 44.562 | 1.00 | 63.16 | C |
| ATOM | 1013 | C | LYS | A | 155 | 4.078 | 73.828 | 45.751 | 1.00 | 62.33 | C |
| ATOM | 1014 | O | LYS | A | 155 | 5.117 | 73.185 | 45.620 | 1.00 | 65.27 | O |
| ATOM | 1015 | CB | LYS | A | 155 | 3.855 | 76.089 | 44.661 | 1.00 | 46.65 | C |
| ATOM | 1016 | N | GLN | A | 156 | 3.422 | 73.899 | 46.906 | 1.00 | 63.04 | N |
| ATOM | 1017 | CA | GLN | A | 156 | 3.895 | 73.198 | 48.097 | 1.00 | 63.93 | C |
| ATOM | 1018 | C | GLN | A | 156 | 3.909 | 71.685 | 47.915 | 1.00 | 63.75 | C |
| ATOM | 1019 | O | GLN | A | 156 | 4.906 | 71.022 | 48.213 | 1.00 | 65.20 | O |
| ATOM | 1020 | CB | GLN | A | 156 | 3.024 | 73.550 | 49.302 | 1.00 | 64.65 | C |
| ATOM | 1021 | CG | GLN | A | 156 | 3.273 | 74.937 | 49.846 | 1.00 | 70.08 | C |
| ATOM | 1022 | CD | GLN | A | 156 | 4.748 | 75.194 | 50.071 | 1.00 | 74.28 | C |
| ATOM | 1023 | OE1 | GLN | A | 156 | 5.504 | 74.282 | 50.431 | 1.00 | 68.16 | O |
| ATOM | 1024 | NE2 | GLN | A | 156 | 5.167 | 76.439 | 49.872 | 1.00 | 70.84 | N |
| ATOM | 1025 | N | ILE | A | 157 | 2.795 | 71.145 | 47.433 | 1.00 | 62.15 | N |
| ATOM | 1026 | CA | ILE | A | 157 | 2.672 | 69.710 | 47.207 | 1.00 | 54.86 | C |
| ATOM | 1027 | C | ILE | A | 157 | 3.635 | 69.228 | 46.128 | 1.00 | 56.26 | C |
| ATOM | 1028 | O | ILE | A | 157 | 4.427 | 68.320 | 46.369 | 1.00 | 61.69 | O |
| ATOM | 1029 | CB | ILE | A | 157 | 1.232 | 69.339 | 46.804 | 1.00 | 52.05 | C |
| ATOM | 1030 | CG1 | ILE | A | 157 | 0.284 | 69.671 | 47.961 | 1.00 | 46.35 | C |
| ATOM | 1031 | CG2 | ILE | A | 157 | 1.159 | 67.867 | 46.405 | 1.00 | 30.56 | C |
| ATOM | 1032 | CD1 | ILE | A | 157 | −1.173 | 69.462 | 47.646 | 1.00 | 42.43 | C |
| ATOM | 1033 | N | ASN | A | 158 | 3.577 | 69.833 | 44.943 | 1.00 | 47.94 | N |
| ATOM | 1034 | CA | ASN | A | 158 | 4.466 | 69.431 | 43.859 | 1.00 | 52.77 | C |
| ATOM | 1035 | C | ASN | A | 158 | 5.921 | 69.434 | 44.303 | 1.00 | 61.41 | C |
| ATOM | 1036 | O | ASN | A | 158 | 6.718 | 68.590 | 43.875 | 1.00 | 67.34 | O |
| ATOM | 1037 | CB | ASN | A | 158 | 4.308 | 70.357 | 42.659 | 1.00 | 53.63 | C |

APPENDIX A-continued

| | | | | | | | | | | |
|---|---|---|---|---|---|---|---|---|---|---|
| ATOM | 1038 | CG | ASN | A | 158 | 2.994 | 70.166 | 41.950 | 1.00 | 53.61 | C |
| ATOM | 1039 | OD1 | ASN | A | 158 | 2.308 | 69.159 | 42.150 | 1.00 | 52.82 | O |
| ATOM | 1040 | ND2 | ASN | A | 158 | 2.637 | 71.123 | 41.101 | 1.00 | 52.30 | N |
| ATOM | 1041 | N | ASP | A | 159 | 6.265 | 70.395 | 45.153 | 1.00 | 63.64 | N |
| ATOM | 1042 | CA | ASP | A | 159 | 7.621 | 70.514 | 45.674 | 1.00 | 65.90 | C |
| ATOM | 1043 | C | ASP | A | 159 | 7.943 | 69.341 | 46.586 | 1.00 | 59.66 | C |
| ATOM | 1044 | O | ASP | A | 159 | 9.010 | 68.743 | 46.479 | 1.00 | 62.06 | O |
| ATOM | 1045 | CB | ASP | A | 159 | 7.781 | 71.829 | 46.445 | 1.00 | 80.71 | C |
| ATOM | 1046 | CG | ASP | A | 159 | 8.196 | 72.984 | 45.550 | 1.00 | 89.94 | C |
| ATOM | 1047 | OD1 | ASP | A | 159 | 7.611 | 73.140 | 44.454 | 1.00 | 91.59 | O |
| ATOM | 1048 | OD2 | ASP | A | 159 | 9.107 | 73.740 | 45.951 | 1.00 | 90.42 | O |
| ATOM | 1049 | N | TYR | A | 160 | 7.018 | 69.014 | 47.482 | 1.00 | 50.69 | N |
| ATOM | 1050 | CA | TYR | A | 160 | 7.222 | 67.905 | 48.397 | 1.00 | 44.72 | C |
| ATOM | 1051 | C | TYR | A | 160 | 7.543 | 66.637 | 47.623 | 1.00 | 50.77 | C |
| ATOM | 1052 | O | TYR | A | 160 | 8.513 | 65.940 | 47.924 | 1.00 | 52.76 | O |
| ATOM | 1053 | CB | TYR | A | 160 | 5.972 | 67.670 | 49.234 | 1.00 | 42.71 | C |
| ATOM | 1054 | CG | TYR | A | 160 | 6.125 | 66.538 | 50.219 | 1.00 | 51.28 | C |
| ATOM | 1055 | CD1 | TYR | A | 160 | 7.100 | 66.588 | 51.209 | 1.00 | 60.26 | C |
| ATOM | 1056 | CD2 | TYR | A | 160 | 5.292 | 65.424 | 50.169 | 1.00 | 49.00 | C |
| ATOM | 1057 | CE1 | TYR | A | 160 | 7.243 | 65.563 | 52.129 | 1.00 | 67.87 | C |
| ATOM | 1058 | CE2 | TYR | A | 160 | 5.427 | 64.388 | 51.087 | 1.00 | 57.76 | C |
| ATOM | 1059 | CZ | TYR | A | 160 | 6.406 | 64.466 | 52.067 | 1.00 | 64.71 | C |
| ATOM | 1060 | OH | TYR | A | 160 | 6.553 | 63.459 | 52.997 | 1.00 | 76.77 | O |
| ATOM | 1061 | N | VAL | A | 161 | 6.714 | 66.351 | 46.622 | 1.00 | 58.65 | N |
| ATOM | 1062 | CA | VAL | A | 161 | 6.873 | 65.167 | 45.785 | 1.00 | 57.95 | C |
| ATOM | 1063 | C | VAL | A | 161 | 8.133 | 65.230 | 44.942 | 1.00 | 59.33 | C |
| ATOM | 1064 | O | VAL | A | 161 | 8.815 | 64.221 | 44.769 | 1.00 | 63.31 | O |
| ATOM | 1065 | CB | VAL | A | 161 | 5.673 | 64.975 | 44.828 | 1.00 | 54.24 | C |
| ATOM | 1066 | CG1 | VAL | A | 161 | 5.898 | 63.745 | 43.947 | 1.00 | 46.53 | C |
| ATOM | 1067 | CG2 | VAL | A | 161 | 4.390 | 64.830 | 45.626 | 1.00 | 43.53 | C |
| ATOM | 1068 | N | GLU | A | 162 | 8.441 | 66.407 | 44.405 | 1.00 | 59.99 | N |
| ATOM | 1069 | CA | GLU | A | 162 | 9.631 | 66.535 | 43.581 | 1.00 | 63.15 | C |
| ATOM | 1070 | C | GLU | A | 162 | 10.873 | 66.273 | 44.417 | 1.00 | 64.98 | C |
| ATOM | 1071 | O | GLU | A | 162 | 11.790 | 65.582 | 43.975 | 1.00 | 69.14 | O |
| ATOM | 1072 | CB | GLU | A | 162 | 9.719 | 67.920 | 42.952 | 1.00 | 63.99 | C |
| ATOM | 1073 | CG | GLU | A | 162 | 10.770 | 67.987 | 41.859 | 1.00 | 71.62 | C |
| ATOM | 1074 | CD | GLU | A | 162 | 10.803 | 69.323 | 41.150 | 1.00 | 80.39 | C |
| ATOM | 1075 | OE1 | GLU | A | 162 | 9.718 | 69.851 | 40.819 | 1.00 | 85.20 | O |
| ATOM | 1076 | OE2 | GLU | A | 162 | 11.916 | 69.839 | 40.911 | 1.00 | 79.50 | O |
| ATOM | 1077 | N | LYS | A | 163 | 10.900 | 66.821 | 45.627 | 1.00 | 61.21 | N |
| ATOM | 1078 | CA | LYS | A | 163 | 12.037 | 66.622 | 46.511 | 1.00 | 56.30 | C |
| ATOM | 1079 | C | LYS | A | 163 | 12.196 | 65.147 | 46.839 | 1.00 | 58.62 | C |
| ATOM | 1080 | O | LYS | A | 163 | 13.266 | 64.575 | 46.639 | 1.00 | 64.92 | O |
| ATOM | 1081 | CB | LYS | A | 163 | 11.868 | 67.417 | 47.807 | 1.00 | 58.42 | C |
| ATOM | 1082 | CG | LYS | A | 163 | 12.139 | 68.916 | 47.675 | 1.00 | 65.98 | C |
| ATOM | 1083 | CD | LYS | A | 163 | 12.363 | 69.554 | 49.045 | 1.00 | 82.62 | C |
| ATOM | 1084 | CE | LYS | A | 163 | 13.545 | 68.897 | 49.765 | 1.00 | 96.54 | C |
| ATOM | 1085 | NZ | LYS | A | 163 | 13.733 | 69.377 | 51.165 | 1.00 | 93.86 | N |
| ATOM | 1086 | N | GLY | A | 164 | 11.123 | 64.535 | 47.331 | 1.00 | 57.63 | N |
| ATOM | 1087 | CA | GLY | A | 164 | 11.161 | 63.125 | 47.688 | 1.00 | 55.15 | C |
| ATOM | 1088 | C | GLY | A | 164 | 11.567 | 62.184 | 46.568 | 1.00 | 55.49 | C |
| ATOM | 1089 | O | GLY | A | 164 | 12.321 | 61.234 | 46.796 | 1.00 | 56.21 | O |
| ATOM | 1090 | N | THR | A | 165 | 11.065 | 62.437 | 45.361 | 1.00 | 57.08 | N |
| ATOM | 1091 | CA | THR | A | 165 | 11.388 | 61.603 | 44.204 | 1.00 | 56.11 | C |
| ATOM | 1092 | C | THR | A | 165 | 12.586 | 62.173 | 43.459 | 1.00 | 60.15 | C |
| ATOM | 1093 | O | THR | A | 165 | 12.748 | 61.946 | 42.261 | 1.00 | 62.27 | O |
| ATOM | 1094 | CB | THR | A | 165 | 10.213 | 61.515 | 43.217 | 1.00 | 51.16 | C |
| ATOM | 1095 | OG1 | THR | A | 165 | 9.972 | 62.807 | 42.645 | 1.00 | 45.05 | O |
| ATOM | 1096 | CG2 | THR | A | 165 | 8.960 | 61.027 | 43.928 | 1.00 | 56.77 | C |
| ATOM | 1097 | N | GLN | A | 166 | 13.408 | 62.928 | 44.184 | 1.00 | 59.45 | N |
| ATOM | 1098 | CA | GLN | A | 166 | 14.618 | 63.545 | 43.646 | 1.00 | 52.50 | C |
| ATOM | 1099 | C | GLN | A | 166 | 14.563 | 64.061 | 42.215 | 1.00 | 50.65 | C |
| ATOM | 1100 | O | GLN | A | 166 | 15.512 | 63.881 | 41.455 | 1.00 | 47.88 | O |
| ATOM | 1101 | CB | GLN | A | 166 | 15.793 | 62.580 | 43.785 | 1.00 | 47.31 | C |
| ATOM | 1102 | CG | GLN | A | 166 | 16.358 | 62.520 | 45.187 | 1.00 | 58.88 | C |
| ATOM | 1103 | CD | GLN | A | 166 | 17.314 | 61.364 | 45.371 | 1.00 | 74.35 | C |
| ATOM | 1104 | OE1 | GLN | A | 166 | 18.127 | 61.065 | 44.489 | 1.00 | 73.51 | O |
| ATOM | 1105 | NE2 | GLN | A | 166 | 17.231 | 60.709 | 46.526 | 1.00 | 76.72 | N |
| ATOM | 1106 | N | GLY | A | 167 | 13.459 | 64.707 | 41.852 | 1.00 | 51.48 | N |
| ATOM | 1107 | CA | GLY | A | 167 | 13.338 | 65.259 | 40.516 | 1.00 | 52.13 | C |
| ATOM | 1108 | C | GLY | A | 167 | 12.664 | 64.379 | 39.487 | 1.00 | 56.17 | C |
| ATOM | 1109 | O | GLY | A | 167 | 12.301 | 64.854 | 38.414 | 1.00 | 64.79 | O |
| ATOM | 1110 | N | LYS | A | 168 | 12.491 | 63.102 | 39.806 | 1.00 | 58.68 | N |
| ATOM | 1111 | CA | LYS | A | 168 | 11.858 | 62.164 | 38.888 | 1.00 | 56.94 | C |
| ATOM | 1112 | C | LYS | A | 168 | 10.397 | 62.524 | 38.594 | 1.00 | 57.46 | C |
| ATOM | 1113 | O | LYS | A | 168 | 9.964 | 62.505 | 37.441 | 1.00 | 60.45 | O |
| ATOM | 1114 | CB | LYS | A | 168 | 11.958 | 60.747 | 39.458 | 1.00 | 62.12 | C |
| ATOM | 1115 | CG | LYS | A | 168 | 13.076 | 59.900 | 38.858 | 1.00 | 65.81 | C |
| ATOM | 1116 | CD | LYS | A | 168 | 12.609 | 59.249 | 37.557 | 1.00 | 80.12 | C |
| ATOM | 1117 | CE | LYS | A | 168 | 13.632 | 58.275 | 36.989 | 1.00 | 76.00 | C |

APPENDIX A-continued

| ATOM | 1118 | NZ | LYS | A | 168 | 14.825 | 58.967 | 36.430 | 1.00 | 81.30 | N |
|---|---|---|---|---|---|---|---|---|---|---|---|
| ATOM | 1119 | N | ILE | A | 169 | 9.636 | 62.854 | 39.629 | 1.00 | 51.91 | N |
| ATOM | 1120 | CA | ILE | A | 169 | 8.240 | 63.214 | 39.423 | 1.00 | 57.55 | C |
| ATOM | 1121 | C | ILE | A | 169 | 8.015 | 64.679 | 39.759 | 1.00 | 63.02 | C |
| ATOM | 1122 | O | ILE | A | 169 | 7.795 | 65.045 | 40.915 | 1.00 | 67.19 | O |
| ATOM | 1123 | CB | ILE | A | 169 | 7.303 | 62.328 | 40.269 | 1.00 | 55.89 | C |
| ATOM | 1124 | CG1 | ILE | A | 169 | 7.422 | 60.877 | 39.803 | 1.00 | 49.76 | C |
| ATOM | 1125 | CG2 | ILE | A | 169 | 5.860 | 62.803 | 40.137 | 1.00 | 54.40 | C |
| ATOM | 1126 | CD1 | ILE | A | 169 | 6.471 | 59.931 | 40.487 | 1.00 | 58.96 | C |
| ATOM | 1127 | N | VAL | A | 170 | 8.067 | 65.513 | 38.727 | 1.00 | 73.35 | N |
| ATOM | 1128 | CA | VAL | A | 170 | 7.894 | 66.951 | 38.878 | 1.00 | 76.76 | C |
| ATOM | 1129 | C | VAL | A | 170 | 6.499 | 67.402 | 39.302 | 1.00 | 84.81 | C |
| ATOM | 1130 | O | VAL | A | 170 | 6.068 | 67.148 | 40.436 | 1.00 | 93.57 | O |
| ATOM | 1131 | CB | VAL | A | 170 | 8.272 | 67.682 | 37.580 | 1.00 | 69.11 | C |
| ATOM | 1132 | CG1 | VAL | A | 170 | 9.778 | 67.603 | 37.372 | 1.00 | 58.85 | C |
| ATOM | 1133 | CG2 | VAL | A | 170 | 7.533 | 67.056 | 36.399 | 1.00 | 77.56 | C |
| ATOM | 1134 | N | ASP | A | 171 | 5.802 | 68.075 | 38.391 | 1.00 | 75.67 | N |
| ATOM | 1135 | CA | ASP | A | 171 | 4.473 | 68.589 | 38.681 | 1.00 | 78.95 | C |
| ATOM | 1136 | C | ASP | A | 171 | 3.404 | 67.513 | 38.719 | 1.00 | 76.00 | C |
| ATOM | 1137 | O | ASP | A | 171 | 2.649 | 67.338 | 37.764 | 1.00 | 80.14 | O |
| ATOM | 1138 | CB | ASP | A | 171 | 4.103 | 69.664 | 37.663 | 1.00 | 88.55 | C |
| ATOM | 1139 | CG | ASP | A | 17I | 5.081 | 70.825 | 37.669 | 1.00 | 101.11 | C |
| ATOM | 1140 | OD1 | ASP | A | 171 | 5.248 | 71.464 | 38.733 | 1.00 | 106.04 | O |
| ATOM | 1141 | OD2 | ASP | A | 171 | 5.688 | 71.100 | 36.612 | 1.00 | 105.71 | O |
| ATOM | 1142 | N | LEU | A | 172 | 3.342 | 66.795 | 39.836 | 1.00 | 72.64 | N |
| ATOM | 1143 | CA | LEU | A | 172 | 2.355 | 65.739 | 40.000 | 1.00 | 71.50 | C |
| ATOM | 1144 | C | LEU | A | 172 | 0.960 | 66.342 | 39.922 | 1.00 | 75.31 | C |
| ATOM | 1145 | O | LEU | A | 172 | 0.110 | 65.871 | 39.164 | 1.00 | 76.39 | O |
| ATOM | 1146 | CB | LEU | A | 172 | 2.533 | 65.041 | 41.349 | 1.00 | 65.60 | C |
| ATOM | 1147 | CG | LEU | A | 172 | 1.544 | 63.904 | 41.620 | 1.00 | 63.22 | C |
| ATOM | 1148 | CD1 | LEU | A | 172 | 1.751 | 62.801 | 40.594 | 1.00 | 62.71 | C |
| ATOM | 1149 | CD2 | LEU | A | 172 | 1.744 | 63.359 | 43.028 | 1.00 | 67.66 | C |
| ATOM | 1150 | N | VAL | A | 173 | 0.735 | 67.386 | 40.715 | 1.00 | 75.31 | N |
| ATOM | 1151 | CA | VAL | A | 173 | −0.554 | 68.066 | 40.745 | 1.00 | 70.37 | C |
| ATOM | 1152 | C | VAL | A | 173 | −0.557 | 69.226 | 39.761 | 1.00 | 77.35 | C |
| ATOM | 1153 | O | VAL | A | 173 | 0.248 | 70.154 | 39.870 | 1.00 | 79.66 | O |
| ATOM | 1154 | CB | VAL | A | 173 | −0.865 | 68.626 | 42.143 | 1.00 | 63.83 | C |
| ATOM | 1155 | CG1 | VAL | A | 173 | −2.299 | 69.135 | 42.185 | 1.00 | 51.87 | C |
| ATOM | 1156 | CG2 | VAL | A | 173 | −0.633 | 67.560 | 43.195 | 1.00 | 61.88 | C |
| ATOM | 1157 | N | LYS | A | 174 | −1.467 | 69.171 | 38.796 | 1.00 | 82.26 | N |
| ATOM | 1158 | CA | LYS | A | 174 | −1.560 | 70.224 | 37.800 | 1.00 | 87.16 | C |
| ATOM | 1159 | C | LYS | A | 174 | −2.901 | 70.931 | 37.907 | 1.00 | 90.52 | C |
| ATOM | 1160 | O | LYS | A | 174 | −3.027 | 72.098 | 37.531 | 1.00 | 94.70 | O |
| ATOM | 1161 | CB | LYS | A | 174 | −1.332 | 69.633 | 36.403 | 1.00 | 83.97 | C |
| ATOM | 1162 | CG | LYS | A | 174 | 0.121 | 69.195 | 36.205 | 1.00 | 83.94 | C |
| ATOM | 1163 | CD | LYS | A | 174 | 0.369 | 68.466 | 34.900 | 1.00 | 82.07 | C |
| ATOM | 1164 | CE | LYS | A | 174 | 1.856 | 68.126 | 34.731 | 1.00 | 88.08 | C |
| ATOM | 1165 | NZ | LYS | A | 174 | 2.720 | 69.319 | 34.478 | 1.00 | 75.48 | N |
| ATOM | 1166 | N | GLU | A | 175 | −3.893 | 70.222 | 38.440 | 1.00 | 90.49 | N |
| ATOM | 1167 | CA | GLU | A | 175 | −5.223 | 70.787 | 38.637 | 1.00 | 89.68 | C |
| ATOM | 1168 | C | GLU | A | 175 | −5.718 | 70.425 | 40.031 | 1.00 | 84.20 | C |
| ATOM | 1169 | O | GLU | A | 175 | −6.074 | 69.278 | 40.302 | 1.00 | 82.60 | O |
| ATOM | 1170 | CB | GLU | A | 175 | −6.205 | 70.266 | 37.581 | 1.00 | 99.06 | C |
| ATOM | 1171 | CG | GLU | A | 175 | −7.619 | 70.846 | 37.696 | 1.00 | 110.36 | C |
| ATOM | 1172 | CD | GLU | A | 175 | −7.642 | 72.371 | 37.783 | 1.00 | 118.50 | C |
| ATOM | 1173 | OE1 | GLU | A | 175 | −7.291 | 72.924 | 38.849 | 1.00 | 119.68 | O |
| ATOM | 1174 | OE2 | GLU | A | 175 | −8.010 | 73.021 | 36.781 | 1.00 | 122.04 | O |
| ATOM | 1175 | N | LEU | A | 176 | −5.734 | 71.419 | 40.912 | 1.00 | 81.54 | N |
| ATOM | 1176 | CA | LEU | A | 176 | −6.168 | 71.228 | 42.288 | 1.00 | 78.44 | C |
| ATOM | 1177 | C | LEU | A | 176 | −7.474 | 71.987 | 42.553 | 1.00 | 78.03 | C |
| ATOM | 1178 | O | LEU | A | 176 | −7.589 | 73.174 | 42.235 | 1.00 | 73.85 | O |
| ATOM | 1179 | CB | LEU | A | 176 | −5.070 | 71.720 | 43.238 | 1.00 | 73.98 | C |
| ATOM | 1180 | CG | LEU | A | 176 | −5.157 | 71.335 | 44.713 | 1.00 | 69.25 | C |
| ATOM | 1181 | CD1 | LEU | A | 176 | −5.004 | 69.831 | 44.856 | 1.00 | 71.50 | C |
| ATOM | 1182 | CD2 | LEU | A | 176 | −4.071 | 72.051 | 45.487 | 1.00 | 66.75 | C |
| ATOM | 1183 | N | ASP | A | 177 | −8.453 | 71.293 | 43.130 | 1.00 | 76.65 | N |
| ATOM | 1184 | CA | ASP | A | 177 | −9.749 | 71.890 | 43.445 | 1.00 | 73.85 | C |
| ATOM | 1185 | C | ASP | A | 177 | −9.572 | 73.046 | 44.428 | 1.00 | 73.19 | C |
| ATOM | 1186 | O | ASP | A | 177 | −8.719 | 72.993 | 45.315 | 1.00 | 68.75 | O |
| ATOM | 1187 | CB | ASP | A | 177 | −10.679 | 70.840 | 44.055 | 1.00 | 76.37 | C |
| ATOM | 1188 | CG | ASP | A | 177 | −12.125 | 71.289 | 44.080 | 1.00 | 85.23 | C |
| ATOM | 1189 | OD1 | ASP | A | 177 | −12.398 | 72.412 | 44.556 | 1.00 | 85.85 | O |
| ATOM | 1190 | OD2 | ASP | A | 177 | −12.991 | 70.513 | 43.624 | 1.00 | 89.30 | O |
| ATOM | 1191 | N | ARG | A | 178 | −10.385 | 74.086 | 44.272 | 1.00 | 74.52 | N |
| ATOM | 1192 | CA | ARG | A | 178 | −10.301 | 75.258 | 45.137 | 1.00 | 77.02 | C |
| ATOM | 1193 | C | ARG | A | 178 | −10.929 | 75.023 | 46.505 | 1.00 | 79.94 | C |
| ATOM | 1194 | O | ARG | A | 178 | −10.527 | 75.636 | 47.497 | 1.00 | 78.30 | O |
| ATOM | 1195 | CB | ARG | A | 178 | −10.966 | 76.448 | 44.460 | 1.00 | 74.14 | C |
| ATOM | 1196 | N | ASP | A | 179 | −11.916 | 74.133 | 46.555 | 1.00 | 83.91 | N |
| ATOM | 1197 | CA | ASP | A | 179 | −12.611 | 73.826 | 47.803 | 1.00 | 86.84 | C |

APPENDIX A-continued

| ATOM | 1198 | C | ASP | A | 179 | −11.985 | 72.643 | 48.537 | 1.00 | 82.83 | C |
|---|---|---|---|---|---|---|---|---|---|---|---|
| ATOM | 1199 | O | ASP | A | 179 | −12.526 | 72.171 | 49.541 | 1.00 | 77.18 | O |
| ATOM | 1200 | CB | ASP | A | 179 | −14.082 | 73.525 | 47.508 | 1.00 | 93.93 | C |
| ATOM | 1201 | CG | ASP | A | 179 | −14.753 | 74.632 | 46.725 | 1.00 | 99.56 | C |
| ATOM | 1202 | OD1 | ASP | A | 179 | −14.879 | 75.748 | 47.270 | 1.00 | 103.54 | O |
| ATOM | 1203 | OD2 | ASP | A | 179 | −15.147 | 74.388 | 45.564 | 1.00 | 106.71 | O |
| ATOM | 1204 | N | THR | A | 180 | −10.847 | 72.172 | 48.029 | 1.00 | 74.51 | N |
| ATOM | 1205 | CA | THR | A | 180 | −10.139 | 71.041 | 48.616 | 1.00 | 67.53 | C |
| ATOM | 1206 | C | THR | A | 180 | −9.869 | 71.241 | 50.101 | 1.00 | 70.06 | C |
| ATOM | 1207 | O | THR | A | 180 | −9.243 | 72.220 | 50.500 | 1.00 | 73.12 | O |
| ATOM | 1208 | CB | THR | A | 180 | −8.806 | 70.796 | 47.894 | 1.00 | 63.87 | C |
| ATOM | 1209 | OG1 | THR | A | 180 | −9.068 | 70.316 | 46.572 | 1.00 | 67.29 | O |
| ATOM | 1210 | CG2 | THR | A | 180 | −7.972 | 69.772 | 48.638 | 1.00 | 66.01 | C |
| ATOM | 1211 | N | VAL | A | 181 | −10.348 | 70.300 | 50.911 | 1.00 | 68.94 | N |
| ATOM | 1212 | CA | VAL | A | 181 | −10.177 | 70.353 | 52.362 | 1.00 | 66.73 | C |
| ATOM | 1213 | C | VAL | A | 181 | −8.814 | 69.803 | 52.778 | 1.00 | 68.60 | C |
| ATOM | 1214 | O | VAL | A | 181 | −8.143 | 70.367 | 53.646 | 1.00 | 67.61 | O |
| ATOM | 1215 | CB | VAL | A | 181 | −11.275 | 69.539 | 53.081 | 1.00 | 63.26 | C |
| ATOM | 1216 | CG1 | VAL | A | 181 | −11.155 | 69.718 | 54.590 | 1.00 | 64.27 | C |
| ATOM | 1217 | CG2 | VAL | A | 181 | −12.642 | 69.974 | 52.591 | 1.00 | 51.43 | C |
| ATOM | 1218 | N | PHE | A | 182 | −8.417 | 68.689 | 52.169 | 1.00 | 65.33 | N |
| ATOM | 1219 | CA | PHE | A | 182 | −7.129 | 68.087 | 52.474 | 1.00 | 62.56 | C |
| ATOM | 1220 | C | PHE | A | 182 | −6.649 | 67.176 | 51.359 | 1.00 | 62.99 | C |
| ATOM | 1221 | O | PHE | A | 182 | −7.449 | 66.555 | 50.661 | 1.00 | 63.51 | O |
| ATOM | 1222 | CB | PHE | A | 182 | −7.182 | 67.297 | 53.793 | 1.00 | 61.02 | C |
| ATOM | 1223 | CG | PHE | A | 182 | −7.830 | 65.939 | 53.681 | 1.00 | 56.62 | C |
| ATOM | 1224 | CD1 | PHE | A | 182 | −9.201 | 65.787 | 53.838 | 1.00 | 62.64 | C |
| ATOM | 1225 | CD2 | PHE | A | 182 | −7.059 | 64.808 | 53.432 | 1.00 | 55.87 | C |
| ATOM | 1226 | CE1 | PHE | A | 182 | −9.793 | 64.527 | 53.755 | 1.00 | 59.31 | C |
| ATOM | 1227 | CE2 | PHE | A | 182 | −7.643 | 63.547 | 53.344 | 1.00 | 48.72 | C |
| ATOM | 1228 | CZ | PHE | A | 182 | −9.010 | 63.408 | 53.506 | 1.00 | 47.03 | C |
| ATOM | 1229 | N | ALA | A | 183 | −5.333 | 67.115 | 51.194 | 1.00 | 60.67 | N |
| ATOM | 1230 | CA | ALA | A | 183 | −4.724 | 66.264 | 50.187 | 1.00 | 54.11 | C |
| ATOM | 1231 | C | ALA | A | 183 | −3.819 | 65.292 | 50.931 | 1.00 | 59.66 | C |
| ATOM | 1232 | O | ALA | A | 183 | −3.088 | 65.682 | 51.845 | 1.00 | 65.32 | O |
| ATOM | 1233 | CB | ALA | A | 183 | −3.921 | 67.094 | 49.217 | 1.00 | 50.43 | C |
| ATOM | 1234 | N | LEU | A | 184 | −3.879 | 64.025 | 50.547 | 1.00 | 58.51 | N |
| ATOM | 1235 | CA | LEU | A | 184 | −3.073 | 62.996 | 51.184 | 1.00 | 60.36 | C |
| ATOM | 1236 | C | LEU | A | 184 | −2.044 | 62.495 | 50.171 | 1.00 | 62.48 | C |
| ATOM | 1237 | O | LEU | A | 184 | −2.299 | 61.548 | 49.431 | 1.00 | 73.04 | O |
| ATOM | 1238 | CB | LEU | A | 184 | −3.990 | 61.862 | 51.653 | 1.00 | 54.07 | C |
| ATOM | 1239 | CG | LEU | A | 184 | −3.467 | 60.816 | 52.636 | 1.00 | 52.45 | C |
| ATOM | 1240 | CD1 | LEU | A | 184 | −4.633 | 60.031 | 53.215 | 1.00 | 55.16 | C |
| ATOM | 1241 | CD2 | LEU | A | 184 | −2.488 | 59.893 | 51.932 | 1.00 | 63.82 | C |
| ATOM | 1242 | N | VAL | A | 185 | −0.880 | 63.140 | 50.142 | 1.00 | 56.28 | N |
| ATOM | 1243 | CA | VAL | A | 185 | 0.182 | 62.784 | 49.208 | 1.00 | 49.45 | C |
| ATOM | 1244 | C | VAL | A | 185 | 1.072 | 61.649 | 49.712 | 1.00 | 50.49 | C |
| ATOM | 1245 | O | VAL | A | 185 | 1.166 | 61.411 | 50.914 | 1.00 | 59.93 | O |
| ATOM | 1246 | CB | VAL | A | 185 | 1.062 | 64.007 | 48.917 | 1.00 | 49.62 | C |
| ATOM | 1247 | CG1 | VAL | A | 185 | 2.000 | 63.719 | 47.771 | 1.00 | 47.07 | C |
| ATOM | 1248 | CG2 | VAL | A | 185 | 0.188 | 65.199 | 48.603 | 1.00 | 51.22 | C |
| ATOM | 1249 | N | ASN | A | 186 | 1.721 | 60.955 | 48.781 | 1.00 | 48.70 | N |
| ATOM | 1250 | CA | ASN | A | 186 | 2.616 | 59.838 | 49.089 | 1.00 | 48.26 | C |
| ATOM | 1251 | C | ASN | A | 186 | 3.602 | 59.629 | 47.942 | 1.00 | 52.28 | C |
| ATOM | 1252 | O | ASN | A | 186 | 3.225 | 59.720 | 46.773 | 1.00 | 58.10 | O |
| ATOM | 1253 | CB | ASN | A | 186 | 1.809 | 58.552 | 49.309 | 1.00 | 45.16 | C |
| ATOM | 1254 | CG | ASN | A | 186 | 2.644 | 57.292 | 49.104 | 1.00 | 49.29 | C |
| ATOM | 1255 | OD1 | ASN | A | 186 | 2.923 | 56.898 | 47.974 | 1.00 | 58.05 | O |
| ATOM | 1256 | ND2 | ASN | A | 186 | 3.053 | 56.662 | 50.198 | 1.00 | 52.29 | N |
| ATOM | 1257 | N | TYR | A | 187 | 4.861 | 59.345 | 48.265 | 1.00 | 48.78 | N |
| ATOM | 1258 | CA | TYR | A | 187 | 5.861 | 59.132 | 47.222 | 1.00 | 49.55 | C |
| ATOM | 1259 | C | TYR | A | 187 | 6.835 | 58.009 | 47.568 | 1.00 | 47.48 | C |
| ATOM | 1260 | O | TYR | A | 187 | 7.019 | 57.671 | 48.737 | 1.00 | 48.07 | O |
| ATOM | 1261 | CB | TYR | A | 187 | 6.637 | 60.433 | 46.965 | 1.00 | 55.04 | C |
| ATOM | 1262 | CG | TYR | A | 187 | 7.613 | 60.794 | 48.059 | 1.00 | 59.50 | C |
| ATOM | 1263 | CD1 | TYR | A | 187 | 8.836 | 60.132 | 48.174 | 1.00 | 58.67 | C |
| ATOM | 1264 | CD2 | TYR | A | 187 | 7.300 | 61.766 | 49.007 | 1.00 | 64.35 | C |
| ATOM | 1265 | CE1 | TYR | A | 187 | 9.723 | 60.427 | 49.209 | 1.00 | 60.04 | C |
| ATOM | 1266 | CE2 | TYR | A | 187 | 8.182 | 62.068 | 50.048 | 1.00 | 67.15 | C |
| ATOM | 1267 | CZ | TYR | A | 187 | 9.389 | 61.393 | 50.141 | 1.00 | 60.82 | C |
| ATOM | 1268 | OH | TYR | A | 187 | 10.258 | 61.678 | 51.167 | 1.00 | 73.18 | O |
| ATOM | 1269 | N | ILE | A | 188 | 7.451 | 57.431 | 46.542 | 1.00 | 43.25 | N |
| ATOM | 1270 | CA | ILE | A | 188 | 8.418 | 56.354 | 46.731 | 1.00 | 45.85 | C |
| ATOM | 1271 | C | ILE | A | 188 | 9.558 | 56.548 | 45.738 | 1.00 | 44.98 | C |
| ATOM | 1272 | O | ILE | A | 188 | 9.326 | 56.805 | 44.555 | 1.00 | 45.54 | O |
| ATOM | 1273 | CB | ILE | A | 188 | 7.773 | 54.960 | 46.516 | 1.00 | 42.73 | C |
| ATOM | 1274 | CG1 | ILE | A | 188 | 8.815 | 53.865 | 46.746 | 1.00 | 43.02 | C |
| ATOM | 1275 | CG2 | ILE | A | 188 | 7.200 | 54.855 | 45.111 | 1.00 | 51.78 | C |
| ATOM | 1276 | CD1 | ILE | A | 188 | 8.268 | 52.459 | 46.650 | 1.00 | 36.07 | C |
| ATOM | 1277 | N | PHE | A | 189 | 10.790 | 56.439 | 46.229 | 1.00 | 46.89 | N |

APPENDIX A-continued

| ATOM | 1278 | CA | PHE | A | 189 | 11.970 | 56.623 | 45.387 | 1.00 | 50.07 | C |
| ATOM | 1279 | C | PHE | A | 189 | 12.899 | 55.421 | 45.434 | 1.00 | 49.41 | C |
| ATOM | 1280 | O | PHE | A | 189 | 13.176 | 54.876 | 46.501 | 1.00 | 48.51 | O |
| ATOM | 1281 | CB | PHE | A | 189 | 12.752 | 57.864 | 45.821 | 1.00 | 44.48 | C |
| ATOM | 1282 | CG | PHE | A | 189 | 13.959 | 58.139 | 44.973 | 1.00 | 53.20 | C |
| ATOM | 1283 | CD1 | PHE | A | 189 | 13.818 | 58.575 | 43.657 | 1.00 | 52.64 | C |
| ATOM | 1284 | CD2 | PHE | A | 189 | 15.239 | 57.939 | 45.476 | 1.00 | 51.80 | C |
| ATOM | 1285 | CE1 | PHE | A | 189 | 14.938 | 58.808 | 42.854 | 1.00 | 50.80 | C |
| ATOM | 1286 | CE2 | PHE | A | 189 | 16.366 | 58.169 | 44.682 | 1.00 | 45.90 | C |
| ATOM | 1287 | CZ | PHE | A | 189 | 16.213 | 58.605 | 43.368 | 1.00 | 44.00 | C |
| ATOM | 1288 | N | PHE | A | 190 | 13.398 | 55.025 | 44.270 | 1.00 | 46.74 | N |
| ATOM | 1289 | CA | PHE | A | 190 | 14.285 | 53.883 | 44.191 | 1.00 | 45.46 | C |
| ATOM | 1290 | C | PHE | A | 190 | 15.383 | 54.068 | 43.163 | 1.00 | 52.29 | C |
| ATOM | 1291 | O | PHE | A | 190 | 15.122 | 54.410 | 42.009 | 1.00 | 51.11 | O |
| ATOM | 1292 | CB | PHE | A | 190 | 13.471 | 52.629 | 43.861 | 1.00 | 52.69 | C |
| ATOM | 1293 | CG | PHE | A | 190 | 14.307 | 51.409 | 43.566 | 1.00 | 60.97 | C |
| ATOM | 1294 | CD1 | PHE | A | 190 | 15.038 | 51.312 | 42.379 | 1.00 | 56.32 | C |
| ATOM | 1295 | CD2 | PHE | A | 190 | 14.353 | 50.350 | 44.469 | 1.00 | 62.97 | C |
| ATOM | 1296 | CE1 | PHE | A | 190 | 15.800 | 50.181 | 42.095 | 1.00 | 57.85 | C |
| ATOM | 1297 | CE2 | PHE | A | 190 | 15.113 | 49.213 | 44.194 | 1.00 | 64.69 | C |
| ATOM | 1298 | CZ | PHE | A | 190 | 15.838 | 49.129 | 43.004 | 1.00 | 64.42 | C |
| ATOM | 1299 | N | LYS | A | 191 | 16.618 | 53.846 | 43.595 | 1.00 | 58.08 | N |
| ATOM | 1300 | CA | LYS | A | 191 | 17.767 | 53.932 | 42.703 | 1.00 | 60.31 | C |
| ATOM | 1301 | C | LYS | A | 191 | 18.758 | 52.861 | 43.114 | 1.00 | 61.74 | C |
| ATOM | 1302 | O | LYS | A | 191 | 19.287 | 52.882 | 44.227 | 1.00 | 60.80 | O |
| ATOM | 1303 | CB | LYS | A | 191 | 18.447 | 55.302 | 42.764 | 1.00 | 55.48 | C |
| ATOM | 1304 | CG | LYS | A | 191 | 19.619 | 55.394 | 41.797 | 1.00 | 52.27 | C |
| ATOM | 1305 | CD | LYS | A | 191 | 20.160 | 56.801 | 41.627 | 1.00 | 53.62 | C |
| ATOM | 1306 | CE | LYS | A | 191 | 21.237 | 56.819 | 40.547 | 1.00 | 57.68 | C |
| ATOM | 1307 | NZ | LYS | A | 191 | 21.822 | 58.170 | 40.320 | 1.00 | 68.94 | N |
| ATOM | 1308 | N | GLY | A | 192 | 18.992 | 51.913 | 42.214 | 1.00 | 62.35 | N |
| ATOM | 1309 | CA | GLY | A | 192 | 19.919 | 50.842 | 42.510 | 1.00 | 67.39 | C |
| ATOM | 1310 | C | GLY | A | 192 | 20.843 | 50.574 | 41.345 | 1.00 | 69.71 | C |
| ATOM | 1311 | O | GLY | A | 192 | 20.577 | 51.001 | 40.222 | 1.00 | 67.56 | O |
| ATOM | 1312 | N | LYS | A | 193 | 21.939 | 49.873 | 41.617 | 1.00 | 75.19 | N |
| ATOM | 1313 | CA | LYS | A | 193 | 22.907 | 49.531 | 40.584 | 1.00 | 74.23 | C |
| ATOM | 1314 | C | LYS | A | 193 | 22.883 | 48.024 | 40.356 | 1.00 | 72.27 | C |
| ATOM | 1315 | O | LYS | A | 193 | 22.747 | 47.240 | 41.299 | 1.00 | 67.95 | O |
| ATOM | 1316 | CB | LYS | A | 193 | 24.309 | 49.976 | 41.006 | 1.00 | 75.02 | C |
| ATOM | 1317 | CG | LYS | A | 193 | 24.430 | 51.472 | 41.221 | 1.00 | 82.27 | C |
| ATOM | 1318 | CD | LYS | A | 193 | 25.745 | 51.853 | 41.880 | 1.00 | 87.19 | C |
| ATOM | 1319 | CE | LYS | A | 193 | 25.795 | 53.350 | 42.161 | 1.00 | 96.36 | C |
| ATOM | 1320 | NZ | LYS | A | 193 | 27.055 | 53.759 | 42.842 | 1.00 | 96.65 | N |
| ATOM | 1321 | N | TRP | A | 194 | 22.988 | 47.619 | 39.098 | 1.00 | 69.22 | N |
| ATOM | 1322 | CA | TRP | A | 194 | 22.994 | 46.202 | 38.776 | 1.00 | 71.41 | C |
| ATOM | 1323 | C | TRP | A | 194 | 24.158 | 45.565 | 39.524 | 1.00 | 74.35 | C |
| ATOM | 1324 | O | TRP | A | 194 | 25.228 | 46.167 | 39.651 | 1.00 | 70.31 | O |
| ATOM | 1325 | CB | TRP | A | 194 | 23.186 | 46.005 | 37.269 | 1.00 | 72.73 | C |
| ATOM | 1326 | CG | TRP | A | 194 | 22.021 | 46.447 | 36.444 | 1.00 | 62.19 | C |
| ATOM | 1327 | CD1 | TRP | A | 194 | 22.053 | 47.246 | 35.334 | 1.00 | 60.96 | C |
| ATOM | 1328 | CD2 | TRP | A | 194 | 20.653 | 46.089 | 36.643 | 1.00 | 52.48 | C |
| ATOM | 1329 | NE1 | TRP | A | 194 | 20.785 | 47.406 | 34.830 | 1.00 | 58.82 | N |
| ATOM | 1330 | CE2 | TRP | A | 194 | 19.907 | 46.705 | 35.614 | 1.00 | 55.96 | C |
| ATOM | 1331 | CE3 | TRP | A | 194 | 19.984 | 45.303 | 37.590 | 1.00 | 47.65 | C |
| ATOM | 1332 | CZ2 | TRP | A | 194 | 18.520 | 46.562 | 35.508 | 1.00 | 59.36 | C |
| ATOM | 1333 | CZ3 | TRP | A | 194 | 18.607 | 45.160 | 37.485 | 1.00 | 50.55 | C |
| ATOM | 1334 | CH2 | TRP | A | 194 | 17.890 | 45.787 | 36.451 | 1.00 | 54.38 | C |
| ATOM | 1335 | N | GLU | A | 195 | 23.951 | 44.357 | 40.031 | 1.00 | 76.18 | N |
| ATOM | 1336 | CA | GLU | A | 195 | 25.019 | 43.666 | 40.738 | 1.00 | 75.11 | C |
| ATOM | 1337 | C | GLU | A | 195 | 26.030 | 43.179 | 39.696 | 1.00 | 74.16 | C |
| ATOM | 1338 | O | GLU | A | 195 | 27.140 | 42.779 | 40.025 | 1.00 | 75.46 | O |
| ATOM | 1339 | CB | GLU | A | 195 | 24.448 | 42.492 | 41.534 | 1.00 | 74.95 | C |
| ATOM | 1340 | CG | GLU | A | 195 | 25.396 | 41.932 | 42.575 | 1.00 | 82.85 | C |
| ATOM | 1341 | CD | GLU | A | 195 | 24.708 | 40.970 | 43.528 | 1.00 | 92.54 | C |
| ATOM | 1342 | OE1 | GLU | A | 195 | 24.231 | 39.909 | 43.071 | 1.00 | 94.36 | O |
| ATOM | 1343 | OE2 | GLU | A | 195 | 24.639 | 41.281 | 44.737 | 1.00 | 96.56 | O |
| ATOM | 1344 | N | ARG | A | 196 | 25.623 | 43.228 | 38.431 | 1.00 | 70.88 | N |
| ATOM | 1345 | CA | ARG | A | 196 | 26.456 | 42.823 | 37.298 | 1.00 | 61.75 | C |
| ATOM | 1346 | C | ARG | A | 196 | 25.971 | 43.636 | 36.094 | 1.00 | 63.41 | C |
| ATOM | 1347 | O | ARG | A | 196 | 25.251 | 43.126 | 35.235 | 1.00 | 66.39 | O |
| ATOM | 1348 | CB | ARG | A | 196 | 26.298 | 41.334 | 37.041 | 1.00 | 49.17 | C |
| ATOM | 1349 | N | PRO | A | 197 | 26.365 | 44.925 | 36.031 | 1.00 | 63.69 | N |
| ATOM | 1350 | CA | PRO | A | 197 | 26.034 | 45.919 | 34.998 | 1.00 | 62.03 | C |
| ATOM | 1351 | C | PRO | A | 197 | 26.371 | 45.547 | 33.564 | 1.00 | 59.67 | C |
| ATOM | 1352 | O | PRO | A | 197 | 26.999 | 44.525 | 33.305 | 1.00 | 67.34 | O |
| ATOM | 1353 | CB | PRO | A | 197 | 26.809 | 47.155 | 35.446 | 1.00 | 60.82 | C |
| ATOM | 1354 | CG | PRO | A | 197 | 26.890 | 46.988 | 36.928 | 1.00 | 65.42 | C |
| ATOM | 1355 | CD | PRO | A | 197 | 27.244 | 45.529 | 37.045 | 1.00 | 58.16 | C |
| ATOM | 1356 | N | PHE | A | 198 | 25.941 | 46.393 | 32.635 | 1.00 | 59.78 | N |
| ATOM | 1357 | CA | PHE | A | 198 | 26.207 | 46.180 | 31.217 | 1.00 | 64.69 | C |

APPENDIX A-continued

| ATOM | 1358 | C | PHE | A | 198 | 27.241 | 47.208 | 30.795 | 1.00 | 68.93 | C |
| --- | --- | --- | --- | --- | --- | --- | --- | --- | --- | --- | --- |
| ATOM | 1359 | O | PHE | A | 198 | 27.278 | 48.305 | 31.343 | 1.00 | 76.85 | O |
| ATOM | 1360 | CB | PHE | A | 198 | 24.945 | 46.400 | 30.377 | 1.00 | 62.99 | C |
| ATOM | 1361 | CG | PHE | A | 198 | 23.805 | 45.483 | 30.715 | 1.00 | 56.22 | C |
| ATOM | 1362 | CD1 | PHE | A | 198 | 23.148 | 45.585 | 31.934 | 1.00 | 54.47 | C |
| ATOM | 1363 | CD2 | PHE | A | 198 | 23.367 | 44.535 | 29.794 | 1.00 | 53.06 | C |
| ATOM | 1364 | CE1 | PHE | A | 198 | 22.069 | 44.764 | 32.228 | 1.00 | 61.54 | C |
| ATOM | 1365 | CE2 | PHE | A | 198 | 22.290 | 43.708 | 30.079 | 1.00 | 50.65 | C |
| ATOM | 1366 | CZ | PHE | A | 198 | 21.639 | 43.821 | 31.298 | 1.00 | 59.45 | C |
| ATOM | 1367 | N | GLU | A | 199 | 28.087 | 46.863 | 29.833 | 1.00 | 75.72 | N |
| ATOM | 1368 | CA | GLU | A | 199 | 29.078 | 47.818 | 29.364 | 1.00 | 80.76 | C |
| ATOM | 1369 | C | GLU | A | 199 | 28.402 | 48.636 | 28.279 | 1.00 | 75.48 | C |
| ATOM | 1370 | O | GLU | A | 199 | 27.778 | 48.090 | 27.369 | 1.00 | 77.98 | O |
| ATOM | 1371 | CB | GLU | A | 199 | 30.316 | 47.104 | 28.817 | 1.00 | 96.09 | C |
| ATOM | 1372 | CG | GLU | A | 199 | 31.099 | 46.341 | 29.880 | 1.00 | 109.28 | C |
| ATOM | 1373 | CD | GLU | A | 199 | 32.394 | 45.756 | 29.350 | 1.00 | 115.78 | C |
| ATOM | 1374 | OE1 | GLU | A | 199 | 33.266 | 46.542 | 28.918 | 1.00 | 116.67 | O |
| ATOM | 1375 | OE2 | GLU | A | 199 | 32.538 | 44.513 | 29.365 | 1.00 | 117.72 | O |
| ATOM | 1376 | N | VAL | A | 200 | 28.517 | 49.952 | 28.396 | 1.00 | 69.54 | N |
| ATOM | 1377 | CA | VAL | A | 200 | 27.897 | 50.880 | 27.458 | 1.00 | 64.74 | C |
| ATOM | 1378 | C | VAL | A | 200 | 28.352 | 50.693 | 26.008 | 1.00 | 70.04 | C |
| ATOM | 1379 | O | VAL | A | 200 | 27.607 | 50.990 | 25.065 | 1.00 | 61.93 | O |
| ATOM | 1380 | CB | VAL | A | 200 | 28.174 | 52.336 | 27.891 | 1.00 | 55.43 | C |
| ATOM | 1381 | CG1 | VAL | A | 200 | 27.358 | 53.296 | 27.054 | 1.00 | 43.37 | C |
| ATOM | 1382 | CG2 | VAL | A | 200 | 27.858 | 52.506 | 29.372 | 1.00 | 54.16 | C |
| ATOM | 1383 | N | LYS | A | 201 | 29.573 | 50.196 | 25.834 | 1.00 | 73.29 | N |
| ATOM | 1384 | CA | LYS | A | 201 | 30.118 | 49.988 | 24.501 | 1.00 | 70.22 | C |
| ATOM | 1385 | C | LYS | A | 201 | 29.417 | 48.847 | 23.785 | 1.00 | 72.44 | C |
| ATOM | 1386 | O | LYS | A | 201 | 29.417 | 48.789 | 22.555 | 1.00 | 74.17 | O |
| ATOM | 1387 | CB | LYS | A | 201 | 31.621 | 49.709 | 24.582 | 1.00 | 75.61 | C |
| ATOM | 1388 | CG | LYS | A | 201 | 32.005 | 48.508 | 25.436 | 1.00 | 73.39 | C |
| ATOM | 1389 | CD | LYS | A | 201 | 33.495 | 48.228 | 25.318 | 1.00 | 72.89 | C |
| ATOM | 1390 | CE | LYS | A | 201 | 33.897 | 46.965 | 26.057 | 1.00 | 78.45 | C |
| ATOM | 1391 | NZ | LYS | A | 201 | 35.354 | 46.666 | 25.910 | 1.00 | 89.99 | N |
| ATOM | 1392 | N | ASP | A | 202 | 28.814 | 47.948 | 24.560 | 1.00 | 72.93 | N |
| ATOM | 1393 | CA | ASP | A | 202 | 28.108 | 46.795 | 24.003 | 1.00 | 76.14 | C |
| ATOM | 1394 | C | ASP | A | 202 | 26.679 | 47.102 | 23.578 | 1.00 | 75.82 | C |
| ATOM | 1395 | O | ASP | A | 202 | 26.108 | 46.401 | 22.740 | 1.00 | 81.22 | O |
| ATOM | 1396 | CB | ASP | A | 202 | 28.076 | 45.643 | 25.008 | 1.00 | 76.82 | C |
| ATOM | 1397 | CG | ASP | A | 202 | 29.444 | 45.058 | 25.273 | 1.00 | 74.96 | C |
| ATOM | 1398 | OD1 | ASP | A | 202 | 30.189 | 44.820 | 24.297 | 1.00 | 66.24 | O |
| ATOM | 1399 | OD2 | ASP | A | 202 | 29.764 | 44.823 | 26.459 | 1.00 | 73.06 | O |
| ATOM | 1400 | N | THR | A | 203 | 26.097 | 48.139 | 24.165 | 1.00 | 72.41 | N |
| ATOM | 1401 | CA | THR | A | 203 | 24.734 | 48.520 | 23.835 | 1.00 | 67.44 | C |
| ATOM | 1402 | C | THR | A | 203 | 24.651 | 48.994 | 22.388 | 1.00 | 67.22 | C |
| ATOM | 1403 | O | THR | A | 203 | 25.316 | 49.953 | 22.000 | 1.00 | 72.13 | O |
| ATOM | 1404 | CB | THR | A | 203 | 24.244 | 49.634 | 24.771 | 1.00 | 62.91 | C |
| ATOM | 1405 | OG1 | THR | A | 203 | 24.372 | 49.195 | 26.128 | 1.00 | 61.88 | O |
| ATOM | 1406 | CG2 | THR | A | 203 | 22.785 | 49.972 | 24.487 | 1.00 | 61.30 | C |
| ATOM | 1407 | N | GLU | A | 204 | 23.843 | 48.300 | 21.592 | 1.00 | 68.70 | N |
| ATOM | 1408 | CA | GLU | A | 204 | 23.645 | 48.635 | 20.183 | 1.00 | 69.45 | C |
| ATOM | 1409 | C | GLU | A | 204 | 22.159 | 48.770 | 19.911 | 1.00 | 70.47 | C |
| ATOM | 1410 | O | GLU | A | 204 | 21.331 | 48.366 | 20.726 | 1.00 | 79.57 | O |
| ATOM | 1411 | CB | GLU | A | 204 | 24.200 | 47.536 | 19.282 | 1.00 | 75.26 | C |
| ATOM | 1412 | CG | GLU | A | 204 | 25.687 | 47.334 | 19.373 | 1.00 | 93.31 | C |
| ATOM | 1413 | CD | GLU | A | 204 | 26.150 | 46.192 | 18.502 | 1.00 | 102.62 | C |
| ATOM | 1414 | OE1 | GLU | A | 204 | 25.739 | 45.042 | 18.768 | 1.00 | 109.34 | O |
| ATOM | 1415 | OE2 | GLU | A | 204 | 26.917 | 46.445 | 17.549 | 1.00 | 111.30 | O |
| ATOM | 1416 | N | GLU | A | 205 | 21.817 | 49.322 | 18.756 | 1.00 | 69.01 | N |
| ATOM | 1417 | CA | GLU | A | 205 | 20.419 | 49.497 | 18.397 | 1.00 | 71.04 | C |
| ATOM | 1418 | C | GLU | A | 205 | 19.899 | 48.243 | 17.698 | 1.00 | 72.15 | C |
| ATOM | 1419 | O | GLU | A | 205 | 20.419 | 47.838 | 16.658 | 1.00 | 71.60 | O |
| ATOM | 1420 | CB | GLU | A | 205 | 20.278 | 50.726 | 17.503 | 1.00 | 75.77 | C |
| ATOM | 1421 | CG | GLU | A | 205 | 18.873 | 51.029 | 17.043 | 1.00 | 88.92 | C |
| ATOM | 1422 | CD | GLU | A | 205 | 18.771 | 52.417 | 16.450 | 1.00 | 98.98 | C |
| ATOM | 1423 | OE1 | GLU | A | 205 | 18.794 | 53.393 | 17.234 | 1.00 | 102.18 | O |
| ATOM | 1424 | OE2 | GLU | A | 205 | 18.685 | 52.531 | 15.207 | 1.00 | 99.42 | O |
| ATOM | 1425 | N | GLU | A | 206 | 18.871 | 47.633 | 18.283 | 1.00 | 75.27 | N |
| ATOM | 1426 | CA | GLU | A | 206 | 18.283 | 46.412 | 17.740 | 1.00 | 73.49 | C |
| ATOM | 1427 | C | GLU | A | 206 | 16.773 | 46.499 | 17.498 | 1.00 | 70.36 | C |
| ATOM | 1428 | O | GLU | A | 206 | 16.139 | 47.524 | 17.759 | 1.00 | 68.83 | O |
| ATOM | 1429 | CB | GLU | A | 206 | 18.582 | 45.238 | 18.681 | 1.00 | 77.07 | C |
| ATOM | 1430 | CG | GLU | A | 206 | 20.058 | 44.937 | 18.845 | 1.00 | 85.02 | C |
| ATOM | 1431 | CD | GLU | A | 206 | 20.702 | 44.484 | 17.549 | 1.00 | 96.44 | C |
| ATOM | 1432 | OE1 | GLU | A | 206 | 20.570 | 45.200 | 16.532 | 1.00 | 104.23 | O |
| ATOM | 1433 | OE2 | GLU | A | 206 | 21.344 | 43.412 | 17.544 | 1.00 | 103.61 | O |
| ATOM | 1434 | N | ASP | A | 207 | 16.208 | 45.408 | 16.988 | 1.00 | 65.41 | N |
| ATOM | 1435 | CA | ASP | A | 207 | 14.782 | 45.332 | 16.711 | 1.00 | 61.28 | C |
| ATOM | 1436 | C | ASP | A | 207 | 14.003 | 44.921 | 17.948 | 1.00 | 62.26 | C |
| ATOM | 1437 | O | ASP | A | 207 | 14.485 | 44.140 | 18.767 | 1.00 | 64.68 | O |

APPENDIX A-continued

| ATOM | 1438 | CB | ASP | A | 207 | 14.485 | 44.301 | 15.611 | 1.00 | 58.24 | C |
|---|---|---|---|---|---|---|---|---|---|---|---|
| ATOM | 1439 | CG | ASP | A | 207 | 14.925 | 44.757 | 14.232 | 1.00 | 64.04 | C |
| ATOM | 1440 | OD1 | ASP | A | 207 | 14.609 | 45.900 | 13.840 | 1.00 | 55.45 | O |
| ATOM | 1441 | OD2 | ASP | A | 207 | 15.575 | 43.957 | 13.528 | 1.00 | 77.25 | O |
| ATOM | 1442 | N | PHE | A | 208 | 12.797 | 45.463 | 18.077 | 1.00 | 63.17 | N |
| ATOM | 1443 | CA | PHE | A | 208 | 11.902 | 45.117 | 19.171 | 1.00 | 60.78 | C |
| ATOM | 1444 | C | PHE | A | 208 | 10.555 | 44.855 | 18.507 | 1.00 | 62.88 | C |
| ATOM | 1445 | O | PHE | A | 208 | 9.973 | 45.744 | 17.884 | 1.00 | 62.33 | O |
| ATOM | 1446 | CB | PHE | A | 208 | 11.780 | 46.248 | 20.195 | 1.00 | 59.04 | C |
| ATOM | 1447 | CG | PHE | A | 208 | 11.017 | 45.852 | 21.428 | 1.00 | 51.95 | C |
| ATOM | 1448 | CD1 | PHE | A | 208 | 9.644 | 45.634 | 21.373 | 1.00 | 47.90 | C |
| ATOM | 1449 | CD2 | PHE | A | 208 | 11.680 | 45.617 | 22.625 | 1.00 | 55.16 | C |
| ATOM | 1450 | CE1 | PHE | A | 208 | 8.943 | 45.182 | 22.489 | 1.00 | 50.54 | C |
| ATOM | 1451 | CE2 | PHE | A | 208 | 10.987 | 45.164 | 23.747 | 1.00 | 60.63 | C |
| ATOM | 1452 | CZ | PHE | A | 208 | 9.615 | 44.944 | 23.676 | 1.00 | 54.42 | C |
| ATOM | 1453 | N | HIS | A | 209 | 10.070 | 43.625 | 18.645 | 1.00 | 67.77 | N |
| ATOM | 1454 | CA | HIS | A | 209 | 8.816 | 43.205 | 18.028 | 1.00 | 66.80 | C |
| ATOM | 1455 | C | HIS | A | 209 | 7.554 | 43.454 | 18.850 | 1.00 | 64.73 | C |
| ATOM | 1456 | O | HIS | A | 209 | 7.267 | 42.730 | 19.806 | 1.00 | 68.03 | O |
| ATOM | 1457 | CB | HIS | A | 209 | 8.923 | 41.724 | 17.658 | 1.00 | 64.57 | C |
| ATOM | 1458 | CG | HIS | A | 209 | 10.150 | 41.400 | 16.865 | 1.00 | 65.00 | C |
| ATOM | 1459 | ND1 | HIS | A | 209 | 10.416 | 41.974 | 15.640 | 1.00 | 68.12 | N |
| ATOM | 1460 | CD2 | HIS | A | 209 | 11.213 | 40.610 | 17.149 | 1.00 | 62.28 | C |
| ATOM | 1461 | CE1 | HIS | A | 209 | 11.592 | 41.556 | 15.206 | 1.00 | 70.85 | C |
| ATOM | 1462 | NE2 | HIS | A | 209 | 12.096 | 40.728 | 16.104 | 1.00 | 69.86 | N |
| ATOM | 1463 | N | VAL | A | 210 | 6.800 | 44.477 | 18.452 | 1.00 | 60.06 | N |
| ATOM | 1464 | CA | VAL | A | 210 | 5.560 | 44.840 | 19.127 | 1.00 | 58.43 | C |
| ATOM | 1465 | C | VAL | A | 210 | 4.434 | 43.911 | 18.677 | 1.00 | 63.95 | C |
| ATOM | 1466 | O | VAL | A | 210 | 3.755 | 43.295 | 19.498 | 1.00 | 62.28 | O |
| ATOM | 1467 | CB | VAL | A | 210 | 5.155 | 46.290 | 18.805 | 1.00 | 51.08 | C |
| ATOM | 1468 | CG1 | VAL | A | 210 | 4.023 | 46.721 | 19.725 | 1.00 | 53.98 | C |
| ATOM | 1469 | CG2 | VAL | A | 210 | 6.359 | 47.213 | 18.944 | 1.00 | 38.06 | C |
| ATOM | 1470 | N | ASP | A | 211 | 4.241 | 43.828 | 17.363 | 1.00 | 70.76 | N |
| ATOM | 1471 | CA | ASP | A | 211 | 3.216 | 42.972 | 16.776 | 1.00 | 73.36 | C |
| ATOM | 1472 | C | ASP | A | 211 | 3.912 | 41.853 | 16.034 | 1.00 | 79.37 | C |
| ATOM | 1473 | O | ASP | A | 211 | 5.138 | 41.767 | 16.035 | 1.00 | 74.90 | O |
| ATOM | 1474 | CB | ASP | A | 211 | 2.359 | 43.747 | 15.775 | 1.00 | 81.75 | C |
| ATOM | 1475 | CG | ASP | A | 211 | 1.585 | 44.877 | 16.418 | 1.00 | 96.07 | C |
| ATOM | 1476 | OD1 | ASP | A | 211 | 0.780 | 44.600 | 17.333 | 1.00 | 97.70 | O |
| ATOM | 1477 | OD2 | ASP | A | 211 | 1.778 | 46.042 | 16.008 | 1.00 | 102.83 | O |
| ATOM | 1478 | N | GLN | A | 212 | 3.123 | 41.002 | 15.390 | 1.00 | 90.81 | N |
| ATOM | 1479 | CA | GLN | A | 212 | 3.670 | 39.893 | 14.619 | 1.00 | 96.58 | C |
| ATOM | 1480 | C | GLN | A | 212 | 3.993 | 40.468 | 13.240 | 1.00 | 99.07 | C |
| ATOM | 1481 | O | GLN | A | 212 | 4.425 | 39.755 | 12.330 | 1.00 | 99.64 | O |
| ATOM | 1482 | CB | GLN | A | 212 | 2.630 | 38.772 | 14.510 | 1.00 | 97.24 | C |
| ATOM | 1483 | CG | GLN | A | 212 | 3.206 | 37.389 | 14.251 | 1.00 | 99.88 | C |
| ATOM | 1484 | CD | GLN | A | 212 | 4.116 | 36.920 | 15.372 | 1.00 | 105.74 | C |
| ATOM | 1485 | OE1 | GLN | A | 212 | 5.202 | 37.462 | 15.573 | 1.00 | 109.44 | O |
| ATOM | 1486 | NE2 | GLN | A | 212 | 3.672 | 35.909 | 16.112 | 1.00 | 106.96 | N |
| ATOM | 1487 | N | VAL | A | 213 | 3.780 | 41.776 | 13.111 | 1.00 | 98.68 | N |
| ATOM | 1488 | CA | VAL | A | 213 | 4.026 | 42.502 | 11.871 | 1.00 | 94.88 | C |
| ATOM | 1489 | C | VAL | A | 213 | 4.365 | 43.961 | 12.163 | 1.00 | 89.26 | C |
| ATOM | 1490 | O | VAL | A | 213 | 4.044 | 44.853 | 11.377 | 1.00 | 85.83 | O |
| ATOM | 1491 | CB | VAL | A | 213 | 2.790 | 42.473 | 10.961 | 1.00 | 102.81 | C |
| ATOM | 1492 | CG1 | VAL | A | 213 | 2.529 | 41.050 | 10.475 | 1.00 | 103.61 | C |
| ATOM | 1493 | CG2 | VAL | A | 213 | 1.583 | 43.019 | 11.722 | 1.00 | 102.87 | C |
| ATOM | 1494 | N | THR | A | 214 | 5.009 | 44.199 | 13.300 | 1.00 | 86.46 | N |
| ATOM | 1495 | CA | THR | A | 214 | 5.397 | 45.549 | 13.694 | 1.00 | 79.98 | C |
| ATOM | 1496 | C | THR | A | 214 | 6.685 | 45.515 | 14.522 | 1.00 | 76.78 | C |
| ATOM | 1497 | O | THR | A | 214 | 6.706 | 45.000 | 15.642 | 1.00 | 76.85 | O |
| ATOM | 1498 | CB | THR | A | 214 | 4.273 | 46.219 | 14.501 | 1.00 | 74.28 | C |
| ATOM | 1499 | OG1 | THR | A | 214 | 3.075 | 46.237 | 13.715 | 1.00 | 79.87 | O |
| ATOM | 1500 | CG2 | THR | A | 214 | 4.653 | 47.644 | 14.867 | 1.00 | 66.43 | C |
| ATOM | 1501 | N | THR | A | 215 | 7.755 | 46.073 | 13.958 | 1.00 | 65.24 | N |
| ATOM | 1502 | CA | THR | A | 215 | 9.061 | 46.096 | 14.605 | 1.00 | 56.63 | C |
| ATOM | 1503 | C | THR | A | 215 | 9.618 | 47.520 | 14.747 | 1.00 | 54.45 | C |
| ATOM | 1504 | O | THR | A | 215 | 9.607 | 48.298 | 13.797 | 1.00 | 56.91 | O |
| ATOM | 1505 | CB | THR | A | 215 | 10.052 | 45.229 | 13.798 | 1.00 | 56.71 | C |
| ATOM | 1506 | OG1 | THR | A | 215 | 11.317 | 45.187 | 14.463 | 1.00 | 59.98 | O |
| ATOM | 1507 | CG2 | THR | A | 215 | 10.236 | 45.797 | 12.394 | 1.00 | 63.33 | C |
| ATOM | 1508 | N | VAL | A | 216 | 10.109 | 47.855 | 15.937 | 1.00 | 59.20 | N |
| ATOM | 1509 | CA | VAL | A | 216 | 10.665 | 49.183 | 16.206 | 1.00 | 55.29 | C |
| ATOM | 1510 | C | VAL | A | 216 | 12.114 | 49.050 | 16.684 | 1.00 | 58.69 | C |
| ATOM | 1511 | O | VAL | A | 216 | 12.436 | 48.122 | 17.422 | 1.00 | 67.07 | O |
| ATOM | 1512 | CB | VAL | A | 216 | 9.874 | 49.906 | 17.321 | 1.00 | 46.67 | C |
| ATOM | 1513 | CG1 | VAL | A | 216 | 10.056 | 51.394 | 17.198 | 1.00 | 65.38 | C |
| ATOM | 1514 | CG2 | VAL | A | 216 | 8.414 | 49.556 | 17.245 | 1.00 | 64.41 | C |
| ATOM | 1515 | N | LYS | A | 217 | 12.983 | 49.971 | 16.271 | 1.00 | 54.87 | N |
| ATOM | 1516 | CA | LYS | A | 217 | 14.388 | 49.942 | 16.692 | 1.00 | 55.31 | C |
| ATOM | 1517 | C | LYS | A | 217 | 14.545 | 50.472 | 18.118 | 1.00 | 55.94 | C |

APPENDIX A-continued

| | | | | | | | | | | | |
|---|---|---|---|---|---|---|---|---|---|---|---|
| ATOM | 1518 | O | LYS | A | 217 | 14.003 | 51.524 | 18.458 | 1.00 | 60.49 | O |
| ATOM | 1519 | CB | LYS | A | 217 | 15.238 | 50.788 | 15.746 | 1.00 | 58.70 | C |
| ATOM | 1520 | CG | LYS | A | 217 | 15.435 | 50.177 | 14.375 | 1.00 | 64.49 | C |
| ATOM | 1521 | CD | LYS | A | 217 | 16.395 | 49.006 | 14.435 | 1.00 | 66.27 | C |
| ATOM | 1522 | CE | LYS | A | 217 | 16.664 | 48.447 | 13.050 | 1.00 | 68.56 | C |
| ATOM | 1523 | NZ | LYS | A | 217 | 17.753 | 47.430 | 13.074 | 1.00 | 82.50 | N |
| ATOM | 1524 | N | VAL | A | 218 | 15.293 | 49.754 | 18.950 | 1.00 | 56.09 | N |
| ATOM | 1525 | CA | VAL | A | 218 | 15.490 | 50.165 | 20.341 | 1.00 | 55.79 | C |
| ATOM | 1526 | C | VAL | A | 218 | 16.912 | 49.889 | 20.830 | 1.00 | 62.26 | C |
| ATOM | 1527 | O | VAL | A | 218 | 17.485 | 48.849 | 20.510 | 1.00 | 68.24 | O |
| ATOM | 1528 | CB | VAL | A | 218 | 14.524 | 49.408 | 21.269 | 1.00 | 53.22 | C |
| ATOM | 1529 | CG1 | VAL | A | 218 | 14.587 | 49.989 | 22.678 | 1.00 | 65.75 | C |
| ATOM | 1530 | CG2 | VAL | A | 218 | 13.117 | 49.467 | 20.712 | 1.00 | 59.73 | C |
| ATOM | 1531 | N | PRO | A | 219 | 17.503 | 50.817 | 21.612 | 1.00 | 62.91 | N |
| ATOM | 1532 | CA | PRO | A | 219 | 18.865 | 50.595 | 22.115 | 1.00 | 63.42 | C |
| ATOM | 1533 | C | PRO | A | 219 | 18.880 | 49.390 | 23.059 | 1.00 | 58.36 | C |
| ATOM | 1534 | O | PRO | A | 219 | 18.421 | 49.462 | 24.198 | 1.00 | 62.66 | O |
| ATOM | 1535 | CB | PRO | A | 219 | 19.199 | 51.915 | 22.812 | 1.00 | 57.84 | C |
| ATOM | 1536 | CG | PRO | A | 219 | 17.865 | 52.402 | 23.258 | 1.00 | 57.49 | C |
| ATOM | 1537 | CD | PRO | A | 219 | 16.994 | 52.124 | 22.058 | 1.00 | 62.38 | C |
| ATOM | 1538 | N | MET | A | 220 | 19.410 | 48.284 | 22.553 | 1.00 | 51.03 | N |
| ATOM | 1539 | CA | MET | A | 220 | 19.472 | 47.024 | 23.274 | 1.00 | 50.97 | C |
| ATOM | 1540 | C | MET | A | 220 | 20.745 | 46.853 | 24.093 | 1.00 | 59.32 | C |
| ATOM | 1541 | O | MET | A | 220 | 21.848 | 46.957 | 23.555 | 1.00 | 60.37 | O |
| ATOM | 1542 | CB | MET | A | 220 | 19.374 | 45.881 | 22.264 | 1.00 | 49.29 | C |
| ATOM | 1543 | CG | MET | A | 220 | 19.070 | 44.537 | 22.869 | 1.00 | 57.98 | C |
| ATOM | 1544 | SD | MET | A | 220 | 17.370 | 44.458 | 23.432 | 1.00 | 64.34 | S |
| ATOM | 1545 | CE | MET | A | 220 | 16.541 | 43.904 | 21.944 | 1.00 | 55.20 | C |
| ATOM | 1546 | N | MET | A | 221 | 20.594 | 46.589 | 25.391 | 1.00 | 65.36 | N |
| ATOM | 1547 | CA | MET | A | 221 | 21.752 | 46.368 | 26.259 | 1.00 | 65.64 | C |
| ATOM | 1548 | C | MET | A | 221 | 22.131 | 44.902 | 26.110 | 1.00 | 70.55 | C |
| ATOM | 1549 | O | MET | A | 221 | 21.254 | 44.042 | 25.984 | 1.00 | 69.96 | O |
| ATOM | 1550 | CB | MET | A | 221 | 21.420 | 46.644 | 27.728 | 1.00 | 61.78 | C |
| ATOM | 1551 | CG | MET | A | 221 | 20.906 | 48.037 | 28.029 | 1.00 | 56.79 | C |
| ATOM | 1552 | SD | MET | A | 221 | 20.838 | 48.336 | 29.806 | 1.00 | 61.80 | S |
| ATOM | 1553 | CE | MET | A | 221 | 19.517 | 47.213 | 30.310 | 1.00 | 57.68 | C |
| ATOM | 1554 | N | LYS | A | 222 | 23.429 | 44.614 | 26.127 | 1.00 | 72.12 | N |
| ATOM | 1555 | CA | LYS | A | 222 | 23.895 | 43.238 | 25.972 | 1.00 | 72.89 | C |
| ATOM | 1556 | C | LYS | A | 222 | 24.967 | 42.861 | 26.981 | 1.00 | 70.34 | C |
| ATOM | 1557 | O | LYS | A | 222 | 25.801 | 43.681 | 27.352 | 1.00 | 81.22 | O |
| ATOM | 1558 | CB | LYS | A | 222 | 24.452 | 43.026 | 24.561 | 1.00 | 67.26 | C |
| ATOM | 1559 | CG | LYS | A | 222 | 23.454 | 43.271 | 23.446 | 1.00 | 68.95 | C |
| ATOM | 1560 | CD | LYS | A | 222 | 24.117 | 43.193 | 22.080 | 1.00 | 63.71 | C |
| ATOM | 1561 | CE | LYS | A | 222 | 23.106 | 43.411 | 20.965 | 1.00 | 68.46 | C |
| ATOM | 1562 | NZ | LYS | A | 222 | 23.738 | 43.340 | 19.620 | 1.00 | 71.77 | N |
| ATOM | 1563 | N | ARG | A | 223 | 24.938 | 41.610 | 27.422 | 1.00 | 68.24 | N |
| ATOM | 1564 | CA | ARG | A | 223 | 25.932 | 41.116 | 28.363 | 1.00 | 72.42 | C |
| ATOM | 1565 | C | ARG | A | 223 | 25.962 | 39.592 | 28.354 | 1.00 | 73.02 | C |
| ATOM | 1566 | O | ARG | A | 223 | 24.924 | 38.930 | 28.407 | 1.00 | 75.03 | O |
| ATOM | 1567 | CB | ARG | A | 223 | 25.650 | 41.615 | 29.784 | 1.00 | 75.82 | C |
| ATOM | 1568 | CG | ARG | A | 223 | 26.760 | 41.262 | 30.767 | 1.00 | 71.56 | C |
| ATOM | 1569 | CD | ARG | A | 223 | 26.202 | 40.781 | 32.093 | 1.00 | 80.24 | C |
| ATOM | 1570 | NE | ARG | A | 223 | 26.975 | 39.655 | 32.611 | 1.00 | 79.45 | N |
| ATOM | 1571 | CZ | ARG | A | 223 | 26.637 | 38.944 | 33.680 | 1.00 | 79.97 | C |
| ATOM | 1572 | NH1 | ARG | A | 223 | 25.535 | 39.240 | 34.356 | 1.00 | 75.78 | N |
| ATOM | 1573 | NH2 | ARG | A | 223 | 27.398 | 37.930 | 34.070 | 1.00 | 87.76 | N |
| ATOM | 1574 | N | LEU | A | 224 | 27.166 | 39.043 | 28.278 | 1.00 | 72.78 | N |
| ATOM | 1575 | CA | LEU | A | 224 | 27.355 | 37.602 | 28.259 | 1.00 | 73.06 | C |
| ATOM | 1576 | C | LEU | A | 224 | 27.916 | 37.161 | 29.610 | 1.00 | 71.05 | C |
| ATOM | 1577 | O | LEU | A | 224 | 28.884 | 37.735 | 30.105 | 1.00 | 73.11 | O |
| ATOM | 1578 | CB | LEU | A | 224 | 28.318 | 37.238 | 27.130 | 1.00 | 73.23 | C |
| ATOM | 1579 | CG | LEU | A | 224 | 28.668 | 35.773 | 26.907 | 1.00 | 70.06 | C |
| ATOM | 1580 | CD1 | LEU | A | 224 | 27.406 | 34.959 | 26.715 | 1.00 | 78.06 | C |
| ATOM | 1581 | CD2 | LEU | A | 224 | 29.566 | 35.669 | 25.689 | 1.00 | 73.21 | C |
| ATOM | 1582 | N | GLY | A | 225 | 27.303 | 36.151 | 30.214 | 1.00 | 68.65 | N |
| ATOM | 1583 | CA | GLY | A | 225 | 27.779 | 35.691 | 31.504 | 1.00 | 69.16 | C |
| ATOM | 1584 | C | GLY | A | 225 | 26.799 | 34.781 | 32.215 | 1.00 | 76.75 | C |
| ATOM | 1585 | O | GLY | A | 225 | 25.907 | 34.203 | 31.591 | 1.00 | 80.00 | O |
| ATOM | 1586 | N | MET | A | 226 | 26.965 | 34.654 | 33.528 | 1.00 | 77.27 | N |
| ATOM | 1587 | CA | MET | A | 226 | 26.097 | 33.801 | 34.329 | 1.00 | 81.89 | C |
| ATOM | 1588 | C | MET | A | 226 | 24.872 | 34.590 | 34.791 | 1.00 | 82.62 | C |
| ATOM | 1589 | O | MET | A | 226 | 25.000 | 35.690 | 35.332 | 1.00 | 87.04 | O |
| ATOM | 1590 | CB | MET | A | 226 | 26.868 | 33.264 | 35.544 | 1.00 | 89.03 | C |
| ATOM | 1591 | CG | MET | A | 226 | 26.747 | 31.753 | 35.761 | 1.00 | 91.59 | C |
| ATOM | 1592 | SD | MET | A | 226 | 27.965 | 30.763 | 34.859 | 1.00 | 85.70 | S |
| ATOM | 1593 | CE | MET | A | 226 | 28.875 | 30.074 | 36.232 | 1.00 | 83.55 | C |
| ATOM | 1594 | N | PHE | A | 227 | 23.687 | 34.026 | 34.574 | 1.00 | 78.94 | N |
| ATOM | 1595 | CA | PHE | A | 227 | 22.440 | 34.677 | 34.966 | 1.00 | 77.64 | C |
| ATOM | 1596 | C | PHE | A | 227 | 21.563 | 33.721 | 35.767 | 1.00 | 77.61 | C |
| ATOM | 1597 | O | PHE | A | 227 | 21.793 | 32.514 | 35.758 | 1.00 | 80.02 | O |

APPENDIX A-continued

| ATOM | 1598 | CB | PHE | A | 227 | 21.680 | 35.152 | 33.720 | 1.00 | 74.03 | C |
|------|------|------|-----|---|-----|--------|--------|--------|------|--------|---|
| ATOM | 1599 | CG | PHE | A | 227 | 22.421 | 36.182 | 32.914 | 1.00 | 61.57 | C |
| ATOM | 1600 | CD1 | PHE | A | 227 | 22.709 | 37.432 | 33.450 | 1.00 | 61.58 | C |
| ATOM | 1601 | CD2 | PHE | A | 227 | 22.843 | 35.899 | 31.621 | 1.00 | 60.56 | C |
| ATOM | 1602 | CE1 | PHE | A | 227 | 23.404 | 38.385 | 32.710 | 1.00 | 59.13 | C |
| ATOM | 1603 | CE2 | PHE | A | 227 | 23.539 | 36.849 | 30.874 | 1.00 | 59.08 | C |
| ATOM | 1604 | CZ | PHE | A | 227 | 23.821 | 38.093 | 31.422 | 1.00 | 50.95 | C |
| ATOM | 1605 | N | ASN | A | 228 | 20.561 | 34.261 | 36.456 | 1.00 | 75.72 | N |
| ATOM | 1606 | CA | ASN | A | 228 | 19.656 | 33.444 | 37.261 | 1.00 | 75.48 | C |
| ATOM | 1607 | C | ASN | A | 228 | 18.439 | 33.033 | 36.433 | 1.00 | 81.82 | C |
| ATOM | 1608 | O | ASN | A | 228 | 17.397 | 32.670 | 36.979 | 1.00 | 87.86 | O |
| ATOM | 1609 | CB | ASN | A | 228 | 19.197 | 34.230 | 38.491 | 1.00 | 76.52 | C |
| ATOM | 1610 | CG | ASN | A | 228 | 18.621 | 33.338 | 39.584 | 1.00 | 79.70 | C |
| ATOM | 1611 | OD1 | ASN | A | 228 | 17.752 | 32.499 | 39.339 | 1.00 | 75.98 | O |
| ATOM | 1612 | ND2 | ASN | A | 228 | 19.103 | 33.530 | 40.805 | 1.00 | 88.96 | N |
| ATOM | 1613 | N | ILE | A | 229 | 18.577 | 33.090 | 35.111 | 1.00 | 84.18 | N |
| ATOM | 1614 | CA | ILE | A | 229 | 17.491 | 32.731 | 34.202 | 1.00 | 84.82 | C |
| ATOM | 1615 | C | ILE | A | 229 | 17.039 | 31.270 | 34.332 | 1.00 | 86.76 | C |
| ATOM | 1616 | O | ILE | A | 229 | 17.853 | 30.370 | 34.533 | 1.00 | 90.31 | O |
| ATOM | 1617 | CB | ILE | A | 229 | 17.890 | 33.011 | 32.738 | 1.00 | 81.71 | C |
| ATOM | 1618 | CG1 | ILE | A | 229 | 16.731 | 32.651 | 31.807 | 1.00 | 89.35 | C |
| ATOM | 1619 | CG2 | ILE | A | 229 | 19.143 | 32.233 | 32.381 | 1.00 | 67.51 | C |
| ATOM | 1620 | CD1 | ILE | A | 229 | 16.997 | 32.955 | 30.355 | 1.00 | 93.35 | C |
| ATOM | 1621 | N | GLN | A | 230 | 15.731 | 31.054 | 34.209 | 1.00 | 87.96 | N |
| ATOM | 1622 | CA | GLN | A | 230 | 15.128 | 29.726 | 34.320 | 1.00 | 89.36 | C |
| ATOM | 1623 | C | GLN | A | 230 | 13.757 | 29.772 | 33.643 | 1.00 | 91.97 | C |
| ATOM | 1624 | O | GLN | A | 230 | 13.128 | 30.828 | 33.596 | 1.00 | 98.53 | O |
| ATOM | 1625 | CB | GLN | A | 230 | 14.962 | 29.362 | 35.795 | 1.00 | 85.59 | C |
| ATOM | 1626 | CG | GLN | A | 230 | 13.995 | 30.281 | 36.521 | 1.00 | 101.01 | C |
| ATOM | 1627 | CD | GLN | A | 230 | 14.140 | 30.238 | 38.027 | 1.00 | 107.76 | C |
| ATOM | 1628 | OE1 | GLN | A | 230 | 13.979 | 29.191 | 38.655 | 1.00 | 107.77 | O |
| ATOM | 1629 | NE2 | GLN | A | 230 | 14.446 | 31.387 | 38.618 | 1.00 | 106.44 | N |
| ATOM | 1630 | N | HIS | A | 231 | 13.286 | 28.642 | 33.125 | 1.00 | 89.15 | N |
| ATOM | 1631 | CA | HIS | A | 231 | 11.984 | 28.619 | 32.462 | 1.00 | 85.18 | C |
| ATOM | 1632 | C | HIS | A | 231 | 10.881 | 27.961 | 33.291 | 1.00 | 84.02 | C |
| ATOM | 1633 | O | HIS | A | 231 | 10.730 | 26.741 | 33.280 | 1.00 | 88.32 | O |
| ATOM | 1634 | CB | HIS | A | 231 | 12.085 | 27.908 | 31.107 | 1.00 | 79.06 | C |
| ATOM | 1635 | CG | HIS | A | 231 | 10.781 | 27.821 | 30.372 | 1.00 | 85.42 | C |
| ATOM | 1636 | ND1 | HIS | A | 231 | 9.668 | 27.200 | 30.899 | 1.00 | 80.29 | N |
| ATOM | 1637 | CD2 | HIS | A | 231 | 10.412 | 28.282 | 29.153 | 1.00 | 84.20 | C |
| ATOM | 1638 | CE1 | HIS | A | 231 | 8.669 | 27.284 | 30.038 | 1.00 | 77.98 | C |
| ATOM | 1639 | NE2 | HIS | A | 231 | 9.095 | 27.936 | 28.970 | 1.00 | 79.51 | N |
| ATOM | 1640 | N | CYS | A | 232 | 10.109 | 28.772 | 34.008 | 1.00 | 80.20 | N |
| ATOM | 1641 | CA | CYS | A | 232 | 9.005 | 28.254 | 34.808 | 1.00 | 78.40 | C |
| ATOM | 1642 | C | CYS | A | 232 | 7.958 | 27.746 | 33.823 | 1.00 | 86.19 | C |
| ATOM | 1643 | O | CYS | A | 232 | 7.576 | 28.460 | 32.896 | 1.00 | 93.12 | O |
| ATOM | 1644 | CB | CYS | A | 232 | 8.409 | 29.369 | 35.670 | 1.00 | 71.70 | C |
| ATOM | 1645 | SG | CYS | A | 232 | 7.021 | 28.885 | 36.723 | 1.00 | 64.82 | S |
| ATOM | 1646 | N | LYS | A | 233 | 7.498 | 26.515 | 34.013 | 1.00 | 91.60 | N |
| ATOM | 1647 | CA | LYS | A | 233 | 6.504 | 25.940 | 33.113 | 1.00 | 90.61 | C |
| ATOM | 1648 | C | LYS | A | 233 | 5.094 | 26.434 | 33.430 | 1.00 | 93.19 | C |
| ATOM | 1649 | O | LYS | A | 233 | 4.253 | 26.548 | 32.535 | 1.00 | 91.14 | O |
| ATOM | 1650 | CB | LYS | A | 233 | 6.556 | 24.425 | 33.187 | 1.00 | 85.09 | C |
| ATOM | 1651 | N | LYS | A | 234 | 4.845 | 26.731 | 34.704 | 1.00 | 95.53 | N |
| ATOM | 1652 | CA | LYS | A | 234 | 3.536 | 27.212 | 35.145 | 1.00 | 95.36 | C |
| ATOM | 1653 | C | LYS | A | 234 | 3.132 | 28.481 | 34.398 | 1.00 | 95.80 | C |
| ATOM | 1654 | O | LYS | A | 234 | 1.996 | 28.613 | 33.941 | 1.00 | 93.85 | O |
| ATOM | 1655 | CB | LYS | A | 234 | 3.553 | 27.474 | 36.657 | 1.00 | 84.44 | C |
| ATOM | 1656 | N | LEU | A | 235 | 4.077 | 29.406 | 34.269 | 1.00 | 98.22 | N |
| ATOM | 1657 | CA | LEU | A | 235 | 3.826 | 30.671 | 33.591 | 1.00 | 92.68 | C |
| ATOM | 1658 | C | LEU | A | 235 | 4.106 | 30.613 | 32.092 | 1.00 | 92.14 | C |
| ATOM | 1659 | O | LEU | A | 235 | 3.799 | 31.560 | 31.370 | 1.00 | 95.18 | O |
| ATOM | 1660 | CB | LEU | A | 235 | 4.682 | 31.776 | 34.216 | 1.00 | 90.99 | C |
| ATOM | 1661 | CG | LEU | A | 235 | 4.589 | 31.969 | 35.732 | 1.00 | 89.59 | C |
| ATOM | 1662 | CD1 | LEU | A | 235 | 5.473 | 33.136 | 36.138 | 1.00 | 89.16 | C |
| ATOM | 1663 | CD2 | LEU | A | 235 | 3.148 | 32.225 | 36.145 | 1.00 | 88.51 | C |
| ATOM | 1664 | N | SER | A | 236 | 4.681 | 29.507 | 31.626 | 1.00 | 90.98 | N |
| ATOM | 1665 | CA | SER | A | 236 | 5.008 | 29.354 | 30.209 | 1.00 | 89.34 | C |
| ATOM | 1666 | C | SER | A | 236 | 5.837 | 30.547 | 29.749 | 1.00 | 84.76 | C |
| ATOM | 1667 | O | SER | A | 236 | 5.622 | 31.089 | 28.661 | 1.00 | 78.33 | O |
| ATOM | 1668 | CB | SER | A | 236 | 3.733 | 29.258 | 29.365 | 1.00 | 90.57 | C |
| ATOM | 1669 | OG | SER | A | 236 | 2.982 | 28.105 | 29.704 | 1.00 | 100.13 | O |
| ATOM | 1670 | N | SER | A | 237 | 6.782 | 30.949 | 30.595 | 1.00 | 80.08 | N |
| ATOM | 1671 | CA | SER | A | 237 | 7.659 | 32.078 | 30.307 | 1.00 | 78.85 | C |
| ATOM | 1672 | C | SER | A | 237 | 9.038 | 31.838 | 30.899 | 1.00 | 75.03 | C |
| ATOM | 1673 | O | SER | A | 237 | 9.227 | 30.947 | 31.724 | 1.00 | 74.83 | O |
| ATOM | 1674 | CB | SER | A | 237 | 7.095 | 33.367 | 30.915 | 1.00 | 75.37 | C |
| ATOM | 1675 | OG | SER | A | 237 | 5.789 | 33.638 | 30.448 | 1.00 | 83.93 | O |
| ATOM | 1676 | N | TRP | A | 238 | 10.002 | 32.639 | 30.469 | 1.00 | 74.08 | N |
| ATOM | 1677 | CA | TRP | A | 238 | 11.353 | 32.539 | 30.987 | 1.00 | 71.90 | C |

APPENDIX A-continued

| | | | | | | | | | | | |
|---|---|---|---|---|---|---|---|---|---|---|---|
| ATOM | 1678 | C | TRP | A | 238 | 11.485 | 33.578 | 32.083 | 1.00 | 70.51 | C |
| ATOM | 1679 | O | TRP | A | 238 | 11.159 | 34.741 | 31.875 | 1.00 | 78.79 | O |
| ATOM | 1680 | CB | TRP | A | 238 | 12.371 | 32.812 | 29.888 | 1.00 | 75.66 | C |
| ATOM | 1681 | CG | TRP | A | 238 | 12.614 | 31.624 | 29.037 | 1.00 | 90.97 | C |
| ATOM | 1682 | CD1 | TRP | A | 238 | 12.006 | 31.312 | 27.854 | 1.00 | 91.41 | C |
| ATOM | 1683 | CD2 | TRP | A | 238 | 13.503 | 30.546 | 29.330 | 1.00 | 97.63 | C |
| ATOM | 1684 | NE1 | TRP | A | 238 | 12.464 | 30.101 | 27.393 | 1.00 | 96.75 | N |
| ATOM | 1685 | CE2 | TRP | A | 238 | 13.383 | 29.610 | 28.282 | 1.00 | 100.79 | C |
| ATOM | 1686 | CE3 | TRP | A | 238 | 14.389 | 30.279 | 30.383 | 1.00 | 97.38 | C |
| ATOM | 1687 | CZ2 | TRP | A | 238 | 14.120 | 28.423 | 28.254 | 1.00 | 108.03 | C |
| ATOM | 1688 | CZ3 | TRP | A | 238 | 15.120 | 29.103 | 30.356 | 1.00 | 100.04 | C |
| ATOM | 1689 | CH2 | TRP | A | 238 | 14.980 | 28.188 | 29.298 | 1.00 | 106.30 | C |
| ATOM | 1690 | N | VAL | A | 239 | 11.950 | 33.166 | 33.253 | 1.00 | 61.22 | N |
| ATOM | 1691 | CA | VAL | A | 239 | 12.091 | 34.106 | 34.348 | 1.00 | 59.13 | C |
| ATOM | 1692 | C | VAL | A | 239 | 13.544 | 34.472 | 34.603 | 1.00 | 61.26 | C |
| ATOM | 1693 | O | VAL | A | 239 | 14.364 | 33.612 | 34.908 | 1.00 | 71.51 | O |
| ATOM | 1694 | CB | VAL | A | 239 | 11.490 | 33.539 | 35.640 | 1.00 | 56.91 | C |
| ATOM | 1695 | CG1 | VAL | A | 239 | 11.451 | 34.625 | 36.714 | 1.00 | 52.51 | C |
| ATOM | 1696 | CG2 | VAL | A | 239 | 10.098 | 32.999 | 35.360 | 1.00 | 52.91 | C |
| ATOM | 1697 | N | LEU | A | 240 | 13.857 | 35.755 | 34.470 | 1.00 | 57.59 | N |
| ATOM | 1698 | CA | LEU | A | 240 | 15.209 | 36.242 | 34.701 | 1.00 | 54.12 | C |
| ATOM | 1699 | C | LEU | A | 240 | 15.264 | 37.076 | 35.985 | 1.00 | 58.04 | C |
| ATOM | 1700 | O | LEU | A | 240 | 14.371 | 37.884 | 36.244 | 1.00 | 64.31 | O |
| ATOM | 1701 | CB | LEU | A | 240 | 15.666 | 37.084 | 33.512 | 1.00 | 37.10 | C |
| ATOM | 1702 | CG | LEU | A | 240 | 16.902 | 37.951 | 33.763 | 1.00 | 44.10 | C |
| ATOM | 1703 | CD1 | LEU | A | 240 | 18.053 | 37.095 | 34.243 | 1.00 | 50.02 | C |
| ATOM | 1704 | CD2 | LEU | A | 240 | 17.274 | 38.678 | 32.488 | 1.00 | 53.53 | C |
| ATOM | 1705 | N | LEU | A | 241 | 16.302 | 36.870 | 36.793 | 1.00 | 55.77 | N |
| ATOM | 1706 | CA | LEU | A | 241 | 16.460 | 37.627 | 38.033 | 1.00 | 55.19 | C |
| ATOM | 1707 | C | LEU | A | 241 | 17.766 | 38.414 | 38.072 | 1.00 | 57.12 | C |
| ATOM | 1708 | O | LEU | A | 241 | 18.852 | 37.843 | 38.032 | 1.00 | 62.42 | O |
| ATOM | 1709 | CB | LEU | A | 241 | 16.396 | 36.708 | 39.255 | 1.00 | 42.73 | C |
| ATOM | 1710 | CG | LEU | A | 241 | 15.030 | 36.135 | 39.629 | 1.00 | 44.62 | C |
| ATOM | 1711 | CD1 | LEU | A | 241 | 14.580 | 35.129 | 38.587 | 1.00 | 48.27 | C |
| ATOM | 1712 | CD2 | LEU | A | 241 | 15.127 | 35.472 | 40.984 | 1.00 | 48.77 | C |
| ATOM | 1713 | N | MET | A | 242 | 17.647 | 39.734 | 38.143 | 1.00 | 60.95 | N |
| ATOM | 1714 | CA | MET | A | 242 | 18.802 | 40.614 | 38.205 | 1.00 | 61.46 | C |
| ATOM | 1715 | C | MET | A | 242 | 18.814 | 41.210 | 39.603 | 1.00 | 69.86 | C |
| ATOM | 1716 | O | MET | A | 242 | 17.850 | 41.856 | 40.014 | 1.00 | 76.58 | O |
| ATOM | 1717 | CB | MET | A | 242 | 18.678 | 41.752 | 37.186 | 1.00 | 58.57 | C |
| ATOM | 1718 | CG | MET | A | 242 | 18.686 | 41.334 | 35.724 | 1.00 | 62.21 | C |
| ATOM | 1719 | SD | MET | A | 242 | 20.337 | 41.283 | 35.025 | 1.00 | 68.05 | S |
| ATOM | 1720 | CE | MET | A | 242 | 20.612 | 42.990 | 34.678 | 1.00 | 53.40 | C |
| ATOM | 1721 | N | LYS | A | 243 | 19.891 | 40.976 | 40.343 | 1.00 | 72.42 | N |
| ATOM | 1722 | CA | LYS | A | 243 | 20.001 | 41.529 | 41.682 | 1.00 | 68.01 | C |
| ATOM | 1723 | C | LYS | A | 243 | 20.571 | 42.936 | 41.586 | 1.00 | 67.35 | C |
| ATOM | 1724 | O | LYS | A | 243 | 21.267 | 43.284 | 40.625 | 1.00 | 61.45 | O |
| ATOM | 1725 | CB | LYS | A | 243 | 20.935 | 40.690 | 42.554 | 1.00 | 77.68 | C |
| ATOM | 1726 | CG | LYS | A | 243 | 20.365 | 39.402 | 43.114 | 1.00 | 77.00 | C |
| ATOM | 1727 | CD | LYS | A | 243 | 21.413 | 38.758 | 44.016 | 1.00 | 78.71 | C |
| ATOM | 1728 | CE | LYS | A | 243 | 20.952 | 37.443 | 44.597 | 1.00 | 81.36 | C |
| ATOM | 1729 | NZ | LYS | A | 243 | 22.054 | 36.810 | 45.368 | 1.00 | 76.85 | N |
| ATOM | 1730 | N | TYR | A | 244 | 20.267 | 43.742 | 42.594 | 1.00 | 65.83 | N |
| ATOM | 1731 | CA | TYR | A | 244 | 20.757 | 45.106 | 42.666 | 1.00 | 65.43 | C |
| ATOM | 1732 | C | TYR | A | 244 | 21.734 | 45.120 | 43.826 | 1.00 | 69.89 | C |
| ATOM | 1733 | O | TYR | A | 244 | 21.515 | 44.429 | 44.821 | 1.00 | 66.25 | O |
| ATOM | 1734 | CB | TYR | A | 244 | 19.616 | 46.071 | 42.992 | 1.00 | 65.19 | C |
| ATOM | 1735 | CG | TYR | A | 244 | 18.643 | 46.354 | 41.871 | 1.00 | 62.59 | C |
| ATOM | 1736 | CD1 | TYR | A | 244 | 18.993 | 47.184 | 40.807 | 1.00 | 62.28 | C |
| ATOM | 1737 | CD2 | TYR | A | 244 | 17.354 | 45.827 | 41.896 | 1.00 | 63.42 | C |
| ATOM | 1738 | CE1 | TYR | A | 244 | 18.077 | 47.486 | 39.799 | 1.00 | 63.68 | C |
| ATOM | 1739 | CE2 | TYR | A | 244 | 16.432 | 46.121 | 40.891 | 1.00 | 56.17 | C |
| ATOM | 1740 | CZ | TYR | A | 244 | 16.799 | 46.949 | 39.851 | 1.00 | 57.90 | C |
| ATOM | 1741 | OH | TYR | A | 244 | 15.888 | 47.240 | 38.865 | 1.00 | 60.28 | O |
| ATOM | 1742 | N | LEU | A | 245 | 22.816 | 45.882 | 43.708 | 1.00 | 74.50 | N |
| ATOM | 1743 | CA | LEU | A | 245 | 23.748 | 45.971 | 44.824 | 1.00 | 74.05 | C |
| ATOM | 1744 | C | LEU | A | 245 | 22.888 | 46.554 | 45.941 | 1.00 | 76.83 | C |
| ATOM | 1745 | O | LEU | A | 245 | 22.453 | 47.707 | 45.866 | 1.00 | 83.60 | O |
| ATOM | 1746 | CB | LEU | A | 245 | 24.910 | 46.923 | 44.512 | 1.00 | 63.18 | C |
| ATOM | 1747 | CG | LEU | A | 245 | 25.927 | 46.502 | 43.450 | 1.00 | 63.62 | C |
| ATOM | 1748 | CD1 | LEU | A | 245 | 26.925 | 47.632 | 43.222 | 1.00 | 60.04 | C |
| ATOM | 1749 | CD2 | LEU | A | 245 | 26.638 | 45.238 | 43.895 | 1.00 | 57.38 | C |
| ATOM | 1750 | N | GLY | A | 246 | 22.621 | 45.747 | 46.959 | 1.00 | 68.52 | N |
| ATOM | 1751 | CA | GLY | A | 246 | 21.799 | 46.208 | 48.055 | 1.00 | 61.59 | C |
| ATOM | 1752 | C | GLY | A | 246 | 20.762 | 45.157 | 48.377 | 1.00 | 65.51 | C |
| ATOM | 1753 | O | GLY | A | 246 | 21.028 | 43.963 | 48.247 | 1.00 | 74.94 | O |
| ATOM | 1754 | N | ASN | A | 247 | 19.574 | 45.593 | 48.778 | 1.00 | 59.87 | N |
| ATOM | 1755 | CA | ASN | A | 247 | 18.513 | 44.665 | 49.137 | 1.00 | 62.02 | C |
| ATOM | 1756 | C | ASN | A | 247 | 17.331 | 44.665 | 48.175 | 1.00 | 69.07 | C |
| ATOM | 1757 | O | ASN | A | 247 | 16.178 | 44.601 | 48.606 | 1.00 | 77.25 | O |

APPENDIX A-continued

| ATOM | 1758 | CB | ASN | A | 247 | 18.031 | 44.963 | 50.563 | 1.00 | 61.21 | C |
| --- | --- | --- | --- | --- | --- | --- | --- | --- | --- | --- | --- |
| ATOM | 1759 | CG | ASN | A | 247 | 17.768 | 46.448 | 50.801 | 1.00 | 62.21 | C |
| ATOM | 1760 | OD1 | ASN | A | 247 | 18.614 | 47.297 | 50.519 | 1.00 | 57.44 | O |
| ATOM | 1761 | ND2 | ASN | A | 247 | 16.594 | 46.762 | 51.335 | 1.00 | 56.87 | N |
| ATOM | 1762 | N | ALA | A | 248 | 17.613 | 44.717 | 46.875 | 1.00 | 69.73 | N |
| ATOM | 1763 | CA | ALA | A | 248 | 16.551 | 44.725 | 45.872 | 1.00 | 65.91 | C |
| ATOM | 1764 | C | ALA | A | 248 | 16.836 | 43.804 | 44.694 | 1.00 | 65.48 | C |
| ATOM | 1765 | O | ALA | A | 248 | 17.993 | 43.564 | 44.347 | 1.00 | 66.59 | O |
| ATOM | 1766 | CB | ALA | A | 248 | 16.330 | 46.139 | 45.371 | 1.00 | 67.35 | C |
| ATOM | 1767 | N | THR | A | 249 | 15.768 | 43.299 | 44.080 | 1.00 | 69.23 | N |
| ATOM | 1768 | CA | THR | A | 249 | 15.875 | 42.412 | 42.922 | 1.00 | 63.48 | C |
| ATOM | 1769 | C | THR | A | 249 | 14.818 | 42.719 | 41.862 | 1.00 | 60.92 | C |
| ATOM | 1770 | O | THR | A | 249 | 13.671 | 43.042 | 42.183 | 1.00 | 55.50 | O |
| ATOM | 1771 | CB | THR | A | 249 | 15.733 | 40.935 | 43.330 | 1.00 | 60.95 | C |
| ATOM | 1772 | OG1 | THR | A | 249 | 16.849 | 40.557 | 44.146 | 1.00 | 73.60 | O |
| ATOM | 1773 | CG2 | THR | A | 249 | 15.673 | 40.041 | 42.095 | 1.00 | 47.90 | C |
| ATOM | 1774 | N | ALA | A | 250 | 15.218 | 42.613 | 40.598 | 1.00 | 61.97 | N |
| ATOM | 1775 | CA | ALA | A | 250 | 14.330 | 42.866 | 39.468 | 1.00 | 59.72 | C |
| ATOM | 1776 | C | ALA | A | 250 | 13.948 | 41.538 | 38.826 | 1.00 | 57.77 | C |
| ATOM | 1777 | O | ALA | A | 250 | 14.805 | 40.692 | 38.595 | 1.00 | 64.36 | O |
| ATOM | 1778 | CB | ALA | A | 250 | 15.035 | 43.756 | 38.446 | 1.00 | 53.80 | C |
| ATOM | 1779 | N | ILE | A | 251 | 12.664 | 41.354 | 38.538 | 1.00 | 58.07 | N |
| ATOM | 1780 | CA | ILE | A | 251 | 12.204 | 40.115 | 37.921 | 1.00 | 56.99 | C |
| ATOM | 1781 | C | ILE | A | 251 | 11.564 | 40.358 | 36.558 | 1.00 | 58.79 | C |
| ATOM | 1782 | O | ILE | A | 251 | 10.527 | 41.010 | 36.463 | 1.00 | 62.58 | O |
| ATOM | 1783 | CB | ILE | A | 251 | 11.175 | 39.414 | 38.803 | 1.00 | 53.59 | C |
| ATOM | 1784 | CG1 | ILE | A | 251 | 11.718 | 39.287 | 40.223 | 1.00 | 52.67 | C |
| ATOM | 1785 | CG2 | ILE | A | 251 | 10.861 | 38.042 | 38.233 | 1.00 | 63.26 | C |
| ATOM | 1786 | CD1 | ILE | A | 251 | 10.769 | 38.590 | 41.168 | 1.00 | 56.99 | C |
| ATOM | 1787 | N | PHE | A | 252 | 12.183 | 39.819 | 35.512 | 1.00 | 57.19 | N |
| ATOM | 1788 | CA | PHE | A | 252 | 11.687 | 39.973 | 34.146 | 1.00 | 59.90 | C |
| ATOM | 1789 | C | PHE | A | 252 | 11.062 | 38.679 | 33.635 | 1.00 | 62.32 | C |
| ATOM | 1790 | O | PHE | A | 252 | 11.725 | 37.643 | 33.598 | 1.00 | 67.52 | O |
| ATOM | 1791 | CB | PHE | A | 252 | 12.836 | 40.371 | 33.214 | 1.00 | 56.66 | C |
| ATOM | 1792 | CG | PHE | A | 252 | 13.479 | 41.677 | 33.567 | 1.00 | 54.74 | C |
| ATOM | 1793 | CD1 | PHE | A | 252 | 12.906 | 42.876 | 33.171 | 1.00 | 61.57 | C |
| ATOM | 1794 | CD2 | PHE | A | 252 | 14.651 | 41.709 | 34.312 | 1.00 | 59.65 | C |
| ATOM | 1795 | CE1 | PHE | A | 252 | 13.497 | 44.090 | 33.510 | 1.00 | 63.98 | C |
| ATOM | 1796 | CE2 | PHE | A | 252 | 15.248 | 42.916 | 34.655 | 1.00 | 56.63 | C |
| ATOM | 1797 | CZ | PHE | A | 252 | 14.669 | 44.108 | 34.255 | 1.00 | 58.63 | C |
| ATOM | 1798 | N | PHE | A | 253 | 9.795 | 38.742 | 33.232 | 1.00 | 59.87 | N |
| ATOM | 1799 | CA | PHE | A | 253 | 9.099 | 37.566 | 32.717 | 1.00 | 55.22 | C |
| ATOM | 1800 | C | PHE | A | 253 | 8.913 | 37.643 | 31.208 | 1.00 | 57.03 | C |
| ATOM | 1801 | O | PHE | A | 253 | 8.125 | 38.451 | 30.720 | 1.00 | 54.76 | O |
| ATOM | 1802 | CB | PHE | A | 253 | 7.724 | 37.422 | 33.363 | 1.00 | 51.09 | C |
| ATOM | 1803 | CG | PHE | A | 253 | 7.746 | 37.458 | 34.859 | 1.00 | 53.71 | C |
| ATOM | 1804 | CD1 | PHE | A | 253 | 8.028 | 38.638 | 35.536 | 1.00 | 55.95 | C |
| ATOM | 1805 | CD2 | PHE | A | 253 | 7.438 | 36.323 | 35.595 | 1.00 | 52.43 | C |
| ATOM | 1806 | CE1 | PHE | A | 253 | 7.996 | 38.688 | 36.927 | 1.00 | 60.01 | C |
| ATOM | 1807 | CE2 | PHE | A | 253 | 7.404 | 36.363 | 36.985 | 1.00 | 62.93 | C |
| ATOM | 1808 | CZ | PHE | A | 253 | 7.683 | 37.549 | 37.653 | 1.00 | 57.28 | C |
| ATOM | 1809 | N | LEU | A | 254 | 9.630 | 36.786 | 30.480 | 1.00 | 63.53 | N |
| ATOM | 1810 | CA | LEU | A | 254 | 9.564 | 36.728 | 29.017 | 1.00 | 62.54 | C |
| ATOM | 1811 | C | LEU | A | 254 | 8.690 | 35.550 | 28.572 | 1.00 | 65.58 | C |
| ATOM | 1812 | O | LEU | A | 254 | 9.145 | 34.405 | 28.536 | 1.00 | 68.53 | O |
| ATOM | 1813 | CB | LEU | A | 254 | 10.974 | 36.572 | 28.441 | 1.00 | 50.37 | C |
| ATOM | 1814 | CG | LEU | A | 254 | 11.125 | 36.614 | 26.922 | 1.00 | 43.14 | C |
| ATOM | 1815 | CD1 | LEU | A | 254 | 10.585 | 37.929 | 26.390 | 1.00 | 49.26 | C |
| ATOM | 1816 | CD2 | LEU | A | 254 | 12.590 | 36.465 | 26.553 | 1.00 | 38.94 | C |
| ATOM | 1817 | N | PRO | A | 255 | 7.424 | 35.826 | 28.210 | 1.00 | 64.84 | N |
| ATOM | 1818 | CA | PRO | A | 255 | 6.439 | 34.831 | 27.767 | 1.00 | 68.25 | C |
| ATOM | 1819 | C | PRO | A | 255 | 6.739 | 34.104 | 26.451 | 1.00 | 73.60 | C |
| ATOM | 1820 | O | PRO | A | 255 | 7.238 | 34.700 | 25.495 | 1.00 | 78.59 | O |
| ATOM | 1821 | CB | PRO | A | 255 | 5.154 | 35.648 | 27.693 | 1.00 | 62.45 | C |
| ATOM | 1822 | CG | PRO | A | 255 | 5.653 | 36.979 | 27.227 | 1.00 | 55.56 | C |
| ATOM | 1823 | CD | PRO | A | 255 | 6.862 | 37.186 | 28.112 | 1.00 | 60.49 | C |
| ATOM | 1824 | N | ASP | A | 256 | 6.426 | 32.811 | 26.410 | 1.00 | 75.85 | N |
| ATOM | 1825 | CA | ASP | A | 256 | 6.649 | 32.020 | 25.206 | 1.00 | 80.39 | C |
| ATOM | 1826 | C | ASP | A | 256 | 5.637 | 32.465 | 24.161 | 1.00 | 81.39 | C |
| ATOM | 1827 | O | ASP | A | 256 | 4.539 | 32.893 | 24.510 | 1.00 | 82.78 | O |
| ATOM | 1828 | CB | ASP | A | 256 | 6.476 | 30.526 | 25.489 | 1.00 | 83.87 | C |
| ATOM | 1829 | CG | ASP | A | 256 | 7.447 | 30.009 | 26.539 | 1.00 | 86.79 | C |
| ATOM | 1830 | OD1 | ASP | A | 256 | 8.651 | 30.346 | 26.468 | 1.00 | 85.16 | O |
| ATOM | 1831 | OD2 | ASP | A | 256 | 7.005 | 29.253 | 27.429 | 1.00 | 85.41 | O |
| ATOM | 1832 | N | GLU | A | 257 | 6.013 | 32.362 | 22.887 | 1.00 | 82.96 | N |
| ATOM | 1833 | CA | GLU | A | 257 | 5.156 | 32.774 | 21.777 | 1.00 | 77.56 | C |
| ATOM | 1834 | C | GLU | A | 257 | 3.680 | 32.574 | 22.084 | 1.00 | 74.15 | C |
| ATOM | 1835 | O | GLU | A | 257 | 3.256 | 31.473 | 22.423 | 1.00 | 75.17 | O |
| ATOM | 1836 | CB | GLU | A | 257 | 5.529 | 32.005 | 20.507 | 1.00 | 83.96 | C |
| ATOM | 1837 | CG | GLU | A | 257 | 4.701 | 32.381 | 19.283 | 1.00 | 96.49 | C |

APPENDIX A-continued

| ATOM | 1838 | CD | GLU | A | 257 | 5.158 | 31.670 | 18.018 | 1.00 | 99.71 | C |
|---|---|---|---|---|---|---|---|---|---|---|---|
| ATOM | 1839 | OE1 | GLU | A | 257 | 5.213 | 30.421 | 18.022 | 1.00 | 101.31 | O |
| ATOM | 1840 | OE2 | GLU | A | 257 | 5.458 | 32.359 | 17.018 | 1.00 | 102.02 | O |
| ATOM | 1841 | N | GLY | A | 258 | 2.907 | 33.652 | 21.973 | 1.00 | 71.88 | N |
| ATOM | 1842 | CA | GLY | A | 258 | 1.481 | 33.591 | 22.243 | 1.00 | 62.55 | C |
| ATOM | 1843 | C | GLY | A | 258 | 1.116 | 33.033 | 23.609 | 1.00 | 61.76 | C |
| ATOM | 1844 | O | GLY | A | 258 | 0.338 | 32.089 | 23.709 | 1.00 | 72.76 | O |
| ATOM | 1845 | N | LYS | A | 259 | 1.669 | 33.613 | 24.666 | 1.00 | 63.73 | N |
| ATOM | 1846 | CA | LYS | A | 259 | 1.383 | 33.154 | 26.020 | 1.00 | 64.57 | C |
| ATOM | 1847 | C | LYS | A | 259 | 1.479 | 34.286 | 27.042 | 1.00 | 70.10 | C |
| ATOM | 1848 | O | LYS | A | 259 | 1.458 | 34.043 | 28.251 | 1.00 | 69.39 | O |
| ATOM | 1849 | CB | LYS | A | 259 | 2.336 | 32.015 | 26.409 | 1.00 | 63.31 | C |
| ATOM | 1850 | CG | LYS | A | 259 | 1.960 | 30.655 | 25.827 | 1.00 | 63.36 | C |
| ATOM | 1851 | CD | LYS | A | 259 | 0.607 | 30.193 | 26.365 | 1.00 | 75.81 | C |
| ATOM | 1852 | CE | LYS | A | 259 | 0.186 | 28.821 | 25.837 | 1.00 | 74.05 | C |
| ATOM | 1853 | NZ | LYS | A | 259 | −1.123 | 28.385 | 26.436 | 1.00 | 66.72 | N |
| ATOM | 1854 | N | LEU | A | 260 | 1.588 | 35.521 | 26.551 | 1.00 | 71.90 | N |
| ATOM | 1855 | CA | LEU | A | 260 | 1.674 | 36.691 | 27.424 | 1.00 | 66.51 | C |
| ATOM | 1856 | C | LEU | A | 260 | 0.395 | 36.807 | 28.238 | 1.00 | 67.69 | C |
| ATOM | 1857 | O | LEU | A | 260 | 0.434 | 36.965 | 29.462 | 1.00 | 70.96 | O |
| ATOM | 1858 | CB | LEU | A | 260 | 1.878 | 37.974 | 26.605 | 1.00 | 49.83 | C |
| ATOM | 1859 | CG | LEU | A | 260 | 1.617 | 39.308 | 27.328 | 1.00 | 36.94 | C |
| ATOM | 1860 | CD1 | LEU | A | 260 | 2.466 | 39.424 | 28.581 | 1.00 | 48.80 | C |
| ATOM | 1861 | CD2 | LEU | A | 260 | 1.919 | 40.453 | 26.390 | 1.00 | 42.60 | C |
| ATOM | 1862 | N | GLN | A | 261 | −0.738 | 36.732 | 27.547 | 1.00 | 67.34 | N |
| ATOM | 1863 | CA | GLN | A | 261 | −2.029 | 36.819 | 28.203 | 1.00 | 68.77 | C |
| ATOM | 1864 | C | GLN | A | 261 | −2.070 | 35.785 | 29.326 | 1.00 | 70.84 | C |
| ATOM | 1865 | O | GLN | A | 261 | −2.562 | 36.053 | 30.422 | 1.00 | 67.04 | O |
| ATOM | 1866 | CB | GLN | A | 261 | −3.145 | 36.550 | 27.193 | 1.00 | 76.02 | C |
| ATOM | 1867 | CG | GLN | A | 261 | −4.521 | 36.511 | 27.818 | 1.00 | 85.51 | C |
| ATOM | 1868 | CD | GLN | A | 261 | −4.902 | 37.834 | 28.438 | 1.00 | 92.98 | C |
| ATOM | 1869 | OE1 | GLN | A | 261 | −5.547 | 37.878 | 29.489 | 1.00 | 88.02 | O |
| ATOM | 1870 | NE2 | GLN | A | 261 | −4.514 | 38.926 | 27.786 | 1.00 | 95.87 | N |
| ATOM | 1871 | N | HIS | A | 262 | −1.529 | 34.605 | 29.039 | 1.00 | 74.30 | N |
| ATOM | 1872 | CA | HIS | A | 262 | −1.482 | 33.512 | 30.001 | 1.00 | 74.02 | C |
| ATOM | 1873 | C | HIS | A | 262 | −0.631 | 33.906 | 31.207 | 1.00 | 72.95 | C |
| ATOM | 1874 | O | HIS | A | 262 | −1.096 | 33.877 | 32.349 | 1.00 | 74.13 | O |
| ATOM | 1875 | CB | HIS | A | 262 | −0.897 | 32.265 | 29.335 | 1.00 | 78.39 | C |
| ATOM | 1876 | CG | HIS | A | 262 | −0.807 | 31.080 | 30.243 | 1.00 | 87.31 | C |
| ATOM | 1877 | ND1 | HIS | A | 262 | −1.918 | 30.492 | 30.811 | 1.00 | 91.10 | N |
| ATOM | 1878 | CD2 | HIS | A | 262 | 0.262 | 30.381 | 30.694 | 1.00 | 87.86 | C |
| ATOM | 1879 | CE1 | HIS | A | 262 | −1.536 | 29.482 | 31.572 | 1.00 | 91.64 | C |
| ATOM | 1880 | NE2 | HIS | A | 262 | −0.219 | 29.393 | 31.519 | 1.00 | 89.22 | N |
| ATOM | 1881 | N | LEU | A | 263 | 0.621 | 34.263 | 30.935 | 1.00 | 70.03 | N |
| ATOM | 1882 | CA | LEU | A | 263 | 1.561 | 34.685 | 31.968 | 1.00 | 66.14 | C |
| ATOM | 1883 | C | LEU | A | 263 | 0.907 | 35.650 | 32.949 | 1.00 | 69.18 | C |
| ATOM | 1884 | O | LEU | A | 263 | 0.919 | 35.426 | 34.161 | 1.00 | 69.38 | O |
| ATOM | 1885 | CB | LEU | A | 263 | 2.764 | 35.375 | 31.321 | 1.00 | 62.67 | C |
| ATOM | 1886 | CG | LEU | A | 263 | 3.506 | 36.392 | 32.196 | 1.00 | 64.56 | C |
| ATOM | 1887 | CD1 | LEU | A | 263 | 4.105 | 35.697 | 33.415 | 1.00 | 55.28 | C |
| ATOM | 1888 | CD2 | LEU | A | 263 | 4.583 | 37.086 | 31.372 | 1.00 | 61.61 | C |
| ATOM | 1889 | N | GLU | A | 264 | 0.343 | 36.725 | 32.405 | 1.00 | 70.57 | N |
| ATOM | 1890 | CA | GLU | A | 264 | −0.311 | 37.754 | 33.202 | 1.00 | 69.51 | C |
| ATOM | 1891 | C | GLU | A | 264 | −1.372 | 37.188 | 34.137 | 1.00 | 70.57 | C |
| ATOM | 1892 | O | GLU | A | 264 | −1.401 | 37.506 | 35.323 | 1.00 | 79.62 | O |
| ATOM | 1893 | CB | GLU | A | 264 | −0.954 | 38.802 | 32.290 | 1.00 | 67.02 | C |
| ATOM | 1894 | CG | GLU | A | 264 | −0.005 | 39.429 | 31.283 | 1.00 | 78.48 | C |
| ATOM | 1895 | CD | GLU | A | 264 | −0.615 | 40.636 | 30.584 | 1.00 | 89.62 | C |
| ATOM | 1896 | OE1 | GLU | A | 264 | −1.774 | 40.535 | 30.128 | 1.00 | 96.49 | O |
| ATOM | 1897 | OE2 | GLU | A | 264 | 0.064 | 41.683 | 30.481 | 1.00 | 83.38 | O |
| ATOM | 1898 | N | ASN | A | 265 | −2.243 | 36.347 | 33.601 | 1.00 | 67.63 | N |
| ATOM | 1899 | CA | ASN | A | 265 | −3.304 | 35.770 | 34.403 | 1.00 | 67.74 | C |
| ATOM | 1900 | C | ASN | A | 265 | −2.812 | 34.747 | 35.415 | 1.00 | 69.50 | C |
| ATOM | 1901 | O | ASN | A | 265 | −3.368 | 34.632 | 36.504 | 1.00 | 68.37 | O |
| ATOM | 1902 | CB | ASN | A | 265 | −4.339 | 35.120 | 33.492 | 1.00 | 74.86 | C |
| ATOM | 1903 | CG | ASN | A | 265 | −4.932 | 36.098 | 32.504 | 1.00 | 82.75 | C |
| ATOM | 1904 | OD1 | ASN | A | 265 | −5.420 | 37.161 | 32.887 | 1.00 | 87.70 | O |
| ATOM | 1905 | ND2 | ASN | A | 265 | −4.900 | 35.743 | 31.223 | 1.00 | 81.94 | N |
| ATOM | 1906 | N | GLU | A | 266 | −1.757 | 34.022 | 35.067 | 1.00 | 73.02 | N |
| ATOM | 1907 | CA | GLU | A | 266 | −1.242 | 32.977 | 35.944 | 1.00 | 81.47 | C |
| ATOM | 1908 | C | GLU | A | 266 | −0.297 | 33.397 | 37.079 | 1.00 | 78.23 | C |
| ATOM | 1909 | O | GLU | A | 266 | 0.219 | 32.541 | 37.800 | 1.00 | 80.40 | O |
| ATOM | 1910 | CB | GLU | A | 266 | −0.567 | 31.894 | 35.093 | 1.00 | 87.12 | C |
| ATOM | 1911 | CG | GLU | A | 266 | −0.878 | 30.465 | 35.536 | 1.00 | 95.08 | C |
| ATOM | 1912 | CD | GLU | A | 266 | −2.309 | 30.049 | 35.228 | 1.00 | 100.59 | C |
| ATOM | 1913 | OE1 | GLU | A | 266 | −3.249 | 30.759 | 35.645 | 1.00 | 102.76 | O |
| ATOM | 1914 | OE2 | GLU | A | 266 | −2.494 | 29.005 | 34.568 | 1.00 | 105.20 | O |
| ATOM | 1915 | N | LEU | A | 267 | −0.076 | 34.693 | 37.261 | 1.00 | 71.70 | N |
| ATOM | 1916 | CA | LEU | A | 267 | 0.827 | 35.145 | 38.318 | 1.00 | 69.74 | C |
| ATOM | 1917 | C | LEU | A | 267 | 0.248 | 35.146 | 39.729 | 1.00 | 71.25 | C |

APPENDIX A-continued

| | | | | | | | | | | | |
|---|---|---|---|---|---|---|---|---|---|---|---|
| ATOM | 1918 | O | LEU | A | 267 | −0.879 | 35.589 | 39.957 | 1.00 | 66.94 | O |
| ATOM | 1919 | CB | LEU | A | 267 | 1.356 | 36.541 | 38.001 | 1.00 | 69.04 | C |
| ATOM | 1920 | CG | LEU | A | 267 | 2.501 | 36.615 | 36.997 | 1.00 | 63.09 | C |
| ATOM | 1921 | CD1 | LEU | A | 267 | 2.860 | 38.071 | 36.763 | 1.00 | 65.56 | C |
| ATOM | 1922 | CD2 | LEU | A | 267 | 3.700 | 35.840 | 37.529 | 1.00 | 62.67 | C |
| ATOM | 1923 | N | THR | A | 268 | 1.043 | 34.657 | 40.677 | 1.00 | 74.83 | N |
| ATOM | 1924 | CA | THR | A | 268 | 0.634 | 34.601 | 42.075 | 1.00 | 80.95 | C |
| ATOM | 1925 | C | THR | A | 268 | 1.831 | 34.855 | 42.976 | 1.00 | 81.67 | C |
| ATOM | 1926 | O | THR | A | 268 | 2.969 | 34.602 | 42.583 | 1.00 | 79.89 | O |
| ATOM | 1927 | CB | THR | A | 268 | 0.074 | 33.232 | 42.440 | 1.00 | 84.34 | C |
| ATOM | 1928 | OG1 | THR | A | 268 | −0.788 | 32.780 | 41.392 | 1.00 | 92.63 | O |
| ATOM | 1929 | CG2 | THR | A | 268 | −0.714 | 33.319 | 43.745 | 1.00 | 92.25 | C |
| ATOM | 1930 | N | HIS | A | 269 | 1.567 | 35.340 | 44.186 | 1.00 | 83.80 | N |
| ATOM | 1931 | CA | HIS | A | 269 | 2.628 | 35.633 | 45.144 | 1.00 | 91.40 | C |
| ATOM | 1932 | C | HIS | A | 269 | 3.657 | 34.510 | 45.263 | 1.00 | 95.12 | C |
| ATOM | 1933 | O | HIS | A | 269 | 4.821 | 34.683 | 44.907 | 1.00 | 96.13 | O |
| ATOM | 1934 | CB | HIS | A | 269 | 2.038 | 35.898 | 46.527 | 1.00 | 94.22 | C |
| ATOM | 1935 | CG | HIS | A | 269 | 3.070 | 36.146 | 47.582 | 1.00 | 103.40 | C |
| ATOM | 1936 | ND1 | HIS | A | 269 | 2.798 | 36.040 | 48.929 | 1.00 | 110.39 | N |
| ATOM | 1937 | CD2 | HIS | A | 269 | 4.374 | 36.500 | 47.489 | 1.00 | 103.96 | C |
| ATOM | 1938 | CE1 | HIS | A | 269 | 3.889 | 36.317 | 49.621 | 1.00 | 109.00 | C |
| ATOM | 1939 | NE2 | HIS | A | 269 | 4.860 | 36.599 | 48.770 | 1.00 | 108.10 | N |
| ATOM | 1940 | N | ASP | A | 270 | 3.218 | 33.369 | 45.784 | 1.00 | 99.42 | N |
| ATOM | 1941 | CA | ASP | A | 270 | 4.079 | 32.205 | 45.981 | 1.00 | 97.84 | C |
| ATOM | 1942 | C | ASP | A | 270 | 4.941 | 31.840 | 44.775 | 1.00 | 92.69 | C |
| ATOM | 1943 | O | ASP | A | 270 | 6.119 | 31.515 | 44.928 | 1.00 | 89.84 | O |
| ATOM | 1944 | CB | ASP | A | 270 | 3.226 | 31.004 | 46.391 | 1.00 | 104.60 | C |
| ATOM | 1945 | CG | ASP | A | 270 | 1.959 | 30.888 | 45.570 | 1.00 | 115.44 | C |
| ATOM | 1946 | OD1 | ASP | A | 270 | 2.058 | 30.736 | 44.332 | 1.00 | 119.96 | O |
| ATOM | 1947 | OD2 | ASP | A | 270 | 0.862 | 30.957 | 46.165 | 1.00 | 123.71 | O |
| ATOM | 1948 | N | ILE | A | 271 | 4.357 | 31.880 | 43.581 | 1.00 | 89.02 | N |
| ATOM | 1949 | CA | ILE | A | 271 | 5.105 | 31.554 | 42.374 | 1.00 | 87.46 | C |
| ATOM | 1950 | C | ILE | A | 271 | 6.346 | 32.436 | 42.320 | 1.00 | 91.60 | C |
| ATOM | 1951 | O | ILE | A | 271 | 7.420 | 31.995 | 41.910 | 1.00 | 92.20 | O |
| ATOM | 1952 | CB | ILE | A | 271 | 4.250 | 31.780 | 41.109 | 1.00 | 85.57 | C |
| ATOM | 1953 | CG1 | ILE | A | 271 | 3.060 | 30.813 | 41.119 | 1.00 | 79.87 | C |
| ATOM | 1954 | CG2 | ILE | A | 271 | 5.100 | 31.584 | 39.860 | 1.00 | 79.54 | C |
| ATOM | 1955 | CD1 | ILE | A | 271 | 2.211 | 30.846 | 39.863 | 1.00 | 80.28 | C |
| ATOM | 1956 | N | ILE | A | 272 | 6.184 | 33.681 | 42.754 | 1.00 | 95.10 | N |
| ATOM | 1957 | CA | ILE | A | 272 | 7.271 | 34.653 | 42.791 | 1.00 | 100.57 | C |
| ATOM | 1958 | C | ILE | A | 272 | 8.209 | 34.348 | 43.961 | 1.00 | 105.54 | C |
| ATOM | 1959 | O | ILE | A | 272 | 9.382 | 34.725 | 43.944 | 1.00 | 105.43 | O |
| ATOM | 1960 | CB | ILE | A | 272 | 6.705 | 36.098 | 42.928 | 1.00 | 102.06 | C |
| ATOM | 1961 | CG1 | ILE | A | 272 | 6.238 | 36.604 | 41.559 | 1.00 | 100.19 | C |
| ATOM | 1962 | CG2 | ILE | A | 272 | 7.747 | 37.033 | 43.529 | 1.00 | 94.44 | C |
| ATOM | 1963 | CD1 | ILE | A | 272 | 5.184 | 35.732 | 40.897 | 1.00 | 104.68 | C |
| ATOM | 1964 | N | THR | A | 273 | 7.683 | 33.661 | 44.974 | 1.00 | 110.10 | N |
| ATOM | 1965 | CA | THR | A | 273 | 8.465 | 33.291 | 46.154 | 1.00 | 108.57 | C |
| ATOM | 1966 | C | THR | A | 273 | 9.400 | 32.137 | 45.813 | 1.00 | 108.74 | C |
| ATOM | 1967 | O | THR | A | 273 | 10.517 | 32.056 | 46.328 | 1.00 | 108.28 | O |
| ATOM | 1968 | CB | THR | A | 273 | 7.554 | 32.848 | 47.324 | 1.00 | 107.55 | C |
| ATOM | 1969 | OG1 | THR | A | 273 | 6.714 | 33.938 | 47.722 | 1.00 | 108.36 | O |
| ATOM | 1970 | CG2 | THR | A | 273 | 8.390 | 32.404 | 48.515 | 1.00 | 107.20 | C |
| ATOM | 1971 | N | LYS | A | 274 | 8.930 | 31.249 | 44.941 | 1.00 | 106.16 | N |
| ATOM | 1972 | CA | LYS | A | 274 | 9.702 | 30.091 | 44.513 | 1.00 | 101.76 | C |
| ATOM | 1973 | C | LYS | A | 274 | 10.971 | 30.491 | 43.760 | 1.00 | 102.87 | C |
| ATOM | 1974 | O | LYS | A | 274 | 12.079 | 30.160 | 44.178 | 1.00 | 103.30 | O |
| ATOM | 1975 | CB | LYS | A | 274 | 8.838 | 29.190 | 43.643 | 1.00 | 90.91 | C |
| ATOM | 1976 | N | PHE | A | 275 | 10.805 | 31.204 | 42.651 | 1.00 | 103.13 | N |
| ATOM | 1977 | CA | PHE | A | 275 | 11.939 | 31.636 | 41.840 | 1.00 | 105.23 | C |
| ATOM | 1978 | C | PHE | A | 275 | 13.107 | 32.127 | 42.676 | 1.00 | 105.50 | C |
| ATOM | 1979 | O | PHE | A | 275 | 14.268 | 31.862 | 42.355 | 1.00 | 110.68 | O |
| ATOM | 1980 | CB | PHE | A | 275 | 11.534 | 32.770 | 40.894 | 1.00 | 110.33 | C |
| ATOM | 1981 | CG | PHE | A | 275 | 10.458 | 32.398 | 39.925 | 1.00 | 115.76 | C |
| ATOM | 1982 | CD1 | PHE | A | 275 | 10.641 | 31.349 | 39.033 | 1.00 | 121.09 | C |
| ATOM | 1983 | CD2 | PHE | A | 275 | 9.257 | 33.099 | 39.902 | 1.00 | 119.63 | C |
| ATOM | 1984 | CE1 | PHE | A | 275 | 9.641 | 30.997 | 38.131 | 1.00 | 127.79 | C |
| ATOM | 1985 | CE2 | PHE | A | 275 | 8.248 | 32.757 | 39.002 | 1.00 | 127.46 | C |
| ATOM | 1986 | CZ | PHE | A | 275 | 8.440 | 31.703 | 38.114 | 1.00 | 128.96 | C |
| ATOM | 1987 | N | LEU | A | 276 | 12.794 | 32.847 | 43.747 | 1.00 | 101.17 | N |
| ATOM | 1988 | CA | LEU | A | 276 | 13.814 | 33.419 | 44.614 | 1.00 | 104.85 | C |
| ATOM | 1989 | C | LEU | A | 276 | 14.623 | 32.412 | 45.423 | 1.00 | 112.60 | C |
| ATOM | 1990 | O | LEU | A | 276 | 15.747 | 32.705 | 45.829 | 1.00 | 112.63 | O |
| ATOM | 1991 | CB | LEU | A | 276 | 13.168 | 34.456 | 45.543 | 1.00 | 99.16 | C |
| ATOM | 1992 | CG | LEU | A | 276 | 12.825 | 35.805 | 44.891 | 1.00 | 91.54 | C |
| ATOM | 1993 | CD1 | LEU | A | 276 | 12.072 | 35.606 | 43.590 | 1.00 | 86.18 | C |
| ATOM | 1994 | CD2 | LEU | A | 276 | 12.002 | 36.626 | 45.853 | 1.00 | 87.09 | C |
| ATOM | 1995 | N | GLU | A | 277 | 14.070 | 31.223 | 45.643 | 1.00 | 120.15 | N |
| ATOM | 1996 | CA | GLU | A | 277 | 14.776 | 30.212 | 46.424 | 1.00 | 122.95 | C |
| ATOM | 1997 | C | GLU | A | 277 | 15.898 | 29.536 | 45.627 | 1.00 | 123.63 | C |

APPENDIX A-continued

| ATOM | 1998 | O | GLU | A | 277 | 16.824 | 28.960 | 46.209 | 1.00 | 126.92 | O |
|---|---|---|---|---|---|---|---|---|---|---|---|
| ATOM | 1999 | CB | GLU | A | 277 | 13.791 | 29.157 | 46.942 | 1.00 | 123.97 | C |
| ATOM | 2000 | CG | GLU | A | 277 | 12.583 | 29.733 | 47.701 | 1.00 | 128.43 | C |
| ATOM | 2001 | CD | GLU | A | 277 | 12.970 | 30.752 | 48.766 | 1.00 | 133.24 | C |
| ATOM | 2002 | OE1 | GLU | A | 277 | 13.747 | 30.402 | 49.682 | 1.00 | 135.66 | O |
| ATOM | 2003 | OE2 | GLU | A | 277 | 12.489 | 31.906 | 48.691 | 1.00 | 133.29 | O |
| ATOM | 2004 | N | ASN | A | 278 | 15.830 | 29.634 | 44.301 | 1.00 | 123.25 | N |
| ATOM | 2005 | CA | ASN | A | 278 | 16.822 | 29.031 | 43.411 | 1.00 | 123.15 | C |
| ATOM | 2006 | C | ASN | A | 278 | 18.262 | 29.264 | 43.875 | 1.00 | 125.27 | C |
| ATOM | 2007 | O | ASN | A | 278 | 18.628 | 30.373 | 44.277 | 1.00 | 125.85 | O |
| ATOM | 2008 | CB | ASN | A | 278 | 16.645 | 29.589 | 42.000 | 1.00 | 120.61 | C |
| ATOM | 2009 | CG | ASN | A | 278 | 17.230 | 28.680 | 40.939 | 1.00 | 122.13 | C |
| ATOM | 2010 | OD1 | ASN | A | 278 | 17.701 | 27.580 | 41.232 | 1.00 | 126.33 | O |
| ATOM | 2011 | ND2 | ASN | A | 278 | 17.201 | 29.137 | 39.693 | 1.00 | 117.43 | N |
| ATOM | 2012 | N | ASP | A | 280 | 20.398 | 28.924 | 41.888 | 1.00 | 93.56 | N |
| ATOM | 2013 | CA | ASP | A | 280 | 21.113 | 28.356 | 40.746 | 1.00 | 98.24 | C |
| ATOM | 2014 | C | ASP | A | 280 | 21.578 | 29.444 | 39.791 | 1.00 | 99.08 | C |
| ATOM | 2015 | O | ASP | A | 280 | 21.383 | 30.632 | 40.045 | 1.00 | 107.64 | O |
| ATOM | 2016 | CB | ASP | A | 280 | 20.225 | 27.387 | 40.005 | 1.00 | 90.98 | C |
| ATOM | 2017 | N | ARG | A | 281 | 22.184 | 29.033 | 38.683 | 1.00 | 93.38 | N |
| ATOM | 2018 | CA | ARG | A | 281 | 22.673 | 29.987 | 37.700 | 1.00 | 89.14 | C |
| ATOM | 2019 | C | ARG | A | 281 | 23.026 | 29.311 | 36.376 | 1.00 | 92.38 | C |
| ATOM | 2020 | O | ARG | A | 281 | 23.056 | 28.085 | 36.294 | 1.00 | 103.28 | O |
| ATOM | 2021 | CB | ARG | A | 281 | 23.879 | 30.740 | 38.265 | 1.00 | 82.93 | C |
| ATOM | 2022 | CG | ARG | A | 281 | 23.691 | 32.247 | 38.238 | 1.00 | 89.76 | C |
| ATOM | 2023 | CD | ARG | A | 281 | 24.843 | 33.008 | 38.890 | 1.00 | 96.57 | C |
| ATOM | 2024 | NE | ARG | A | 281 | 24.666 | 34.452 | 38.744 | 1.00 | 110.57 | N |
| ATOM | 2025 | CZ | ARG | A | 281 | 23.645 | 35.134 | 39.255 | 1.00 | 118.44 | C |
| ATOM | 2026 | NH1 | ARG | A | 281 | 22.712 | 34.503 | 39.956 | 1.00 | 119.06 | N |
| ATOM | 2027 | NH2 | ARG | A | 281 | 23.537 | 36.441 | 39.039 | 1.00 | 122.19 | N |
| ATOM | 2028 | N | ARG | A | 282 | 23.294 | 30.105 | 35.341 | 1.00 | 89.05 | N |
| ATOM | 2029 | CA | ARG | A | 282 | 23.599 | 29.550 | 34.023 | 1.00 | 83.50 | C |
| ATOM | 2030 | C | ARG | A | 282 | 24.191 | 30.551 | 33.035 | 1.00 | 83.96 | C |
| ATOM | 2031 | O | ARG | A | 282 | 23.834 | 31.731 | 33.030 | 1.00 | 85.93 | O |
| ATOM | 2032 | CB | ARG | A | 282 | 22.327 | 28.934 | 33.426 | 1.00 | 74.20 | C |
| ATOM | 2033 | CG | ARG | A | 282 | 22.427 | 28.555 | 31.955 | 1.00 | 90.03 | C |
| ATOM | 2034 | CD | ARG | A | 282 | 21.532 | 27.367 | 31.580 | 1.00 | 103.03 | C |
| ATOM | 2035 | NE | ARG | A | 282 | 20.104 | 27.576 | 31.823 | 1.00 | 105.65 | N |
| ATOM | 2036 | CZ | ARG | A | 282 | 19.516 | 27.512 | 33.017 | 1.00 | 111.83 | C |
| ATOM | 2037 | NH1 | ARG | A | 282 | 20.222 | 27.246 | 34.109 | 1.00 | 111.63 | N |
| ATOM | 2038 | NH2 | ARG | A | 282 | 18.207 | 27.692 | 33.118 | 1.00 | 113.89 | N |
| ATOM | 2039 | N | SER | A | 283 | 25.091 | 30.061 | 32.191 | 1.00 | 79.08 | N |
| ATOM | 2040 | CA | SER | A | 283 | 25.736 | 30.893 | 31.192 | 1.00 | 78.78 | C |
| ATOM | 2041 | C | SER | A | 283 | 24.766 | 31.194 | 30.052 | 1.00 | 81.77 | C |
| ATOM | 2042 | O | SER | A | 283 | 24.101 | 30.291 | 29.537 | 1.00 | 81.74 | O |
| ATOM | 2043 | CB | SER | A | 283 | 26.972 | 30.182 | 30.648 | 1.00 | 75.69 | C |
| ATOM | 2044 | OG | SER | A | 283 | 27.581 | 30.945 | 29.625 | 1.00 | 79.35 | O |
| ATOM | 2045 | N | ALA | A | 284 | 24.691 | 32.468 | 29.670 | 1.00 | 79.60 | N |
| ATOM | 2046 | CA | ALA | A | 284 | 23.808 | 32.912 | 28.596 | 1.00 | 70.71 | C |
| ATOM | 2047 | C | ALA | A | 284 | 24.194 | 34.308 | 28.118 | 1.00 | 69.11 | C |
| ATOM | 2048 | O | ALA | A | 284 | 24.887 | 35.042 | 28.819 | 1.00 | 69.25 | O |
| ATOM | 2049 | CB | ALA | A | 284 | 22.371 | 32.916 | 29.079 | 1.00 | 64.04 | C |
| ATOM | 2050 | N | SER | A | 285 | 23.747 | 34.662 | 26.916 | 1.00 | 69.52 | N |
| ATOM | 2051 | CA | SER | A | 285 | 24.020 | 35.981 | 26.343 | 1.00 | 73.51 | C |
| ATOM | 2052 | C | SER | A | 285 | 22.707 | 36.756 | 26.380 | 1.00 | 75.86 | C |
| ATOM | 2053 | O | SER | A | 285 | 21.819 | 36.532 | 25.555 | 1.00 | 77.62 | O |
| ATOM | 2054 | CB | SER | A | 285 | 24.508 | 35.848 | 24.895 | 1.00 | 74.21 | C |
| ATOM | 2055 | OG | SER | A | 285 | 24.870 | 37.108 | 24.354 | 1.00 | 72.57 | O |
| ATOM | 2056 | N | LEU | A | 286 | 22.592 | 37.670 | 27.339 | 1.00 | 73.47 | N |
| ATOM | 2057 | CA | LEU | A | 286 | 21.371 | 38.450 | 27.515 | 1.00 | 72.94 | C |
| ATOM | 2058 | C | LEU | A | 286 | 21.251 | 39.766 | 26.752 | 1.00 | 77.66 | C |
| ATOM | 2059 | O | LEU | A | 286 | 22.198 | 40.553 | 26.670 | 1.00 | 74.59 | O |
| ATOM | 2060 | CB | LEU | A | 286 | 21.153 | 38.733 | 29.002 | 1.00 | 67.04 | C |
| ATOM | 2061 | CG | LEU | A | 286 | 19.991 | 39.672 | 29.334 | 1.00 | 58.04 | C |
| ATOM | 2062 | CD1 | LEU | A | 286 | 18.673 | 39.005 | 28.957 | 1.00 | 57.42 | C |
| ATOM | 2063 | CD2 | LEU | A | 286 | 20.024 | 40.019 | 30.812 | 1.00 | 57.48 | C |
| ATOM | 2064 | N | HIS | A | 287 | 20.056 | 39.989 | 26.209 | 1.00 | 79.34 | N |
| ATOM | 2065 | CA | HIS | A | 287 | 19.728 | 41.207 | 25.480 | 1.00 | 73.44 | C |
| ATOM | 2066 | C | HIS | A | 287 | 18.541 | 41.843 | 26.189 | 1.00 | 70.30 | C |
| ATOM | 2067 | O | HIS | A | 287 | 17.414 | 41.354 | 26.092 | 1.00 | 72.24 | O |
| ATOM | 2068 | CB | HIS | A | 287 | 19.354 | 40.895 | 24.031 | 1.00 | 69.51 | C |
| ATOM | 2069 | CG | HIS | A | 287 | 20.508 | 40.448 | 23.193 | 1.00 | 72.27 | C |
| ATOM | 2070 | ND1 | HIS | A | 287 | 20.620 | 40.763 | 21.856 | 1.00 | 74.64 | N |
| ATOM | 2071 | CD2 | HIS | A | 287 | 21.595 | 39.702 | 23.497 | 1.00 | 74.43 | C |
| ATOM | 2072 | CE1 | HIS | A | 287 | 21.728 | 40.231 | 21.373 | 1.00 | 78.92 | C |
| ATOM | 2073 | NE2 | HIS | A | 287 | 22.338 | 39.581 | 22.348 | 1.00 | 76.87 | N |
| ATOM | 2074 | N | LEU | A | 288 | 18.801 | 42.924 | 26.914 | 1.00 | 62.28 | N |
| ATOM | 2075 | CA | LEU | A | 288 | 17.756 | 43.617 | 27.656 | 1.00 | 59.94 | C |
| ATOM | 2076 | C | LEU | A | 288 | 17.717 | 45.064 | 27.193 | 1.00 | 64.65 | C |
| ATOM | 2077 | O | LEU | A | 288 | 18.703 | 45.789 | 27.314 | 1.00 | 68.16 | O |

APPENDIX A-continued

| ATOM | 2078 | CB | LEU | A | 288 | 18.053 | 43.554 | 29.156 | 1.00 | 48.45 | C |
|---|---|---|---|---|---|---|---|---|---|---|---|
| ATOM | 2079 | CG | LEU | A | 288 | 16.932 | 43.928 | 30.119 | 1.00 | 46.62 | C |
| ATOM | 2080 | CD1 | LEU | A | 288 | 15.785 | 42.946 | 29.949 | 1.00 | 43.24 | C |
| ATOM | 2081 | CD2 | LEU | A | 288 | 17.448 | 43.897 | 31.551 | 1.00 | 44.22 | C |
| ATOM | 2082 | N | PRO | A | 289 | 16.573 | 45.507 | 26.650 | 1.00 | 66.22 | N |
| ATOM | 2083 | CA | PRO | A | 289 | 16.480 | 46.890 | 26.183 | 1.00 | 64.96 | C |
| ATOM | 2084 | C | PRO | A | 289 | 16.517 | 47.874 | 27.335 | 1.00 | 64.81 | C |
| ATOM | 2085 | O | PRO | A | 289 | 16.029 | 47.580 | 28.426 | 1.00 | 68.74 | O |
| ATOM | 2086 | CB | PRO | A | 289 | 15.143 | 46.912 | 25.446 | 1.00 | 57.87 | C |
| ATOM | 2087 | CG | PRO | A | 289 | 14.322 | 45.963 | 26.254 | 1.00 | 59.81 | C |
| ATOM | 2088 | CD | PRO | A | 289 | 15.281 | 44.813 | 26.498 | 1.00 | 64.77 | C |
| ATOM | 2089 | N | LYS | A | 290 | 17.121 | 49.032 | 27.104 | 1.00 | 65.05 | N |
| ATOM | 2090 | CA | LYS | A | 290 | 17.166 | 50.051 | 28.135 | 1.00 | 66.03 | C |
| ATOM | 2091 | C | LYS | A | 290 | 15.836 | 50.781 | 27.998 | 1.00 | 65.63 | C |
| ATOM | 2092 | O | LYS | A | 290 | 15.392 | 51.071 | 26.883 | 1.00 | 66.34 | O |
| ATOM | 2093 | CB | LYS | A | 290 | 18.357 | 50.988 | 27.918 | 1.00 | 60.43 | C |
| ATOM | 2094 | CG | LYS | A | 290 | 18.407 | 51.632 | 26.561 | 1.00 | 63.01 | C |
| ATOM | 2095 | CD | LYS | A | 290 | 19.730 | 52.339 | 26.360 | 1.00 | 69.06 | C |
| ATOM | 2096 | CE | LYS | A | 290 | 19.980 | 53.382 | 27.435 | 1.00 | 61.71 | C |
| ATOM | 2097 | NZ | LYS | A | 290 | 21.231 | 54.133 | 27.151 | 1.00 | 66.63 | N |
| ATOM | 2098 | N | LEU | A | 291 | 15.196 | 51.058 | 29.132 | 1.00 | 66.79 | N |
| ATOM | 2099 | CA | LEU | A | 291 | 13.888 | 51.700 | 29.133 | 1.00 | 58.21 | C |
| ATOM | 2100 | C | LEU | A | 291 | 13.776 | 53.061 | 29.804 | 1.00 | 58.53 | C |
| ATOM | 2101 | O | LEU | A | 291 | 14.513 | 53.395 | 30.732 | 1.00 | 60.89 | O |
| ATOM | 2102 | CB | LEU | A | 291 | 12.870 | 50.772 | 29.789 | 1.00 | 55.33 | C |
| ATOM | 2103 | CG | LEU | A | 291 | 12.879 | 49.318 | 29.335 | 1.00 | 49.62 | C |
| ATOM | 2104 | CD1 | LEU | A | 291 | 11.855 | 48.550 | 30.143 | 1.00 | 49.47 | C |
| ATOM | 2105 | CD2 | LEU | A | 291 | 12.585 | 49.232 | 27.851 | 1.00 | 46.93 | C |
| ATOM | 2106 | N | SER | A | 292 | 12.811 | 53.827 | 29.314 | 1.00 | 56.42 | N |
| ATOM | 2107 | CA | SER | A | 292 | 12.495 | 55.149 | 29.821 | 1.00 | 52.43 | C |
| ATOM | 2108 | C | SER | A | 292 | 10.997 | 55.211 | 29.591 | 1.00 | 53.99 | C |
| ATOM | 2109 | O | SER | A | 292 | 10.546 | 55.609 | 28.518 | 1.00 | 66.92 | O |
| ATOM | 2110 | CB | SER | A | 292 | 13.183 | 56.232 | 28.991 | 1.00 | 49.27 | C |
| ATOM | 2111 | OG | SER | A | 292 | 14.569 | 55.975 | 28.858 | 1.00 | 74.13 | O |
| ATOM | 2112 | N | ILE | A | 293 | 10.227 | 54.773 | 30.578 | 1.00 | 49.10 | N |
| ATOM | 2113 | CA | ILE | A | 293 | 8.779 | 54.788 | 30.454 | 1.00 | 53.23 | C |
| ATOM | 2114 | C | ILE | A | 293 | 8.142 | 55.334 | 31.720 | 1.00 | 58.22 | C |
| ATOM | 2115 | O | ILE | A | 293 | 8.721 | 55.233 | 32.807 | 1.00 | 54.89 | O |
| ATOM | 2116 | CB | ILE | A | 293 | 8.225 | 53.374 | 30.158 | 1.00 | 50.20 | C |
| ATOM | 2117 | CG1 | ILE | A | 293 | 8.451 | 52.456 | 31.349 | 1.00 | 42.39 | C |
| ATOM | 2118 | CG2 | ILE | A | 293 | 8.918 | 52.790 | 28.933 | 1.00 | 55.77 | C |
| ATOM | 2119 | CD1 | ILE | A | 293 | 8.191 | 51.008 | 31.028 | 1.00 | 50.52 | C |
| ATOM | 2120 | N | THR | A | 294 | 6.961 | 55.932 | 31.567 | 1.00 | 60.86 | N |
| ATOM | 2121 | CA | THR | A | 294 | 6.232 | 56.505 | 32.696 | 1.00 | 57.67 | C |
| ATOM | 2122 | C | THR | A | 294 | 4.732 | 56.271 | 32.585 | 1.00 | 52.57 | C |
| ATOM | 2123 | O | THR | A | 294 | 4.157 | 56.409 | 31.509 | 1.00 | 54.53 | O |
| ATOM | 2124 | CB | THR | A | 294 | 6.476 | 58.041 | 32.831 | 1.00 | 57.75 | C |
| ATOM | 2125 | OG1 | THR | A | 294 | 5.246 | 58.750 | 32.613 | 1.00 | 51.50 | O |
| ATOM | 2126 | CG2 | THR | A | 294 | 7.523 | 58.515 | 31.831 | 1.00 | 55.51 | C |
| ATOM | 2127 | N | GLY | A | 295 | 4.111 | 55.918 | 33.709 | 1.00 | 56.08 | N |
| ATOM | 2128 | CA | GLY | A | 295 | 2.679 | 55.688 | 33.745 | 1.00 | 52.45 | C |
| ATOM | 2129 | C | GLY | A | 295 | 1.962 | 56.736 | 34.584 | 1.00 | 56.82 | C |
| ATOM | 2130 | O | GLY | A | 295 | 2.461 | 57.150 | 35.635 | 1.00 | 56.96 | O |
| ATOM | 2131 | N | THR | A | 296 | 0.799 | 57.178 | 34.111 | 1.00 | 58.22 | N |
| ATOM | 2132 | CA | THR | A | 296 | −0.009 | 58.173 | 34.817 | 1.00 | 51.73 | C |
| ATOM | 2133 | C | THR | A | 296 | −1.421 | 57.617 | 34.888 | 1.00 | 49.70 | C |
| ATOM | 2134 | O | THR | A | 296 | −1.975 | 57.224 | 33.869 | 1.00 | 61.71 | O |
| ATOM | 2135 | CB | THR | A | 296 | −0.042 | 59.498 | 34.059 | 1.00 | 47.69 | C |
| ATOM | 2136 | OG1 | THR | A | 296 | 1.287 | 59.845 | 33.644 | 1.00 | 56.50 | O |
| ATOM | 2137 | CG2 | THR | A | 296 | −0.586 | 60.596 | 34.958 | 1.00 | 40.05 | C |
| ATOM | 2138 | N | TYR | A | 297 | −2.020 | 57.600 | 36.075 | 1.00 | 55.78 | N |
| ATOM | 2139 | CA | TYR | A | 297 | −3.353 | 57.019 | 36.216 | 1.00 | 54.04 | C |
| ATOM | 2140 | C | TYR | A | 297 | −4.392 | 57.774 | 37.043 | 1.00 | 56.80 | C |
| ATOM | 2141 | O | TYR | A | 297 | −4.058 | 58.482 | 37.994 | 1.00 | 59.98 | O |
| ATOM | 2142 | CB | TYR | A | 297 | −3.209 | 55.609 | 36.803 | 1.00 | 50.75 | C |
| ATOM | 2143 | CG | TYR | A | 297 | −2.264 | 54.729 | 36.019 | 1.00 | 45.87 | C |
| ATOM | 2144 | CD1 | TYR | A | 297 | −2.645 | 54.195 | 34.790 | 1.00 | 44.57 | C |
| ATOM | 2145 | CD2 | TYR | A | 297 | −0.972 | 54.479 | 36.476 | 1.00 | 34.32 | C |
| ATOM | 2146 | CE1 | TYR | A | 297 | −1.765 | 53.439 | 34.031 | 1.00 | 48.63 | C |
| ATOM | 2147 | CE2 | TYR | A | 297 | −0.082 | 53.723 | 35.724 | 1.00 | 44.98 | C |
| ATOM | 2148 | CZ | TYR | A | 297 | −0.485 | 53.207 | 34.498 | 1.00 | 50.58 | C |
| ATOM | 2149 | OH | TYR | A | 297 | 0.390 | 52.475 | 33.723 | 1.00 | 53.18 | O |
| ATOM | 2150 | N | ASP | A | 298 | −5.657 | 57.610 | 36.656 | 1.00 | 58.07 | N |
| ATOM | 2151 | CA | ASP | A | 298 | −6.790 | 58.180 | 37.383 | 1.00 | 59.88 | C |
| ATOM | 2152 | C | ASP | A | 298 | −7.430 | 56.905 | 37.924 | 1.00 | 61.13 | C |
| ATOM | 2153 | O | ASP | A | 298 | −8.348 | 56.342 | 37.322 | 1.00 | 67.07 | O |
| ATOM | 2154 | CB | ASP | A | 298 | −7.767 | 58.892 | 36.448 | 1.00 | 72.37 | C |
| ATOM | 2155 | CG | ASP | A | 298 | −8.773 | 59.756 | 37.205 | 1.00 | 89.50 | C |
| ATOM | 2156 | OD1 | ASP | A | 298 | −9.284 | 59.299 | 38.255 | 1.00 | 94.27 | O |
| ATOM | 2157 | OD2 | ASP | A | 298 | −9.054 | 60.888 | 36.746 | 1.00 | 91.84 | O |

APPENDIX A-continued

| ATOM | 2158 | N | LEU | A | 299 | −6.909 | 56.447 | 39.054 | 1.00 | 62.57 | N |
|---|---|---|---|---|---|---|---|---|---|---|---|
| ATOM | 2159 | CA | LEU | A | 299 | −7.345 | 55.208 | 39.684 | 1.00 | 65.93 | C |
| ATOM | 2160 | C | LEU | A | 299 | −8.801 | 55.092 | 40.090 | 1.00 | 69.28 | C |
| ATOM | 2161 | O | LEU | A | 299 | −9.186 | 54.080 | 40.670 | 1.00 | 77.46 | O |
| ATOM | 2162 | CB | LEU | A | 299 | −6.469 | 54.914 | 40.908 | 1.00 | 60.84 | C |
| ATOM | 2163 | CG | LEU | A | 299 | −4.962 | 54.829 | 40.654 | 1.00 | 60.01 | C |
| ATOM | 2164 | CD1 | LEU | A | 299 | −4.243 | 54.586 | 41.967 | 1.00 | 65.40 | C |
| ATOM | 2165 | CD2 | LEU | A | 299 | −4.661 | 53.720 | 39.656 | 1.00 | 48.22 | C |
| ATOM | 2166 | N | LYS | A | 300 | −9.623 | 56.094 | 39.799 | 1.00 | 67.89 | N |
| ATOM | 2167 | CA | LYS | A | 300 | −11.020 | 55.985 | 40.194 | 1.00 | 68.41 | C |
| ATOM | 2168 | C | LYS | A | 300 | −11.730 | 54.832 | 39.480 | 1.00 | 68.87 | C |
| ATOM | 2169 | O | LYS | A | 300 | −12.369 | 53.996 | 40.127 | 1.00 | 66.83 | O |
| ATOM | 2170 | CB | LYS | A | 300 | −11.777 | 57.290 | 39.937 | 1.00 | 73.46 | C |
| ATOM | 2171 | CG | LYS | A | 300 | −13.171 | 57.268 | 40.559 | 1.00 | 74.64 | C |
| ATOM | 2172 | CD | LYS | A | 300 | −13.991 | 58.500 | 40.232 | 1.00 | 82.29 | C |
| ATOM | 2173 | CE | LYS | A | 300 | −15.405 | 58.354 | 40.782 | 1.00 | 81.04 | C |
| ATOM | 2174 | NZ | LYS | A | 300 | −16.295 | 59.490 | 40.412 | 1.00 | 88.34 | N |
| ATOM | 2175 | N | SER | A | 301 | −11.605 | 54.784 | 38.154 | 1.00 | 71.20 | N |
| ATOM | 2176 | CA | SER | A | 301 | −12.241 | 53.744 | 37.337 | 1.00 | 68.52 | C |
| ATOM | 2177 | C | SER | A | 301 | −11.765 | 52.339 | 37.677 | 1.00 | 67.58 | C |
| ATOM | 2178 | O | SER | A | 301 | −12.567 | 51.418 | 37.839 | 1.00 | 64.66 | O |
| ATOM | 2179 | CB | SER | A | 301 | −11.971 | 54.001 | 35.854 | 1.00 | 71.87 | C |
| ATOM | 2180 | OG | SER | A | 301 | −12.355 | 55.312 | 35.484 | 1.00 | 94.70 | O |
| ATOM | 2181 | N | VAL | A | 302 | −10.450 | 52.187 | 37.771 | 1.00 | 72.44 | N |
| ATOM | 2182 | CA | VAL | A | 302 | −9.825 | 50.905 | 38.072 | 1.00 | 66.57 | C |
| ATOM | 2183 | C | VAL | A | 302 | −10.122 | 50.405 | 39.485 | 1.00 | 67.22 | C |
| ATOM | 2184 | O | VAL | A | 302 | −10.519 | 49.254 | 39.667 | 1.00 | 65.57 | O |
| ATOM | 2185 | CB | VAL | A | 302 | −8.302 | 50.998 | 37.890 | 1.00 | 64.44 | C |
| ATOM | 2186 | CG1 | VAL | A | 302 | −7.678 | 49.634 | 38.043 | 1.00 | 73.10 | C |
| ATOM | 2187 | CG2 | VAL | A | 302 | −7.982 | 51.581 | 36.528 | 1.00 | 64.41 | C |
| ATOM | 2188 | N | LEU | A | 303 | −9.923 | 51.267 | 40.480 | 1.00 | 66.92 | N |
| ATOM | 2189 | CA | LEU | A | 303 | −10.170 | 50.898 | 41.874 | 1.00 | 67.67 | C |
| ATOM | 2190 | C | LEU | A | 303 | −11.639 | 50.605 | 42.153 | 1.00 | 66.46 | C |
| ATOM | 2191 | O | LEU | A | 303 | −11.962 | 49.810 | 43.037 | 1.00 | 70.17 | O |
| ATOM | 2192 | CB | LEU | A | 303 | −9.673 | 51.998 | 42.818 | 1.00 | 59.26 | C |
| ATOM | 2193 | CG | LEU | A | 303 | −8.153 | 52.100 | 42.942 | 1.00 | 49.90 | C |
| ATOM | 2194 | CD1 | LEU | A | 303 | −7.777 | 53.351 | 43.710 | 1.00 | 46.02 | C |
| ATOM | 2195 | CD2 | LEU | A | 303 | −7.621 | 50.854 | 43.626 | 1.00 | 33.27 | C |
| ATOM | 2196 | N | GLY | A | 304 | −12.530 | 51.258 | 41.418 | 1.00 | 63.78 | N |
| ATOM | 2197 | CA | GLY | A | 304 | −13.937 | 50.989 | 41.615 | 1.00 | 66.41 | C |
| ATOM | 2198 | C | GLY | A | 304 | −14.161 | 49.539 | 41.225 | 1.00 | 68.47 | C |
| ATOM | 2199 | O | GLY | A | 304 | −14.885 | 48.790 | 41.889 | 1.00 | 66.51 | O |
| ATOM | 2200 | N | GLN | A | 305 | −13.502 | 49.140 | 40.142 | 1.00 | 67.50 | N |
| ATOM | 2201 | CA | GLN | A | 305 | −13.607 | 47.785 | 39.623 | 1.00 | 66.33 | C |
| ATOM | 2202 | C | GLN | A | 305 | −13.192 | 46.742 | 40.659 | 1.00 | 63.54 | C |
| ATOM | 2203 | O | GLN | A | 305 | −13.556 | 45.573 | 40.549 | 1.00 | 60.68 | O |
| ATOM | 2204 | CB | GLN | A | 305 | −12.755 | 47.646 | 38.358 | 1.00 | 69.12 | C |
| ATOM | 2205 | CG | GLN | A | 305 | −13.400 | 46.775 | 37.302 | 1.00 | 77.58 | C |
| ATOM | 2206 | CD | GLN | A | 305 | −14.719 | 47.349 | 36.816 | 1.00 | 82.43 | C |
| ATOM | 2207 | OE1 | GLN | A | 305 | −15.592 | 46.619 | 36.342 | 1.00 | 83.09 | O |
| ATOM | 2208 | NE2 | GLN | A | 305 | −14.866 | 48.666 | 36.922 | 1.00 | 85.51 | N |
| ATOM | 2209 | N | LEU | A | 306 | −12.423 | 47.165 | 41.658 | 1.00 | 64.38 | N |
| ATOM | 2210 | CA | LEU | A | 306 | −11.985 | 46.264 | 42.720 | 1.00 | 63.13 | C |
| ATOM | 2211 | C | LEU | A | 306 | −12.845 | 46.452 | 43.966 | 1.00 | 64.36 | C |
| ATOM | 2212 | O | LEU | A | 306 | −12.447 | 46.076 | 45.074 | 1.00 | 65.26 | O |
| ATOM | 2213 | CB | LEU | A | 306 | −10.516 | 46.499 | 43.078 | 1.00 | 60.91 | C |
| ATOM | 2214 | CG | LEU | A | 306 | −9.445 | 45.857 | 42.198 | 1.00 | 57.45 | C |
| ATOM | 2215 | CD1 | LEU | A | 306 | −9.529 | 46.410 | 40.791 | 1.00 | 57.04 | C |
| ATOM | 2216 | CD2 | LEU | A | 306 | −8.078 | 46.132 | 42.800 | 1.00 | 57.44 | C |
| ATOM | 2217 | N | GLY | A | 307 | −14.018 | 47.051 | 43.777 | 1.00 | 63.23 | N |
| ATOM | 2218 | CA | GLY | A | 307 | −14.932 | 47.257 | 44.886 | 1.00 | 66.08 | C |
| ATOM | 2219 | C | GLY | A | 307 | −14.908 | 48.625 | 45.532 | 1.00 | 64.49 | C |
| ATOM | 2220 | O | GLY | A | 307 | −15.895 | 49.035 | 46.142 | 1.00 | 73.26 | O |
| ATOM | 2221 | N | ILE | A | 308 | −13.790 | 49.331 | 45.401 | 1.00 | 56.68 | N |
| ATOM | 2222 | CA | ILE | A | 308 | −13.644 | 50.658 | 45.988 | 1.00 | 49.36 | C |
| ATOM | 2223 | C | ILE | A | 308 | −14.425 | 51.730 | 45.220 | 1.00 | 52.05 | C |
| ATOM | 2224 | O | ILE | A | 308 | −13.940 | 52.274 | 44.221 | 1.00 | 52.15 | O |
| ATOM | 2225 | CB | ILE | A | 308 | −12.161 | 51.062 | 46.041 | 1.00 | 43.86 | C |
| ATOM | 2226 | CG1 | ILE | A | 308 | −11.351 | 49.962 | 46.724 | 1.00 | 46.74 | C |
| ATOM | 2227 | CG2 | ILE | A | 308 | −12.005 | 52.349 | 46.818 | 1.00 | 45.83 | C |
| ATOM | 2228 | CD1 | ILE | A | 308 | −9.877 | 50.262 | 46.826 | 1.00 | 44.60 | C |
| ATOM | 2229 | N | THR | A | 309 | −15.631 | 52.033 | 45.694 | 1.00 | 51.53 | N |
| ATOM | 2230 | CA | THR | A | 309 | −16.482 | 53.040 | 45.056 | 1.00 | 60.98 | C |
| ATOM | 2231 | C | THR | A | 309 | −17.043 | 54.066 | 46.042 | 1.00 | 60.93 | C |
| ATOM | 2232 | O | THR | A | 309 | −17.130 | 55.257 | 45.734 | 1.00 | 54.94 | O |
| ATOM | 2233 | CB | THR | A | 309 | −17.674 | 52.386 | 44.317 | 1.00 | 61.59 | C |
| ATOM | 2234 | OG1 | THR | A | 309 | −18.255 | 51.374 | 45.148 | 1.00 | 70.08 | O |
| ATOM | 2235 | CG2 | THR | A | 309 | −17.224 | 51.776 | 43.000 | 1.00 | 62.62 | C |
| ATOM | 2236 | N | LYS | A | 310 | −17.422 | 53.594 | 47.224 | 1.00 | 63.16 | N |
| ATOM | 2237 | CA | LYS | A | 310 | −17.984 | 54.446 | 48.263 | 1.00 | 60.89 | C |

APPENDIX A-continued

| ATOM | 2238 | C | LYS | A | 310 | −17.239 | 55.756 | 48.477 | 1.00 | 61.93 | C |
|---|---|---|---|---|---|---|---|---|---|---|---|
| ATOM | 2239 | O | LYS | A | 310 | −17.822 | 56.831 | 48.340 | 1.00 | 61.75 | O |
| ATOM | 2240 | CB | LYS | A | 310 | −18.045 | 53.677 | 49.579 | 1.00 | 70.76 | C |
| ATOM | 2241 | CG | LYS | A | 310 | −19.330 | 52.901 | 49.784 | 1.00 | 81.65 | C |
| ATOM | 2242 | CD | LYS | A | 310 | −20.496 | 53.859 | 49.936 | 1.00 | 91.96 | C |
| ATOM | 2243 | CE | LYS | A | 310 | −21.770 | 53.138 | 50.330 | 1.00 | 97.34 | C |
| ATOM | 2244 | NZ | LYS | A | 310 | −22.882 | 54.108 | 50.552 | 1.00 | 101.10 | N |
| ATOM | 2245 | N | VAL | A | 311 | −15.955 | 55.658 | 48.815 | 1.00 | 63.63 | N |
| ATOM | 2246 | CA | VAL | A | 311 | −15.116 | 56.829 | 49.068 | 1.00 | 62.16 | C |
| ATOM | 2247 | C | VAL | A | 311 | −15.131 | 57.872 | 47.956 | 1.00 | 65.36 | C |
| ATOM | 2248 | O | VAL | A | 311 | −14.858 | 59.045 | 48.202 | 1.00 | 73.47 | O |
| ATOM | 2249 | CB | VAL | A | 311 | −13.655 | 56.409 | 49.347 | 1.00 | 59.63 | C |
| ATOM | 2250 | CG1 | VAL | A | 311 | −12.733 | 57.612 | 49.300 | 1.00 | 63.96 | C |
| ATOM | 2251 | CG2 | VAL | A | 311 | −13.570 | 55.774 | 50.715 | 1.00 | 72.37 | C |
| ATOM | 2252 | N | PHE | A | 312 | −15.456 | 57.455 | 46.737 | 1.00 | 64.39 | N |
| ATOM | 2253 | CA | PHE | A | 312 | −15.500 | 58.376 | 45.604 | 1.00 | 62.95 | C |
| ATOM | 2254 | C | PHE | A | 312 | −16.898 | 58.954 | 45.372 | 1.00 | 65.31 | C |
| ATOM | 2255 | O | PHE | A | 312 | −17.077 | 59.841 | 44.530 | 1.00 | 64.70 | O |
| ATOM | 2256 | CB | PHE | A | 312 | −15.050 | 57.662 | 44.329 | 1.00 | 65.66 | C |
| ATOM | 2257 | CG | PHE | A | 312 | −13.579 | 57.363 | 44.276 | 1.00 | 71.31 | C |
| ATOM | 2258 | CD1 | PHE | A | 312 | −12.653 | 58.384 | 44.084 | 1.00 | 72.83 | C |
| ATOM | 2259 | CD2 | PHE | A | 312 | −13.117 | 56.054 | 44.394 | 1.00 | 69.18 | C |
| ATOM | 2260 | CE1 | PHE | A | 312 | −11.289 | 58.106 | 44.008 | 1.00 | 70.60 | C |
| ATOM | 2261 | CE2 | PHE | A | 312 | −11.756 | 55.767 | 44.321 | 1.00 | 65.97 | C |
| ATOM | 2262 | CZ | PHE | A | 312 | −10.840 | 56.793 | 44.126 | 1.00 | 62.86 | C |
| ATOM | 2263 | N | SER | A | 313 | −17.881 | 58.456 | 46.122 | 1.00 | 67.37 | N |
| ATOM | 2264 | CA | SER | A | 313 | −19.270 | 58.892 | 45.965 | 1.00 | 71.15 | C |
| ATOM | 2265 | C | SER | A | 313 | −19.766 | 59.922 | 46.968 | 1.00 | 71.63 | C |
| ATOM | 2266 | O | SER | A | 313 | −19.070 | 60.278 | 47.921 | 1.00 | 77.36 | O |
| ATOM | 2267 | CB | SER | A | 313 | −20.208 | 57.684 | 46.028 | 1.00 | 67.93 | C |
| ATOM | 2268 | OG | SER | A | 313 | −20.235 | 57.144 | 47.339 | 1.00 | 58.09 | O |
| ATOM | 2269 | N | ASN | A | 314 | −20.990 | 60.390 | 46.733 | 1.00 | 68.17 | N |
| ATOM | 2270 | CA | ASN | A | 314 | −21.635 | 61.358 | 47.607 | 1.00 | 67.10 | C |
| ATOM | 2271 | C | ASN | A | 314 | −22.216 | 60.612 | 48.799 | 1.00 | 74.03 | C |
| ATOM | 2272 | O | ASN | A | 314 | −23.195 | 61.044 | 49.413 | 1.00 | 75.57 | O |
| ATOM | 2273 | CB | ASN | A | 314 | −22.749 | 62.091 | 46.868 | 1.00 | 61.19 | C |
| ATOM | 2274 | CG | ASN | A | 314 | −22.220 | 63.067 | 45.854 | 1.00 | 61.74 | C |
| ATOM | 2275 | OD1 | ASN | A | 314 | −21.477 | 63.986 | 46.194 | 1.00 | 70.92 | O |
| ATOM | 2276 | ND2 | ASN | A | 314 | −22.598 | 62.877 | 44.597 | 1.00 | 70.23 | N |
| ATOM | 2277 | N | GLY | A | 315 | −21.600 | 59.476 | 49.107 | 1.00 | 77.57 | N |
| ATOM | 2278 | CA | GLY | A | 315 | −22.032 | 58.665 | 50.226 | 1.00 | 73.69 | C |
| ATOM | 2279 | C | GLY | A | 315 | −20.807 | 58.235 | 50.998 | 1.00 | 68.13 | C |
| ATOM | 2280 | O | GLY | A | 315 | −20.879 | 57.420 | 51.914 | 1.00 | 74.41 | O |
| ATOM | 2281 | N | ALA | A | 316 | −19.666 | 58.789 | 50.612 | 1.00 | 64.92 | N |
| ATOM | 2282 | CA | ALA | A | 316 | −18.415 | 58.462 | 51.268 | 1.00 | 65.46 | C |
| ATOM | 2283 | C | ALA | A | 316 | −18.447 | 59.002 | 52.688 | 1.00 | 65.04 | C |
| ATOM | 2284 | O | ALA | A | 316 | −18.976 | 60.086 | 52.930 | 1.00 | 64.27 | O |
| ATOM | 2285 | CB | ALA | A | 316 | −17.261 | 59.072 | 50.502 | 1.00 | 67.17 | C |
| ATOM | 2286 | N | ASP | A | 317 | −17.889 | 58.242 | 53.626 | 1.00 | 66.34 | N |
| ATOM | 2287 | CA | ASP | A | 317 | −17.852 | 58.664 | 55.021 | 1.00 | 66.14 | C |
| ATOM | 2288 | C | ASP | A | 317 | −16.420 | 58.906 | 55.481 | 1.00 | 67.88 | C |
| ATOM | 2289 | O | ASP | A | 317 | −15.668 | 57.961 | 55.723 | 1.00 | 65.92 | O |
| ATOM | 2290 | CB | ASP | A | 317 | −18.499 | 57.613 | 55.918 | 1.00 | 68.99 | C |
| ATOM | 2291 | CG | ASP | A | 317 | −18.535 | 58.039 | 57.367 | 1.00 | 74.44 | C |
| ATOM | 2292 | OD1 | ASP | A | 317 | −19.099 | 59.116 | 57.643 | 1.00 | 79.76 | O |
| ATOM | 2293 | OD2 | ASP | A | 317 | −18.001 | 57.308 | 58.229 | 1.00 | 77.39 | O |
| ATOM | 2294 | N | LEU | A | 318 | −16.048 | 60.178 | 55.599 | 1.00 | 69.44 | N |
| ATOM | 2295 | CA | LEU | A | 318 | −14.704 | 60.547 | 56.028 | 1.00 | 62.34 | C |
| ATOM | 2296 | C | LEU | A | 318 | −14.715 | 61.191 | 57.415 | 1.00 | 61.50 | C |
| ATOM | 2297 | O | LEU | A | 318 | −13.875 | 62.033 | 57.723 | 1.00 | 58.42 | O |
| ATOM | 2298 | CB | LEU | A | 318 | −14.075 | 61.496 | 55.002 | 1.00 | 64.47 | C |
| ATOM | 2299 | CG | LEU | A | 318 | −13.875 | 60.913 | 53.595 | 1.00 | 64.14 | C |
| ATOM | 2300 | CD1 | LEU | A | 318 | −13.391 | 61.985 | 52.646 | 1.00 | 66.95 | C |
| ATOM | 2301 | CD2 | LEU | A | 318 | −12.872 | 59.779 | 53.650 | 1.00 | 69.09 | C |
| ATOM | 2302 | N | SER | A | 319 | −15.670 | 60.780 | 58.247 | 1.00 | 63.67 | N |
| ATOM | 2303 | CA | SER | A | 319 | −15.811 | 61.298 | 59.606 | 1.00 | 62.41 | C |
| ATOM | 2304 | C | SER | A | 319 | −14.494 | 61.260 | 60.367 | 1.00 | 68.63 | C |
| ATOM | 2305 | O | SER | A | 319 | −14.203 | 62.161 | 61.154 | 1.00 | 72.23 | O |
| ATOM | 2306 | CB | SER | A | 319 | −16.837 | 60.475 | 60.383 | 1.00 | 62.02 | C |
| ATOM | 2307 | OG | SER | A | 319 | −18.041 | 60.357 | 59.658 | 1.00 | 70.29 | O |
| ATOM | 2308 | N | GLY | A | 320 | −13.714 | 60.206 | 60.137 | 1.00 | 66.38 | N |
| ATOM | 2309 | CA | GLY | A | 320 | −12.436 | 60.046 | 60.813 | 1.00 | 68.87 | C |
| ATOM | 2310 | C | GLY | A | 320 | −11.440 | 61.173 | 60.598 | 1.00 | 72.67 | C |
| ATOM | 2311 | O | GLY | A | 320 | −10.510 | 61.353 | 61.391 | 1.00 | 70.78 | O |
| ATOM | 2312 | N | VAL | A | 321 | −11.627 | 61.931 | 59.522 | 1.00 | 72.14 | N |
| ATOM | 2313 | CA | VAL | A | 321 | −10.739 | 63.041 | 59.212 | 1.00 | 67.31 | C |
| ATOM | 2314 | C | VAL | A | 321 | −11.257 | 64.321 | 59.869 | 1.00 | 68.60 | C |
| ATOM | 2315 | O | VAL | A | 321 | −10.533 | 64.968 | 60.627 | 1.00 | 66.77 | O |
| ATOM | 2316 | CB | VAL | A | 321 | −10.627 | 63.248 | 57.682 | 1.00 | 61.84 | C |
| ATOM | 2317 | CG1 | VAL | A | 321 | −9.602 | 64.318 | 57.372 | 1.00 | 59.66 | C |

APPENDIX A-continued

| ATOM | 2318 | CG2 | VAL | A | 321 | −10.239 | 61.945 | 57.015 | 1.00 | 54.74 | C |
|---|---|---|---|---|---|---|---|---|---|---|---|
| ATOM | 2319 | N | THR | A | 322 | −12.512 | 64.672 | 59.591 | 1.00 | 69.68 | N |
| ATOM | 2320 | CA | THR | A | 322 | −13.112 | 65.878 | 60.158 | 1.00 | 69.88 | C |
| ATOM | 2321 | C | THR | A | 322 | −14.623 | 65.752 | 60.376 | 1.00 | 69.10 | C |
| ATOM | 2322 | O | THR | A | 322 | −15.353 | 65.289 | 59.497 | 1.00 | 66.53 | O |
| ATOM | 2323 | CB | THR | A | 322 | −12.848 | 67.100 | 59.251 | 1.00 | 72.46 | C |
| ATOM | 2324 | OG1 | THR | A | 322 | −13.196 | 68.304 | 59.949 | 1.00 | 78.22 | O |
| ATOM | 2325 | CG2 | THR | A | 322 | −13.674 | 67.001 | 57.970 | 1.00 | 79.99 | C |
| ATOM | 2326 | N | GLU | A | 323 | −15.078 | 66.174 | 61.554 | 1.00 | 74.84 | N |
| ATOM | 2327 | CA | GLU | A | 323 | −16.495 | 66.132 | 61.916 | 1.00 | 76.80 | C |
| ATOM | 2328 | C | GLU | A | 323 | −17.231 | 67.283 | 61.234 | 1.00 | 80.65 | C |
| ATOM | 2329 | O | GLU | A | 323 | −18.457 | 67.294 | 61.179 | 1.00 | 82.56 | O |
| ATOM | 2330 | CB | GLU | A | 323 | −16.670 | 66.291 | 63.430 | 1.00 | 83.11 | C |
| ATOM | 2331 | CG | GLU | A | 323 | −15.746 | 65.445 | 64.293 | 1.00 | 95.95 | C |
| ATOM | 2332 | CD | GLU | A | 323 | −16.176 | 63.994 | 64.384 | 1.00 | 104.08 | C |
| ATOM | 2333 | OE1 | GLU | A | 323 | −16.210 | 63.312 | 63.335 | 1.00 | 109.77 | O |
| ATOM | 2334 | OE2 | GLU | A | 323 | −16.477 | 63.535 | 65.509 | 1.00 | 96.33 | O |
| ATOM | 2335 | N | GLU | A | 324 | −16.469 | 68.253 | 60.732 | 1.00 | 88.84 | N |
| ATOM | 2336 | CA | GLU | A | 324 | −17.013 | 69.439 | 60.066 | 1.00 | 91.54 | C |
| ATOM | 2337 | C | GLU | A | 324 | −18.110 | 69.102 | 59.061 | 1.00 | 87.24 | C |
| ATOM | 2338 | O | GLU | A | 324 | −19.245 | 68.816 | 59.438 | 1.00 | 86.38 | O |
| ATOM | 2339 | CB | GLU | A | 324 | −15.886 | 70.199 | 59.355 | 1.00 | 101.20 | C |
| ATOM | 2340 | CG | GLU | A | 324 | −15.822 | 71.692 | 59.663 | 1.00 | 112.44 | C |
| ATOM | 2341 | CD | GLU | A | 324 | −15.591 | 71.976 | 61.137 | 1.00 | 121.86 | C |
| ATOM | 2342 | OE1 | GLU | A | 324 | −16.539 | 71.804 | 61.935 | 1.00 | 124.19 | O |
| ATOM | 2343 | OE2 | GLU | A | 324 | −14.457 | 72.364 | 61.500 | 1.00 | 122.98 | O |
| ATOM | 2344 | N | ALA | A | 325 | −17.769 | 69.154 | 57.780 | 1.00 | 83.34 | N |
| ATOM | 2345 | CA | ALA | A | 325 | −18.725 | 68.844 | 56.729 | 1.00 | 79.05 | C |
| ATOM | 2346 | C | ALA | A | 325 | −18.378 | 67.484 | 56.157 | 1.00 | 78.43 | C |
| ATOM | 2347 | O | ALA | A | 325 | −17.284 | 66.965 | 56.388 | 1.00 | 75.68 | O |
| ATOM | 2348 | CB | ALA | A | 325 | −18.671 | 69.902 | 55.628 | 1.00 | 71.37 | C |
| ATOM | 2349 | N | PRO | A | 326 | −19.315 | 66.877 | 55.414 | 1.00 | 80.66 | N |
| ATOM | 2350 | CA | PRO | A | 326 | −19.062 | 65.566 | 54.817 | 1.00 | 80.26 | C |
| ATOM | 2351 | C | PRO | A | 326 | −18.078 | 65.731 | 53.658 | 1.00 | 77.41 | C |
| ATOM | 2352 | O | PRO | A | 326 | −18.054 | 66.778 | 53.000 | 1.00 | 70.59 | O |
| ATOM | 2353 | CB | PRO | A | 326 | −20.455 | 65.125 | 54.368 | 1.00 | 80.14 | C |
| ATOM | 2354 | CG | PRO | A | 326 | −21.098 | 66.417 | 53.994 | 1.00 | 78.08 | C |
| ATOM | 2355 | CD | PRO | A | 326 | −20.689 | 67.327 | 55.128 | 1.00 | 78.16 | C |
| ATOM | 2356 | N | LEU | A | 327 | −17.269 | 64.704 | 53.415 | 1.00 | 77.11 | N |
| ATOM | 2357 | CA | LEU | A | 327 | −16.272 | 64.757 | 52.350 | 1.00 | 75.03 | C |
| ATOM | 2358 | C | LEU | A | 327 | −16.288 | 63.524 | 51.443 | 1.00 | 71.33 | C |
| ATOM | 2359 | O | LEU | A | 327 | −17.065 | 62.591 | 51.651 | 1.00 | 74.27 | O |
| ATOM | 2360 | CB | LEU | A | 327 | −14.874 | 64.920 | 52.965 | 1.00 | 68.23 | C |
| ATOM | 2361 | CG | LEU | A | 327 | −14.627 | 66.119 | 53.887 | 1.00 | 62.62 | C |
| ATOM | 2362 | CD1 | LEU | A | 327 | −13.240 | 66.026 | 54.500 | 1.00 | 56.94 | C |
| ATOM | 2363 | CD2 | LEU | A | 327 | −14.774 | 67.406 | 53.101 | 1.00 | 54.97 | C |
| ATOM | 2364 | N | LYS | A | 328 | −15.420 | 63.544 | 50.435 | 1.00 | 67.28 | N |
| ATOM | 2365 | CA | LYS | A | 328 | −15.277 | 62.447 | 49.481 | 1.00 | 66.52 | C |
| ATOM | 2366 | C | LYS | A | 328 | −14.063 | 62.732 | 48.598 | 1.00 | 67.67 | C |
| ATOM | 2367 | O | LYS | A | 328 | −13.580 | 63.858 | 48.549 | 1.00 | 73.60 | O |
| ATOM | 2368 | CB | LYS | A | 328 | −16.517 | 62.331 | 48.594 | 1.00 | 58.01 | C |
| ATOM | 2369 | CG | LYS | A | 328 | −16.651 | 63.460 | 47.602 | 1.00 | 51.35 | C |
| ATOM | 2370 | CD | LYS | A | 328 | −17.675 | 63.139 | 46.549 | 1.00 | 51.66 | C |
| ATOM | 2371 | CE | LYS | A | 328 | −17.763 | 64.257 | 45.528 | 1.00 | 57.09 | C |
| ATOM | 2372 | NZ | LYS | A | 328 | −18.731 | 63.939 | 44.442 | 1.00 | 58.00 | N |
| ATOM | 2373 | N | LEU | A | 329 | −13.570 | 61.712 | 47.906 | 1.00 | 68.53 | N |
| ATOM | 2374 | CA | LEU | A | 329 | −12.425 | 61.878 | 47.014 | 1.00 | 68.19 | C |
| ATOM | 2375 | C | LEU | A | 329 | −12.902 | 62.350 | 45.641 | 1.00 | 71.15 | C |
| ATOM | 2376 | O | LEU | A | 329 | −13.811 | 61.757 | 45.055 | 1.00 | 77.26 | O |
| ATOM | 2377 | CB | LEU | A | 329 | −11.672 | 60.550 | 46.860 | 1.00 | 61.73 | C |
| ATOM | 2378 | CG | LEU | A | 329 | −10.375 | 60.318 | 47.640 | 1.00 | 56.51 | C |
| ATOM | 2379 | CD1 | LEU | A | 329 | −10.583 | 60.611 | 49.111 | 1.00 | 61.27 | C |
| ATOM | 2380 | CD2 | LEU | A | 329 | −9.918 | 58.884 | 47.435 | 1.00 | 46.07 | C |
| ATOM | 2381 | N | SER | A | 330 | −12.299 | 63.416 | 45.126 | 1.00 | 68.84 | N |
| ATOM | 2382 | CA | SER | A | 330 | −12.687 | 63.914 | 43.812 | 1.00 | 75.77 | C |
| ATOM | 2383 | C | SER | A | 330 | −11.930 | 63.132 | 42.731 | 1.00 | 79.17 | C |
| ATOM | 2384 | O | SER | A | 330 | −12.332 | 63.104 | 41.565 | 1.00 | 79.75 | O |
| ATOM | 2385 | CB | SER | A | 330 | −12.387 | 65.412 | 43.693 | 1.00 | 70.03 | C |
| ATOM | 2386 | OG | SER | A | 330 | −10.995 | 65.656 | 43.653 | 1.00 | 84.36 | O |
| ATOM | 2387 | N | LYS | A | 331 | −10.835 | 62.491 | 43.135 | 1.00 | 76.89 | N |
| ATOM | 2388 | CA | LYS | A | 331 | −10.017 | 61.695 | 42.226 | 1.00 | 69.40 | C |
| ATOM | 2389 | C | LYS | A | 331 | −8.808 | 61.078 | 42.926 | 1.00 | 69.70 | C |
| ATOM | 2390 | O | LYS | A | 331 | −8.450 | 61.463 | 44.043 | 1.00 | 66.62 | O |
| ATOM | 2391 | CB | LYS | A | 331 | −9.537 | 62.545 | 41.044 | 1.00 | 65.33 | C |
| ATOM | 2392 | CG | LYS | A | 331 | −8.831 | 63.839 | 41.425 | 1.00 | 58.02 | C |
| ATOM | 2393 | CD | LYS | A | 331 | −7.846 | 64.243 | 40.340 | 1.00 | 56.19 | C |
| ATOM | 2394 | CE | LYS | A | 331 | −7.907 | 65.729 | 40.035 | 1.00 | 61.07 | C |
| ATOM | 2395 | NZ | LYS | A | 331 | −7.667 | 66.555 | 41.237 | 1.00 | 55.30 | N |
| ATOM | 2396 | N | ALA | A | 332 | −8.186 | 60.111 | 42.257 | 1.00 | 66.32 | N |
| ATOM | 2397 | CA | ALA | A | 332 | −7.008 | 59.435 | 42.788 | 1.00 | 62.22 | C |

APPENDIX A-continued

| | | | | | | | | | | | |
|---|---|---|---|---|---|---|---|---|---|---|---|
| ATOM | 2398 | C | ALA | A | 332 | −5.961 | 59.309 | 41.681 | 1.00 | 62.65 | C |
| ATOM | 2399 | O | ALA | A | 332 | −5.978 | 58.354 | 40.906 | 1.00 | 64.38 | O |
| ATOM | 2400 | CB | ALA | A | 332 | −7.388 | 58.056 | 43.320 | 1.00 | 57.80 | C |
| ATOM | 2401 | N | VAL | A | 333 | −5.053 | 60.281 | 41.616 | 1.00 | 61.39 | N |
| ATOM | 2402 | CA | VAL | A | 333 | −4.006 | 60.297 | 40.598 | 1.00 | 56.27 | C |
| ATOM | 2403 | C | VAL | A | 333 | −2.714 | 59.620 | 41.033 | 1.00 | 55.81 | C |
| ATOM | 2404 | O | VAL | A | 333 | −2.188 | 59.888 | 42.113 | 1.00 | 53.94 | O |
| ATOM | 2405 | CB | VAL | A | 333 | −3.657 | 61.738 | 40.181 | 1.00 | 52.06 | C |
| ATOM | 2406 | CG1 | VAL | A | 333 | −2.629 | 61.717 | 39.066 | 1.00 | 44.80 | C |
| ATOM | 2407 | CG2 | VAL | A | 333 | −4.909 | 62.468 | 39.739 | 1.00 | 50.28 | C |
| ATOM | 2408 | N | HIS | A | 334 | −2.204 | 58.743 | 40.174 | 1.00 | 56.26 | N |
| ATOM | 2409 | CA | HIS | A | 334 | −0.961 | 58.034 | 40.443 | 1.00 | 51.03 | C |
| ATOM | 2410 | C | HIS | A | 334 | −0.022 | 58.193 | 39.260 | 1.00 | 50.03 | C |
| ATOM | 2411 | O | HIS | A | 334 | −0.431 | 58.066 | 38.108 | 1.00 | 51.68 | O |
| ATOM | 2412 | CB | HIS | A | 334 | −1.218 | 56.539 | 40.680 | 1.00 | 48.51 | C |
| ATOM | 2413 | CG | HIS | A | 334 | 0.032 | 55.736 | 40.884 | 1.00 | 52.26 | C |
| ATOM | 2414 | ND1 | HIS | A | 334 | 0.909 | 55.970 | 41.922 | 1.00 | 52.28 | N |
| ATOM | 2415 | CD2 | HIS | A | 334 | 0.562 | 54.713 | 40.169 | 1.00 | 52.43 | C |
| ATOM | 2416 | CE1 | HIS | A | 334 | 1.926 | 55.130 | 41.838 | 1.00 | 53.16 | C |
| ATOM | 2417 | NE2 | HIS | A | 334 | 1.740 | 54.357 | 40.782 | 1.00 | 51.17 | N |
| ATOM | 2418 | N | LYS | A | 335 | 1.238 | 58.492 | 39.546 | 1.00 | 52.10 | N |
| ATOM | 2419 | CA | LYS | A | 335 | 2.224 | 58.621 | 38.489 | 1.00 | 46.83 | C |
| ATOM | 2420 | C | LYS | A | 335 | 3.511 | 57.910 | 38.908 | 1.00 | 47.60 | C |
| ATOM | 2421 | O | LYS | A | 335 | 4.002 | 58.076 | 40.026 | 1.00 | 47.49 | O |
| ATOM | 2422 | CB | LYS | A | 335 | 2.519 | 60.088 | 38.182 | 1.00 | 45.82 | C |
| ATOM | 2423 | CG | LYS | A | 335 | 3.349 | 60.240 | 36.921 | 1.00 | 51.73 | C |
| ATOM | 2424 | CD | LYS | A | 335 | 3.938 | 61.622 | 36.766 | 1.00 | 49.93 | C |
| ATOM | 2425 | CE | LYS | A | 335 | 4.864 | 61.659 | 35.559 | 1.00 | 60.21 | C |
| ATOM | 2426 | NZ | LYS | A | 335 | 5.614 | 62.939 | 35.441 | 1.00 | 72.47 | N |
| ATOM | 2427 | N | ALA | A | 336 | 4.044 | 57.100 | 38.007 | 1.00 | 40.39 | N |
| ATOM | 2428 | CA | ALA | A | 336 | 5.269 | 56.373 | 38.278 | 1.00 | 43.74 | C |
| ATOM | 2429 | C | ALA | A | 336 | 6.203 | 56.578 | 37.085 | 1.00 | 49.83 | C |
| ATOM | 2430 | O | ALA | A | 336 | 5.747 | 56.721 | 35.954 | 1.00 | 45.00 | O |
| ATOM | 2431 | CB | ALA | A | 336 | 4.958 | 54.900 | 38.475 | 1.00 | 37.82 | C |
| ATOM | 2432 | N | VAL | A | 337 | 7.507 | 56.611 | 37.336 | 1.00 | 51.58 | N |
| ATOM | 2433 | CA | VAL | A | 337 | 8.466 | 56.810 | 36.260 | 1.00 | 51.06 | C |
| ATOM | 2434 | C | VAL | A | 337 | 9.654 | 55.872 | 36.415 | 1.00 | 57.58 | C |
| ATOM | 2435 | O | VAL | A | 337 | 10.284 | 55.820 | 37.475 | 1.00 | 55.63 | O |
| ATOM | 2436 | CB | VAL | A | 337 | 8.964 | 58.253 | 36.240 | 1.00 | 46.14 | C |
| ATOM | 2437 | CG1 | VAL | A | 337 | 9.783 | 58.500 | 34.993 | 1.00 | 63.65 | C |
| ATOM | 2438 | CG2 | VAL | A | 337 | 7.789 | 59.193 | 36.294 | 1.00 | 51.43 | C |
| ATOM | 2439 | N | LEU | A | 338 | 9.956 | 55.143 | 35.344 | 1.00 | 56.99 | N |
| ATOM | 2440 | CA | LEU | A | 338 | 11.047 | 54.176 | 35.338 | 1.00 | 53.20 | C |
| ATOM | 2441 | C | LEU | A | 338 | 12.158 | 54.472 | 34.338 | 1.00 | 53.43 | C |
| ATOM | 2442 | O | LEU | A | 338 | 11.910 | 54.932 | 33.226 | 1.00 | 55.84 | O |
| ATOM | 2443 | CB | LEU | A | 338 | 10.494 | 52.778 | 35.042 | 1.00 | 56.02 | C |
| ATOM | 2444 | CG | LEU | A | 338 | 11.508 | 51.667 | 34.733 | 1.00 | 60.64 | C |
| ATOM | 2445 | CD1 | LEU | A | 338 | 12.211 | 51.246 | 36.015 | 1.00 | 57.51 | C |
| ATOM | 2446 | CD2 | LEU | A | 338 | 10.803 | 50.477 | 34.098 | 1.00 | 52.05 | C |
| ATOM | 2447 | N | THR | A | 339 | 13.388 | 54.190 | 34.756 | 1.00 | 59.14 | N |
| ATOM | 2448 | CA | THR | A | 339 | 14.568 | 54.357 | 33.912 | 1.00 | 58.17 | C |
| ATOM | 2449 | C | THR | A | 339 | 15.453 | 53.134 | 34.153 | 1.00 | 52.16 | C |
| ATOM | 2450 | O | THR | A | 339 | 15.823 | 52.840 | 35.290 | 1.00 | 45.55 | O |
| ATOM | 2451 | CB | THR | A | 339 | 15.363 | 55.648 | 34.254 | 1.00 | 59.52 | C |
| ATOM | 2452 | OG1 | THR | A | 339 | 14.544 | 56.798 | 34.011 | 1.00 | 68.10 | O |
| ATOM | 2453 | CG2 | THR | A | 339 | 16.606 | 55.758 | 33.384 | 1.00 | 52.12 | C |
| ATOM | 2454 | N | ILE | A | 340 | 15.749 | 52.406 | 33.080 | 1.00 | 53.00 | N |
| ATOM | 2455 | CA | ILE | A | 340 | 16.590 | 51.214 | 33.144 | 1.00 | 56.88 | C |
| ATOM | 2456 | C | ILE | A | 340 | 17.719 | 51.345 | 32.136 | 1.00 | 60.90 | C |
| ATOM | 2457 | O | ILE | A | 340 | 17.484 | 51.336 | 30.931 | 1.00 | 60.54 | O |
| ATOM | 2458 | CB | ILE | A | 340 | 15.803 | 49.913 | 32.805 | 1.00 | 49.74 | C |
| ATOM | 2459 | CG1 | ILE | A | 340 | 14.876 | 49.535 | 33.959 | 1.00 | 51.53 | C |
| ATOM | 2460 | CG2 | ILE | A | 340 | 16.768 | 48.770 | 32.535 | 1.00 | 44.53 | C |
| ATOM | 2461 | CD1 | ILE | A | 340 | 14.226 | 48.182 | 33.783 | 1.00 | 37.74 | C |
| ATOM | 2462 | N | ASP | A | 341 | 18.944 | 51.482 | 32.632 | 1.00 | 67.25 | N |
| ATOM | 2463 | CA | ASP | A | 341 | 20.106 | 51.589 | 31.761 | 1.00 | 67.33 | C |
| ATOM | 2464 | C | ASP | A | 341 | 21.090 | 50.494 | 32.131 | 1.00 | 66.22 | C |
| ATOM | 2465 | O | ASP | A | 341 | 20.724 | 49.522 | 32.800 | 1.00 | 65.22 | O |
| ATOM | 2466 | CB | ASP | A | 341 | 20.773 | 52.964 | 31.886 | 1.00 | 69.27 | C |
| ATOM | 2467 | CG | ASP | A | 341 | 20.981 | 53.387 | 33.324 | 1.00 | 79.30 | C |
| ATOM | 2468 | OD1 | ASP | A | 341 | 21.349 | 52.527 | 34.153 | 1.00 | 86.81 | O |
| ATOM | 2469 | OD2 | ASP | A | 341 | 20.789 | 54.586 | 33.625 | 1.00 | 78.94 | O |
| ATOM | 2470 | N | GLU | A | 342 | 22.335 | 50.650 | 31.696 | 1.00 | 65.42 | N |
| ATOM | 2471 | CA | GLU | A | 342 | 23.363 | 49.661 | 31.980 | 1.00 | 65.59 | C |
| ATOM | 2472 | C | GLU | A | 342 | 23.879 | 49.713 | 33.416 | 1.00 | 68.38 | C |
| ATOM | 2473 | O | GLU | A | 342 | 24.302 | 48.691 | 33.962 | 1.00 | 68.97 | O |
| ATOM | 2474 | CB | GLU | A | 342 | 24.529 | 49.816 | 31.004 | 1.00 | 60.34 | C |
| ATOM | 2475 | CG | GLU | A | 342 | 24.656 | 51.185 | 30.349 | 1.00 | 66.98 | C |
| ATOM | 2476 | CD | GLU | A | 342 | 23.872 | 51.284 | 29.052 | 1.00 | 67.00 | C |
| ATOM | 2477 | OE1 | GLU | A | 342 | 23.857 | 50.292 | 28.295 | 1.00 | 65.06 | O |

APPENDIX A-continued

| ATOM | 2478 | OE2 | GLU | A | 342 | 23.285 | 52.352 | 28.780 | 1.00 | 69.45 | O |
|------|------|-----|-----|---|-----|--------|--------|--------|------|-------|---|
| ATOM | 2479 | N | LYS | A | 343 | 23.835 | 50.896 | 34.027 | 1.00 | 67.92 | N |
| ATOM | 2480 | CA | LYS | A | 343 | 24.300 | 51.074 | 35.404 | 1.00 | 62.32 | C |
| ATOM | 2481 | C | LYS | A | 343 | 23.366 | 50.381 | 36.384 | 1.00 | 62.69 | C |
| ATOM | 2482 | O | LYS | A | 343 | 23.811 | 49.731 | 37.331 | 1.00 | 64.19 | O |
| ATOM | 2483 | CB | LYS | A | 343 | 24.381 | 52.565 | 35.754 | 1.00 | 62.39 | C |
| ATOM | 2484 | CG | LYS | A | 343 | 25.119 | 53.411 | 34.721 | 1.00 | 80.86 | C |
| ATOM | 2485 | CD | LYS | A | 343 | 26.509 | 52.855 | 34.432 | 1.00 | 93.43 | C |
| ATOM | 2486 | CE | LYS | A | 343 | 27.167 | 53.569 | 33.260 | 1.00 | 99.01 | C |
| ATOM | 2487 | NZ | LYS | A | 343 | 28.471 | 52.947 | 32.886 | 1.00 | 94.47 | N |
| ATOM | 2488 | N | GLY | A | 344 | 22.066 | 50.532 | 36.145 | 1.00 | 68.24 | N |
| ATOM | 2489 | CA | GLY | A | 344 | 21.062 | 49.928 | 37.005 | 1.00 | 62.18 | C |
| ATOM | 2490 | C | GLY | A | 344 | 19.662 | 50.445 | 36.720 | 1.00 | 56.63 | C |
| ATOM | 2491 | O | GLY | A | 344 | 19.283 | 50.635 | 35.560 | 1.00 | 55.85 | O |
| ATOM | 2492 | N | THR | A | 345 | 18.895 | 50.680 | 37.781 | 1.00 | 46.13 | N |
| ATOM | 2493 | CA | THR | A | 345 | 17.527 | 51.164 | 37.645 | 1.00 | 47.56 | C |
| ATOM | 2494 | C | THR | A | 345 | 17.168 | 52.274 | 38.629 | 1.00 | 52.31 | C |
| ATOM | 2495 | O | THR | A | 345 | 17.581 | 52.263 | 39.793 | 1.00 | 50.90 | O |
| ATOM | 2496 | CB | THR | A | 345 | 16.506 | 50.016 | 37.847 | 1.00 | 51.93 | C |
| ATOM | 2497 | OG1 | THR | A | 345 | 16.650 | 49.049 | 36.800 | 1.00 | 58.62 | O |
| ATOM | 2498 | CG2 | THR | A | 345 | 15.080 | 50.556 | 37.849 | 1.00 | 49.55 | C |
| ATOM | 2499 | N | GLU | A | 346 | 16.388 | 53.232 | 38.142 | 1.00 | 56.67 | N |
| ATOM | 2500 | CA | GLU | A | 346 | 15.916 | 54.344 | 38.952 | 1.00 | 54.28 | C |
| ATOM | 2501 | C | GLU | A | 346 | 14.419 | 54.419 | 38.700 | 1.00 | 52.63 | C |
| ATOM | 2502 | O | GLU | A | 346 | 13.980 | 54.350 | 37.551 | 1.00 | 53.09 | O |
| ATOM | 2503 | CB | GLU | A | 346 | 16.581 | 55.651 | 38.529 | 1.00 | 51.46 | C |
| ATOM | 2504 | CG | GLU | A | 346 | 16.109 | 56.852 | 39.332 | 1.00 | 70.65 | C |
| ATOM | 2505 | CD | GLU | A | 346 | 16.808 | 58.134 | 38.931 | 1.00 | 78.43 | C |
| ATOM | 2506 | OE1 | GLU | A | 346 | 16.836 | 58.439 | 37.720 | 1.00 | 75.69 | O |
| ATOM | 2507 | OE2 | GLU | A | 346 | 17.324 | 58.837 | 39.826 | 1.00 | 84.47 | O |
| ATOM | 2508 | N | ALA | A | 347 | 13.640 | 54.547 | 39.771 | 1.00 | 49.36 | N |
| ATOM | 2509 | CA | ALA | A | 347 | 12.189 | 54.604 | 39.660 | 1.00 | 40.55 | C |
| ATOM | 2510 | C | ALA | A | 347 | 11.543 | 55.385 | 40.791 | 1.00 | 47.12 | C |
| ATOM | 2511 | O | ALA | A | 347 | 11.952 | 55.296 | 41.951 | 1.00 | 50.67 | O |
| ATOM | 2512 | CB | ALA | A | 347 | 11.622 | 53.196 | 39.630 | 1.00 | 38.51 | C |
| ATOM | 2513 | N | ALA | A | 348 | 10.515 | 56.144 | 40.447 | 1.00 | 47.94 | N |
| ATOM | 2514 | CA | ALA | A | 348 | 9.800 | 56.929 | 41.434 | 1.00 | 44.59 | C |
| ATOM | 2515 | C | ALA | A | 348 | 8.304 | 56.742 | 41.228 | 1.00 | 43.51 | C |
| ATOM | 2516 | O | ALA | A | 348 | 7.848 | 56.493 | 40.110 | 1.00 | 42.89 | O |
| ATOM | 2517 | CB | ALA | A | 348 | 10.171 | 58.390 | 41.300 | 1.00 | 46.21 | C |
| ATOM | 2518 | N | GLY | A | 349 | 7.553 | 56.844 | 42.319 | 1.00 | 40.83 | N |
| ATOM | 2519 | CA | GLY | A | 349 | 6.112 | 56.699 | 42.259 | 1.00 | 39.32 | C |
| ATOM | 2520 | C | GLY | A | 349 | 5.512 | 57.725 | 43.195 | 1.00 | 45.99 | C |
| ATOM | 2521 | O | GLY | A | 349 | 6.073 | 57.990 | 44.262 | 1.00 | 49.17 | O |
| ATOM | 2522 | N | ALA | A | 350 | 4.386 | 58.313 | 42.805 | 1.00 | 44.47 | N |
| ATOM | 2523 | CA | ALA | A | 350 | 3.734 | 59.320 | 43.632 | 1.00 | 43.57 | C |
| ATOM | 2524 | C | ALA | A | 350 | 2.227 | 59.196 | 43.554 | 1.00 | 51.11 | C |
| ATOM | 2525 | O | ALA | A | 350 | 1.658 | 58.990 | 42.484 | 1.00 | 55.23 | O |
| ATOM | 2526 | CB | ALA | A | 350 | 4.159 | 60.711 | 43.200 | 1.00 | 41.74 | C |
| ATOM | 2527 | N | MET | A | 351 | 1.588 | 59.330 | 44.705 | 1.00 | 59.55 | N |
| ATOM | 2528 | CA | MET | A | 351 | 0.144 | 59.229 | 44.811 | 1.00 | 63.19 | C |
| ATOM | 2529 | C | MET | A | 351 | −0.361 | 60.584 | 45.295 | 1.00 | 69.80 | C |
| ATOM | 2530 | O | MET | A | 351 | 0.186 | 61.160 | 46.236 | 1.00 | 76.01 | O |
| ATOM | 2531 | CB | MET | A | 351 | −0.201 | 58.136 | 45.821 | 1.00 | 66.28 | C |
| ATOM | 2532 | CG | MET | A | 351 | −1.644 | 57.673 | 45.830 | 1.00 | 73.91 | C |
| ATOM | 2533 | SD | MET | A | 351 | −2.033 | 56.597 | 44.452 | 1.00 | 71.07 | S |
| ATOM | 2534 | CE | MET | A | 351 | −3.622 | 57.238 | 44.003 | 1.00 | 77.40 | C |
| ATOM | 2535 | N | PHE | A | 352 | −1.400 | 61.098 | 44.650 | 1.00 | 78.08 | N |
| ATOM | 2536 | CA | PHE | A | 352 | −1.963 | 62.392 | 45.019 | 1.00 | 82.58 | C |
| ATOM | 2537 | C | PHE | A | 352 | −3.485 | 62.333 | 45.068 | 1.00 | 81.70 | C |
| ATOM | 2538 | O | PHE | A | 352 | −4.060 | 61.350 | 44.560 | 1.00 | 84.51 | O |
| ATOM | 2539 | CB | PHE | A | 352 | −1.505 | 63.455 | 44.011 | 1.00 | 92.17 | C |
| ATOM | 2540 | CG | PHE | A | 352 | −2.548 | 64.492 | 43.700 | 1.00 | 99.05 | C |
| ATOM | 2541 | CD1 | PHE | A | 352 | −2.934 | 65.427 | 44.659 | 1.00 | 99.79 | C |
| ATOM | 2542 | CD2 | PHE | A | 352 | −3.174 | 64.505 | 42.456 | 1.00 | 101.24 | C |
| ATOM | 2543 | CE1 | PHE | A | 352 | −3.934 | 66.356 | 44.385 | 1.00 | 104.69 | C |
| ATOM | 2544 | CE2 | PHE | A | 352 | −4.172 | 65.430 | 42.171 | 1.00 | 103.62 | C |
| ATOM | 2545 | CZ | PHE | A | 352 | −4.554 | 66.358 | 43.138 | 1.00 | 108.18 | C |
| ATOM | 2546 | OXT | PHE | A | 352 | −4.090 | 63.277 | 45.613 | 1.00 | 80.28 | O |
| TER | 2547 | | PHE | A | 352 | | | | | | |
| ATOM | 2548 | N | LEU | B | 353 | 50.029 | 32.289 | 26.227 | 1.00 | 95.13 | N |
| ATOM | 2549 | CA | LEU | B | 353 | 48.576 | 32.231 | 26.553 | 1.00 | 91.03 | C |
| ATOM | 2550 | C | LEU | B | 353 | 48.049 | 30.876 | 26.086 | 1.00 | 93.21 | C |
| ATOM | 2551 | O | LEU | B | 353 | 48.324 | 30.464 | 24.957 | 1.00 | 98.03 | O |
| ATOM | 2552 | CB | LEU | B | 353 | 47.848 | 33.359 | 25.822 | 1.00 | 88.05 | C |
| ATOM | 2553 | CG | LEU | B | 353 | 48.714 | 34.592 | 25.552 | 1.00 | 75.52 | C |
| ATOM | 2554 | CD1 | LEU | B | 353 | 47.947 | 35.571 | 24.693 | 1.00 | 78.37 | C |
| ATOM | 2555 | CD2 | LEU | B | 353 | 49.136 | 35.228 | 26.865 | 1.00 | 79.94 | C |
| ATOM | 2556 | N | GLU | B | 354 | 47.312 | 30.173 | 26.946 | 1.00 | 91.29 | N |
| ATOM | 2557 | CA | GLU | B | 354 | 46.767 | 28.873 | 26.561 | 1.00 | 81.27 | C |

APPENDIX A-continued

| | | | | | | | | | | |
|---|---|---|---|---|---|---|---|---|---|---|
| ATOM | 2558 | C | GLU | B | 354 | 45.293 | 29.009 | 26.202 | 1.00 | 70.33 | C |
| ATOM | 2559 | O | GLU | B | 354 | 44.487 | 29.486 | 27.001 | 1.00 | 62.24 | O |
| ATOM | 2560 | CB | GLU | B | 354 | 46.938 | 27.839 | 27.680 | 1.00 | 83.67 | C |
| ATOM | 2561 | CG | GLU | B | 354 | 45.933 | 27.943 | 28.806 | 1.00 | 91.27 | C |
| ATOM | 2562 | CD | GLU | B | 354 | 45.898 | 26.690 | 29.654 | 1.00 | 96.64 | C |
| ATOM | 2563 | OE1 | GLU | B | 354 | 46.932 | 26.370 | 30.273 | 1.00 | 105.63 | O |
| ATOM | 2564 | OE2 | GLU | B | 354 | 44.843 | 26.020 | 29.698 | 1.00 | 96.86 | O |
| ATOM | 2565 | N | ALA | B | 355 | 44.958 | 28.595 | 24.985 | 1.00 | 64.59 | N |
| ATOM | 2566 | CA | ALA | B | 355 | 43.593 | 28.670 | 24.488 | 1.00 | 60.28 | C |
| ATOM | 2567 | C | ALA | B | 355 | 42.929 | 27.304 | 24.508 | 1.00 | 63.52 | C |
| ATOM | 2568 | O | ALA | B | 355 | 43.539 | 26.301 | 24.142 | 1.00 | 72.50 | O |
| ATOM | 2569 | CB | ALA | B | 355 | 43.588 | 29.224 | 23.077 | 1.00 | 45.56 | C |
| ATOM | 2570 | N | ILE | B | 356 | 41.673 | 27.277 | 24.944 | 1.00 | 67.54 | N |
| ATOM | 2571 | CA | ILE | B | 356 | 40.893 | 26.049 | 25.016 | 1.00 | 64.16 | C |
| ATOM | 2572 | C | ILE | B | 356 | 39.570 | 26.267 | 24.287 | 1.00 | 67.55 | C |
| ATOM | 2573 | O | ILE | B | 356 | 39.162 | 27.404 | 24.051 | 1.00 | 69.17 | O |
| ATOM | 2574 | CB | ILE | B | 356 | 40.592 | 25.659 | 26.483 | 1.00 | 57.39 | C |
| ATOM | 2575 | CG1 | ILE | B | 356 | 39.745 | 26.739 | 27.150 | 1.00 | 58.27 | C |
| ATOM | 2576 | CG2 | ILE | B | 356 | 41.884 | 25.498 | 27.257 | 1.00 | 60.36 | C |
| ATOM | 2577 | CD1 | ILE | B | 356 | 39.253 | 26.359 | 28.527 | 1.00 | 73.33 | C |
| ATOM | 2578 | N | PRO | B | 357 | 38.886 | 25.180 | 23.904 | 1.00 | 72.48 | N |
| ATOM | 2579 | CA | PRO | B | 357 | 37.608 | 25.344 | 23.207 | 1.00 | 75.51 | C |
| ATOM | 2580 | C | PRO | B | 357 | 36.606 | 26.111 | 24.077 | 1.00 | 80.95 | C |
| ATOM | 2581 | O | PRO | B | 357 | 36.662 | 26.041 | 25.309 | 1.00 | 76.05 | O |
| ATOM | 2582 | CB | PRO | B | 357 | 37.186 | 23.903 | 22.926 | 1.00 | 74.28 | C |
| ATOM | 2583 | CG | PRO | B | 357 | 37.846 | 23.128 | 24.039 | 1.00 | 76.63 | C |
| ATOM | 2584 | CD | PRO | B | 357 | 39.208 | 23.756 | 24.090 | 1.00 | 73.62 | C |
| ATOM | 2585 | N | ARG | B | 358 | 35.694 | 26.837 | 23.434 | 1.00 | 86.69 | N |
| ATOM | 2586 | CA | ARG | B | 358 | 34.703 | 27.640 | 24.149 | 1.00 | 88.68 | C |
| ATOM | 2587 | C | ARG | B | 358 | 33.381 | 26.905 | 24.395 | 1.00 | 90.32 | C |
| ATOM | 2588 | O | ARG | B | 358 | 33.385 | 25.741 | 24.793 | 1.00 | 96.13 | O |
| ATOM | 2589 | CB | ARG | B | 358 | 34.442 | 28.929 | 23.376 | 1.00 | 89.72 | C |
| ATOM | 2590 | CG | ARG | B | 358 | 33.760 | 30.006 | 24.181 | 1.00 | 90.31 | C |
| ATOM | 2591 | CD | ARG | B | 358 | 32.813 | 30.773 | 23.295 | 1.00 | 88.80 | C |
| ATOM | 2592 | NE | ARG | B | 358 | 33.500 | 31.330 | 22.138 | 1.00 | 88.77 | N |
| ATOM | 2593 | CZ | ARG | B | 358 | 32.876 | 31.867 | 21.098 | 1.00 | 94.65 | C |
| ATOM | 2594 | NH1 | ARG | B | 358 | 31.551 | 31.917 | 21.073 | 1.00 | 94.75 | N |
| ATOM | 2595 | NH2 | ARG | B | 358 | 33.577 | 32.346 | 20.080 | 1.00 | 103.31 | N |
| ATOM | 2596 | N | SER | B | 359 | 32.251 | 27.577 | 24.169 | 1.00 | 88.88 | N |
| ATOM | 2597 | CA | SER | B | 359 | 30.957 | 26.938 | 24.401 | 1.00 | 84.85 | C |
| ATOM | 2598 | C | SER | B | 359 | 29.732 | 27.592 | 23.756 | 1.00 | 89.26 | C |
| ATOM | 2599 | O | SER | B | 359 | 28.649 | 27.004 | 23.768 | 1.00 | 101.29 | O |
| ATOM | 2600 | CB | SER | B | 359 | 30.701 | 26.812 | 25.903 | 1.00 | 73.54 | C |
| ATOM | 2601 | OG | SER | B | 359 | 30.391 | 28.073 | 26.461 | 1.00 | 66.56 | O |
| ATOM | 2602 | N | ILE | B | 360 | 29.878 | 28.793 | 23.205 | 1.00 | 83.46 | N |
| ATOM | 2603 | CA | ILE | B | 360 | 28.741 | 29.468 | 22.568 | 1.00 | 82.87 | C |
| ATOM | 2604 | C | ILE | B | 360 | 27.454 | 29.410 | 23.415 | 1.00 | 80.23 | C |
| ATOM | 2605 | O | ILE | B | 360 | 26.576 | 28.579 | 23.168 | 1.00 | 79.67 | O |
| ATOM | 2606 | CB | ILE | B | 360 | 28.423 | 28.845 | 21.179 | 1.00 | 71.55 | C |
| ATOM | 2607 | CG1 | ILE | B | 360 | 29.666 | 28.878 | 20.291 | 1.00 | 76.51 | C |
| ATOM | 2608 | CG2 | ILE | B | 360 | 27.293 | 29.614 | 20.506 | 1.00 | 68.52 | C |
| ATOM | 2609 | CD1 | ILE | B | 360 | 29.439 | 28.340 | 18.895 | 1.00 | 78.92 | C |
| ATOM | 2610 | N | PRO | B | 361 | 27.325 | 30.294 | 24.421 | 1.00 | 74.64 | N |
| ATOM | 2611 | CA | PRO | B | 361 | 26.123 | 30.289 | 25.261 | 1.00 | 70.59 | C |
| ATOM | 2612 | C | PRO | B | 361 | 24.891 | 30.687 | 24.451 | 1.00 | 71.77 | C |
| ATOM | 2613 | O | PRO | B | 361 | 25.011 | 31.300 | 23.390 | 1.00 | 72.63 | O |
| ATOM | 2614 | CB | PRO | B | 361 | 26.448 | 31.321 | 26.341 | 1.00 | 71.94 | C |
| ATOM | 2615 | CG | PRO | B | 361 | 27.943 | 31.345 | 26.376 | 1.00 | 67.16 | C |
| ATOM | 2616 | CD | PRO | B | 361 | 28.296 | 31.282 | 24.919 | 1.00 | 73.99 | C |
| ATOM | 2617 | N | PRO | B | 362 | 23.688 | 30.345 | 24.942 | 1.00 | 69.01 | N |
| ATOM | 2618 | CA | PRO | B | 362 | 22.448 | 30.684 | 24.235 | 1.00 | 66.98 | C |
| ATOM | 2619 | C | PRO | B | 362 | 22.038 | 32.145 | 24.449 | 1.00 | 71.15 | C |
| ATOM | 2620 | O | PRO | B | 362 | 22.334 | 32.737 | 25.490 | 1.00 | 76.44 | O |
| ATOM | 2621 | CB | PRO | B | 362 | 21.451 | 29.706 | 24.833 | 1.00 | 51.94 | C |
| ATOM | 2622 | CG | PRO | B | 362 | 21.896 | 29.652 | 26.256 | 1.00 | 52.16 | C |
| ATOM | 2623 | CD | PRO | B | 362 | 23.399 | 29.533 | 26.138 | 1.00 | 60.56 | C |
| ATOM | 2624 | N | GLU | B | 363 | 21.358 | 32.718 | 23.459 | 1.00 | 67.23 | N |
| ATOM | 2625 | CA | GLU | B | 363 | 20.910 | 34.103 | 23.532 | 1.00 | 62.78 | C |
| ATOM | 2626 | C | GLU | B | 363 | 19.517 | 34.232 | 24.134 | 1.00 | 66.80 | C |
| ATOM | 2627 | O | GLU | B | 363 | 18.571 | 33.614 | 23.651 | 1.00 | 75.56 | O |
| ATOM | 2628 | CB | GLU | B | 363 | 20.870 | 34.718 | 22.140 | 1.00 | 59.52 | C |
| ATOM | 2629 | CG | GLU | B | 363 | 22.182 | 34.728 | 21.408 | 1.00 | 76.59 | C |
| ATOM | 2630 | CD | GLU | B | 363 | 22.034 | 35.276 | 20.005 | 1.00 | 86.01 | C |
| ATOM | 2631 | OE1 | GLU | B | 363 | 21.233 | 34.710 | 19.227 | 1.00 | 89.71 | O |
| ATOM | 2632 | OE2 | GLU | B | 363 | 22.715 | 36.273 | 19.681 | 1.00 | 92.17 | O |
| ATOM | 2633 | N | VAL | B | 364 | 19.393 | 35.035 | 25.185 | 1.00 | 65.56 | N |
| ATOM | 2634 | CA | VAL | B | 364 | 18.094 | 35.278 | 25.809 | 1.00 | 62.34 | C |
| ATOM | 2635 | C | VAL | B | 364 | 17.781 | 36.746 | 25.529 | 1.00 | 63.44 | C |
| ATOM | 2636 | O | VAL | B | 364 | 18.358 | 37.645 | 26.148 | 1.00 | 60.98 | O |
| ATOM | 2637 | CB | VAL | B | 364 | 18.131 | 35.042 | 27.328 | 1.00 | 62.33 | C |

APPENDIX A-continued

| ATOM | 2638 | CG1 | VAL | B | 364 | 16.744 | 35.232 | 27.917 | 1.00 | 49.01 | C |
|------|------|-----|-----|---|-----|--------|--------|--------|------|-------|---|
| ATOM | 2639 | CG2 | VAL | B | 364 | 18.649 | 33.650 | 27.617 | 1.00 | 62.45 | C |
| ATOM | 2640 | N | LYS | B | 365 | 16.871 | 36.980 | 24.585 | 1.00 | 61.44 | N |
| ATOM | 2641 | CA | LYS | B | 365 | 16.514 | 38.335 | 24.181 | 1.00 | 58.75 | C |
| ATOM | 2642 | C | LYS | B | 365 | 15.083 | 38.772 | 24.510 | 1.00 | 60.24 | C |
| ATOM | 2643 | O | LYS | B | 365 | 14.111 | 38.172 | 24.049 | 1.00 | 62.72 | O |
| ATOM | 2644 | CB | LYS | B | 365 | 16.773 | 38.492 | 22.675 | 1.00 | 47.91 | C |
| ATOM | 2645 | N | PHE | B | 366 | 14.963 | 39.823 | 25.315 | 1.00 | 61.45 | N |
| ATOM | 2646 | CA | PHE | B | 366 | 13.660 | 40.372 | 25.668 | 1.00 | 63.78 | C |
| ATOM | 2647 | C | PHE | B | 366 | 13.326 | 41.429 | 24.605 | 1.00 | 68.18 | C |
| ATOM | 2648 | O | PHE | B | 366 | 13.302 | 42.629 | 24.891 | 1.00 | 70.73 | O |
| ATOM | 2649 | CB | PHE | B | 366 | 13.691 | 41.040 | 27.053 | 1.00 | 60.35 | C |
| ATOM | 2650 | CG | PHE | B | 366 | 13.816 | 40.077 | 28.202 | 1.00 | 54.80 | C |
| ATOM | 2651 | CD1 | PHE | B | 366 | 15.031 | 39.470 | 28.496 | 1.00 | 55.43 | C |
| ATOM | 2652 | CD2 | PHE | B | 366 | 12.712 | 39.787 | 29.002 | 1.00 | 60.31 | C |
| ATOM | 2653 | CE1 | PHE | B | 366 | 15.147 | 38.587 | 29.571 | 1.00 | 46.88 | C |
| ATOM | 2654 | CE2 | PHE | B | 366 | 12.816 | 38.905 | 30.081 | 1.00 | 51.44 | C |
| ATOM | 2655 | CZ | PHE | B | 366 | 14.037 | 38.306 | 30.365 | 1.00 | 51.73 | C |
| ATOM | 2656 | N | ASN | B | 367 | 13.089 | 40.982 | 23.375 | 1.00 | 66.20 | N |
| ATOM | 2657 | CA | ASN | B | 367 | 12.756 | 41.892 | 22.279 | 1.00 | 65.12 | C |
| ATOM | 2658 | C | ASN | B | 367 | 11.300 | 41.705 | 21.843 | 1.00 | 63.33 | C |
| ATOM | 2659 | O | ASN | B | 367 | 10.962 | 41.788 | 20.659 | 1.00 | 58.17 | O |
| ATOM | 2660 | CB | ASN | B | 367 | 13.716 | 41.661 | 21.110 | 1.00 | 60.14 | C |
| ATOM | 2661 | CG | ASN | B | 367 | 13.709 | 40.231 | 20.623 | 1.00 | 64.97 | C |
| ATOM | 2662 | OD1 | ASN | B | 367 | 13.275 | 39.319 | 21.328 | 1.00 | 69.86 | O |
| ATOM | 2663 | ND2 | ASN | B | 367 | 14.182 | 40.027 | 19.402 | 1.00 | 59.35 | N |
| ATOM | 2664 | N | ALA | B | 368 | 10.448 | 41.447 | 22.829 | 1.00 | 59.54 | N |
| ATOM | 2665 | CA | ALA | B | 368 | 9.023 | 41.247 | 22.616 | 1.00 | 57.86 | C |
| ATOM | 2666 | C | ALA | B | 368 | 8.324 | 41.684 | 23.905 | 1.00 | 62.84 | C |
| ATOM | 2667 | O | ALA | B | 368 | 8.948 | 41.743 | 24.969 | 1.00 | 66.25 | O |
| ATOM | 2668 | CB | ALA | B | 368 | 8.731 | 39.771 | 22.325 | 1.00 | 38.04 | C |
| ATOM | 2669 | N | PRO | B | 369 | 7.024 | 42.003 | 23.830 | 1.00 | 59.07 | N |
| ATOM | 2670 | CA | PRO | B | 369 | 6.324 | 42.425 | 25.046 | 1.00 | 54.01 | C |
| ATOM | 2671 | C | PRO | B | 369 | 6.575 | 41.492 | 26.229 | 1.00 | 53.41 | C |
| ATOM | 2672 | O | PRO | B | 369 | 6.289 | 40.297 | 26.161 | 1.00 | 58.70 | O |
| ATOM | 2673 | CB | PRO | B | 369 | 4.868 | 42.435 | 24.609 | 1.00 | 51.46 | C |
| ATOM | 2674 | CG | PRO | B | 369 | 4.968 | 42.868 | 23.170 | 1.00 | 50.22 | C |
| ATOM | 2675 | CD | PRO | B | 369 | 6.127 | 42.042 | 22.661 | 1.00 | 47.55 | C |
| ATOM | 2676 | N | PHE | B | 370 | 7.119 | 42.049 | 27.307 | 1.00 | 54.35 | N |
| ATOM | 2677 | CA | PHE | B | 370 | 7.404 | 41.281 | 28.512 | 1.00 | 53.26 | C |
| ATOM | 2678 | C | PHE | B | 370 | 6.895 | 41.986 | 29.766 | 1.00 | 53.29 | C |
| ATOM | 2679 | O | PHE | B | 370 | 6.573 | 43.173 | 29.744 | 1.00 | 63.98 | O |
| ATOM | 2680 | CB | PHE | B | 370 | 8.907 | 41.012 | 28.627 | 1.00 | 52.15 | C |
| ATOM | 2681 | CG | PHE | B | 370 | 9.749 | 42.253 | 28.754 | 1.00 | 56.31 | C |
| ATOM | 2682 | CD1 | PHE | B | 370 | 9.883 | 42.899 | 29.981 | 1.00 | 62.15 | C |
| ATOM | 2683 | CD2 | PHE | B | 370 | 10.435 | 42.761 | 27.650 | 1.00 | 58.24 | C |
| ATOM | 2684 | CE1 | PHE | B | 370 | 10.692 | 44.034 | 30.111 | 1.00 | 55.38 | C |
| ATOM | 2685 | CE2 | PHE | B | 370 | 11.247 | 43.896 | 27.766 | 1.00 | 51.88 | C |
| ATOM | 2686 | CZ | PHE | B | 370 | 11.375 | 44.531 | 28.999 | 1.00 | 53.97 | C |
| ATOM | 2687 | N | VAL | B | 371 | 6.822 | 41.242 | 30.861 | 1.00 | 49.67 | N |
| ATOM | 2688 | CA | VAL | B | 371 | 6.338 | 41.775 | 32.128 | 1.00 | 45.42 | C |
| ATOM | 2689 | C | VAL | B | 371 | 7.481 | 41.836 | 33.124 | 1.00 | 45.69 | C |
| ATOM | 2690 | O | VAL | B | 371 | 8.509 | 41.201 | 32.926 | 1.00 | 54.69 | O |
| ATOM | 2691 | CB | VAL | B | 371 | 5.238 | 40.872 | 32.702 | 1.00 | 45.31 | C |
| ATOM | 2692 | CG1 | VAL | B | 371 | 4.705 | 41.447 | 34.004 | 1.00 | 43.96 | C |
| ATOM | 2693 | CG2 | VAL | B | 371 | 4.131 | 40.707 | 31.677 | 1.00 | 40.34 | C |
| ATOM | 2694 | N | PHE | B | 372 | 7.304 | 42.596 | 34.197 | 1.00 | 50.62 | N |
| ATOM | 2695 | CA | PHE | B | 372 | 8.349 | 42.706 | 35.207 | 1.00 | 55.28 | C |
| ATOM | 2696 | C | PHE | B | 372 | 7.897 | 43.442 | 36.460 | 1.00 | 53.84 | C |
| ATOM | 2697 | O | PHE | B | 372 | 6.954 | 44.235 | 36.431 | 1.00 | 54.69 | O |
| ATOM | 2698 | CB | PHE | B | 372 | 9.571 | 43.433 | 34.638 | 1.00 | 55.53 | C |
| ATOM | 2699 | CG | PHE | B | 372 | 9.407 | 44.925 | 34.569 | 1.00 | 58.14 | C |
| ATOM | 2700 | CD1 | PHE | B | 372 | 8.666 | 45.513 | 33.550 | 1.00 | 65.56 | C |
| ATOM | 2701 | CD2 | PHE | B | 372 | 9.964 | 45.740 | 35.549 | 1.00 | 55.03 | C |
| ATOM | 2702 | CE1 | PHE | B | 372 | 8.477 | 46.893 | 33.507 | 1.00 | 65.07 | C |
| ATOM | 2703 | CE2 | PHE | B | 372 | 9.781 | 47.119 | 35.517 | 1.00 | 62.70 | C |
| ATOM | 2704 | CZ | PHE | B | 372 | 9.036 | 47.698 | 34.493 | 1.00 | 65.70 | C |
| ATOM | 2705 | N | LEU | B | 373 | 8.584 | 43.165 | 37.561 | 1.00 | 52.17 | N |
| ATOM | 2706 | CA | LEU | B | 373 | 8.299 | 43.826 | 38.822 | 1.00 | 62.46 | C |
| ATOM | 2707 | C | LEU | B | 373 | 9.572 | 43.929 | 39.645 | 1.00 | 61.03 | C |
| ATOM | 2708 | O | LEU | B | 373 | 10.540 | 43.209 | 39.398 | 1.00 | 56.08 | O |
| ATOM | 2709 | CB | LEU | B | 373 | 7.205 | 43.091 | 39.613 | 1.00 | 62.40 | C |
| ATOM | 2710 | CG | LEU | B | 373 | 7.226 | 41.580 | 39.841 | 1.00 | 65.96 | C |
| ATOM | 2711 | CD1 | LEU | B | 373 | 8.594 | 41.128 | 40.304 | 1.00 | 78.73 | C |
| ATOM | 2712 | CD2 | LEU | B | 373 | 6.161 | 41.225 | 40.877 | 1.00 | 50.90 | C |
| ATOM | 2713 | N | MET | B | 374 | 9.571 | 44.849 | 40.607 | 1.00 | 63.46 | N |
| ATOM | 2714 | CA | MET | B | 374 | 10.721 | 45.056 | 41.473 | 1.00 | 59.62 | C |
| ATOM | 2715 | C | MET | B | 374 | 10.365 | 44.715 | 42.910 | 1.00 | 59.44 | C |
| ATOM | 2716 | O | MET | B | 374 | 9.374 | 45.201 | 43.460 | 1.00 | 52.08 | O |
| ATOM | 2717 | CB | MET | B | 374 | 11.222 | 46.496 | 41.355 | 1.00 | 58.63 | C |

APPENDIX A-continued

| ATOM | 2718 | CG | MET | B | 374 | 11.904 | 46.771 | 40.020 | 1.00 | 65.14 | C |
|---|---|---|---|---|---|---|---|---|---|---|---|
| ATOM | 2719 | SD | MET | B | 374 | 12.509 | 48.453 | 39.822 | 1.00 | 62.08 | S |
| ATOM | 2720 | CE | MET | B | 374 | 11.262 | 49.118 | 38.754 | 1.00 | 73.29 | C |
| ATOM | 2721 | N | ILE | B | 375 | 11.195 | 43.868 | 43.506 | 1.00 | 58.37 | N |
| ATOM | 2722 | CA | ILE | B | 375 | 10.974 | 43.400 | 44.858 | 1.00 | 56.10 | C |
| ATOM | 2723 | C | ILE | B | 375 | 12.065 | 43.783 | 45.834 | 1.00 | 61.08 | C |
| ATOM | 2724 | O | ILE | B | 375 | 13.254 | 43.758 | 45.504 | 1.00 | 61.59 | O |
| ATOM | 2725 | CB | ILE | B | 375 | 10.861 | 41.879 | 44.865 | 1.00 | 57.62 | C |
| ATOM | 2726 | CG1 | ILE | B | 375 | 9.730 | 41.458 | 43.931 | 1.00 | 58.50 | C |
| ATOM | 2727 | CG2 | ILE | B | 375 | 10.637 | 41.375 | 46.282 | 1.00 | 64.27 | C |
| ATOM | 2728 | CD1 | ILE | B | 375 | 9.579 | 39.969 | 43.798 | 1.00 | 71.61 | C |
| ATOM | 2729 | N | GLU | B | 376 | 11.645 | 44.129 | 47.045 | 1.00 | 62.90 | N |
| ATOM | 2730 | CA | GLU | B | 376 | 12.569 | 44.489 | 48.108 | 1.00 | 63.82 | C |
| ATOM | 2731 | C | GLU | B | 376 | 12.863 | 43.153 | 48.796 | 1.00 | 66.05 | C |
| ATOM | 2732 | O | GLU | B | 376 | 11.962 | 42.506 | 49.326 | 1.00 | 63.09 | O |
| ATOM | 2733 | CB | GLU | B | 376 | 11.896 | 45.484 | 49.057 | 1.00 | 61.50 | C |
| ATOM | 2734 | CG | GLU | B | 376 | 12.839 | 46.189 | 50.005 | 1.00 | 62.97 | C |
| ATOM | 2735 | CD | GLU | B | 376 | 13.232 | 45.324 | 51.182 | 1.00 | 69.20 | C |
| ATOM | 2736 | OE1 | GLU | B | 376 | 12.352 | 45.022 | 52.016 | 1.00 | 67.57 | O |
| ATOM | 2737 | OE2 | GLU | B | 376 | 14.419 | 44.945 | 51.272 | 1.00 | 69.44 | O |
| ATOM | 2738 | N | GLN | B | 377 | 14.127 | 42.742 | 48.766 | 1.00 | 68.41 | N |
| ATOM | 2739 | CA | GLN | B | 377 | 14.555 | 41.462 | 49.327 | 1.00 | 66.29 | C |
| ATOM | 2740 | C | GLN | B | 377 | 14.149 | 41.101 | 50.753 | 1.00 | 65.40 | C |
| ATOM | 2741 | O | GLN | B | 377 | 13.887 | 39.937 | 51.033 | 1.00 | 68.37 | O |
| ATOM | 2742 | CB | GLN | B | 377 | 16.066 | 41.316 | 49.143 | 1.00 | 63.89 | C |
| ATOM | 2743 | CG | GLN | B | 377 | 16.450 | 41.329 | 47.662 | 1.00 | 88.59 | C |
| ATOM | 2744 | CD | GLN | B | 377 | 17.923 | 41.081 | 47.404 | 1.00 | 97.38 | C |
| ATOM | 2745 | OE1 | GLN | B | 377 | 18.788 | 41.782 | 47.930 | 1.00 | 108.24 | O |
| ATOM | 2746 | NE2 | GLN | B | 377 | 18.216 | 40.082 | 46.577 | 1.00 | 102.65 | N |
| ATOM | 2747 | N | ASN | B | 378 | 14.092 | 42.076 | 51.650 | 1.00 | 65.80 | N |
| ATOM | 2748 | CA | ASN | B | 378 | 13.691 | 41.804 | 53.026 | 1.00 | 66.74 | C |
| ATOM | 2749 | C | ASN | B | 378 | 12.202 | 41.510 | 53.112 | 1.00 | 75.92 | C |
| ATOM | 2750 | O | ASN | B | 378 | 11.791 | 40.380 | 53.378 | 1.00 | 82.52 | O |
| ATOM | 2751 | CB | ASN | B | 378 | 14.025 | 42.994 | 53.917 | 1.00 | 71.59 | C |
| ATOM | 2752 | CG | ASN | B | 378 | 15.476 | 43.021 | 54.320 | 1.00 | 81.04 | C |
| ATOM | 2753 | OD1 | ASN | B | 378 | 15.821 | 42.664 | 55.446 | 1.00 | 98.82 | O |
| ATOM | 2754 | ND2 | ASN | B | 378 | 16.340 | 43.431 | 53.400 | 1.00 | 75.57 | N |
| ATOM | 2755 | N | THR | B | 379 | 11.398 | 42.541 | 52.882 | 1.00 | 81.20 | N |
| ATOM | 2756 | CA | THR | B | 379 | 9.944 | 42.426 | 52.935 | 1.00 | 79.37 | C |
| ATOM | 2757 | C | THR | B | 379 | 9.382 | 41.583 | 51.795 | 1.00 | 73.68 | C |
| ATOM | 2758 | O | THR | B | 379 | 8.246 | 41.109 | 51.861 | 1.00 | 69.33 | O |
| ATOM | 2759 | CB | THR | B | 379 | 9.278 | 43.822 | 52.886 | 1.00 | 82.38 | C |
| ATOM | 2760 | OG1 | THR | B | 379 | 9.719 | 44.528 | 51.717 | 1.00 | 84.78 | O |
| ATOM | 2761 | CG2 | THR | B | 379 | 9.641 | 44.629 | 54.126 | 1.00 | 87.13 | C |
| ATOM | 2762 | N | LYS | B | 380 | 10.186 | 41.394 | 50.754 | 1.00 | 69.47 | N |
| ATOM | 2763 | CA | LYS | B | 380 | 9.765 | 40.622 | 49.594 | 1.00 | 70.86 | C |
| ATOM | 2764 | C | LYS | B | 380 | 8.489 | 41.226 | 48.994 | 1.00 | 72.76 | C |
| ATOM | 2765 | O | LYS | B | 380 | 7.677 | 40.517 | 48.400 | 1.00 | 73.01 | O |
| ATOM | 2766 | CB | LYS | B | 380 | 9.533 | 39.165 | 49.993 | 1.00 | 56.44 | C |
| ATOM | 2767 | N | SER | B | 381 | 8.323 | 42.540 | 49.154 | 1.00 | 73.08 | N |
| ATOM | 2768 | CA | SER | B | 381 | 7.154 | 43.247 | 48.631 | 1.00 | 68.78 | C |
| ATOM | 2769 | C | SER | B | 381 | 7.424 | 43.843 | 47.243 | 1.00 | 69.37 | C |
| ATOM | 2770 | O | SER | B | 381 | 8.568 | 44.156 | 46.896 | 1.00 | 65.30 | O |
| ATOM | 2771 | CB | SER | B | 381 | 6.728 | 44.357 | 49.596 | 1.00 | 70.68 | C |
| ATOM | 2772 | OG | SER | B | 381 | 7.749 | 45.329 | 49.739 | 1.00 | 75.62 | O |
| ATOM | 2773 | N | PRO | B | 382 | 6.362 | 44.012 | 46.435 | 1.00 | 66.38 | N |
| ATOM | 2774 | CA | PRO | B | 382 | 6.439 | 44.559 | 45.079 | 1.00 | 62.68 | C |
| ATOM | 2775 | C | PRO | B | 382 | 6.525 | 46.077 | 45.036 | 1.00 | 61.73 | C |
| ATOM | 2776 | O | PRO | B | 382 | 5.507 | 46.767 | 45.047 | 1.00 | 65.27 | O |
| ATOM | 2777 | CB | PRO | B | 382 | 5.158 | 44.047 | 44.446 | 1.00 | 63.17 | C |
| ATOM | 2778 | CG | PRO | B | 382 | 4.189 | 44.190 | 45.579 | 1.00 | 60.70 | C |
| ATOM | 2779 | CD | PRO | B | 382 | 4.971 | 43.644 | 46.764 | 1.00 | 68.49 | C |
| ATOM | 2780 | N | LEU | B | 383 | 7.744 | 46.596 | 44.984 | 1.00 | 57.74 | N |
| ATOM | 2781 | CA | LEU | B | 383 | 7.939 | 48.034 | 44.930 | 1.00 | 52.26 | C |
| ATOM | 2782 | C | LEU | B | 383 | 7.319 | 48.612 | 43.659 | 1.00 | 50.43 | C |
| ATOM | 2783 | O | LEU | B | 383 | 6.582 | 49.593 | 43.716 | 1.00 | 52.38 | O |
| ATOM | 2784 | CB | LEU | B | 383 | 9.432 | 48.357 | 44.985 | 1.00 | 50.04 | C |
| ATOM | 2785 | CG | LEU | B | 383 | 10.062 | 48.533 | 46.369 | 1.00 | 44.19 | C |
| ATOM | 2786 | CD1 | LEU | B | 383 | 9.577 | 47.465 | 47.321 | 1.00 | 49.77 | C |
| ATOM | 2787 | CD2 | LEU | B | 383 | 11.573 | 48.498 | 46.229 | 1.00 | 40.45 | C |
| ATOM | 2788 | N | PHE | B | 384 | 7.616 | 47.989 | 42.521 | 1.00 | 53.06 | N |
| ATOM | 2789 | CA | PHE | B | 384 | 7.107 | 48.429 | 41.222 | 1.00 | 47.58 | C |
| ATOM | 2790 | C | PHE | B | 384 | 6.757 | 47.215 | 40.363 | 1.00 | 48.65 | C |
| ATOM | 2791 | O | PHE | B | 384 | 7.209 | 46.102 | 40.632 | 1.00 | 49.46 | O |
| ATOM | 2792 | CB | PHE | B | 384 | 8.171 | 49.262 | 40.492 | 1.00 | 45.93 | C |
| ATOM | 2793 | CG | PHE | B | 384 | 8.519 | 50.561 | 41.179 | 1.00 | 60.02 | C |
| ATOM | 2794 | CD1 | PHE | B | 384 | 7.744 | 51.703 | 40.979 | 1.00 | 51.91 | C |
| ATOM | 2795 | CD2 | PHE | B | 384 | 9.616 | 50.638 | 42.042 | 1.00 | 60.04 | C |
| ATOM | 2796 | CE1 | PHE | B | 384 | 8.056 | 52.904 | 41.630 | 1.00 | 56.20 | C |
| ATOM | 2797 | CE2 | PHE | B | 384 | 9.936 | 51.833 | 42.698 | 1.00 | 58.17 | C |

APPENDIX A-continued

| ATOM | 2798 | CZ | PHE | B | 384 | 9.154 | 52.968 | 42.492 | 1.00 | 51.30 | C |
|---|---|---|---|---|---|---|---|---|---|---|---|
| ATOM | 2799 | N | MET | B | 385 | 5.943 | 47.440 | 39.336 | 1.00 | 45.48 | N |
| ATOM | 2800 | CA | MET | B | 385 | 5.541 | 46.389 | 38.404 | 1.00 | 44.49 | C |
| ATOM | 2801 | C | MET | B | 385 | 5.088 | 47.028 | 37.106 | 1.00 | 48.73 | C |
| ATOM | 2802 | O | MET | B | 385 | 4.614 | 48.165 | 37.104 | 1.00 | 54.71 | O |
| ATOM | 2803 | CB | MET | B | 385 | 4.389 | 45.557 | 38.964 | 1.00 | 51.58 | C |
| ATOM | 2804 | CG | MET | B | 385 | 3.872 | 44.513 | 37.976 | 1.00 | 51.67 | C |
| ATOM | 2805 | SD | MET | B | 385 | 2.476 | 43.533 | 38.582 | 1.00 | 63.04 | S |
| ATOM | 2806 | CE | MET | B | 385 | 2.600 | 42.057 | 37.513 | 1.00 | 42.76 | C |
| ATOM | 2807 | N | GLY | B | 386 | 5.225 | 46.302 | 36.001 | 1.00 | 48.45 | N |
| ATOM | 2808 | CA | GLY | B | 386 | 4.801 | 46.854 | 34.730 | 1.00 | 46.55 | C |
| ATOM | 2809 | C | GLY | B | 386 | 4.960 | 45.928 | 33.545 | 1.00 | 45.82 | C |
| ATOM | 2810 | O | GLY | B | 386 | 5.377 | 44.779 | 33.687 | 1.00 | 48.98 | O |
| ATOM | 2811 | N | LYS | B | 387 | 4.600 | 46.430 | 32.371 | 1.00 | 40.84 | N |
| ATOM | 2812 | CA | LYS | B | 387 | 4.724 | 45.670 | 31.140 | 1.00 | 41.72 | C |
| ATOM | 2813 | C | LYS | B | 387 | 5.253 | 46.577 | 30.045 | 1.00 | 50.34 | C |
| ATOM | 2814 | O | LYS | B | 387 | 4.757 | 47.690 | 29.853 | 1.00 | 51.02 | O |
| ATOM | 2815 | CB | LYS | B | 387 | 3.381 | 45.105 | 30.692 | 1.00 | 42.47 | C |
| ATOM | 2816 | CG | LYS | B | 387 | 3.432 | 44.571 | 29.263 | 1.00 | 42.00 | C |
| ATOM | 2817 | CD | LYS | B | 387 | 2.147 | 43.887 | 28.851 | 1.00 | 41.97 | C |
| ATOM | 2818 | CE | LYS | B | 387 | 1.014 | 44.871 | 28.707 | 1.00 | 50.19 | C |
| ATOM | 2819 | NZ | LYS | B | 387 | −0.220 | 44.167 | 28.285 | 1.00 | 59.67 | N |
| ATOM | 2820 | N | VAL | B | 388 | 6.258 | 46.095 | 29.326 | 1.00 | 50.31 | N |
| ATOM | 2821 | CA | VAL | B | 388 | 6.854 | 46.862 | 28.243 | 1.00 | 49.53 | C |
| ATOM | 2822 | C | VAL | B | 388 | 6.309 | 46.336 | 26.926 | 1.00 | 48.85 | C |
| ATOM | 2823 | O | VAL | B | 388 | 6.668 | 45.247 | 26.491 | 1.00 | 60.31 | O |
| ATOM | 2824 | CB | VAL | B | 388 | 8.396 | 46.731 | 28.249 | 1.00 | 47.89 | C |
| ATOM | 2825 | CG1 | VAL | B | 388 | 9.010 | 47.665 | 27.214 | 1.00 | 38.61 | C |
| ATOM | 2826 | CG2 | VAL | B | 388 | 8.934 | 47.037 | 29.639 | 1.00 | 45.88 | C |
| ATOM | 2827 | N | VAL | B | 389 | 5.436 | 47.111 | 26.295 | 1.00 | 46.81 | N |
| ATOM | 2828 | CA | VAL | B | 389 | 4.842 | 46.714 | 25.027 | 1.00 | 43.83 | C |
| ATOM | 2829 | C | VAL | B | 389 | 5.572 | 47.308 | 23.820 | 1.00 | 44.34 | C |
| ATOM | 2830 | O | VAL | B | 389 | 5.605 | 46.712 | 22.745 | 1.00 | 47.08 | O |
| ATOM | 2831 | CB | VAL | B | 389 | 3.371 | 47.131 | 24.977 | 1.00 | 37.41 | C |
| ATOM | 2832 | CG1 | VAL | B | 389 | 2.763 | 46.743 | 23.632 | 1.00 | 54.79 | C |
| ATOM | 2833 | CG2 | VAL | B | 389 | 2.620 | 46.469 | 26.120 | 1.00 | 42.63 | C |
| ATOM | 2834 | N | ASN | B | 390 | 6.156 | 48.483 | 24.008 | 1.00 | 48.40 | N |
| ATOM | 2835 | CA | ASN | B | 390 | 6.884 | 49.175 | 22.951 | 1.00 | 50.66 | C |
| ATOM | 2836 | C | ASN | B | 390 | 7.725 | 50.247 | 23.626 | 1.00 | 58.21 | C |
| ATOM | 2837 | O | ASN | B | 390 | 7.228 | 51.329 | 23.953 | 1.00 | 59.89 | O |
| ATOM | 2838 | CB | ASN | B | 390 | 5.901 | 49.817 | 21.969 | 1.00 | 55.71 | C |
| ATOM | 2839 | CG | ASN | B | 390 | 6.589 | 50.674 | 20.919 | 1.00 | 63.17 | C |
| ATOM | 2840 | OD1 | ASN | B | 390 | 7.818 | 50.764 | 20.868 | 1.00 | 73.12 | O |
| ATOM | 2841 | ND2 | ASN | B | 390 | 5.790 | 51.311 | 20.072 | 1.00 | 64.31 | N |
| ATOM | 2842 | N | PRO | B | 391 | 9.017 | 49.958 | 23.848 | 1.00 | 62.88 | N |
| ATOM | 2843 | CA | PRO | B | 391 | 9.943 | 50.891 | 24.496 | 1.00 | 63.09 | C |
| ATOM | 2844 | C | PRO | B | 391 | 10.026 | 52.289 | 23.903 | 1.00 | 57.56 | C |
| ATOM | 2845 | O | PRO | B | 391 | 10.475 | 53.218 | 24.578 | 1.00 | 62.77 | O |
| ATOM | 2846 | CB | PRO | B | 391 | 11.279 | 50.147 | 24.447 | 1.00 | 61.96 | C |
| ATOM | 2847 | CG | PRO | B | 391 | 11.126 | 49.220 | 23.287 | 1.00 | 64.15 | C |
| ATOM | 2848 | CD | PRO | B | 391 | 9.718 | 48.730 | 23.441 | 1.00 | 62.61 | C |
| ATOM | 2849 | N | THR | B | 392 | 9.582 | 52.441 | 22.658 | 1.00 | 53.31 | N |
| ATOM | 2850 | CA | THR | B | 392 | 9.622 | 53.739 | 21.985 | 1.00 | 60.90 | C |
| ATOM | 2851 | C | THR | B | 392 | 8.392 | 54.595 | 22.292 | 1.00 | 60.82 | C |
| ATOM | 2852 | O | THR | B | 392 | 8.427 | 55.821 | 22.178 | 1.00 | 56.87 | O |
| ATOM | 2853 | CB | THR | B | 392 | 9.742 | 53.565 | 20.456 | 1.00 | 59.19 | C |
| ATOM | 2854 | OG1 | THR | B | 392 | 8.540 | 52.988 | 19.935 | 1.00 | 61.04 | O |
| ATOM | 2855 | CG2 | THR | B | 392 | 10.909 | 52.649 | 20.126 | 1.00 | 59.90 | C |
| ATOM | 2856 | N | GLN | B | 393 | 7.311 | 53.932 | 22.687 | 1.00 | 63.31 | N |
| ATOM | 2857 | CA | GLN | B | 393 | 6.059 | 54.599 | 23.019 | 1.00 | 58.71 | C |
| ATOM | 2858 | C | GLN | B | 393 | 6.256 | 55.539 | 24.203 | 1.00 | 56.16 | C |
| ATOM | 2859 | O | GLN | B | 393 | 6.842 | 55.161 | 25.215 | 1.00 | 63.66 | O |
| ATOM | 2860 | CB | GLN | B | 393 | 4.998 | 53.550 | 23.353 | 1.00 | 61.67 | C |
| ATOM | 2861 | CG | GLN | B | 393 | 3.597 | 54.101 | 23.569 | 1.00 | 72.76 | C |
| ATOM | 2862 | CD | GLN | B | 393 | 2.555 | 52.993 | 23.641 | 1.00 | 76.15 | C |
| ATOM | 2863 | OE1 | GLN | B | 393 | 2.294 | 52.429 | 24.707 | 1.00 | 81.40 | O |
| ATOM | 2864 | NE2 | GLN | B | 393 | 1.957 | 52.674 | 22.499 | 1.00 | 61.63 | N |
| ATOM | 2865 | N | LYS | B | 394 | 5.760 | 56.764 | 24.073 | 1.00 | 59.78 | N |
| ATOM | 2866 | CA | LYS | B | 394 | 5.887 | 57.770 | 25.124 | 1.00 | 64.60 | C |
| ATOM | 2867 | C | LYS | B | 394 | 4.548 | 58.110 | 25.787 | 1.00 | 69.52 | C |
| ATOM | 2868 | O | LYS | B | 394 | 4.548 | 58.370 | 27.011 | 1.00 | 74.15 | O |
| ATOM | 2869 | CB | LYS | B | 394 | 6.521 | 59.045 | 24.551 | 1.00 | 62.16 | C |
| ATOM | 2870 | CG | LYS | B | 394 | 7.877 | 59.423 | 25.148 | 1.00 | 69.11 | C |
| ATOM | 2871 | CD | LYS | B | 394 | 8.976 | 58.392 | 24.864 | 1.00 | 81.72 | C |
| ATOM | 2872 | CE | LYS | B | 394 | 8.928 | 57.196 | 25.818 | 1.00 | 85.23 | C |
| ATOM | 2873 | NZ | LYS | B | 394 | 10.041 | 56.223 | 25.582 | 1.00 | 77.70 | N |
| ATOM | 2874 | OXT | LYS | B | 394 | 3.516 | 58.134 | 25.080 | 1.00 | 70.18 | O |
| TER | 2875 | | LYS | B | 394 | | | | | | |
| HETATM | 2876 | O | HOH | | 395 | −10.656 | 42.320 | 34.264 | 1.00 | 49.27 | O |
| HETATM | 2877 | O | HOH | | 396 | 23.473 | 57.530 | 48.807 | 1.00 | 64.10 | O |

APPENDIX A-continued

| | | | | | | | | | | | |
|---|---|---|---|---|---|---|---|---|---|---|---|
| HETATM | 2878 | O | HOH | | | 398 | 25.100 | 59.122 | 39.798 | 1.00 | 59.10 | O |
| HETATM | 2879 | O | HOH | | | 399 | −13.670 | 73.163 | 56.639 | 1.00 | 62.14 | O |
| HETATM | 2880 | O | HOH | | | 401 | −11.462 | 61.960 | 38.251 | 1.00 | 57.44 | O |
| HETATM | 2881 | O | HOH | | | 402 | 11.147 | 65.235 | 50.537 | 1.00 | 57.34 | O |
| HETATM | 2882 | O | HOH | | | 403 | −17.698 | 44.938 | 40.522 | 1.00 | 42.40 | O |
| HETATM | 2883 | O | HOH | | | 408 | 1.577 | 45.248 | 69.638 | 1.00 | 77.47 | O |
| HETATM | 2884 | O | HOH | | | 411 | 5.603 | 72.238 | 53.126 | 1.00 | 61.59 | O |
| HETATM | 2885 | O | HOH | | | 415 | −13.252 | 73.873 | 59.714 | 1.00 | 80.74 | O |
| HETATM | 2886 | O | HOH | | | 419 | 11.507 | 56.942 | 57.916 | 1.00 | 72.00 | O |
| HETATM | 2887 | O | HOH | | | 420 | −10.743 | 53.147 | 61.393 | 1.00 | 54.65 | O |
| HETATM | 2888 | O | HOH | | | 421 | 11.461 | 28.122 | 25.052 | 1.00 | 59.32 | O |
| HETATM | 2889 | O | HOH | | | 423 | 18.508 | 34.775 | 16.870 | 1.00 | 73.36 | O |
| HETATM | 2890 | O | HOH | | | 424 | 21.301 | 42.453 | 46.188 | 1.00 | 66.54 | O |
| HETATM | 2891 | O | HOH | | | 425 | −5.506 | 74.396 | 39.900 | 1.00 | 102.94 | O |
| HETATM | 2892 | O | HOH | | | 426 | 2.458 | 63.761 | 67.339 | 1.00 | 55.91 | O |
| MASTER | 316 | 0 | 0 | 11 | 14 | 0 | 1 | 6 | 2890 | 2 | 0 | 30 |
| END | | | | | | | | | | | | |

What is claimed is:

1. A method of healing, alleviating, relieving, altering, remedying, ameliorating, improving, or affecting alpha-1 antitrypsin (AAT) deficiency in a subject in need of such treatment, the method comprising administering to the subject a compound capable of disrupting polymerization of the mutant Z form of AAT under conditions such that AAT deficiency is treated, wherein the compound is selected from the group consisting of: 5-(2-Bromo-ethoxy-methyl)-auinolin-8-ol, 3,4-methylenedioxy-6-nitrocinnamic acid, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl -benzene, 2-acetyl-5-chlorothiophene, or 1,9-decadiene; or a pharmaceutically acceptable salt thereof.

2. A method of reducing the accumulation of the mutant Z form of alpha-1 antitrypsin (AAT) in a cell, the method comprising contacting the cell with a compound capable of disrupting polymerization of the mutant Z form of AAT under conditions such that accumulation of the mutant Z form of alpha-1 antitrypsin in the cell is reduced, wherein the compound is selected from the group consisting of: 5-(2-Bromo-ethoxy-methyl)-auinolin-8-ol, 3,4-methylenedioxy-6-nitrocinnamic acid, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl-benzene, 2-acetyl-5-chlorothiophene, or 1,9-decadiene; or a pharmaceutically acceptable salt thereof.

3. The method of claim 1, wherein the compound is 1,9-decadiene.

4. A method of healing, alleviating, relieving, altering, remedying, ameliorating, improving, or affecting lung damage or preserving lung function in a subject suffering from alpha-1 antitrypsin (AAT) deficiency, the method comprising administering to the subject a compound capable of disrupting polymerization of the mutant Z form of AAT, under conditions such that lung damage in the subject is treated or lung function is preserved, wherein the compound is selected from the group consisting of: 5-(2-Bromo-ethoxy-methyl)-quinolin-8-ol, 3,4-methylenedioxy-6-nitrocinnamic acid, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl-benzene, 2-acetyl-5-chlorothiophene, or 1,9-decadiene; or a pharmaceutically acceptable salt thereof.

5. The method of claim 4, wherein the method further comprises the step of identifying the subject as suffering from AAT-deficiency-related lung damage prior to the step of administering to the subject the compound capable of disrupting polymerization of the mutant Z form of AAT.

6. The method of claim 4, wherein the method further comprises the step of determining the efficacy of administration to the subject of the compound capable of disrupting polymerization of the mutant Z form of AAT.

7. The method of claim 6, wherein the step of determining the efficacy of administration to the subject of the compound comprises testing lung function of the subject before and after administration of the compound, and comparing the lung function determined before administration of the compound and after administration of the compound.

8. A method of reducing the accumulation of the mutant Z form of alpha-1 antitrypsin (AAT) in a cell, the method comprising contacting the cell with a compound selected from the group consisting of: 5-(2-Bromo-ethoxy-methyl)-quinolin-8-ol, 3,4-methylenedioxy-6-nitrocinnamic acid, 5-Nitro-1-naphthol, 3'-acetoxy acetophenone, 2-Ethyl-3-methyl-3-thiophen-2-yl-oxirane-2-carboxylic acid, sodium salt, 2-Bromo-1,5-dimethoxy-3-methyl-benzene, 2-acetyl-5-chlorothiophene, or 1,9-decadiene, or a pharmaceutically acceptable salt thereof, under conditions such that accumulation of the mutant Z form of alpha-1 antitrypsin in the cell is reduced.

* * * * *